（12）United States Patent
Arai et al.

(10) Patent No.: US 7,956,060 B2
(45) Date of Patent: Jun. 7, 2011

(54) PYRIMIDINE DERIVATIVE COMPOUND

(75) Inventors: Hitoshi Arai, Nishinomiya (JP);
Tsutomu Matsumura, Sakai (JP);
Syoichi Isami, Susono (JP); Hiroshi Ishida, Sunto-gun (JP); Koji Hagihara, Sakai (JP); Hiroshi Umehara, Sunto-gun (JP); Yoshinori Yamashita, Sunto-gun (JP); Nana Oiwa, Sunto-gun (JP); Yukimasa Shiotsu, Sunto-gun (JP); Tomoki Naoe, Aichi (JP); Hitoshi Kiyoi, Aichi (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 1110 days.

(21) Appl. No.: 10/594,369

(22) PCT Filed: Mar. 30, 2005

(86) PCT No.: PCT/JP2005/006034
§ 371 (c)(1),
(2), (4) Date: Sep. 27, 2006

(87) PCT Pub. No.: WO2005/095382
PCT Pub. Date: Oct. 13, 2005

(65) Prior Publication Data
US 2009/0012060 A1    Jan. 8, 2009

(30) Foreign Application Priority Data

Mar. 30, 2004 (JP) ................. 2004-097434

(51) Int. Cl.
| C07D 471/04 | (2006.01) |
| C07D 471/22 | (2006.01) |
| C07D 487/04 | (2006.01) |
| C07D 239/70 | (2006.01) |
| C07D 471/00 | (2006.01) |
| C07D 487/00 | (2006.01) |
| C07D 401/00 | (2006.01) |
| C07D 403/00 | (2006.01) |
| C07D 405/00 | (2006.01) |
| C07D 409/00 | (2006.01) |
| C07D 411/00 | (2006.01) |
| C07D 413/00 | (2006.01) |
| C07D 417/00 | (2006.01) |
| C07D 419/00 | (2006.01) |
| A61K 31/505 | (2006.01) |
| A01N 43/56 | (2006.01) |

(52) U.S. Cl. ........ 514/257; 514/275; 514/403; 544/245; 544/324; 548/143
(58) Field of Classification Search .......... 514/257, 514/275, 403; 544/245, 324; 548/143
See application file for complete search history.

(56) References Cited

U.S. PATENT DOCUMENTS
| 6,593,326 B1 | 7/2003 | Bradbury et al. ........ 514/235.8 |
| 2003/0137263 A1 | 7/2003 | Peterson ............... 318/445 |

FOREIGN PATENT DOCUMENTS
| JP | 61-91184 | 5/1986 |
| JP | 2002-533446 | 10/2002 |
| WO | WO 03/009101 | 1/2003 |
| WO | WO 03/063794 | 8/2003 |

*Primary Examiner* — Brandon J Fetterolf
*Assistant Examiner* — Paul Zarek
(74) *Attorney, Agent, or Firm* — Fitzpatrick, Cella, Harper & Scinto

(57) ABSTRACT

The present invention provides an antitumor agent and the like, which comprises as an active ingredient, a pyrimidine derivative represented by Formula (I):

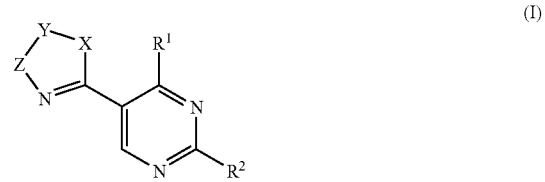

[wherein —X—Y—Z— represents —O—$CR^3$=N— (wherein $R^3$ represents a hydrogen atom, a substituted or unsubstituted aromatic heterocyclic group and the like) and the like, $R^1$ represents —$NR^{10}R^{11}$ (wherein $R^{10}$ and $R^{11}$ may be the same or different, and each represents a hydrogen atom, substituted or unsubstituted lower alkyl and the like) and the like, $R^2$ represents —$NR^{13}R^{14}$ (wherein $R^{13}$ and $R^{14}$ may be the same or different, and each represents a hydrogen atom, substituted or unsubstituted lower alkyl and the like)] or a pharmaceutically acceptable salt thereof.

8 Claims, No Drawings

PYRIMIDINE DERIVATIVE COMPOUND

TECHNICAL FIELD

The present invention relates to antitumor agents, and pyrimidine derivatives having antitumor activity, and the like, or pharmaceutically acceptable salts thereof.

BACKGROUND ART

Examples of known pyrimidine derivatives having a heterocyclic group at 5-position include compounds having LTB4 inhibiting activity (Patent Document 1), compounds having NO production inhibiting activity (Patent Documents 2 and 3), compounds having neurodegeneration inhibiting activity (Patent Document 4), compounds having modulating activity of function of acetylcholine receptor (Patent Document 5), compounds having anti-inflammatory activity (Patent Document 6), compounds having antiviral activity (Patent Document 7), compounds having inhibitory activity against cyclin-dependent serine/threonine kinases, and the like (Patent Document 8), compounds having tyrosine kinase inhibiting activity (Patent Document 9), compounds having glycogen synthase kinase 3 inhibiting activity (Patent Document 10), compounds having protein kinase inhibiting activity (Patent Documents 11 to 13), compounds having modulating activity of CCR4 function (Patent Document 14), compounds having protein kinase inhibiting activity (Patent Document 15), compounds having kinase inhibiting activity (Patent Document 16), and compounds having SRC kinase inhibiting activity (Patent Documents 17 and 18).
Patent Document 1: WO92/01675
Patent Document 2: WO94/14780
Patent Document 3: Japanese Published Unexamined Patent Application No. 87492/1998
Patent Document 4: WO99/19305
Patent Document 5: WO99/32117
Patent Document 6: U.S. Pat. No. 5,935,966 specification
Patent Document 7: WO99/41253
Patent Document 8: WO00/39101
Patent Document 9: WO01/17995
Patent Document 10: WO02/20495
Patent Document 11: WO02/22601
Patent Document 12: WO02/22602
Patent Document 13: WO02/22608
Patent Document 14: WO02/30358
Patent Document 15: WO02/62789
Patent Document 16: WO03/30909
Patent Document 17: WO01/00213
Patent Document 18: Japanese Translation of PCT International Application No. 2003-523942

DISCLOSURE OF INVENTION

Problems to be Solved by the Invention

An object of the present invention is to provide an antitumor agent which comprises, as an active ingredient, a pyrimidine derivative or a pharmaceutically acceptable salt thereof; a pyrimidine derivative or a pharmaceutically acceptable salt thereof, having an antitumor activity, and the like; and the like.

Means for Solving the Problems

The present invention relates to the following (1) to (35):
(1) An antitumor agent which comprises, as an active ingredient, a pyrimidine derivative represented by Formula (I):

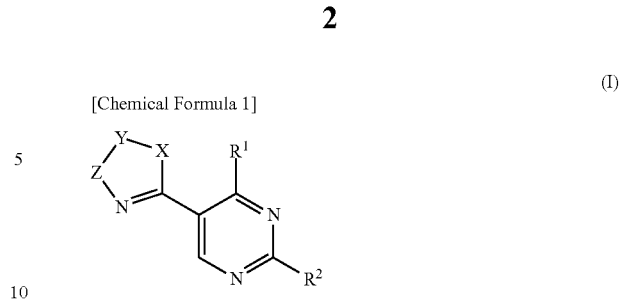

(I)

[wherein —X—Y—Z— represents —O—CR$^3$=N— {wherein R$^3$ represents a hydrogen atom, hydroxy, carboxy, lower alkyl, lower alkyl substituted with one to four substituents, which may be the same or different and selected from the following substituent group A [substituent group A: halogen, amino, aminosulfonyl, nitro, hydroxy, mercapto, cyano, formyl, carboxy, carbamoyl, lower alkanoyloxy, lower alkanoylamino, mono- or di-(lower alkyl)aminocarbonyl, lower alkoxycarbonyl, mono- or di-(lower alkyl)amino, N-aryl-N-(lower alkyl)amino, lower alkylsulfonyl, lower alkylsulfinyl, mono- or di-(lower alkylsulfonyl)amino, mono- or di-(arylsulfonyl)amino, tri(lower alkyl)silyl, lower alkylthio, aromatic heterocyclic alkylthio, lower alkanoyl, lower alkanoyl substituted with one to three substituents, which may be the same or different and selected from the following substituent group a (substituent group a: halogen and hydroxy), lower alkoxy, lower alkoxy substituted with one to three substituents, which may be the same or different and selected from the substituent group a, aryloxy, aryloxy substituted with one to three substituents, which may be the same or different and selected from the substituent group a, aralkyloxy, and aralkyloxy substituted with one to three substituents, which may be the same or different and selected from the substituent group a; wherein, when the substituted lower alkyl is substituted methyl, substituted ethyl, or substituted propyl, the substituent may be —NR$^4$R$^5$ (wherein R$^4$ and R$^5$ may be the same or different, and each represents a hydrogen atom, substituted or unsubstituted lower alkyl, substituted or unsubstituted lower alkenyl, substituted or unsubstituted lower alkynyl, substituted or unsubstituted aralkyl, substituted or unsubstituted aromatic heterocyclic alkyl, substituted or unsubstituted heteroalicyclic alkyl, substituted or unsubstituted aryl, a substituted or unsubstituted aromatic heterocyclic group, or a substituted or unsubstituted heteroalicyclic group)], substituted or unsubstituted lower alkenyl, substituted or unsubstituted lower alkynyl, substituted or unsubstituted aralkyl, substituted or unsubstituted aromatic heterocyclic alkyl, substituted or unsubstituted heteroalicyclic alkyl, substituted or unsubstituted aryl, a substituted or unsubstituted aromatic heterocyclic group, a substituted or unsubstituted heteroalicyclic group, substituted or unsubstituted lower alkoxy, substituted or unsubstituted lower alkoxycarbonyl, substituted or unsubstituted lower alkylthio, substituted or unsubstituted lower alkanoyl, or —C(=O)NR$^6$R$^7$ (wherein R$^6$ and R$^7$ may be the same or different, and each represents a hydrogen atom, substituted or unsubstituted lower alkyl, substituted or unsubstituted lower alkenyl, substituted or unsubstituted lower alkynyl, substituted or unsubstituted aralkyl, substituted or unsubstituted aromatic heterocyclic alkyl, substituted or unsubstituted heteroalicyclic alkyl, substituted or unsubstituted aryl, a substituted or unsubstituted aromatic heterocyclic group, or a substituted or unsubstituted heteroalicyclic group, or R$^6$ and R$^7$ are combined together with the adjacent nitrogen atom thereto to form a substituted or unsubstituted heteroalicyclic group)}, —N=CR$^{3a}$—O— (wherein R$^{3a}$ has the same definition as $R^3$ described above), —O—N=$CR^{3b}$— (wherein $R^{3b}$ has the same definition as $R^3$ described above), —O—C (=O)—$NR^8$— (wherein $R^8$ represents a hydrogen atom, lower alkyl, lower alkyl substituted with one to four substituents, which may be the same or different and selected from the substituent group A, or substituted or unsubstituted heteroalicyclic alkyl), —N=N—$NR^9$— (wherein $R^9$ represents substituted or unsubstituted lower alkyl or substituted or unsubstituted heteroalicyclic alkyl), or —$NR^{9a}$—N=N— (wherein $R^{9a}$ has the same definition as $R^9$ described above); $R^1$ represents —$NR^{10}R^{11}$ (wherein $R^{10}$ and $R^{11}$ may be the same or different, and each represents a hydrogen atom, substituted or unsubstituted lower alkyl, substituted or unsubstituted lower alkenyl, substituted or unsubstituted lower alkynyl, substituted or unsubstituted aralkyl, substituted or unsubstituted aromatic heterocyclic alkyl, substituted or unsubstituted heteroalicyclic alkyl, substituted or unsubstituted monocyclic aryl, a substituted or unsubstituted aromatic monoheterocyclic group, or a substituted or unsubstituted heteroalicyclic group, or $R^{10}$ and $R^{11}$ are combined together with the adjacent nitrogen atom thereto to form a substituted or unsubstituted heteroalicyclic group; wherein, when one of $R^{10}$ and $R^{11}$ is a hydrogen atom, the other of $R^{10}$ and $R^{11}$ is not a group selected from substituted or unsubstituted pyrazol-3-yl and substituted or unsubstituted 1,2,4-triazol-3-yl), or —$OR^{12}$ (wherein $R^{12}$ represents a hydrogen atom, substituted or unsubstituted lower alkyl, substituted or unsubstituted lower alkenyl, substituted or unsubstituted lower alkynyl, substituted or unsubstituted aralkyl, substituted or unsubstituted aromatic heterocyclic alkyl, substituted or unsubstituted heteroalicyclic alkyl, substituted or unsubstituted aryl, a substituted or unsubstituted aromatic heterocyclic group, or a substituted or unsubstituted heteroalicyclic group); and $R^2$ represents —$NR^{13}R^{14}$ (wherein $R^{13}$ and $R^{14}$ may be the same or different, and each represents a hydrogen atom, substituted or unsubstituted lower alkyl, substituted or unsubstituted lower alkenyl, substituted or unsubstituted lower alkynyl, substituted or unsubstituted aralkyl, substituted or unsubstituted aromatic heterocyclic alkyl, substituted or unsubstituted heteroalicyclic alkyl, substituted or unsubstituted monocyclic aryl, a substituted or unsubstituted aromatic monoheterocyclic group, or a substituted or unsubstituted heteroalicyclic group, or $R^{13}$ and $R^{14}$ are combined together with the adjacent nitrogen atom thereto to form a substituted or unsubstituted heteroalicyclic group or a substituted or unsubstituted aromatic heterocyclic group; wherein. $R^{13}$ and $R^{14}$ do not simultaneously represent a hydrogen atom, and when one of $R^{13}$ and $R^{14}$ is a hydrogen atom, the other of $R^{13}$ and $R^{14}$ is not substituted or unsubstituted pyrazol-3-yl)] or a pharmaceutically acceptable salt thereof.

(2) The antitumor agent according to (1), wherein the tumor is a hematopoietic tumor.

(3) A therapeutic agent for leukemia, which comprises, as an active ingredient, the pyrimidine derivative or the pharmaceutically acceptable salt thereof described in (1).

(4) A pyrimidine derivative represented by Formula (IA):

[Chemical Formula 2]

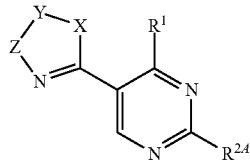

(IA)

[wherein —X—Y—Z— and $R^1$ have the same definitions as described above, respectively;

$R^{2A}$ represents —$NR^{13A}R^{14A}$ {wherein $R^{13A}$ and $R^{14A}$ may be the same or different, and each represents a hydrogen atom, lower alkyl, lower alkyl substituted with one to four substituents, which may be the same or different and selected from the following substituent group B [substituent group B: halogen, amino, aminosulfonyl, nitro, hydroxy, mercapto, cyano, formyl, carboxy, carbamoyl, lower alkanoyloxy, lower alkanoylamino, mono- or di-(lower alkyl)aminocarbonyl, lower alkoxycarbonyl, mono- or di-(lower alkyl)amino, N-aryl-N-(lower alkyl)amino, lower alkylsulfonyl, lower alkylsulfinyl, mono- or di-(lower alkylsulfonyl)amino, mono- or di-(arylsulfonyl)amino, tri-(lower alkyl)silyl, lower alkylthio, aromatic heterocyclic alkylthio, lower alkanoyl, lower alkanoyl substituted with one to three substituents, which may be the same or different and selected from the following substituent group a (substituent group a: halogen and hydroxy), lower alkoxy, lower alkoxy substituted with one to three substituents, which may be the same or different and selected from the substituent group a, aryloxy, aryloxy substituted with one to three substituents, which may be the same or different and selected from the substituent group a, aralkyloxy, and aralkyloxy substituted with one to three substituents, which may be the same or different and selected from the substituent group a], substituted or unsubstituted lower alkenyl, substituted or unsubstituted lower alkynyl, substituted or unsubstituted heteroalicyclic-alkyl, substituted or unsubstituted monocyclic aryl, or a substituted or unsubstituted heteroalicyclic group, or $R^{13A}$ and $R^{14A}$ are combined together with the adjacent nitrogen atom thereto to form a substituted or unsubstituted heteroalicyclic group or a substituted or unsubstituted aromatic heterocyclic group, wherein $R^{13A}$ and $R^{14A}$ do not simultaneously represent a hydrogen atom}, —$NR^{15}CR^{16A}R^{16B}$—Ar {wherein $R^{15}$ represents a hydrogen atom or lower alkyl; $R^{16A}$ and $R^{16B}$ may be the same or different, and each represents a hydrogen atom, lower alkyl, or lower alkyl substituted with one to three substituents, which may be the same or different and selected from the following substituent group b (substituent group b: halogen, hydroxy, and hydroxymethyl); and Ar represents aryl, aryl substituted with one to three substituents, which may be the same or different and selected from the following substituent group C [substituent group C: halogen, amino, nitro, hydroxy, mercapto, cyano, carboxy, aminosulfonyl, lower alkyl, lower alkyl substituted with one to three substituents, which may be the same or different and selected from the substituent group b, lower alkoxy, lower alkylthio, mono- or di-(lower alkyl)amino, lower alkanoylamino, mono- or di-(lower alkylsulfonyl)amino, lower alkoxycarbonylamino, heteroalicyclic alkyloxy, and alkylenedioxy], an aromatic heterocyclic group, or an aromatic heterocyclic group substituted with one to three substituents, which may be the same or different and selected from the substituent group C}, or —$NR^{15}CR^{16A}R^{16B}CR^{17A}R^{17B}$—Ar (wherein $R^{15}$, $R^{16A}$, $R^{16B}$, and Ar have the same definitions as described above, respectively; and $R^{17A}$ and $R^{17B}$ have the same definition as $R^{16A}$ and $R^{16B}$ described above, respectively)] or a pharmaceutically acceptable salt thereof.

(5) The pyrimidine derivative or the pharmaceutically acceptable salt thereof according to (4), wherein —X—Y—Z— is —O—$CR^3$=N— (wherein $R^3$ has the same definition as described above).

(6) The pyrimidine derivative or the pharmaceutically acceptable salt thereof according to (4), wherein —X—Y—Z— is —O—$CR^{3A}$=N— (wherein $R^{3A}$ represents lower alkyl, lower alkyl substituted with one to four substituents, which may be the same or different and selected from the substituent group A, or heteroalicyclic alkyl).

(7) The pyrimidine derivative or the pharmaceutically acceptable salt thereof according to (5) or (6), wherein $R^1$ is —$NR^{10}R^{11}$ (wherein $R^{10}$ and $R^{11}$ have the same definitions as described above, respectively), and $R^{2A}$ is —$NR^{15}CR^{16A}R^{16B}$—Ar (wherein $R^{15}$, $R^{16A}$, $R^{16B}$, and Ar have the same definitions as described above, respectively) or —$NR^{15}CR^{16A}R^{16B}CR^{17A}R^{17B}$—Ar (wherein $R^{15}$, $R^{16A}$, $R^{16B}$, $R^{17A}$, $R^{17B}$, and Ar have the same definitions as described above, respectively).

(8) The pyrimidine derivative or the pharmaceutically acceptable salt thereof according to any of (5) to (7), wherein $R^1$ is —$NHR^{10A}$ (wherein $R^{10A}$ represents substituted or unsubstituted lower alkyl or substituted or unsubstituted monocyclic aryl).

(9) The pyrimidine derivative or the pharmaceutically acceptable salt thereof according to any of (5) to (8), wherein $R^{2A}$ is —$NH(CH_2)_2$—Ar (wherein Ar has the same definition as described above).

(10) The pyrimidine derivative or the pharmaceutically acceptable salt thereof according to any of (5) to (8), wherein $R^{2A}$ is —$NH(CH_2)_2$—$Ar^1$ (wherein $Ar^1$ represents phenyl or phenyl substituted with one to three substituents, which may be the same or different and selected from the substituent group C).

(11) The pyrimidine derivative or the pharmaceutically acceptable salt thereof according to any of (5) to (8), wherein $R^{2A}$ is —$NH(CH_2)_2$—$Ar^2$ (wherein $Ar^2$ represents pyridyl or pyridyl substituted with one to three substituents, which may be the same or different and selected from the substituent group C).

(12) The pyrimidine derivative or the pharmaceutically acceptable salt thereof according to (4), wherein —X—Y—Z— is —O—C(=O)—$NR^8$— (wherein $R^8$ has the same definition as described above).

(13) The pyrimidine derivative or the pharmaceutically acceptable salt thereof according to (12), wherein $R^1$ is —$NR^{10}R^{11}$ (wherein $R^{10}$ and $R^{11}$ have the same definitions as described above, respectively), and $R^{2A}$ is —$NR^{15}CR^{16A}R^{16B}$—Ar (wherein $R^{15}$, $R^{16A}$, $R^{16B}$, and Ar have the same definitions as described above, respectively) or —$NR^{15}CR^{16A}R^{16B}CR^{17A}R^{17B}$—Ar (wherein $R^{15}$, $R^{16A}$, $R^{16B}$, $R^{17A}$, $R^{17B}$, and Ar have the same definitions as described above, respectively).

(14) The pyrimidine derivative or the pharmaceutically acceptable salt thereof according to (12), wherein $R^1$ is —$NHR^{10B}$ (wherein $R^{10B}$ represents substituted or unsubstituted lower alkyl), and $R^{2A}$ is —$NH(CH_2)_2$—Ar (wherein Ar has the same definition as described above).

(15) The pyrimidine derivative or the pharmaceutically acceptable salt thereof according to any of (12) to (14), wherein $R^{2A}$ is

[Chemical Formula 3]

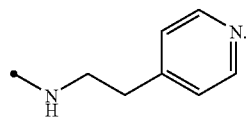

(16) The pyrimidine derivative or the pharmaceutically acceptable salt thereof according to (4), wherein —X—Y—Z— is —N=N—$NR^9$— (wherein $R^9$ has the same definition as described above) or —$NR^{9a}$—N=N— (wherein $R^{9a}$ has the same definition as described above).

(17) The pyrimidine derivative or the pharmaceutically acceptable salt thereof according to (16), wherein $R^1$ is —$NR^{10}R^{11}$ (wherein $R^{10}$ and $R^{11}$ have the same definitions as described above, respectively), and $R^{2A}$ is —$NR^{15}(CH_2)_n$—Ar (wherein $R^{15}$ and Ar have the same definitions as described above, respectively; and n represents 1 or 2).

(18) The pyrimidine derivative or the pharmaceutically acceptable salt thereof according to (16), wherein $R^1$ is —$NHR^{10B}$ (wherein $R^{10B}$ has the same definition as described above), and $R^{2A}$ is —$NH(CH_2)_2$—Ar (wherein Ar has the same definition as described above).

(19) The pyrimidine derivative or the pharmaceutically acceptable salt thereof according to (16), wherein $R^1$ is —$NHR^{10B}$ (wherein $R^{10B}$ has the same definition as described above), and $R^{2A}$ is

[Chemical Formula 4]

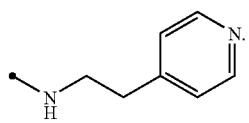

(20) A pharmaceutical composition which comprises, as an active ingredient, the pyrimidine derivative or the pharmaceutically acceptable salt thereof according to any of (4) to (19).

(21) An antitumor agent which comprises, as an active ingredient, the pyrimidine derivative or the pharmaceutically acceptable salt thereof according to any of (4) to (19).

(22) The antitumor agent according to (21), wherein the tumor is a hematopoietic tumor.

(23) A therapeutic agent for leukemia, which comprises, as an active ingredient, the pyrimidine derivative or the pharmaceutically acceptable salt thereof according to any of (4) to (19).

(24) A method for treating a tumor, which comprises a step of administering an effective amount of the pyrimidine derivative or the pharmaceutically acceptable salt thereof according to (1).

(25) A method for treating a hematopoietic tumor, which comprises a step of administering an effective amount of the pyrimidine derivative or the pharmaceutically acceptable, salt thereof according to (1).

(26) A method for treating leukemia, which comprises a step of administering an effective amount of the pyrimidine derivative or the pharmaceutically acceptable salt thereof according to (1).

(27) A method for treating a tumor, which comprises a step of administering an effective amount of the pyrimidine derivative or the pharmaceutically acceptable salt thereof according to any of (4) to (19).

(28) A method for treating a hematopoietic tumor, which comprises a step of administering an effective amount of the pyrimidine derivative or the pharmaceutically acceptable salt thereof according to any of (4) to (19).

(29) A method for treating leukemia, which comprises a step of administering an effective amount of the pyrimidine derivative or the pharmaceutically acceptable salt thereof according to any of (4) to (19).

(30) Use of the pyrimidine derivative or the pharmaceutically acceptable salt thereof according to (1) for a manufacture of an antitumor agent.

(31) Use of the pyrimidine derivative or the pharmaceutically acceptable salt thereof according to (1) for a manufacture of a therapeutic agent for a hematopoietic tumor.

(32) Use of the pyrimidine derivative or the pharmaceutically acceptable salt thereof according to (1) for a manufacture of a therapeutic agent for leukemia.

(33) Use of the pyrimidine derivative or the pharmaceutically acceptable salt thereof according to any of (4) to (19) for a manufacture of an antitumor agent.

(34) Use of the pyrimidine derivative or the pharmaceutically acceptable salt thereof according to any of (4) to (19) for a manufacture of therapeutic agent for a hematopoietic tumor.

(35) Use of the pyrimidine derivative or the pharmaceutically acceptable salt thereof according to any of (4) to (19) for a manufacture of a therapeutic agent for leukemia.

Effects of the Invention

The present invention provides an antitumor agent, which comprises, as an active ingredient, a pyrimidine derivative or a pharmaceutically acceptable salt thereof; a pyrimidine derivative or a pharmaceutically acceptable salt thereof, having an antitumor activity, and the like; and the like.

BEST MODE FOR CARRYING OUT THE INVENTION

Hereinafter, compounds represented by Formula (I) are referred to as Compound (I). This applies to compounds of other formula numbers.

In the definitions of each groups in Compound (I) and Compound (IA):

(i) The halogen represents each atoms of fluorine, chlorine, bromine, and iodine.

(ii) Examples of the lower alkyl and the lower alkyl moieties of the lower alkoxy, the lower alkoxycarbonyl, the lower alkoxycarbonylamino, the lower alkylthio, the lower alkylsulfonyl, the lower alkylsulfinyl, the mono- or di-(lower alkyl)amino, the mono- or di-(lower alkyl)aminocarbonyl, the N-aryl-N-(lower alkyl)amino, the lower alkanoyl, the lower alkanoylamino, the lower alkanoyloxy, the mono- or di-(lower alkylsulfonyl)amino, and the tri-(lower alkyl)silyl include, for example, linear, branched or cyclic alkyl or alkyl comprising these alkyls in combination, having 1 to 10 carbon atom(s). More specific examples thereof are as follows.

(ii-a) Examples of the linear or branched lower alkyl include, for example, methyl, ethyl, n-propyl, isopropyl, n-butyl, isobutyl, sec-butyl, tert-butyl, n-pentyl, neopentyl, n-hexyl, n-heptyl, n-octyl, n-nonyl, n-decyl and the like;

(ii-b) examples of the cyclic lower alkyl include, for example, cyclopropyl, cyclobutyl, cyclopentyl, cyclohexyl, cycloheptyl, cyclooctyl, cyclodecyl, noradamantyl, adamantyl, bicyclo[2.2.1]heptyl, bicyclo[2.2.2]octyl, bicyclo[3.3.0]octyl, bicyclo[3.3.1]nonyl and the like; and (ii-c) examples of the lower alkyl comprising a combination of linear or branched alkyl and cyclic alkyl include, for example, cyclopropylmethyl, cyclopentylmethyl cyclooctylethyl, and the like.

The two lower alkyl moieties of the di-(lower alkyl)amino, the di-(lower alkyl)aminocarbonyl, and the di-(lower alkylsulfonyl)amino and the three lower alkyl moieties of the tri-(lower alkyl)silyl may be the same or different.

(iii) Examples of the lower alkenyl include, for example, linear, branched or cyclic alkenyl having 2 to 8 carbon atoms. More specific examples thereof include vinyl, allyl, 1-propenyl, butenyl, pentenyl, hexenyl, heptenyl, octenyl, cyclohexenyl, 2,6-octadienyl and the like.

(iv) Examples of the lower alkynyl include, for example, linear or branched alkynyl having 2 to 8 carbon atoms. More specific examples thereof include ethynyl, 1-propynyl, propargyl, butynyl, pentynyl, hexynyl, heptynyl, octynyl and the like.

(v) Examples of the aryl and the aryl moieties of the N-aryl-N-(lower alkyl)amino, the aryloxy, and the mono- or di-(arylsulfonyl)amino include, for example, monocyclic, bicyclic or tricyclic aryl having 6 to 14 carbon atoms. More specific examples thereof include phenyl, naphthyl, indenyl, anthranil and the like. The monocyclic aryl only includes above-mentioned examples which are monocyclic.

The two aryl moieties of the di-(arylsulfonyl)amino may be the same or different.

(vi) The alkylene moieties of the aralkyl, the aralkyloxy, the heteroalicyclic alkyl, the heteroalicyclic alkyloxy, the aromatic heterocyclic alkyl, and the aromatic heterocyclic alkylthio have the same definitions as the group formed by removing one hydrogen atom from the lower alkyl (ii) described above.

(vii) In addition to the groups defined in the above aryl (v) described above, examples of the aryl moieties of the aralkyl and the aralkyloxy include, for example, the group formed by removing one hydrogen atom from the fused ring, in which, aryl and the cycloalkyl are fused. Specific examples thereof include, indanyl, 1,2,3,4-tetrahydronaphtyl, 6,7,8,9-tetrahydro-5H-benzocycloheptyl and the like.

(viii) Examples of the aromatic heterocyclic group and the aromatic heterocyclic moieties of the aromatic heterocyclic alkyl and the aromatic heterocyclic alkylthio include, for example, 5- or 6-membered monocyclic aromatic heterocyclic group containing at least one atom selected from the nitrogen atom, oxygen atom, and sulfur atom, bicyclic or tricyclic fused aromatic heterocyclic group containing at least one atom selected from the nitrogen atom, oxygen atom, and sulfur atom in which 3- to 8-membered rings are fused and the like. More specific examples include, for example, pyridyl, pyrazinyl, pyrimidinyl, pyridazinyl, benzimidazolyl, 2-oxobenzimidazolyl, benzotriazolyl, benzofuryl, benzothienyl, purinyl, benzoxazolyl, benzothiazolyl, benzodioxolyl indazolyl, indolyl, isoindolyl, purinyl, quinolyl, isoquinolyl, phthalazinyl, naphthyridinyl, quinoxalinyl, pyrrolyl, pyrazolyl, quinazolinyl, cinnolinyl, triazolyl, tetrazolyl, imidazolyl, oxazolyl, isoxazolyl, thiazolyl, isothiazolyl, thienyl, furyl and the like. The monocyclic aromatic heterocyclic group only includes above-mentioned examples which are monocyclic. When aromatic heterocyclic group is a nitrogen-containing aromatic heterocyclic group, then the nitrogen atoms in the ring may be oxidized.

(ix) Examples of the aromatic heterocyclic group formed together with the adjacent nitrogen atom include, for example, 5- or 6-membered monocyclic aromatic heterocyclic group containing at least one nitrogen atom (the monocyclic aromatic heterocyclic group may further contain any other of a nitrogen atom, an oxygen atom, or a sulfur atom), bicyclic or tricyclic fused aromatic heterocyclic group containing at least one nitrogen atom in which 3- to 8-membered rings are fused (the fused aromatic heterocyclic group may further contain any other of a nitrogen atom, an oxygen atom, or a sulfur atom) and the like. More specific examples include, for example, pyrrolyl, imidazolyl, pyrazolyl, indolyl, isoindolyl, indazolyl, purinyl, carbazolyl, carborinyl and the like.

(x) Examples of the heteroalicyclic group, the heteroalicyclic moieties of the heteroalicyclic alkyl and the heteroalicyclic alkyloxy include, for example, 5- or 6-membered monocyclic heteroalicyclic group containing at least one atom selected from a nitrogen atom, an oxygen atom and a sulfur atom, bicyclic or tricyclic fused heteroalicyclic group or cross-linked heteroalicyclic group containing at least one atom selected from a nitrogen atom, an oxygen atom, and a sulfur atom, in which 3- to 8-membered rings are fused or cross-linked and the like. More specific examples include, for example, pyrrolidinyl, 2,5-dioxopyrrolidinyl, thiazolidinyl, oxazolidinyl, piperidyl, piperidino, piperazinyl, homopiperazinyl, homopiperidyl, homopiperidino, morpholinyl, morpholino, thiomorpholinyl, thiomorpholino, pyranyl, tetrahydropyridyl, tetrahydropyranyl, tetrahydrofuranyl, tetrahydroquinolyl, tetrahydroisoquinolyl, octahydroquinolyl, indolinyl, isoindolinyl, perhydroazepinyl, perhydroazocinyl, 8-azabicyclo[3.2.1]octanyl, and the like.

(xi) Examples of the heteroalicyclic group formed together with the adjacent nitrogen atom include, for example, 5- or 6-membered monocyclic heteroalicyclic group containing at least one nitrogen atom (the monocyclic heteroalicyclic group may further contain any other of a nitrogen atom, an oxygen atom, and a sulfur atom), a bicyclic or tricyclic fused heteroalicyclic group containing at least one nitrogen atom, in which 3 to 8-membered rings are fused (the fused heteroalicyclic group may further contain any other of a nitrogen atom, an oxygen atom, and a sulfur atom) and the like. More specific examples include, for example, pyrrolidinyl, 2,5-dioxopyrrolidinyl, thiazolidinyl, oxazolidinyl, piperidino, piperazinyl, homopiperazinyl, homopiperidino, morpholino, thiomorpholino, pyranyl, tetrahydropyridyl, tetrahydroquinolyl, tetrahydroisoquinolyl, octahydroquinolyl, indolinyl, isoindolinyl, perhydroazepinyl, perhydroazocinyl, and the like.

(xii) Examples of the alkylenedioxy include, for example, methylenedioxy, ethylenedioxy and the like.

(xiii) Examples of the substituents in the substituted lower alkyl, the substituted lower alkoxy, the substituted lower alkoxycarbonyl, the substituted lower alkylthio, and the substituted lower alkanoyl, which may be the same or different and in number of 1 to 4, include, for example, halogen, amino, nitro, hydroxy, mercapto, cyano, formyl, carboxy, carbamoyl, aminosulfonyl, lower alkanoyloxy, lower alkanoylamino, mono- or di-(lower alkyl)aminocarbonyl, lower alkoxycarbonyl, lower alkoxycarbonylamino, lower alkylthio, N-aryl-N-(lower alkyl)amino, lower alkylsulfonyl, lower alkylsulfinyl, mono- or di-(lower alkylsulfonyl)amino, mono- or di-(arylsulfonyl)amino, tri-(lower alkyl)silyl, aromatic heterocyclic alkylthio, lower alkanoyl, substituted lower alkanoyl [the substituent (a) in the substituted lower alkanoyl, which may be the same or different and 1 to 3 in number is, for example, halogen, hydroxy, hydroxymethyl, lower alkoxy and the like], lower alkoxy, substituted lower alkoxy [the substituent in the substituted lower alkoxy has the same definition as the substituent (a) described above], aryloxy, substituted aryloxy [the substituent in the substituted aryloxy has the same definition as the substituent (a) described above], aralkyloxy, substituted aralkyloxy [the substituent in the substituted aralkyloxy has the same definition as the substituent (a) described above], mono- or di-(substituted or unsubstituted lower alkyl)amino [the substituent in the mono- or di-(substituted lower alkyl)amino has the same definition as the substituent (a) described above] and the like.

Here, halogen; the lower alkyl moieties of the lower alkanoyloxy, the lower alkanoylamino, the mono- or di-(lower alkyl)aminocarbonyl, the lower alkoxycarbonyl, the lower alkoxycarbonylamino, the lower alkylthio, the N-aryl-N-(lower alkyl)amino, the lower alkylsulfonyl, the lower alkylsulfinyl, the mono- or di-(arylsulfonyl)amino, the tri-(lower alkyl)silyl, the lower alkanoyl, the lower alkoxy, and the mono- or di-(lower alkyl)amino; the aryl moieties of the N-aryl-N-(lower alkyl)amino, the mono- or di-(arylsulfonyl)amino and the aryloxy; the alkylene moieties of the aromatic heterocyclic alkylthio and the aralkyloxy; aryl moieties of the aralkyloxy; and the aromatic heterocyclic moieties of the aromatic heterocyclic alkylthio have the same definitions as the halogen (i), the lower alkyl (ii), the aryl (v), the alkylene moieties of the aralkyl (vi), the aryl moieties of the aralkyl (vii), and the aromatic heterocyclic group (viii) described above, respectively. The two lower alkyl moieties of the di-(lower alkyl)aminocarbonyl and the di-(lower alkylsulfonyl)amino, the two substituted or unsubstituted lower alkyl moieties of the di-(substituted or unsubstituted lower alkyl)amino, the three lower alkyl moieties of the tri-(lower alkyl)silyl and the two aryl moieties of the di-(arylsulfonyl)amino may each be the same or different.

(xiv) The substituents of the substituted aryl, the substituted monocyclic aryl, the substituted aralkyl, the substituted lower alkenyl, the substituted lower alkynyl, the substituted aromatic heterocyclic group, the substituted monocyclic aromatic heterocyclic group, the substituted heteroalicyclic group, the substituted aromatic heterocyclic alkyl, the substituted heteroalicyclic alkyl, the substituted heteroalicyclic group formed together with the adjacent nitrogen atom, the substituted aromatic heterocyclic group formed together with the adjacent nitrogen atom, the substituted pyrazol-3-yl and the substituted 1,2,4-triazol-3-yl include, in addition to the groups mentioned in the definition of the substituent (xiii) in the above substituted lower alkyl, for example, the lower alkyl, the substituted lower alkyl [the substituent in the substituted lower alkyl has the same definition as the substituent (a) described above], the aryl, the substituted aryl {the substituent (b) in the substituted aryl include, for example, halogen, hydroxy, lower alkyl, the substituted lower alkyl [the substituent in the substituted lower alkyl has the same definition as the substituent (a) described above], lower alkoxy and the like, which may be the same or different and in number of 1 to 3}, the aralkyl, the substituted aralkyl [the substituent in the substituted aralkyl has the same definition as the substituent (b) described above], the aromatic heterocyclic group, the substituted aromatic heterocyclic group [the substituent in the substituted aromatic heterocyclic group has the same definition as the substituent (b) described above], the heteroalicyclic group, the substituted heteroalicyclic group [the substituent in the substituted heteroalicyclic group has the same definition as the substituent (b) described above], the aromatic heterocyclic alkyl, the substituted aromatic heterocyclic alkyl [the substituent in the substituted aromatic heterocyclic alkyl has the same definition as the substituent (b) described above], the heteroalicyclic alkyl, the substituted heteroalicyclic alkyl [the substituent in the substituted heteroalicyclic alkyl has the same definition as the substituent (b) described above], and the like. The substituent in the substituted heteroalicyclic group and the substituted heteroalicyclic alkyl may be oxo, in addition to the substituents described above. The substituent in the substituted aryl, the substituted monocyclic aryl, the substituted aromatic heterocyclic group and the substituted monocyclic aromatic heterocyclic group may be heteroalicyclic alkyloxy or alkylenedioxy, in addition to the substituents described above.

Here, the halogen; the lower alkyl and the lower alkyl moieties of the lower alkoxy; the aryl; the aromatic heterocyclic group and the aromatic heterocyclic moieties of the aromatic heterocyclic alkyl; the heteroalicyclic group; the heteroalicyclic moieties of the heteroalicyclic alkyl and the heteroalicyclic alkyloxy; the alkylene moieties of the aralkyl, the aromatic heterocyclic alkyl, the heteroalicyclic alkyl and the heteroalicyclic alkyloxy; the aryl moieties of the aralkyl;

and the alkylenedioxy have the same definitions as the halogen (i), the lower alkyl (ii), the aryl (v), the aromatic heterocyclic group (viii), the heteroalicyclic group (x), the alkylene moieties of the aralkyl (vi), the aryl moieties of the aralkyl (vii) and the alkylenedioxy (xii) described above, respectively.

Examples of the pharmaceutically acceptable salts of Compound (I) include, for example, pharmaceutically acceptable acid addition salts, metal salts, ammonium salts, organic amine addition salts, amino acid addition salts and the like. The pharmaceutically acceptable acid addition salts include, for example, inorganic acid salts such as hydrochlorides, sulfates and phosphates; and organic acid salts such as acetate, maleate, fumarate, tartrates, citrates, lactates, aspartates, and glutamates. The pharmaceutically acceptable metal salts include, for example, alkali metal salts such as sodium salts and potassium salts; alkaline earth metal salts such as magnesium salts and calcium salts; as well as aluminum salts, zinc salts and the like. The pharmaceutically acceptable ammonium salts include, for example, salts of ammonium, tetramethylammonium and the like. The pharmaceutically acceptable organic amine addition salts include, for example, addition salts of morpholine, piperidine and the like. The pharmaceutically acceptable amino acid addition salts include, for example, addition salts of lysine, glycine, phenylalanine and the like.

The hematopoietic tumor refers to tumors typically in hemocytes and the like. Examples of pathosis based on the hematopoietic tumor are leukemia such as chronic myeloid leukemia and acute myeloid leukemia; myeloma such as multiple myeloma; lymphoma and the like.

Production methods of Compound (I) will now be described.

In any of the production methods shown below, when a defined group changes under reaction conditions or is not suitable for carrying out the method, production can be easily performed by employing a process commonly used in synthetic organic chemistry, such as protection of functional groups and deprotection thereof [for example, refer to Protective Groups in Organic Synthesis, third edition, T. W. Greene, John Wiley & Sons Inc. (1999) and the like]. If necessary, the order of reaction steps, such as introduction of substituents, can be changed.

Compound (I) can be obtained, for example, by the production methods described below.

Production Method 1: Compound (IB), i.e., Compound (I) in which —X—Y—Z— is —O—CR$^{3B}$=N— (wherein R$^{3B}$ has the same definition as R$^3$ described above except that a hydrogen atom is removed), can be obtained, for example, by the following production method:

[Chemical Formula 5]

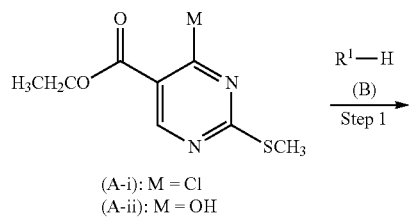

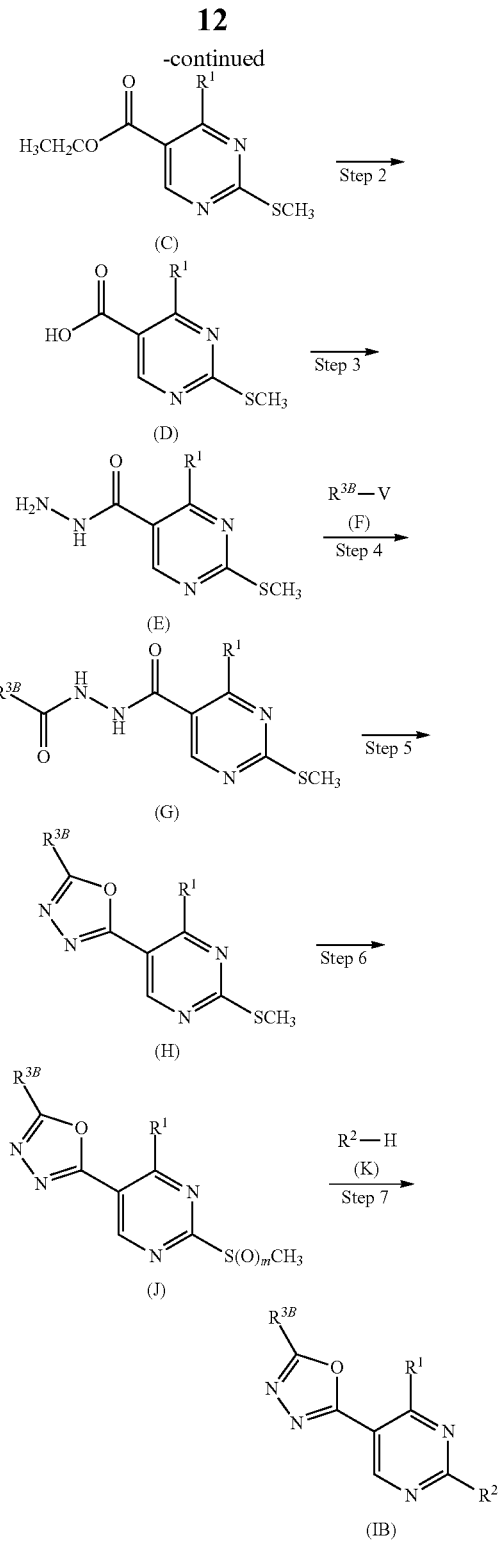

[wherein R$^1$, R$^2$, and R$^{3B}$ have the same definitions as described above, respectively; M represents a chlorine atom or hydroxy; V represents carboxy, —COCl, or —CO$_2$COR$^{3B}$ (wherein R$^{3B}$ has the same definition as described above; and m represents 1 or 2)]

Step 1

Compound (C) can be obtained by reacting commercially available Compound (A-i) with 1 equivalent to a large excess, preferably 1 to 3 equivalents, of R$^1$—H [wherein R$^1$ has the same definition as described above: Compound (B)], in an inert solvent, in the presence or absence of 1 equivalent to a large excess, preferably 1 to 10 equivalents, of a base.

Compound (B) can be obtained as a commercially available product or by a known method [for example, a method described in Comprehensive Organic Transformations, second edition, R. C. Larock, John Wiley & Sons Inc. (1999), or the like] or a modified method thereof.

The inert solvent is not particularly limited as long as it is inert to the reaction. Examples thereof include tetrahydrofuran (THF), dioxane, 1,2-dimethoxyethane, diethyl ether, diisopropyl ether, benzene, toluene, xylene, ethyl acetate, acetonitrile, dichloromethane, chloroform, 1,2-dichloroethane, dimethylformamide (DMF), dimethylacetamide (DMA), N-methylpyrrolidone (NMP), dimethyl sulfoxide (DMSO), pyridine, and the like. These solvents may be used alone or in combination. In particular, THF, dichloromethane, chloroform, or a mixed solvent thereof is preferable.

Examples of the base include organic bases, such as triethylamine, diisopropylethylamine, 1,8-diazabicyclo[5.4.0]undec-7-ene (DBU), N,N-dimethylaniline, pyridine, and quinoline; inorganic bases, such as potassium carbonate, sodium carbonate, lithium carbonate, sodium hydrogencarbonate, potassium hydroxide, sodium hydroxide, lithium hydroxide, potassium tert-butoxide, sodium hydride, potassium hydride, and lithium hydride; basic anion exchange resins, such as Amberlyst A-21 (Rohm and Haas Company) and AG1-X8 (Bio-Rad Laboratories, Inc.); solid phase-supported bases, such as poly(4-vinylpyridine) and morpholinomethyl polystyrene; and the like. In particular, triethylamine or DBU is preferable.

The reaction is carried out at a temperature between 0° C. and 100° C., preferably at a temperature between 20° C. and 50° C., usually for 1 to 48 hours.

Furthermore, in the step described above, when Compound (B) in which $R^1$ represents $-OR^{12}$ (wherein $R^{12}$ is the same as that defined above) is used, Compound (C) can be synthesized by a method using the Mitsunobu reaction described below, in addition to the method described above.

Compound (C) can be obtained by subjecting Compound (A-ii) obtained by a known method [for example, a method described in Journal of Heterocyclic Chemistry, vol. 38, p. 93 (2001) or the like] or a modified method thereof, together with 1 to 5 equivalents of $R^{12}OH$ [wherein $R^{12}$ is the same as that defined above: Compound (B)], to the Mitsunobu reaction in an inert solvent.

The inert solvent is not particularly limited as long as it is inert to the reaction. Examples thereof include dichloromethane, chloroform, dichloroethane, DMF, DMA, NMP, DMSO, THF, dioxane, diethyl ether, diisopropyl ether, benzene, toluene, xylene, ethyl acetate, acetonitrile, and the like. These solvents may be used alone or in combination. In particular, THF is preferable.

As a condensing agent used in the Mitsunobu reaction, any condensing agent generally used in the reaction can be used. For example, a combination of 1 to 10 equivalents of dialkyl azodicarboxylate and 1 to 10 equivalents of triphenylphosphine or trialkylphosphine, 1 to 10 equivalents of (cyanomethylene)triphenyl phosphorane, or the like can be used. In particular, a combination of 1 to 3 equivalents of diethyl azodicarboxylate (DEAD) and 1 to 3 equivalents of triphenylphosphine is preferable.

The reaction is carried out at a temperature between 0° C. and 100° C., preferably at a temperature between 20° C. and 60° C., usually for 1 to 50 hours.

Step 2

Compound (D) can be obtained by treating Compound (C) obtained in Step 1, in a solvent, with 1 to 10 equivalents, preferably 1 to 5 equivalents, of a base.

The solvent is not particularly limited. For example, protic solvents, such as water, methanol, ethanol, propanol, and butanol, may be used alone or in combination. Alternatively, an aprotic solvent, such as THF or dioxane, may be mixed thereto. In particular, a mixed solvent of ethanol and water is preferable.

Examples of the base include inorganic bases, such as sodium hydroxide, lithium hydroxide, potassium hydroxide, sodium carbonate, potassium carbonate, and lithium carbonate; basic anion exchange resins, such as Amberlyst A-21 (Rohm and Haas Company) and AG1-X8 (Bio-Rad Laboratories, Inc.); and the like.

The reaction is carried out at a temperature between 0° C. and 150° C., preferably at a temperature between 20° C. and the boiling point of the solvent, usually for 1 to 48 hours.

Step 3

Compound (E) can be obtained by reacting Compound (D) obtained in Step 2 with 1 to 20 equivalents, preferably 2 to 5 equivalents of hydrazine hydrate, in an inert solvent, in the presence of 1 to 10 equivalents, preferably 1 to 2 equivalents, of carbonyldiimidazole.

The inert solvent is not particularly limited as long as it is inert to the reaction. Examples thereof include THF, dioxane, 1,2-dimethoxyethane, benzene, toluene, xylene, ethyl acetate, acetonitrile, dichloromethane, chloroform, 1,2-dichloroethane, DMF, DMA, NMP, DMSO, pyridine, and the like. These solvents may be used alone or in combination. In particular, THF, dichloromethane, chloroform, or a mixed solvent thereof is preferable.

The reaction is carried out at a temperature between 0° C. and 100° C., preferably at a temperature between 20° C. and 50° C., usually for 1 to 48 hours.

Step 4

Compound (G) can be obtained by reacting Compound (E) obtained in Step 3 with $R^{3B}$—V [wherein $R^{3B}$ and V have the same definitions as described above, respectively: Compound (F)], in a solvent inactive in the reaction, in the presence or absence of a base or a condensing agent.

Step 4-1: when V is —COCl or —CO$_2$COR$^{3B}$ (Wherein $R^{3B}$ has the Same Definition as Described Above) in Compound (F)

Compound (G) can be obtained by reacting Compound (E) obtained in Step 4 with 1 to 5 equivalents, preferably 1 to 2 equivalents, of Compound (F), in an inert solvent, in the presence of 1 to 10 equivalents, preferably 1 to 4 equivalents, of a base.

Compound (F) can be obtained as a commercially available product or by a known method [for example, a method described in Comprehensive Organic Transformations, second edition, R. C. Larock, John Wiley & Sons Inc. (1999), or the like] or a modified method thereof.

Examples of the base include organic bases, such as triethylamine, diisopropylethylamine, DBU, N,N-dimethylaniline, pyridine, quinoline, and lithium diisopropylamide (LDA); inorganic bases, such as potassium carbonate, sodium carbonate, sodium hydrogencarbonate, potassium hydroxide, sodium hydroxide, potassium tert-butoxide, sodium hydride, and potassium hydride; basic anion exchange resins, such as Amberlyst A-21 (Rohm and Haas Company) and AG1-X8 (Bio-Rad Laboratories, Inc.); solid-phase-supported bases, such as piperidinomethyl polystyrene and morpholinomethyl polystyrene; and the like. In particular, morpholinomethyl polystyrene or triethylamine is preferable.

The inert solvent is not particularly limited as long as it is inert to the reaction. Examples thereof include dichloromethane, 1,2-dichloroethane, chloroform, THF, dioxane, 1,2-dimethoxyethane, benzene, toluene, xylene, ethyl acetate, DMF, DMA, NMP, DMSO, acetonitrile, water, and the like. These solvents may be used alone or in combination. In particular, THF or dichloromethane is preferable.

The reaction is carried out at a temperature between 0° C. and 100° C., preferably at a temperature between room temperature and 50° C., usually for 1 to 48 hours.

Step 4-2: when V Represents Carboxy in Compound (F)

Compound (G) can be obtained by reacting Compound (E) with 1 to 5 equivalent of Compound (F) in an inert solvent, in the presence of 1 to 10 equivalents of a condensation agent.

Examples of the condensing agent include dicyclohexylcarbodiimide, diisopropylcarbodiimide, N-ethyl-N'-(3-dimethylaminopropyl)carbodiimide (EDC) or a hydrochloride thereof, polystyrene-supported EDC, polystyrene-supported N-benzyl-N'-cyclohexylcarbodiimide, benzotriazol-1-yloxytris(dimethylamino)phosphonium hexafluorophosphate, diphenylphosphoryl azide, and the like. In particular, EDC, a hydrochloride thereof, or polystyrene-supported EDC is preferable.

This reaction may be carried out also in the presence of 1 to 5 equivalents of an additive. Examples of the additive include N-hydroxysuccinimide, 1-hydroxybenzotriazole, 3-hydroxy-4-oxo-3,4-dihydro-1,2,3-benzotriazine, and the like. In particular, 1-hydroxybenzotriazole is preferable.

The inert solvent is not particularly limited as long as it is inert to the reaction. Examples thereof include dichloromethane, chloroform, dichloroethane, DMF, DMA, NMP, DMSO, THF, 2-methyltetrahydrofuran, dioxane, diethyl ether, benzene, toluene, xylene, ethyl acetate, acetonitrile, and the like. These solvents may be used alone or in combination. In particular, chloroform, THF, or a mixed solvent thereof is preferable.

The reaction is carried out at a temperature between 0° C. and 150° C., preferably at a temperature between room temperature and 80° C., usually for 1 to 120 hours.

Compound (F) can be obtained as a commercially available product or by a known method [for example, a method described in Comprehensive Organic Transformations, second edition, R. C. Larock, John Wiley & Sons Inc. (1999) or the like] or a modified method thereof.

Step 5

Compound (H) can be obtained by treating Compound (G) obtained in Step 4 with 1 equivalent to a large excess, preferably 1 to 10 equivalents, of a chlorinating agent in an inert solvent, in the presence of 1 equivalent to a large excess, preferably 1 to 10 equivalents, of a base.

As the chlorinating agent, for example, phosphorus oxychloride or the like can be used alone. Alternatively, a combination of carbon tetrachloride and triphenylphosphine or triphenylphosphine polystyrene, or the like can be used.

The inert solvent is not particularly limited as long as it is inert to the reaction. Examples thereof include dichloromethane, chloroform, dichloroethane, THF, 2-methyltetrahydrofuran, dioxane, diethyl ether, benzene, toluene, xylene, acetonitrile, and the like. These solvents may be used alone or in combination. In particular, chloroform, dichloromethane, or acetonitrile is preferable.

The reaction is carried out at a temperature between 0° C. and the boiling point of the solvent, preferably at a temperature between room temperature and 50° C., usually for 1 to 120 hours.

Step 6

Compound (J) can be obtained by treating Compound (H) obtained in Step 5 with 1 equivalent to a large excess, preferably 1 to 5 equivalents, of an oxidizing agent in an inert solvent.

The inert solvent is not particularly limited as long as it is inert to the reaction. Examples thereof include dichloromethane, chloroform, 1,2-dichloroethane, THF, dioxane, diethyl ether, diisopropyl ether, methanol, ethanol, 2-propanol, benzene, toluene, xylene, ethyl acetate, acetonitrile, water, and the like. These solvents may be used alone or in combination. In particular, dichloromethane is preferable.

Examples of the oxidizing agent include metachloroperbenzoic acid (mCPBA), benzoyl peroxide, peracetic acid, aqueous hydrogen peroxide, sodium periodate, and the like. In particular, mCPBA is preferable.

The reaction is carried out at a temperature between 0° C. and 100° C., preferably at a temperature between 0° C. and 50° C., usually for 10 minutes to 24 hours.

With respect to Compound (J), either a compound in which m represents 1 or a compound in which m represents 2 may be selectively obtained by adjusting the reaction conditions, for example, the equivalent of the oxidizing agent, temperature, and the like, or a mixture of these may be obtained. In each case, the resulting product can be used as it is in the subsequent step. When Compound (J) is obtained as a mixture, the mixture ratio is not particularly limited.

Step 7

Compound (IB) can be obtained by reacting Compound (J) obtained in Step 6 with 1 to 5 equivalents of $R^2$—H [wherein $R^2$ has the same definition as described above: Compound (K)] in an inert solvent.

The inert solvent is not particularly limited as long as it is inert to the reaction. Examples thereof include dichloromethane, chloroform, 1,2-dichloroethane, DMF, DMA, NMP, DMSO, THF, dioxane, diethyl ether, diisopropyl ether, benzene, toluene, xylene, ethyl acetate, acetonitrile, and the like. These solvents may be used alone or in combination. In particular, THF is preferable.

The reaction is carried out at a temperature between 0° C. and 100° C., preferably at a temperature between 20° C. and 60° C., usually for 1 to 72 hours.

Compound (K) can be obtained as a commercially available product or by a known method [for example, a method described in Comprehensive Organic Transformations, second edition, R. C. Larock, John Wiley & Sons Inc. (1999), or the like] or a modified method thereof.

Production Method 2: Compound (IC), i.e., Compound (I) in which $R^3$ is —$CH_2NR^4R^5$ (wherein $R^4$ and $R^5$ have the same as described above, respectively), can be also obtained by the production method described below, in addition to Production Method 1 described above.

[Chemical Formula 6]

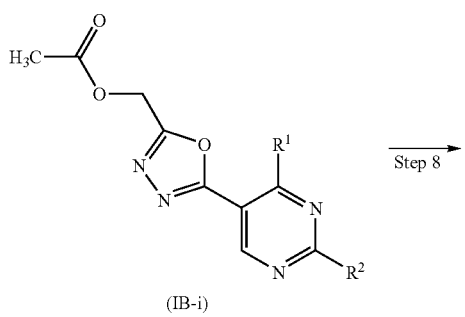

(IB-i)

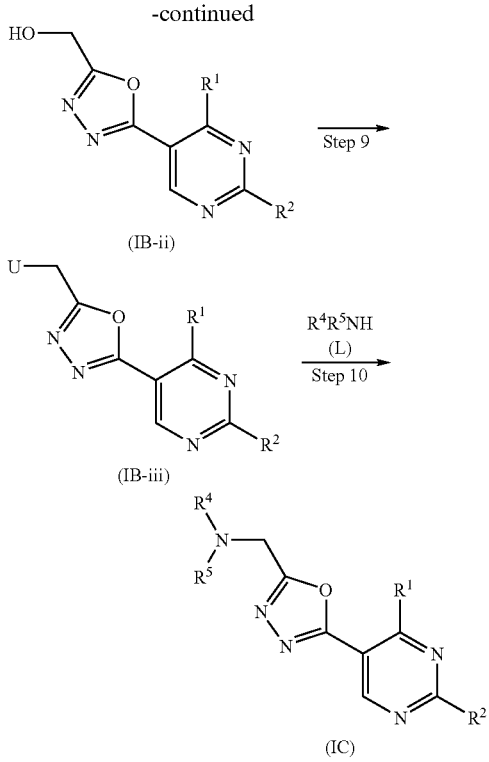

{wherein $R^1$, $R^2$, $R^4$, and $R^5$ have the same definitions as described above, respectively; and U represents lower alkylsulfonyloxy [wherein the lower alkyl moiety of the lower alkylsulfonyloxy has the same definition as the lower alkyl (ii) described above] or substituted or unsubstituted arylsulfonyloxy [wherein the aryl moiety of the arylsulfonyloxy has the same definition as the aryl (v) described above, and examples of the substituent of the substituted arylsulfonyloxy which may be the same or different, and in number 1 to 3, include lower alkyl (wherein the lower alkyl has the same definition as the lower alkyl (ii) described above)]}

Step 8

Compound (IB-ii) can be obtained by treating Compound (IB-i) obtained in Production Method 1, with 1 to 10 equivalents, preferably 1 to 5 equivalents, of a base, in a solvent, in a similar manner to Step 2 of Production Method 1.

The optimum reaction conditions, the solvent, the base, and the like are the same as those described in Step 2 of Production Method 1.

Step 9

Compound (IB-iii) can be obtained by reacting Compound (IB-ii) obtained in Step 8 with 1 equivalent to a large excess, preferably 1 to 3 equivalents, of a sulfonyl halide or a sulfonic anhydride, in an inert solvent, in the presence of 1 equivalent to a large excess, preferably 1 to 10 equivalents, of a base.

The inert solvent is not particularly limited as long as it is inert to the reaction. Examples thereof include THF, dioxane, diethyl ether, diisopropyl ether, benzene, toluene, xylene, ethyl acetate, acetonitrile, dichloromethane, chloroform, dichloroethane, DMF, DMA, NMP, DMSO, pyridine, and the like. These solvents may be used alone or in combination. In particular, dichloromethane is preferable.

Examples of the base include organic bases, such as triethylamine, diisopropylethylamine, DBU, N,N-dimethylaniline, pyridine, and quinoline; inorganic bases, such as potassium carbonate, sodium carbonate, lithium carbonate, sodium hydrogencarbonate, potassium hydroxide, sodium hydroxide, lithium hydroxide, potassium tert-butoxide; basic anion exchange resins, such as Amberlyst A-21 (Rohm and Haas Company) and AG1-X8 (Bio-Rad Laboratories, Inc.); solid-phase-supported bases, such as poly(4-vinylpyridine) and morpholinomethyl polystyrene; and the like. In particular, triethylamine is preferable.

As the sulfonyl halide or the sulfonic anhydride, for example, methanesulfonyl chloride, benzenesulfonyl chloride, p-toluenesulfonyl chloride, methanesulfonic anhydride, benzenesulfonic anhydride, toluenesulfonic anhydride, or the like can be used. In particular, methanesulfonyl chloride or methanesulfonic anhydride is preferable.

The reaction is carried out at a temperature between 0° C. and 150° C., preferably at a temperature between 0° C. and 50° C., usually for 1 to 48 hours.

Step 10

Compound (IC) can be obtained by reacting Compound (IB-iii) obtained in Step 9 with 1 to 10 equivalents, preferably 1 to 5 equivalents, of $R^4R^5NH$ [wherein $R^4$ and $R^5$ have the same definitions as described above, respectively: Compound (L)], in an inert solvent, in the presence or absence of 1 equivalent to a large excess, preferably 1 to 10 equivalents, of a base.

The inert solvent is not particularly limited as long as it is inert to the reaction. Examples thereof include THF, dioxane, diethyl ether, diisopropyl ether, benzene, toluene, xylene, ethyl acetate, acetonitrile, dichloromethane, chloroform, dichloroethane, DMF, DMA, NMP, DMSO, pyridine, and the like. These solvents may be used alone or in combination. In particular, THF, chloroform, or a mixed solvent thereof is preferable.

Examples of the base include organic bases, such as triethylamine, diisopropylethylamine, DBU, N,N-dimethylaniline, pyridine, and quinoline; inorganic bases, such as potassium carbonate, sodium carbonate, lithium carbonate, sodium hydrogencarbonate, potassium hydroxide, sodium hydroxide, lithium hydroxide, and potassium tert-butoxide; basic anion exchange resins, such as Amberlyst A-21 (Rohm and Haas Company) and AG1-X8 (Bio-Rad Laboratories, Inc.); solid phase-supported bases, such as poly(4-vinylpyridine) and morpholinomethyl polystyrene; and the like. In particular, poly(4-vinylpyridine) is preferable.

The reaction is carried out at a temperature between 0° C. and 100° C., preferably at a temperature between 20° C. and 50° C., usually for 1 to 100 hours.

Production Method 3: Compound (ID), i.e., Compound (I) in which $R^3$ is carboxy, can be obtained, for example, by the method shown below.

[Chemical Formula 7]

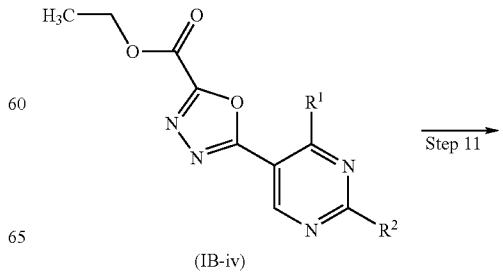

-continued

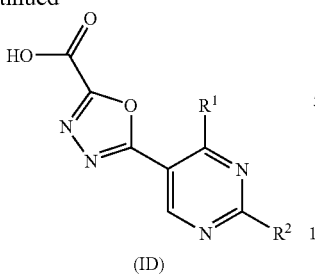

(wherein R¹ and R² are the same as those defined above, respectively)

Step 11

Compound (ID) can be obtained by treating Compound (IB-iv) obtained in Production Method 1, with 1 to 10 equivalents, preferably 1 to 5 equivalents, of a base, in a solvent, in a similar manner to Step 2 of Production Method 1.

The reaction conditions, the solvent, the base, and the like are the same as those described in Step 2 of Production Method 1.

Production Method 4: Compound (IE), i.e., Compound (I) in which R³ is —C(=O)NR⁶R⁷ (wherein R⁶ and R⁷ have the same definitions as described above, respectively), can be, obtained, for example, by the method shown below.

[Chemical Formula 8]

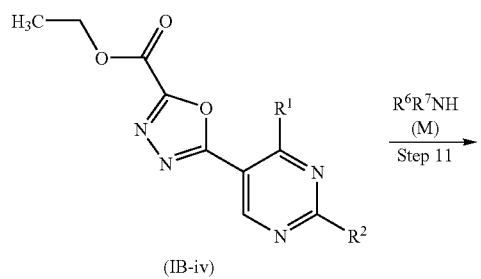

(wherein R¹, R², R⁶, and R⁷ have the same definitions as described above, respectively)

Step 12

Compound (IE) can be obtained by reacting Compound (IB-iv) obtained by Production Method 1 with 1 to 10 equivalents, preferably 1 to 5 equivalents, of R⁶R⁷NH [wherein R⁶ and R⁷ have the same definitions as described above, respectively: Compound (M)] in an inert solvent.

The inert solvent is not particularly limited as long as it is inert to the reaction. Examples thereof include dichloromethane, chloroform, 1,2-dichloroethane, DMF, DMA, NMP, DMSO, THF, dioxane, diethyl ether, diisopropyl ether, benzene, toluene, xylene, ethyl acetate, acetonitrile, and the like. These solvents may be used alone or in combination. In particular, THF is preferable.

The reaction is carried out at a temperature between 20° C. and the boiling point of the solvent, preferably at a temperature between 50° C. and 100° C., usually for 1 hour to 1 week.

Compound (M) can be obtained as a commercially available product or by a known method [for example, a method described in Comprehensive Organic Transformations, second edition, R. C. Larock, John Wiley & Sons Inc. (1999). or the like] or a modified method thereof.

Production Method 5: Compound (IF), i.e., Compound (I) in which —X—Y—Z— is —O—(C=O)—NR⁸— (wherein R⁸ has the same definition as described above), can be obtained, for example, by the following production method:

[Chemical Formula 9]

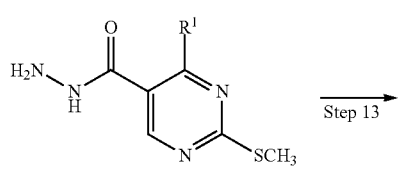

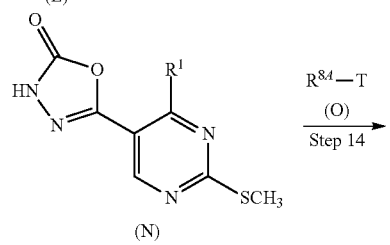

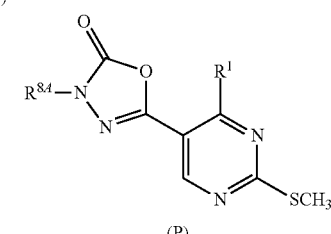

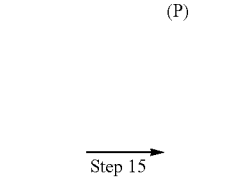

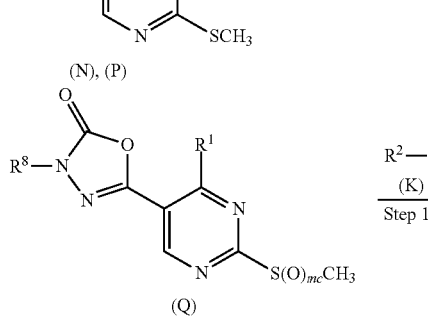

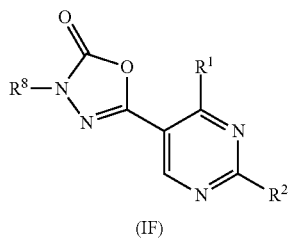

{wherein R¹, R², and mc have the same definitions as described above, respectively; $R^{8A}$ has the same definition as $R^8$ described above except that a hydrogen atom is removed; and T represents a chlorine atom, a bromine atom, an iodine atom, hydroxy, lower alkylsulfonyloxy [wherein the lower alkyl moiety of the lower alkylsulfonyloxy has the same definition as the lower alkyl (ii) described above], or substituted or unsubstituted arylsulfonyloxy [wherein the aryl moiety of the arylsulfonyloxy has the same definition as the aryl (v) described above, and examples of the substituent of the substituted arylsulfonyloxy which may be the same or different, and in number 1 to 3, include lower alkyl (wherein the lower alkyl has the same definition as the lower alkyl (ii) described above)]}

Step 13

Compound (N) can be obtained by reacting Compound (E) obtained in Step 3 of Production Method 1 with 1 to 5 equivalents, preferably 1 to 3 equivalents, of carbonyldiimidazole in an inert solvent, in the presence of 1 to 10 equivalents, preferably 1 to 5 equivalents, of a base.

The inert solvent is not particularly limited as long as it is inert to the reaction. Examples thereof include dichloromethane, chloroform, 1,2-dichloroethane, DMF, DMA, NMP, DMSO, THF, dioxane, diethyl ether, diisopropyl ether, benzene, toluene, xylene, ethyl acetate, acetonitrile, and the like. These solvents may be used alone or in combination. In particular, THF is preferable.

Examples of the base include organic bases, such as triethylamine, diisopropylethylamine, DBU, N,N-dimethylaniline, pyridine, and quinoline; inorganic bases, such as potassium carbonate, sodium carbonate, lithium carbonate, sodium hydrogencarbonate, potassium hydroxide, sodium hydroxide, lithium hydroxide, and potassium tert-butoxide; basic anion exchange resins, such as Amberlyst A-21 (Rohm and Haas Company) and AG1-X8 (Bio-Rad Laboratories, Inc.); solid-phase-supported bases, such as poly(4-vinylpyridine) and morpholinomethyl polystyrene; and the like. In particular, triethylamine is preferable.

The reaction is carried out at a temperature between 0° C. and 100° C., preferably at a temperature between 20° C. and 60° C., usually for 1 to 100 hours.

Step 14

Compound (P) can be obtained by reacting Compound (N) obtained in Step 13 with 1 to 5 equivalents of $R^{8A}$-T {wherein $R^{8A}$ and T have the same definitions as described above, respectively: Compound (O)} in an inert solvent.

Step 14-1: when T Represents Hydroxyl in Compound (O)

Compound (P) can be obtained by subjecting Compound (N) obtained in Step 13, together with 1 to 5 equivalents of $R^{8A}$—OH (wherein $R^{8A}$ has the same definition as described above), to the Mitsunobu reaction in an inert solvent.

The inert solvent is not particularly limited as long as it is inert to the reaction. Examples thereof include dichloromethane, chloroform, dichloroethane, DMF, DMA, NMP, DMSO, THF, dioxane, diethyl ether, diisopropyl ether, benzene, toluene, xylene, ethyl acetate, acetonitrile, and the like. These solvents may be used alone or in combination. In particular, THF is preferable.

As a condensing agent used in the Mitsunobu reaction, any condensing agent generally used in the reaction can be used. For example, a combination of 1 to 10 equivalents of dialkyl azodicarboxylate and 1 to 10 equivalents of triphenylphosphine or trialkylphosphine, 1 to 10 equivalents of (cyanomethylene)triphenyl phosphorane, or the like can be used. In particular, a combination of 1 to 3 equivalents of DEAD and 1 to 3 equivalents of triphenylphosphine is preferable.

The reaction is carried out at a temperature between 0° C. and 100° C., preferably at a temperature between 20° C. and 60° C., usually for 1 to 50 hours.

Step 14-2: when T Represents a Group Other than Hydroxy in Compound (o).

Compound (P) can be obtained by reacting Compound (N) obtained in Step 13 with 1 to 5 equivalents of $R^{8A}$-$T^A$ (wherein $R^{8A}$ has the same definition as described above, and $T^A$ has the same definition as T described above except that hydroxy is removed) in an inert solvent, in the presence of 1 equivalent to a large excess, preferably 1 to 10 equivalents, of a base.

The inert solvent and the base are the same as those described in Step 10 of Production Method 2.

The reaction is carried out at a temperature between 0° C. and the boiling point of the solvent, preferably at a temperature between 20° C. and 100° C., usually for 1 hour to 1 week.

Step 15

Compound (Q) can be obtained by treating Compound (N) and Compound (P) obtained by Step 13 and Step 14, respectively, in a similar manner to Step 6 of Production Method 1.

The reaction conditions, the solvent, the reagent, and the like are the same as those described in Step 6 of Production Method 1.

Step 16

Compound (IF) can be obtained by reacting Compound (Q) obtained in Step 15 to react with Compound (K) in a similar manner to Step 7 of Production Method 1.

The reaction conditions, the solvent, the reagent, and the like are the same as those described in Step 7 of Production Method 1.

Production Method 6: Compound (IF-ii), i.e., Compound (IF) in which $R^8$ represents —$(CH_2)_{n1}NR^4R^5$ (wherein $R^4$ and $R^5$ have the same definitions as described above, respectively, and n1 represents an integer of 1 to 3), can be obtained, for example, by the production method shown below, in addition to Production Method 5.

[Chemical Formula 10]

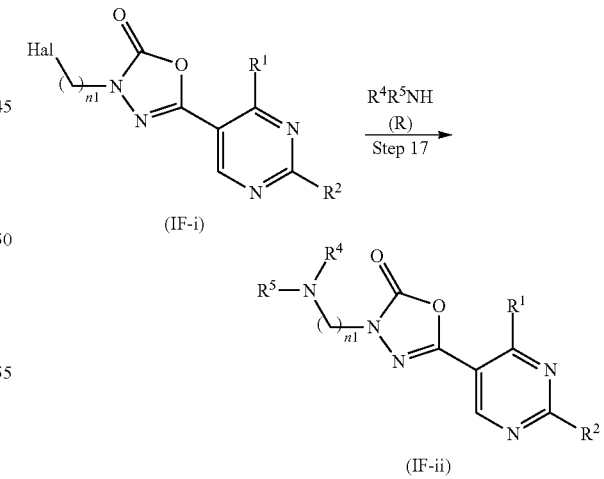

[wherein $R^4$, $R^5$, and n1 have the same definitions as described above, respectively, and Hal represents a halogen. Here, the halogen has the same definition as the halogen (i) described above]

Step 17

Compound (IF-ii) can be obtained by reacting Compound (IF-i) obtained in Production Method 5 with 1 to 5 equivalents of Compound (R) in an inert solvent, in the presence of 1 equivalent to a large excess, preferably 1 to 10 equivalents, of a base.

The inert solvent and the base are the same as those described in Step 10 of Production Method 2.

The reaction is carried out at a temperature between 20° C. and the boiling point of the solvent, preferably at a temperature between 50° C. and 100° C., usually for 1 hour to 1 week.

Production Method 7: Compound (IG-i), i.e., Compound (I) in which —X—Y—Z— is —N=N—NR$^9$— (wherein R$^9$ has the same definition as described above), and/or Compound (IG-ii), i.e., Compound (I) in which —X—Y—Z— is —NR$^{9a}$—N=N— (wherein R$^{9a}$ has the same definition as described above), can be produced, for example, by the production method shown below.

[Chemical Formula 11]

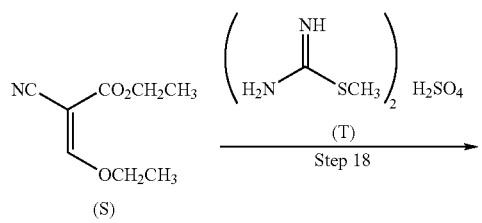

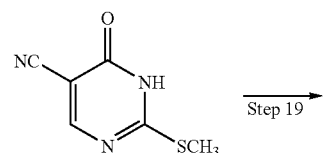

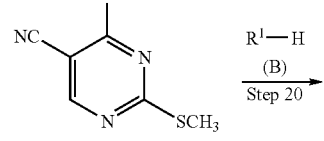

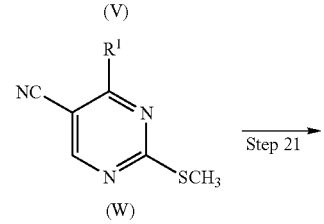

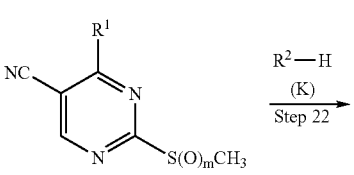

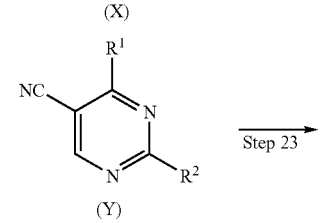

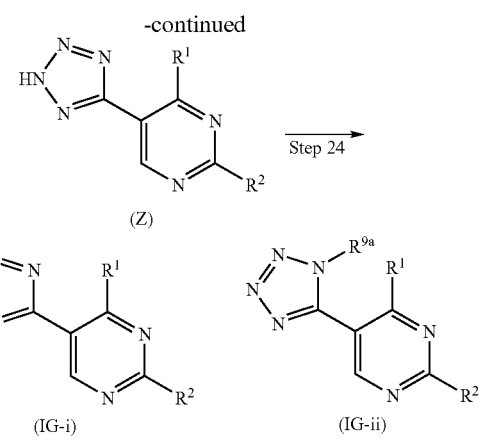

(wherein R$^1$, R$^2$, R$^{11}$, and m have the same definitions as described above, respectively)

Step 18

Compound (U) can be obtained by reacting ethyl 2-ethoxymethylene-2-cyanoacetate (S) with 0.5 equivalents to a large excess, preferably 0.5 to 2 equivalents, of methyl-isothiourea sulfate (T) in a solvent, in the presence of an alkali or metal alkoxide solution.

The solvent is not particularly limited. Examples thereof include methanol, ethanol, 2-propanol, THF, 1,4-dioxane, and the like. These solvents may be used alone or in combination. In particular, ethanol is preferable.

Examples of the alkali or metal alkoxide solution include aqueous alkali solutions, such as an aqueous lithium hydroxide solution, an aqueous potassium hydroxide solution, an aqueous sodium hydroxide solution, an aqueous magnesium hydroxide solution, and an aqueous calcium hydroxide solution; an aqueous solution, a THF solution, or a 2-methyl-2-propanol solution of potassium tert-butoxide; an aqueous solution or a methanol solution of sodium methoxide; and the like. In particular, an aqueous sodium hydroxide solution is preferable.

The reaction is carried out at a temperature between 0° C. and 50° C., preferably at a temperature between 0° C. and 15° C., usually for 1 to 48 hours.

Step 19

Compound (V) can be obtained by reacting Compound (U) obtained in Step 18 with 1 equivalent to a large excess of a chlorinating agent in an inert solvent or not.

As the chlorinating agent, for example, phosphorus oxychloride or the like is used.

The inert solvent is not particularly limited as long as it is inert to the reaction. Examples thereof include 1,2-dichloroethane, THF, dioxane, chloroform, benzene, toluene, xylene, ethyl acetate, triethylamine, pyridine, N,N-dimethylaniline, and the like. These solvents may be used alone or in combination.

The reaction is carried out at a temperature between 0° C. and the boiling point of the solvent, preferably at a temperature between 50° C. and the boiling point of the solvent, usually for 1 to 48 hours.

Compound (V) obtained in this step can also be obtained by a method described in, for example, Journal of Heterocyclic Chemistry, 8(3), 445 (1971), WO99/61444, or the like, or a similar method thereto, in addition to the method described above.

Step 20

Compound (W) can be obtained by reacting Compound (V) obtained in Step 19 with 1 equivalent to a large excess, preferably 1 to 3 equivalents, of Compound (B) in an inert solvent.

The inert solvent is not particularly limited as long as it is inert to the reaction. Examples thereof include THF, dioxane, diethyl ether, diisopropyl ether, benzene, toluene, xylene, ethyl acetate, acetonitrile, dichloromethane, chloroform, 1,2-dichloroethane, DMF, DMA, NMP, DMSO, and the like. These solvents may be used alone or in combination. In particular, THF, chloroform, or a mixed solvent thereof is preferable.

The reaction is carried out at a temperature between 0° C. and 100° C., preferably at a temperature between 0° C. and 50° C., usually for 10 minutes to 48 hours.

If necessary, the reaction may be carried out by adding 1 equivalent to a large excess, preferably 1 to 10 equivalents, of a base. Examples of the base include organic bases, such as triethylamine, diisopropylethylamine, DBU, N,N-dimethylaniline, pyridine, and quinoline; inorganic bases, such as potassium carbonate, sodium carbonate, lithium carbonate, sodium hydrogencarbonate, potassium hydroxide, sodium hydroxide, lithium hydroxide, and potassium tert-butoxide; basic anion exchange resins, such as Amberlyst A-21 (Rohm and Haas Company) and AG1-X8 (Bio-Rad Laboratories, Inc.); solid phase-supported bases, such as poly(4-vinylpyridine) and morpholinomethyl polystyrene; and the like. When the reaction is carried out using combinatorial chemistry techniques, in particular, morpholinomethyl polystyrene is preferable.

Compound (B) can be obtained as a commercially available product or by a known method [for example, a method described in Comprehensive Organic Transformations, second edition, R. C. Larock, John Wiley & Sons Inc. (1999), or the like] or a modified method thereof.

Step 21

Compound (X) can be obtained by treating Compound (W) obtained in Step 20 in a similar manner to Step 6 of Production Method 1.

The optimum reaction conditions, the solvent, the reagent, and the like are the same as those described in Step 6 of Production Method 1.

Step 22

Compound (Y) can be obtained by reacting Compound (X) obtained in Step 21 with 1 to 5 equivalents of Compound (K) in an inert solvent.

The inert solvent is not particularly limited as long as it is inert to the reaction. Examples thereof include dichloromethane, chloroform, 1,2-dichloroethane, DMF, DMA, NMP, DMSO, THF, dioxane, diethyl ether, diisopropyl ether, benzene, toluene, xylene, ethyl acetate, acetonitrile, and the like. These solvents may be used alone or in combination. In particular, THF is preferable.

The reaction is carried out at a temperature between 0° C. and 100° C., preferably at a temperature between 20° C. and 60° C., usually for 1 to 72 hours.

Compound (K) can be obtained as a commercially available product or by a known method [for example, a method described in Comprehensive Organic Transformations, second edition, R. C. Larock, John Wiley & Sons Inc. (1999), or the like] or a similar method thereto.

Step 23

Compound (Z) can be obtained by reacting Compound (Y) obtained in Step 22 with 1 to 10 equivalents of sodium azide or ammonium azide in an inert solvent.

The inert solvent is not particularly limited as long as it is inert to the reaction. Examples thereof include chloroform, 1,2-dichloroethane, DMF, DMA, NMP, DMSO, THF, dioxane, diisopropyl ether, benzene, toluene, xylene, ethyl acetate, acetonitrile, and the like. These solvents may be used alone or in combination. In particular, DMF is preferable. Furthermore, in order to accelerate the reaction, 1 equivalent or more of ammonium chloride, ethylammonium chloride, or the like can be added to the reaction system.

The reaction is carried out at a temperature between 0° C. and 180° C., preferably at a temperature between 50° C. and 120° C., usually for 1 to 72 hours.

Step 24

Compound (IG-i) and/or Compound (IG-ii) can be obtained by subjecting Compound (Z) obtained in Step 23, together with 1 to 5 equivalents of $R^9$—OH (wherein $R^9$ is the same as that defined above) or $R^{9a}$—OH (wherein $R^{9a}$ is the same as that defined above), to the Mitsunobu reaction in an inert solvent.

The reaction conditions, the solvent, the reagent, and the like are the same as those described in Step 14-1 of Production Method 5.

According to this reaction, Compound (IG-i) or Compound (IG-ii) is obtained independently, or as a mixture thereof. The ratio of these compounds varies depending on the types of Compound (Z) and $R^9$—OH (wherein $R^9$ has the same definition as described above) or $R^{9a}$—OH (wherein $R^{9a}$ has the same definition as described above), the reagent, the reaction conditions, and the like.

Production Method 8: Although Compound (I) can be obtained according to any of Production Methods 1 to 7 described above, it is also possible to obtain Compound (I) from Compound (IH) by changing the order of introduction of each groups as shown in the method described below. Similarly, it is also possible to obtain Compound (AD), which is a intermediate, from Compound (AA).

[Chemical Formula 12]

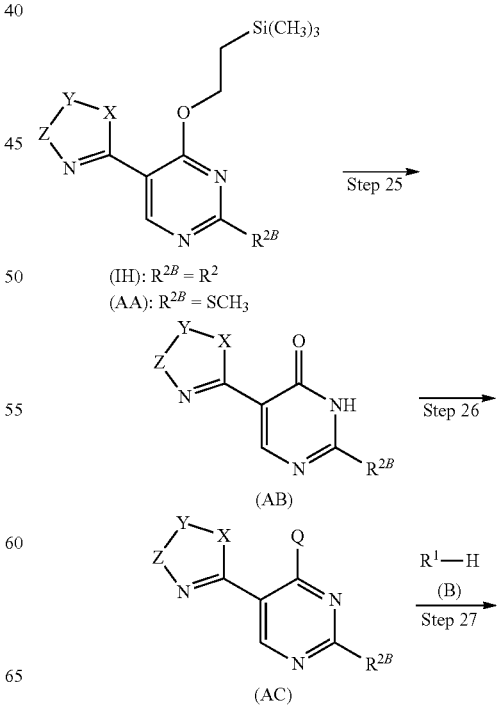

-continued

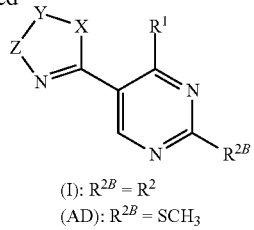

(I): $R^{2B} = R^2$
(AD): $R^{2B} = SCH_3$

{wherein —X—Y—Z— has the same definition as described above; $R^{2B}$ is the same as that obtained by adding methylthio to the definition of $R^2$ described above; and Q represents a chlorine atom, lower alkylsulfonyloxy [wherein the lower alkyl moiety of the lower alkylsulfonyloxy has the same definition as the lower alkyl (ii) described above], or substituted or unsubstituted arylsulfonyloxy [wherein the aryl moiety of the arylsulfonyloxy has the same definition as the aryl (v) described above, and examples of the substituent of the substituted arylsulfonyloxy which may be the same or different, and in number of 1 to 3, include lower alkyl (wherein the lower alkyl has the same definition as the lower alkyl (ii) described above)]}

Step 25

Compound (AB) can be obtained by reacting Compound (IH) obtained according to Production Methods 1 to 7 described above and Compound (AA) obtained in each step of Production Methods 1, 5, and 7 with 1 to 10 equivalents, preferably 1 to 3 equivalents, of a quaternary ammonium fluoride salt in an inert solvent.

The inert solvent is not particularly limited as long as it is inert to the reaction. Examples thereof include dichloromethane, chloroform, 1,2-dichloroethane, DMF, DMA, NMP, DMSO, THF, dioxane, diethyl ether, diisopropyl ether, benzene, toluene, xylene, ethyl acetate, acetonitrile, methanol, ethanol, n-propanol, 2-propanol, water, and the like. These solvents may be used alone or in combination. In particular, THF is preferable.

As the quaternary ammonium fluoride salt, for example, tetrabutylammonium fluoride (TBAF), tetraethylammonium fluoride, or the like can be used. It is also possible to prepare a quaternary ammonium fluoride salt in the reaction system using both tetrabutylammonium chloride and potassium fluoride or the like.

The reaction is carried out at a temperature between 0° C. and 100° C., preferably at a temperature between 20° C. and 60° C., usually for 10 minutes to 24 hours.

Step 26

Compound (AC) can be obtained by allowing Compound (AB) obtained in Step 25 to react with an excess amount of a chlorinating agent in the presence or absence of a solvent inactive in the reaction or to react with a sulfonic acid halide or a sulfonic acid anhydride in a solvent inactive in the reaction.

Step 26-1: when Q Represents a Chlorine Atom in Compound (AC)

Compound (AC) can be obtained by allowing Compound (AB) obtained in Step 25 to react with an excess amount of a chlorinating agent in an inert solvent or not.

As the chlorinating agent, for example, phosphorus oxychloride, phosphorus pentachloride, or the like is used.

The inert solvent is not particularly limited as long as it is inert to the reaction. Examples thereof include 1,2-dichloroethane, THF, dioxane, 1,2-dimethoxyethane, chloroform, benzene, toluene, xylene, ethyl acetate, triethylamine, pyridine, N,N-dimethylaniline, and the like. These solvents may be used alone or in combination.

The reaction is carried out at a temperature between 0° C. and the boiling point of the solvent, preferably at a temperature between 50° C. and 110° C., usually for 1 to 24 hours.

Step 26-2: when Q Represents a Group Other than a Chlorine Atom in Compound (AC)

Compound (AC) can be obtained by reacting compound (AB) obtained in Step 25 with a sulfonyl halide or a sulfonic anhydride in an inert solvent.

The reaction conditions, the solvent, the reagent, and the like are the same as those described in Step 9 of Production Method 2.

Step 27

Compound (I) or Compound (AD) can be obtained by reacting Compound (AC) obtained in Step 26 with Compound (B) in a similar manner to Step 1 of Production Method 1.

Furthermore, conversion of the functional groups in Compound (I), the intermediate, and the starting compound can be performed by a known method [for example, a method described in Comprehensive Organic Transformations, second edition, R. C. Larock, John Wiley & Sons Inc. (1999), or the like] or a similar method thereto.

By appropriately combining the methods described above and the like, it is possible to obtain Compound (I) which has a desired functional group at a desired position.

Isolation and purification of the products and the intermediates in the production methods described above can be performed by appropriately combining processes that are usually used in organic synthesis, for example, filtration, extraction, washing, drying, concentration, crystallization, various chromatographies, and the like. It is also possible to perform purification by a purification process generally used in combinatorial chemistry and the like using a resin, for example, a scavenger resin, such as benzoyl chloride polymer-bound, poly(4-vinylpyridine), benzaldehyde polymer-bound, or trityl chloride polymer-bound; an ion exchange resin, such as AG1-X8 (manufactured by Bio-Rad Laboratories, Inc.); or the like. Furthermore, the intermediate may be subjected to the subsequent reaction without purification.

In Compound (I), isomers, such as positional isomers, regioisomers, or optical isomers, may be present. All possible isomers including these and mixtures at any ratio of the isomers can be used for the antitumor agent and the like of the present invention.

To obtain a salt of Compound (I), when Compound (I) is obtained in the form of a salt, the salt of Compound (I) may be purified as it is. Further, when Compound (I) is obtained in a free form, Compound (I) may be dissolved or suspended in a suitable solvent, followed by addition of an acid or a base to form a salt. Then, the resulting salt may be isolated and purified.

Compound (I) or pharmaceutically acceptable salt thereof may exist in the form of adducts with water or solvents. These adducts may also be used in the antitumor agent of the present invention.

Specific examples of Compound (I) are shown in Tables 1 to 7, which by no means limit the scope of the present invention.

[Table 1-1]

TABLE 1-1

*General structure: R³-oxadiazole-pyrimidine with HN-CH₂CH₂CH₃ (n-propyl amine) and R² substituent*

| Compound Number | —R² | —R³ | Analytical Data |
|---|---|---|---|
| 1-1 | —NH—CH₂CH₂—N(CH₃)₂ | —CH₃ | MS m/z 306 (M + H)⁺ |
| 1-2 | —NH—CH₂CH₂CH₂—N(CH₃)₂ | —CH₃ | MS m/z 320 (M + H)⁺ |
| 1-3 | —NH—CH₂CH₂-(2-thienyl) | —CH₃ | MS m/z 345 (M + H)⁺ |
| 1-4 | —NH—CH₂CH₂CH₂-(pyrrolidin-1-yl) | —CH₃ | MS m/z 346 (M + H)⁺ |
| 1-5 | —NH—CH₂CH₂-(piperidin-1-yl) | —CH₃ | MS m/z 346 (M + H)⁺ |
| 1-6 | —NH—CH₂CH₂CH₂-(morpholin-4-yl) | —CH₃ | MS m/z 362 (M + H)⁺ |
| 1-7 | —NH—CH₂CH₂-(pyridin-2-yl) | —CH₃ | MS m/z 340 (M + H)⁺ |
| 1-8 | —NH—CH₂CH₂-(pyridin-3-yl) | —CH₃ | MS m/z 340 (M + H)⁺ |
| 1-9 | —NH—CH₂CH₂-(pyridin-4-yl) | —CH₃ | MS m/z 340 (M + H)⁺ |
| 1-10 | —NH—CH₂CH₂—C₆H₅ | —CH₃ | MS m/z 339 (M + H)⁺ |

[Table 1-2]

TABLE 1-2

| Compound Number | —R² | —R³ | Analytical Data |
|---|---|---|---|
| 1-11 | —NH—CH₂CH₂—N(CH₃)₂ | —CH₂CH₃ | MS m/z 320 (M + H)⁺ |
| 1-12 | —NH—CH₂CH₂CH₂—N(CH₃)₂ | —CH₂CH₃ | MS m/z 334 (M + H)⁺ |
| 1-13 | —NH—CH₂CH₂-(2-thienyl) | —CH₂CH₃ | MS m/z 359 (M + H)⁺ |
| 1-14 | —NH—CH₂CH₂CH₂-(pyrrolidin-1-yl) | —CH₂CH₃ | MS m/z 360 (M + H)⁺ |
| 1-15 | —NH—CH₂CH₂-(piperidin-1-yl) | —CH₂CH₃ | MS m/z 360 (M + H)⁺ |
| 1-16 | —NH—CH₂CH₂CH₂-(morpholin-4-yl) | —CH₂CH₃ | MS m/z 376 (M + H)⁺ |
| 1-17 | —NH—CH₂CH₂-(pyridin-2-yl) | —CH₂CH₃ | MS m/z 354 (M + H)⁺ |
| 1-18 | —NH—CH₂CH₂-(pyridin-3-yl) | —CH₂CH₃ | MS m/z 354 (M + H)⁺ |
| 1-19 | —NH—CH₂CH₂-(pyridin-4-yl) | —CH₂CH₃ | MS m/z 354 (M + H)⁺ |
| 1-20 | —NH—CH₂CH₂—C₆H₅ | —CH₂CH₃ | MS m/z 353 (M + H)⁺ |

[Table 1-3]
TABLE 1-3
| Compound Number | •—R² | •—R³ | Analytical Data |
|---|---|---|---|
| 1-21 |  |  | MS m/z 334 (M + H)⁺ |
| 1-22 |  |  | MS m/z 348 (M + H)⁺ |
| 1-23 |  |  | MS m/z 373 (M + H)⁺ |
| 1-24 |  |  | MS m/z 374 (M + H)⁺ |
| 1-25 |  |  | MS m/z 374 (M + H)⁺ |
| 1-26 |  |  | MS m/z 390 (M + H)⁺ |
| 1-27 |  |  | MS m/z 368 (M + H)⁺ |
| 1-28 |  |  | MS m/z 368 (M + H)⁺ |
| 1-29 |  |  | MS m/z 368 (M + H)⁺ |
| 1-30 |  |  | MS m/z 367 (M + H)⁺ |

[Table 1-4]

TABLE 1-4

| Compound Number | —R² | —R³ | Analytical Data |
|---|---|---|---|
| 1-31 | •—NH—CH₂CH₂—N(CH₃)₂ | —CH(CH₃)₂ | MS m/z 334 (M + H)⁺ |
| 1-32 | •—NH—(CH₂)₃—N(CH₃)₂ | —CH(CH₃)₂ | MS m/z 348 (M + H)⁺ |
| 1-33 | •—NH—CH₂CH₂-(2-thienyl) | —CH(CH₃)₂ | MS m/z 373 (M + H)⁺ |
| 1-34 | •—NH—(CH₂)₃-(1-pyrrolidinyl) | —CH(CH₃)₂ | MS m/z 374 (M + H)⁺ |
| 1-35 | •—NH—CH₂CH₂-(1-piperidinyl) | —CH(CH₃)₂ | MS m/z 374 (M + H)⁺ |

TABLE 1-4-continued

| Compound Number | —R² | —R³ | Analytical Data |
|---|---|---|---|
| 1-36 | •—NH—(CH₂)₃-(4-morpholinyl) | —CH(CH₃)₂ | MS m/z 390 (M + H)⁺ |
| 1-37 | •—NH—CH₂CH₂-(2-pyridyl) | —CH(CH₃)₂ | MS m/z 368 (M + H)⁺ |
| 1-38 | •—NH—CH₂CH₂-(3-pyridyl) | —CH(CH₃)₂ | MS m/z 368 (M + H)⁺ |
| 1-39 | •—NH—CH₂CH₂-(4-pyridyl) | —CH(CH₃)₂ | MS m/z 368 (M + H)⁺ |
| 1-40 | •—NH—CH₂CH₂-phenyl | —CH(CH₃)₂ | MS m/z 367 (M + H)⁺ |

[Table 1-5]

TABLE 1-5

| Compound Number | —R² | —R³ | Analytical Data |
|---|---|---|---|
| 1-41 | •—NH—CH₂CH₂—N(CH₃)₂ | —C(CH₃)₃ | MS m/z 348 (M + H)⁺ |
| 1-42 | •—NH—(CH₂)₃—N(CH₃)₂ | —C(CH₃)₃ | MS m/z 362 (M + H)⁺ |
| 1-43 | •—NH—CH₂CH₂-(2-thienyl) | —C(CH₃)₃ | MS m/z 387 (M + H)⁺ |
| 1-44 | •—NH—(CH₂)₃-(1-pyrrolidinyl) | —C(CH₃)₃ | MS m/z 388 (M + H)⁺ |
| 1-45 | •—NH—CH₂CH₂-(1-piperidinyl) | —C(CH₃)₃ | MS m/z 388 (M + H)⁺ |

TABLE 1-5-continued
| Compound Number | —R² | —R³ | Analytical Data |
|---|---|---|---|
| 1-46 | 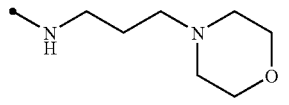 | 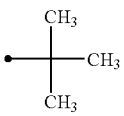 | MS m/z 404 (M + H)⁺ |
| 1-47 | 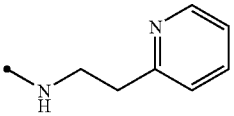 | 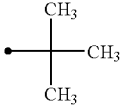 | MS m/z 382 (M + H)⁺ |
| 1-48 | 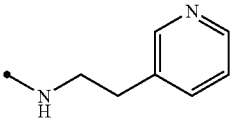 | 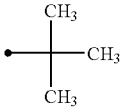 | MS m/z 382 (M + H)⁺ |
| 1-49 | 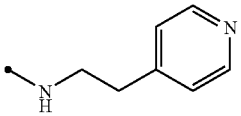 | 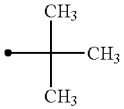 | MS m/z 382 (M + H)⁺ |
| 1-50 | 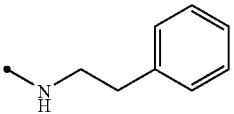 | 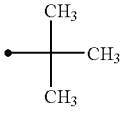 | MS m/z 381 (M + H)⁺ |
[Table 1-6]
TABLE 1-6
| Compound Number | —R² | —R³ | Analytical Data |
|---|---|---|---|
| 1-51 | 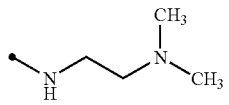 | 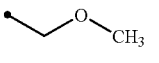 | MS m/z 336 (M + H)⁺ |
| 1-52 | 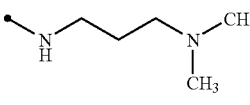 | 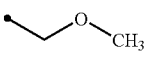 | MS m/z 350 (M + H)⁺ |
| 1-53 | 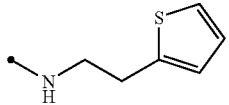 | 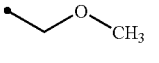 | MS m/z 375 (M + H)⁺ |
| 1-54 | 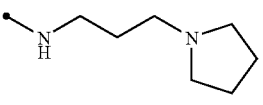 | 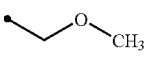 | MS m/z 376 (M + H)⁺ |

TABLE 1-6-continued

| Compound Number | —R² | —R³ | Analytical Data |
|---|---|---|---|
| 1-55 | *-NH-CH₂CH₂-(N-piperidine) | *-O-CH₂-O-CH₃ | MS m/z 376 (M + H)⁺ |
| 1-56 | *-NH-CH₂CH₂CH₂-(N-morpholine) | *-O-CH₂-O-CH₃ | MS m/z 392 (M + H)⁺ |
| 1-57 | *-NH-CH₂CH₂-(2-pyridyl) | *-O-CH₂-O-CH₃ | MS m/z 370 (M + H)⁺ |
| 1-58 | *-NH-CH₂CH₂-(3-pyridyl) | *-O-CH₂-O-CH₃ | MS m/z 370 (M + H)⁺ |
| 1-59 | *-NH-CH₂CH₂-(4-pyridyl) | *-O-CH₂-O-CH₃ | MS m/z 370 (M + H)⁺ |
| 1-60 | *-NH-CH₂CH₂-phenyl | *-O-CH₂-O-CH₃ | MS m/z 369 (M + H)⁺ |

[Table 1-7]

TABLE 1-7

| Compound Number | —R² | —R³ | Analytical Data |
|---|---|---|---|
| 1-61 | *-NH-CH₂CH₂-N(CH₃)₂ | *-cyclopropyl | MS m/z 332 (M + H)⁺ |
| 1-62 | *-NH-CH₂CH₂CH₂-N(CH₃)₂ | *-cyclopropyl | MS m/z 346 (M + H)⁺ |
| 1-63 | *-NH-CH₂CH₂-(2-thienyl) | *-cyclopropyl | MS m/z 371 (M + H)⁺ |
| 1-64 | *-NH-CH₂CH₂CH₂-(N-pyrrolidine) | *-cyclopropyl | MS m/z 372 (M + H)⁺ |
| 1-65 | *-NH-CH₂CH₂-(N-piperidine) | *-cyclopropyl | MS m/z 372 (M + H)⁺ |

TABLE 1-7-continued

| Compound Number | —R² | —R³ | Analytical Data |
|---|---|---|---|
| 1-66 | *-NH-CH₂CH₂CH₂-(N-morpholine) | *-cyclopropyl | MS m/z 388 (M + H)⁺ |
| 1-67 | *-NH-CH₂CH₂-(2-pyridyl) | *-cyclopropyl | MS m/z 366 (M + H)⁺ |
| 1-68 | *-NH-CH₂CH₂-(3-pyridyl) | *-cyclopropyl | MS m/z 366 (M + H)⁺ |
| 1-69 | *-NH-CH₂CH₂-(4-pyridyl) | *-cyclopropyl | MS m/z 366 (M + H)⁺ |
| 1-70 | *-NH-CH₂CH₂-phenyl | *-cyclopropyl | MS m/z 365 (M + H)⁺ |

[Table 1-8]
TABLE 1-8
| Compound Number | •—R² | •—R³ | Analytical Data |
|---|---|---|---|
| 1-71 | 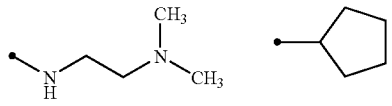 | 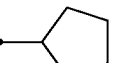 | MS m/z 360 (M + H)⁺ |
| 1-72 | 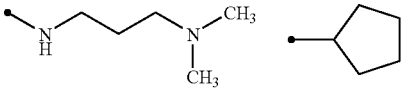 | 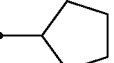 | MS m/z 374 (M + H)⁺ |
| 1-73 | 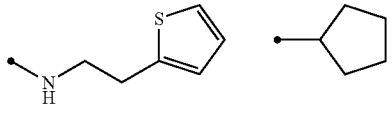 | 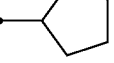 | MS m/z 399 (M + H)⁺ |
| 1-74 | 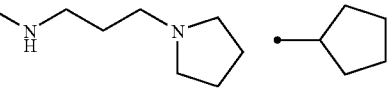 | 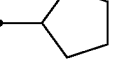 | MS m/z 400 (M + H)⁺ |
| 1-75 | 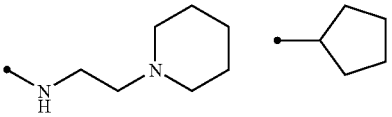 | 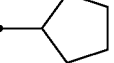 | MS m/z 400 (M + H)⁺ |
| 1-76 | 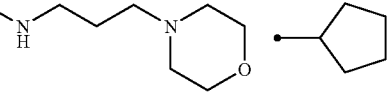 | 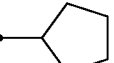 | MS m/z 416 (M + H)⁺ |
| 1-77 | 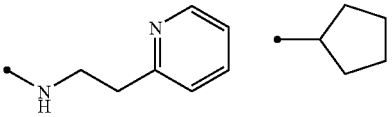 | 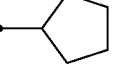 | MS m/z 394 (M + H)⁺ |
| 1-78 | 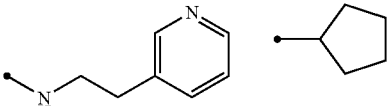 | 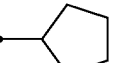 | MS m/z 394 (M + H)⁺ |
| 1-79 | 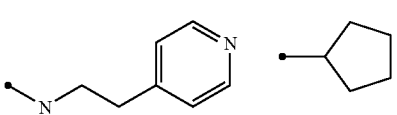 | 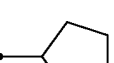 | MS m/z 394 (M + H)⁺ |
| 1-80 | 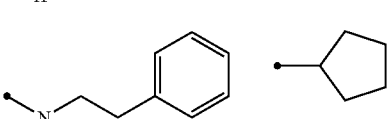 | 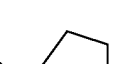 | MS m/z 393 (M + H)⁺ |
[Table 1-9]
TABLE 1-9
| Compound Number | •—R² | •—R³ | Analytical Data |
|---|---|---|---|
| 1-81 | 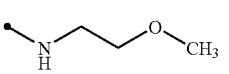 | •—CH₃ | MS m/z 307 (M + H)⁺ |

TABLE 1-9-continued
| Compound Number | —R² | —R³ | Analytical Data |
|---|---|---|---|
| 1-82 | 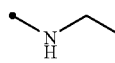 | —CH₃ | MS m/z 302 (M + H)⁺ |
| 1-83 |  | —CH₃ | MS m/z 353 (M + H)⁺ |
| 1-84 | 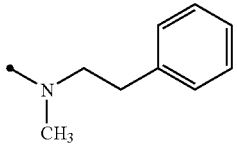 | —CH₃ | MS m/z 318 (M + H)⁺ |
| 1-85 |  | —CH₃ | MS m/z 348 (M + H)⁺ |
| 1-86 | 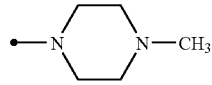 | —CH₃ | MS m/z 415 (M + H)⁺ |
| 1-87 |  | —CH₃ | MS m/z 414 (M + H)⁺ |
| 1-88 | 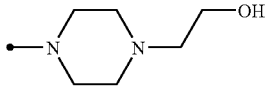 | —CH₃ | MS m/z 408 (M + H)⁺ |
| 1-89 |  | —CH₃ | MS m/z 400 (M + H)⁺ |
| 1-90 | 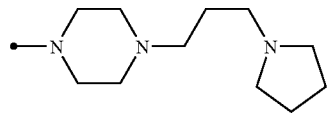 | —CH₃ | MS m/z 339 (M + H)⁺ |
| 1-91 |  | —CH₃ | MS m/z 279 (M + H)⁺ |
| 1-92 | 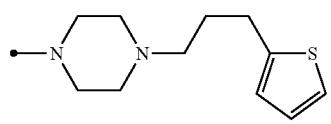 | —CH₃ | MS m/z 293 (M + H)⁺ |
[Table 1-10]
TABLE 1-10
| Compound Number | —R² | —R³ | Analytical Data |
|---|---|---|---|
| 1-93 |  | 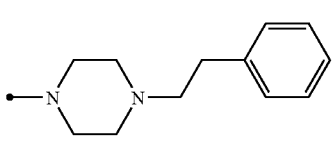 | MS m/z 321 (M + H)⁺ |

TABLE 1-10-continued

| Compound Number | —R² | —R³ | Analytical Data |
|---|---|---|---|
| 1-94 | -NH-CH₂CH₂-CN | -CH₃ | MS m/z 316 (M + H)⁺ |
| 1-95 | -N(CH₃)-CH₂CH₂-Ph | -CH₃ | MS m/z 367 (M + H)⁺ |
| 1-96 | -N(piperazine)-N-CH₃ | -CH₃ | MS m/z 332 (M + H)⁺ |
| 1-97 | -N(piperazine)-N-CH₂CH₂-OH | -CH₃ | MS m/z 362 (M + H)⁺ |
| 1-98 | -N(piperazine)-N-CH₂CH₂CH₂-N(pyrrolidine) | -CH₃ | MS m/z 429 (M + H)⁺ |
| 1-99 | -N(piperazine)-N-CH₂CH₂CH₂-(2-thienyl) | -CH₃ | MS m/z 428 (M + H)⁺ |
| 1-100 | -N(piperazine)-N-CH₂CH₂-Ph | -CH₃ | MS m/z 421 (M + H)⁺ |
| 1-101 | -N(piperidine)-4-CH₂CH₂-N(pyrrolidine) | -CH₃ | MS m/z 414 (M + H)⁺ |
| 1-102 | -NH-CH(CH₃)-Ph | -CH₃ | MS m/z 353 (M + H)⁺ |
| 1-103 | -NH-CH₂CH₂-OH | -CH₃ | MS m/z 293 (M + H)⁺ |
| 1-104 | -NH-CH₂CH₂CH₂-OH | -CH₃ | MS m/z 307 (M + H)⁺ |

[Table 1-11]

TABLE 1-11

| Compound Number | —R² | —R³ | Analytical Data |
|---|---|---|---|
| 1-105 | -NH-CH₂CH₂-O-CH₃ | -CH₂CH₃ | MS m/z 335 (M + H)⁺ |

TABLE 1-11-continued

| Compound Number | —R² | —R³ | Analytical Data |
|---|---|---|---|
| 1-106 | •−NH−CH₂CH₂−CN | •−CH₂CH₂CH₂−CH₃ | MS m/z 330 (M + H)⁺ |
| 1-107 | •−N(CH₃)−CH₂CH₂−Ph | •−CH₂CH₂CH₂−CH₃ | MS m/z 381 (M + H)⁺ |
| 1-108 | •−N(piperazine)N−CH₃ | •−CH₂CH₂CH₂−CH₃ | MS m/z 346 (M + H)⁺ |
| 1-109 | •−N(piperazine)N−CH₂CH₂−OH | •−CH₂CH₂CH₂−CH₃ | MS m/z 376 (M + H)⁺ |
| 1-110 | •−N(piperazine)N−CH₂CH₂CH₂−pyrrolidine | •−CH₂CH₂CH₂−CH₃ | MS m/z 443 (M + H)⁺ |
| 1-111 | •−N(piperazine)N−CH₂CH₂CH₂−(2-thienyl) | •−CH₂CH₂CH₂−CH₃ | MS m/z 442 (M + H)⁺ |
| 1-112 | •−N(piperazine)N−CH₂CH₂−Ph | •−CH₂CH₂CH₂−CH₃ | MS m/z 436 (M + H)⁺ |
| 1-113 | •−N(piperazine)N−CH₂CH₂−pyrrolidine | •−CH₂CH₂CH₂−CH₃ | MS m/z 428 (M + H)⁺ |
| 1-114 | •−NH−CH(CH₃)−Ph | •−CH₂CH₂CH₂−CH₃ | MS m/z 367 (M + H)⁺ |
| 1-115 | •−NH−CH₂CH₂−OH | •−CH₂CH₂CH₂−CH₃ | MS m/z 307 (M + H)⁺ |
| 1-116 | •−NH−CH₂CH₂CH₂−OH | •−CH₂CH₂CH₂−CH₃ | MS m/z 321 (M + H)⁺ |

[Table 1-12]

TABLE 1-12

| Compound Number | —R² | —R³ | Analytical Data |
|---|---|---|---|
| 1-117 | •−NH−CH₂CH₂−O−CH₃ | •−CH(CH₃)−CH₃ | MS m/z 335 (M + H)⁺ |

TABLE 1-12-continued
| Compound Number | —R² | —R³ | Analytical Data |
|---|---|---|---|
| 1-118 | 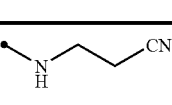 | 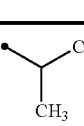 | MS m/z 330 (M + H)⁺ |
| 1-119 | 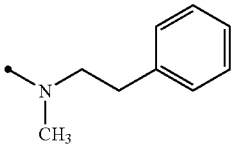 |  | MS m/z 381 (M + H)⁺ |
| 1-120 | 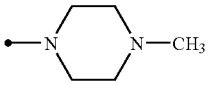 |  | MS m/z 346 (M + H)⁺ |
| 1-121 | 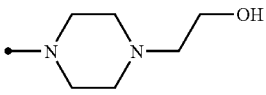 |  | MS m/z 376 (M + H)⁺ |
| 1-122 | 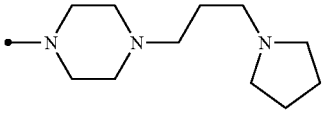 |  | MS m/z 443 (M + H)⁺ |
| 1-123 | 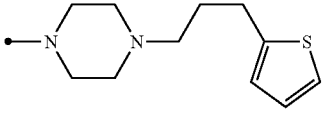 |  | MS m/z 442 (M + H)⁺ |
| 1-124 | 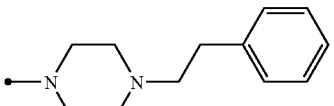 |  | MS m/z 436 (M + H)⁺ |
| 1-125 | 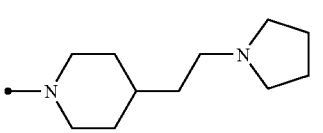 |  | MS m/z 428 (M + H)⁺ |
| 1-126 | 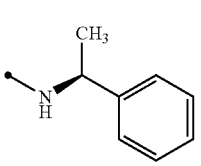 |  | MS m/z 367 (M + H)⁺ |
| 1-127 | 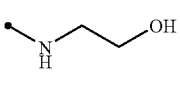 |  | MS m/z 307 (M + H)⁺ |
| 1-128 | 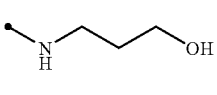 |  | MS m/z 321 (M + H)⁺ |

[Table 1-13]

TABLE 1-13

| Compound Number | —R² | —R³ | Analytical Data |
|---|---|---|---|
| 1-129 | •—NH—CH₂CH₂—O—CH₃ | •—C(CH₃)₃ | MS m/z 349 (M + H)⁺ |
| 1-130 | •—NH—CH₂—CN | •—C(CH₃)₃ | MS m/z 344 (M + H)⁺ |
| 1-131 | •—N(CH₃)—CH₂CH₂—Ph | •—C(CH₃)₃ | MS m/z 395 (M + H)⁺ |
| 1-132 | •—N(piperazine)N—CH₃ | •—C(CH₃)₃ | MS m/z 360 (M + H)⁺ |
| 1-133 | •—N(piperazine)N—CH₂CH₂—OH | •—C(CH₃)₃ | MS m/z 390 (M + H)⁺ |
| 1-134 | •—N(piperazine)N—CH₂CH₂CH₂—N(pyrrolidine) | •—C(CH₃)₃ | MS m/z 457 (M + H)⁺ |
| 1-135 | •—N(piperazine)N—CH₂CH₂—(thiophene) | •—C(CH₃)₃ | MS m/z 456 (M + H)⁺ |
| 1-136 | •—N(piperazine)N—CH₂CH₂—Ph | •—C(CH₃)₃ | MS m/z 450 (M + H)⁺ |
| 1-137 | •—N(piperidine)—CH₂CH₂—N(pyrrolidine) | •—C(CH₃)₃ | MS m/z 442 (M + H)⁺ |
| 1-138 | •—NH—CH(CH₃)—Ph | •—C(CH₃)₃ | MS m/z 381 (M + H)⁺ |
| 1-139 | •—NH—CH₂CH₂—OH | •—C(CH₃)₃ | MS m/z 321 (M + H)⁺ |

TABLE 1-13-continued

| Compound Number | —R² | —R³ | Analytical Data |
|---|---|---|---|
| 1-140 | •—NH—CH₂CH₂CH₂—OH | •—C(CH₃)₃ | MS m/z 335 (M + H)⁺ |

[Table 1-14]

TABLE 1-14

| Compound Number | —R² | —R³ | Analytical Data |
|---|---|---|---|
| 1-141 | •—NH—CH₂CH₂—O—CH₃ | •—O—CH₂—O—CH₃ | MS m/z 337 (M + H)⁺ |
| 1-142 | •—NH—CH₂CH₂—CN | •—O—CH₂—O—CH₃ | MS m/z 332 (M + H)⁺ |
| 1-143 | •—N(CH₃)—CH₂CH₂—Ph | •—O—CH₂—O—CH₃ | MS m/z 383 (M + H)⁺ |
| 1-144 | •—N(piperazine)—CH₃ | •—O—CH₂—O—CH₃ | MS m/z 348 (M + H)⁺ |
| 1-145 | •—N(piperazine)—CH₂CH₂—OH | •—O—CH₂—O—CH₃ | MS m/z 378 (M + H)⁺ |
| 1-146 | •—N(piperazine)—CH₂CH₂CH₂—N(pyrrolidine) | •—O—CH₂—O—CH₃ | MS m/z 445 (M + H)⁺ |
| 1-147 | •—N(piperazine)—CH₂CH₂—(2-thienyl) | •—O—CH₂—O—CH₃ | MS m/z 444 (M + H)⁺ |
| 1-148 | •—N(piperazine)—CH₂CH₂—Ph | •—O—CH₂—O—CH₃ | MS m/z 438 (M + H)⁺ |
| 1-149 | •—N(piperidine-4-yl)—CH₂CH₂—N(pyrrolidine) | •—O—CH₂—O—CH₃ | MS m/z 430 (M + H)⁺ |
| 1-150 | •—NH—CH(CH₃)—Ph | •—O—CH₂—O—CH₃ | MS m/z 369 (M + H)⁺ |
| 1-151 | •—NH—CH₂CH₂—OH | •—O—CH₂—O—CH₃ | MS m/z 309 (M + H)⁺ |

TABLE 1-14-continued

| Compound Number | —R² | —R³ | Analytical Data |
|---|---|---|---|
| 1-152 | •―NH―CH₂CH₂CH₂―OH | •―O―CH₃ (methoxymethyl) | MS m/z 323 (M + H)⁺ |

[Table 1-15]

TABLE 1-15

| Compound Number | —R² | —R³ | Analytical Data |
|---|---|---|---|
| 1-153 | •―NH―CH₂CH₂―O―CH₃ | cyclopropyl | MS m/z 333 (M + H)⁺ |
| 1-154 | •―NH―CH₂CH₂―CN | cyclopropyl | MS m/z 328 (M + H)⁺ |
| 1-155 | •―N(CH₃)―CH₂CH₂―Ph | cyclopropyl | MS m/z 379 (M + H)⁺ |
| 1-156 | •―N-piperazinyl-N'―CH₃ | cyclopropyl | MS m/z 344 (M + H)⁺ |
| 1-157 | •―N-piperazinyl-N'―CH₂CH₂―OH | cyclopropyl | MS m/z 374 (M + H)⁺ |
| 1-158 | •―N-piperazinyl-N'―CH₂CH₂CH₂―(pyrrolidin-1-yl) | cyclopropyl | MS m/z 441 (M + H)⁺ |
| 1-159 | •―N-piperazinyl-N'―CH₂CH₂―(thiophen-2-yl) | cyclopropyl | MS m/z 440 (M + H)⁺ |
| 1-160 | •―N-piperazinyl-N'―CH₂CH₂―Ph | cyclopropyl | MS m/z 434 (M + H)⁺ |
| 1-161 | •―N-piperazinyl-N'―CH₂CH₂―(pyrrolidin-1-yl) | cyclopropyl | MS m/z 426 (M + H)⁺ |
| 1-162 | •―NH―CH(CH₃)―Ph | cyclopropyl | MS m/z 365 (M + H)⁺ |
| 1-163 | •―NH―CH₂CH₂―OH | cyclopropyl | MS m/z 305 (M + H)⁺ |

TABLE 1-15-continued

| Compound Number | —R² | —R³ | Analytical Data |
|---|---|---|---|
| 1-164 | •—NH—CH₂CH₂CH₂—OH | cyclopropyl | MS m/z 319 (M + H)⁺ |

[Table 1-16]

TABLE 1-16

| Compound Number | —R² | —R³ | Analytical Data |
|---|---|---|---|
| 1-165 | •—NH—CH₂CH₂—O—CH₃ | cyclopentyl | MS m/z 361 (M + H)⁺ |
| 1-166 | •—NH—CH₂CH₂—CN | cyclopentyl | MS m/z 356 (M + H)⁺ |
| 1-167 | •—N(CH₃)—CH₂CH₂—Ph | cyclopentyl | MS m/z 407 (M + H)⁺ |
| 1-168 | •—N(piperazine)N—CH₃ | cyclopentyl | MS m/z 372 (M + H)⁺ |
| 1-169 | •—N(piperazine)N—CH₂CH₂OH | cyclopentyl | MS m/z 402 (M + H)⁺ |
| 1-170 | •—N(piperazine)N—CH₂CH₂CH₂—N(pyrrolidine) | cyclopentyl | MS m/z 469 (M + H)⁺ |
| 1-171 | •—N(piperazine)N—CH₂CH₂—(2-thienyl) | cyclopentyl | MS m/z 468 (M + H)⁺ |
| 1-172 | •—N(piperazine)N—CH₂CH₂—Ph | cyclopentyl | MS m/z 462 (M + H)⁺ |
| 1-173 | •—N(piperidine)—CH₂CH₂—N(pyrrolidine) (4-substituted) | cyclopentyl | MS m/z 454 (M + H)⁺ |
| 1-174 | •—NH—CH(CH₃)—Ph | cyclopentyl | MS m/z 393 (M + H)⁺ |
| 1-175 | •—NH—CH₂CH₂—OH | cyclopentyl | MS m/z 333 (M + H)⁺ |

TABLE 1-16-continued

| Compound Number | •—R² | •—R³ | Analytical Data |
|---|---|---|---|
| 1-176 | •—NH—CH₂CH₂CH₂—OH | •—cyclopentyl | MS m/z 347 (M + H)⁺ |

[Table 1-17]

TABLE 1-17

| Compound Number | •—R² | •—R³ | Analytical Data |
|---|---|---|---|
| 1-177 | •—NH—CH₂-(4-pyridyl) | •—CH₃ | MS m/z 326 (M + H)⁺ |
| 1-178 | •—NH—CH₂CH₂-(4-bromophenyl) | •—CH₃ | MS m/z 418 (M + H)⁺ |
| 1-179 | •—NH—CH₂CH₂-(4-chlorophenyl) | •—CH₃ | MS m/z 373 (M + H)⁺ |
| 1-180 | •—NH—CH₂CH₂-(4-fluorophenyl) | •—CH₃ | MS m/z 357 (M + H)⁺ |
| 1-181 | •—NH—CH₂CH₂-(4-methoxyphenyl) | •—CH₃ | MS m/z 369 (M + H)⁺ |
| 1-182 | •—NH—CH₂CH₂-(4-sulfamoylphenyl) | •—CH₃ | MS m/z 418 (M + H)⁺ |
| 1-183 | •—NH—CH₂CH₂—O-phenyl | •—CH₃ | MS m/z 355 (M + H)⁺ |
| 1-184 | •—NH—CH₂CH₂-(1H-indol-3-yl) | •—CH₃ | MS m/z 378 (M + H)⁺ |
| 1-185 | •—NH—CH₂CH₂-(2,4-dichlorophenyl) | •—CH₃ | MS m/z 407 (M + H)⁺ |

TABLE 1-17-continued
| Compound Number | •—R² | •—R³ | Analytical Data |
|---|---|---|---|
| 1-186 | 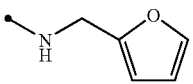 | •—CH₃ | MS m/z 315 (M + H)⁺ |
| 1-187 | 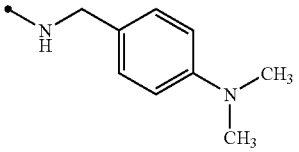 | •—CH₃ | MS m/z 368 (M + H)⁺ |
| 1-188 | 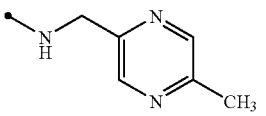 | •—CH₃ | MS m/z 341 (M + H)⁺ |
[Table 1-18]
TABLE 1-18
| Compound Number | •—R² | •—R³ | Analytical Data |
|---|---|---|---|
| 1-189 | 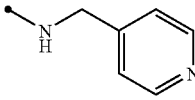 | •—CH₃ | MS m/z 340 (M + H)⁺ |
| 1-190 | 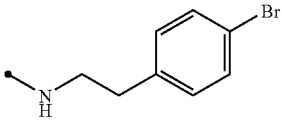 | •—CH₃ | MS m/z 432 (M + H)⁺ |
| 1-191 | 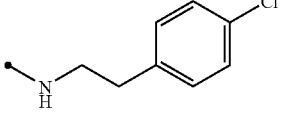 | •—CH₃ | MS m/z 387 (M + H)⁺ |
| 1-192 | 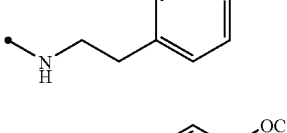 | •—CH₃ | MS m/z 371 (M + H)⁺ |
| 1-193 | 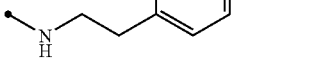 | •—CH₃ | MS m/z 383 (M + H)⁺ |
| 1-194 | 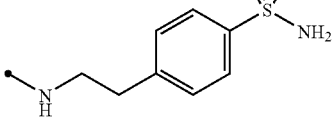 | •—CH₃ | MS m/z 432 (M + H)⁺ |
| 1-195 | 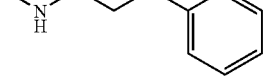 | •—CH₃ | MS m/z 369 (M + H)⁺ |

TABLE 1-18-continued

| Compound Number | —R² | —R³ | Analytical Data |
|---|---|---|---|
| 1-196 | (1H-indol-3-yl)ethyl-NH— | —CH₃ | MS m/z 392 (M + H)⁺ |
| 1-197 | 2,4-dichlorobenzyl-NH— (ethylene linker) | —CH₃ | MS m/z 421 (M + H)⁺ |
| 1-198 | furan-2-ylmethyl-NH— | —CH₃ | MS m/z 329 (M + H)⁺ |
| 1-199 | 4-(dimethylamino)benzyl-NH— | —CH₃ | MS m/z 382 (M + H)⁺ |
| 1-200 | (5-methylpyrazin-2-yl)methyl-NH— | —CH₃ | MS m/z 355 (M + H)⁺ |

[Table 1-19]

TABLE 1-19

| Compound Number | —R² | —R³ | Analytical Data |
|---|---|---|---|
| 1-201 | pyridin-4-ylmethyl-NH— | —CH₂CH₂CH₃ | MS m/z 354 (M + H)⁺ |
| 1-202 | 4-bromophenethyl-NH— | —CH₂CH₂CH₃ | MS m/z 446 (M + H)⁺ |
| 1-203 | 4-chlorophenethyl-NH— | —CH₂CH₂CH₃ | MS m/z 401 (M + H)⁺ |
| 1-204 | 4-fluorophenethyl-NH— | —CH₂CH₂CH₃ | MS m/z 385 (M + H)⁺ |
| 1-205 | 4-methoxyphenethyl-NH— | —CH₂CH₂CH₃ | MS m/z 397 (M + H)⁺ |

TABLE 1-19-continued

| Compound Number | •—R² | •—R³ | Analytical Data |
|---|---|---|---|
| 1-206 | 4-sulfamoylphenethylamino (•—NH—CH₂CH₂—C₆H₄—SO₂NH₂) | •—CH₂CH₂CH₂CH₃ | MS m/z 446 (M + H)⁺ |
| 1-207 | 2-phenoxyethylamino (•—NH—CH₂CH₂—O—C₆H₅) | •—CH₂CH₂CH₂CH₃ | MS m/z 383 (M + H)⁺ |
| 1-208 | 2-(1H-indol-3-yl)ethylamino | •—CH₂CH₂CH₂CH₃ | MS m/z 406 (M + H)⁺ |
| 1-209 | 2-(2,4-dichlorophenyl)ethylamino | •—CH₂CH₂CH₂CH₃ | MS m/z 435 (M + H)⁺ |
| 1-210 | (furan-2-ylmethyl)amino | •—CH₂CH₂CH₂CH₃ | MS m/z 343 (M + H)⁺ |
| 1-211 | [4-(dimethylamino)benzyl]amino | •—CH₂CH₂CH₂CH₃ | MS m/z 396 (M + H)⁺ |
| 1-212 | [(5-methylpyrazin-2-yl)methyl]amino | •—CH₂CH₂CH₂CH₃ | MS m/z 369 (M + H)⁺ |

[Table 1-20]

TABLE 1-20

| Compound Number | •—R² | •—R³ | Analytical Data |
|---|---|---|---|
| 1-213 | (pyridin-4-ylmethyl)amino | •—CH(CH₃)₂ | MS m/z 354 (M + H)⁺ |
| 1-214 | 2-(4-bromophenyl)ethylamino | •—CH(CH₃)₂ | MS m/z 446 (M + H)⁺ |
| 1-215 | 2-(4-chlorophenyl)ethylamino | •—CH(CH₃)₂ | MS m/z 401 (M + H)⁺ |

TABLE 1-20-continued
| Compound Number | —R² | —R³ | Analytical Data |
|---|---|---|---|
| 1-216 | 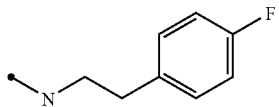 |  | MS m/z 385 (M + H)⁺ |
| 1-217 | 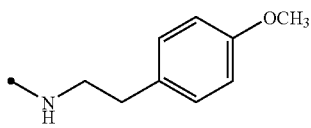 |  | MS m/z 397 (M + H)⁺ |
| 1-218 | 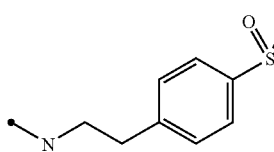 |  | MS m/z 446 (M + H)⁺ |
| 1-219 | 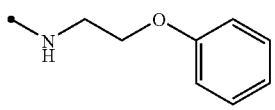 |  | MS m/z 383 (M + H)⁺ |
| 1-220 | 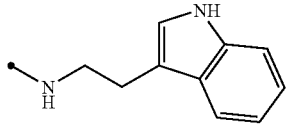 |  | MS m/z 406 (M + H)⁺ |
| 1-221 | 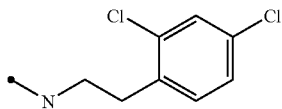 |  | MS m/z 435 (M + H)⁺ |
| 1-222 | 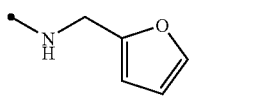 |  | MS m/z 343 (M + H)⁺ |
| 1-223 | 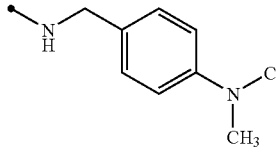 |  | MS m/z 396 (M + H)⁺ |
| 1-224 | 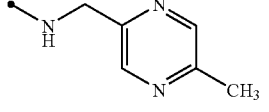 |  | MS m/z 369 (M + H)⁺ |
[Table 1-21]
TABLE 1-21
| Compound Number | —R² | —R³ | Analytical Data |
|---|---|---|---|
| 1-225 | 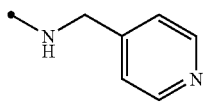 | 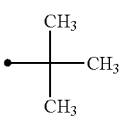 | MS m/z 368 (M + H)⁺ |

TABLE 1-21-continued
| Compound Number | —R² | —R³ | Analytical Data |
|---|---|---|---|
| 1-226 |  | 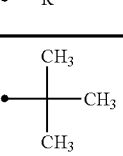 | MS m/z 460 (M + H)⁺ |
| 1-227 | 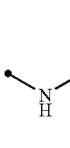 | 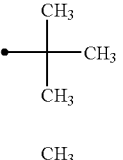 | MS m/z 415 (M + H)⁺ |
| 1-228 | 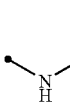 | 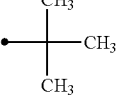 | MS m/z 399 (M + H)⁺ |
| 1-229 | 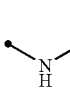 | 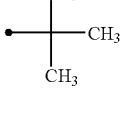 | MS m/z 411 (M + H)⁺ |
| 1-230 | 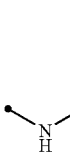 | 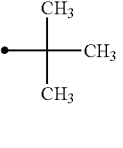 | MS m/z 460 (M + H)⁺ |
| 1-231 |  | 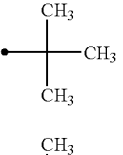 | MS m/z 397 (M + H)⁺ |
| 1-232 | 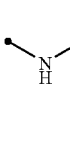 | 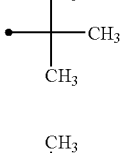 | MS m/z 420 (M + H)⁺ |
| 1-233 | 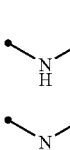 | 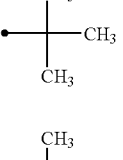 | MS m/z 449 (M + H)⁺ |
| 1-234 |  | 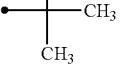 | MS m/z 357 (M + H)⁺ |
| 1-235 |  | 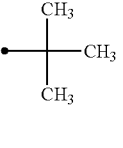 | MS m/z 410 (M + H)⁺ |
| 1-236 | 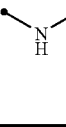 | 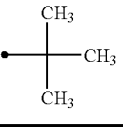 | MS m/z 383 (M + H)⁺ |

TABLE 1-22

| Compound Number | —R² | —R³ | Analytical Data |
|---|---|---|---|
| 1-237 | •—NH—CH₂-(4-pyridyl) | •—O—CH₂—O—CH₃ | MS m/z 356 (M + H)⁺ |
| 1-238 | •—NH—CH₂CH₂-(4-Br-phenyl) | •—O—CH₂—O—CH₃ | MS m/z 448 (M + H)⁺ |
| 1-239 | •—NH—CH₂CH₂-(4-Cl-phenyl) | •—O—CH₂—O—CH₃ | MS m/z 403 (M + H)⁺ |
| 1-240 | •—NH—CH₂CH₂-(4-F-phenyl) | •—O—CH₂—O—CH₃ | MS m/z 387 (M + H)⁺ |
| 1-241 | •—NH—CH₂CH₂-(4-OCH₃-phenyl) | •—O—CH₂—O—CH₃ | MS m/z 399 (M + H)⁺ |
| 1-242 | •—NH—CH₂CH₂-(4-SO₂NH₂-phenyl) | •—O—CH₂—O—CH₃ | MS m/z 448 (M + H)⁺ |
| 1-243 | •—NH—CH₂CH₂—O-phenyl | •—O—CH₂—O—CH₃ | MS m/z 385 (M + H)⁺ |
| 1-244 | •—NH—CH₂CH₂-(1H-indol-3-yl) | •—O—CH₂—O—CH₃ | MS m/z 408 (M + H)⁺ |
| 1-245 | •—NH—CH₂CH₂-(3,4-diCl-phenyl) | •—O—CH₂—O—CH₃ | MS m/z 437 (M + H)⁺ |
| 1-246 | •—NH—CH₂-(furan-2-yl) | •—O—CH₂—O—CH₃ | MS m/z 345 (M + H)⁺ |
| 1-247 | •—NH—CH₂-(4-N(CH₃)₂-phenyl) | •—O—CH₂—O—CH₃ | MS m/z 398 (M + H)⁺ |

TABLE 1-22-continued

| Compound Number | •—R² | •—R³ | Analytical Data |
|---|---|---|---|
| 1-248 | •−NH−CH₂− (5-methylpyrazin-2-yl) | •−O−CH₃ (methoxymethyl) | MS m/z 371 (M + H)⁺ |

[Table 1-23]

TABLE 1-23

| Compound Number | •—R² | •—R³ | Analytical Data |
|---|---|---|---|
| 1-249 | •−NH−CH₂−(pyridin-4-yl) | cyclopropyl | MS m/z 352 (M + H)⁺ |
| 1-250 | •−NH−CH₂CH₂−(4-bromophenyl) | cyclopropyl | MS m/z 444 (M + H)⁺ |
| 1-251 | •−NH−CH₂CH₂−(4-chlorophenyl) | cyclopropyl | MS m/z 399 (M + H)⁺ |
| 1-252 | •−NH−CH₂CH₂−(4-fluorophenyl) | cyclopropyl | MS m/z 383 (M + H)⁺ |
| 1-253 | •−NH−CH₂CH₂−(4-methoxyphenyl) | cyclopropyl | MS m/z 395 (M + H)⁺ |
| 1-254 | •−NH−CH₂CH₂−(4-sulfamoylphenyl) | cyclopropyl | MS m/z 444 (M + H)⁺ |
| 1-255 | •−NH−CH₂CH₂−O−phenyl | cyclopropyl | MS m/z 381 (M + H)⁺ |
| 1-256 | •−NH−CH₂CH₂−(1H-indol-3-yl) | cyclopropyl | MS m/z 404 (M + H)⁺ |
| 1-257 | •−NH−CH₂CH₂−(2,4-dichlorophenyl) | cyclopropyl | MS m/z 433 (M + H)⁺ |

TABLE 1-23-continued
| Compound Number | —R² | —R³ | Analytical Data |
|---|---|---|---|
| 1-258 | 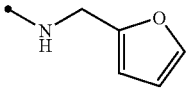 |  | MS m/z 341 (M + H)⁺ |
| 1-259 | 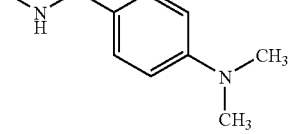 |  | MS m/z 394 (M + H)⁺ |
| 1-260 | 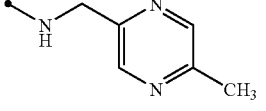 |  | MS m/z 367 (M + H)⁺ |
[Table 1-24]
TABLE 1-24
| Compound Number | —R² | —R³ | Analytical Data |
|---|---|---|---|
| 1-261 | 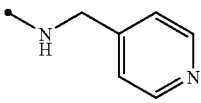 | 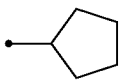 | MS m/z 380 (M + H)⁺ |
| 1-262 | 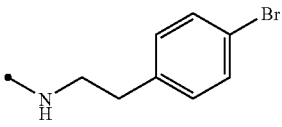 | 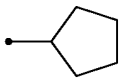 | MS m/z 472 (M + H)⁺ |
| 1-263 | 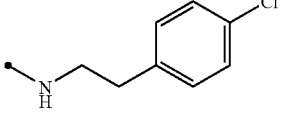 | 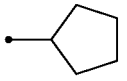 | MS m/z 427 (M + H)⁺ |
| 1-264 | 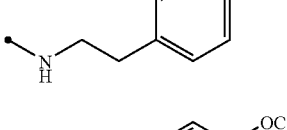 | 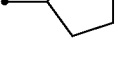 | MS m/z 411 (M + H)⁺ |
| 1-265 | 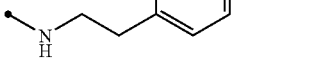 | 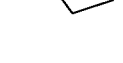 | MS m/z 423 (M + H)⁺ |
| 1-266 | 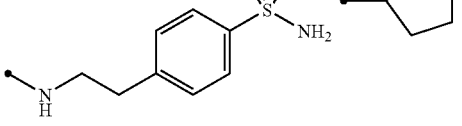 | 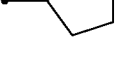 | MS m/z 472 (M + H)⁺ |
| 1-267 | 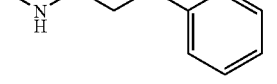 | 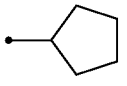 | MS m/z 409 (M + H)⁺ |

TABLE 1-24-continued

| Compound Number | —R² | —R³ | Analytical Data |
|---|---|---|---|
| 1-268 | •—NH—CH₂CH₂—(1H-indol-3-yl) | cyclopentyl | MS m/z 432 (M + H)⁺ |
| 1-269 | •—NH—CH₂CH₂—(2,4-dichlorophenyl) | cyclopentyl | MS m/z 461 (M + H)⁺ |
| 1-270 | •—NH—CH₂—(furan-2-yl) | cyclopentyl | MS m/z 369 (M + H)⁺ |
| 1-271 | •—NH—CH₂—(4-(N,N-dimethylamino)phenyl) | cyclopentyl | MS m/z 422 (M + H)⁺ |
| 1-272 | •—NH—CH₂—(5-methylpyrazin-2-yl) | cyclopentyl | MS m/z 395 (M + H)⁺ |

[Table 1-25]

TABLE 1-25

| Compound Number | —R² | —R³ | Analytical Data |
|---|---|---|---|
| 1-273 | •—NH—CH₂CH₂—S—CH₂—(furan-2-yl) | •—CH₃ | MS m/z 375 (M + H)⁺ |
| 1-274 | •—NH—CH₂CH₂CH₂—N(CH₃)—phenyl | •—CH₃ | MS m/z 382 (M + H)⁺ |
| 1-275 | •—NH—CH₂—(benzo[1,3]dioxol-5-yl) | •—CH₃ | MS m/z 369 (M + H)⁺ |
| 1-276 | •—NH—CH(CH₂OH)—CH₂—phenyl | •—CH₃ | MS m/z 370 (M + H)⁺ |
| 1-277 | •—NH—(1-benzylpiperidin-4-yl) | •—CH₃ | MS m/z 408 (M + H)⁺ |

TABLE 1-25-continued
| Compound Number | —R² | —R³ | Analytical Data |
|---|---|---|---|
| 1-278 | 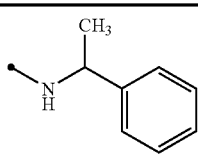 | —CH₃ | MS m/z 339 (M + H)⁺ |
| 1-279 | 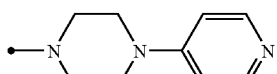 | —CH₃ | MS m/z 381 (M + H)⁺ |
| 1-280 | 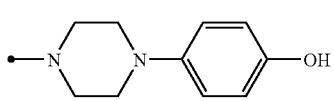 | —CH₃ | MS m/z 396 (M + H)⁺ |
| 1-281 | 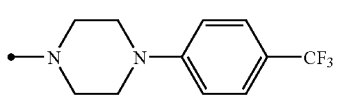 | —CH₃ | MS m/z 448 (M + H)⁺ |
| 1-282 | 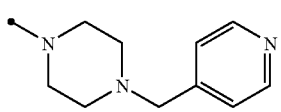 | —CH₃ | MS m/z 395 (M + H)⁺ |
| 1-283 | 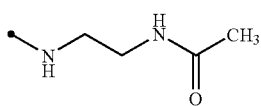 | —CH₃ | MS m/z 320 (M + H)⁺ |
| 1-284 | 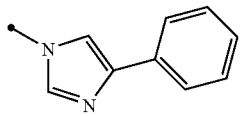 | —CH₃ | MS m/z 362 (M + H)⁺ |
[Table 1-26]
TABLE 1-26
| Compound Number | —R² | —R³ | Analytical Data |
|---|---|---|---|
| 1-285 | 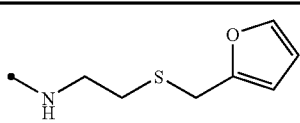 | —CH₃ | MS m/z 389 (M + H)⁺ |
| 1-286 | 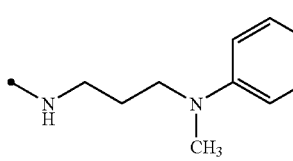 | —CH₃ | MS m/z 396 (M + H)⁺ |
| 1-287 | 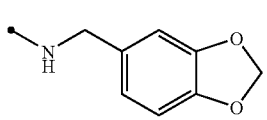 | —CH₃ | MS m/z 383 (M + H)⁺ |
| 1-288 | 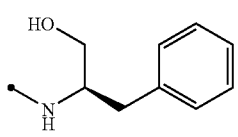 | —CH₃ | MS m/z 384 (M + H)⁺ |

TABLE 1-26-continued

| Compound Number | —R² | —R³ | Analytical Data |
|---|---|---|---|
| 1-289 | piperidine-N-benzyl, NH linker | CH₃ | MS m/z 422 (M + H)⁺ |
| 1-290 | NH-CH(CH₃)-phenyl | CH₃ | MS m/z 353 (M + H)⁺ |
| 1-291 | piperazine-pyridin-4-yl | CH₃ | MS m/z 395 (M + H)⁺ |
| 1-292 | piperazine-(4-hydroxyphenyl) | CH₃ | MS m/z 410 (M + H)⁺ |
| 1-293 | piperazine-(4-CF₃-phenyl) | CH₃ | MS m/z 462 (M + H)⁺ |
| 1-294 | piperazine-CH₂-pyridin-4-yl | CH₃ | MS m/z 409 (M + H)⁺ |
| 1-295 | NH-CH₂CH₂-NH-C(O)CH₃ | CH₃ | MS m/z 334 (M + H)⁺ |
| 1-296 | N-(4-phenyl-imidazol-1-yl) | CH₃ | MS m/z 376 (M + H)⁺ |

[Table 1-27]

TABLE 1-27

| Compound Number | —R² | —R³ | Analytical Data |
|---|---|---|---|
| 1-297 | NH-CH₂CH₂-S-CH₂-furan-2-yl | CH₂CH₂CH₃ | MS m/z 403 (M + H)⁺ |
| 1-298 | NH-CH₂CH₂CH₂-N(CH₃)-phenyl | CH₂CH₂CH₃ | MS m/z 410 (M + H)⁺ |
| 1-299 | NH-CH₂-benzo[1,3]dioxol-5-yl | CH₂CH₂CH₃ | MS m/z 397 (M + H)⁺ |

TABLE 1-27-continued
| Compound Number | —R² | —R³ | Analytical Data |
|---|---|---|---|
| 1-300 |  |  | MS m/z 398 (M + H)⁺ |
| 1-301 | 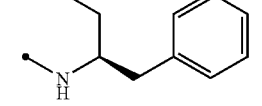 |  | MS m/z 436 (M + H)⁺ |
| 1-302 | 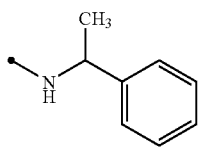 |  | MS m/z 367 (M + H)⁺ |
| 1-303 | 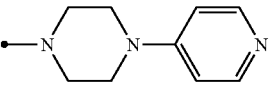 |  | MS m/z 409 (M + H)⁺ |
| 1-304 | 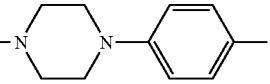 |  | MS m/z 424 (M + H)⁺ |
| 1-305 | 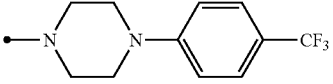 |  | MS m/z 476 (M + H)⁺ |
| 1-306 | 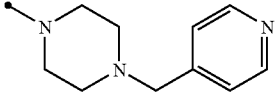 |  | MS m/z 423 (M + H)⁺ |
| 1-307 | 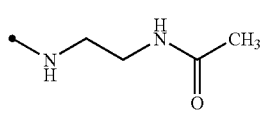 |  | MS m/z 348 (M + H)⁺ |
| 1-308 | 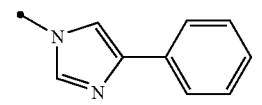 |  | MS m/z 390 (M + H)⁺ |
[Table 1-28]
TABLE 1-28
| Compound Number | —R² | —R³ | Analytical Data |
|---|---|---|---|
| 1-309 | 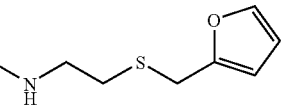 |  | MS m/z 403 (M + H)⁺ |
| 1-310 | 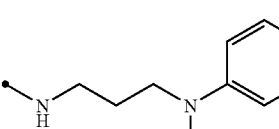 |  | MS m/z 410 (M + H)⁺ |

TABLE 1-28-continued
| Compound Number | —R² | —R³ | Analytical Data |
|---|---|---|---|
| 1-311 | 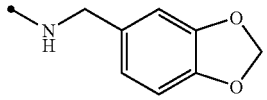 |  | MS m/z 397 (M + H)⁺ |
| 1-312 | 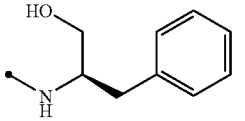 |  | MS m/z 398 (M + H)⁺ |
| 1-313 | 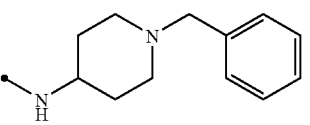 |  | MS m/z 436 (M + H)⁺ |
| 1-314 | 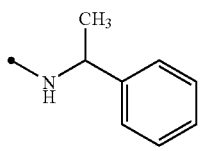 |  | MS m/z 367 (M + H)⁺ |
| 1-315 | 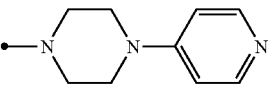 |  | MS m/z 409 (M + H)⁺ |
| 1-316 | 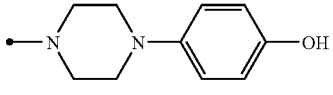 |  | MS m/z 424 (M + H)⁺ |
| 1-317 | 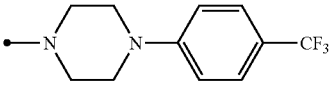 |  | MS m/z 476 (M + H)⁺ |
| 1-318 | 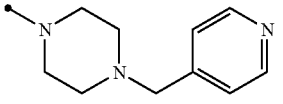 |  | MS m/z 423 (M + H)⁺ |
| 1-319 | 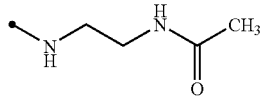 |  | MS m/z 348 (M + H)⁺ |
| 1-320 | 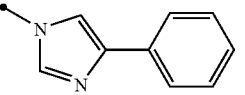 |  | MS m/z 390 (M + H)⁺ |
[Table 1-29]
TABLE 1-29
| Compound Number | —R² | —R³ | Analytical Data |
|---|---|---|---|
| 1-321 | 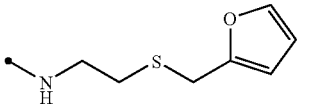 | 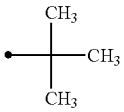 | MS m/z 417 (M + H)⁺ |

TABLE 1-29-continued

| Compound Number | —R² | —R³ | Analytical Data |
|---|---|---|---|
| 1-322 | •—NH—CH₂CH₂CH₂—N(CH₃)—C₆H₅ | —C(CH₃)₃ | MS m/z 424 (M + H)⁺ |
| 1-323 | •—NH—CH₂—(benzo[1,3]dioxol-5-yl) | —C(CH₃)₃ | MS m/z 411 (M + H)⁺ |
| 1-324 | •—NH—CH(CH₂OH)—CH₂—C₆H₅ | —C(CH₃)₃ | MS m/z 412 (M + H)⁺ |
| 1-325 | •—NH—(1-benzylpiperidin-4-yl) | —C(CH₃)₃ | MS m/z 450 (M + H)⁺ |
| 1-326 | •—NH—CH(CH₃)—C₆H₅ | —C(CH₃)₃ | MS m/z 381 (M + H)⁺ |
| 1-327 | •—(4-(pyridin-4-yl)piperazin-1-yl) | —C(CH₃)₃ | MS m/z 423 (M + H)⁺ |
| 1-328 | •—(4-(4-hydroxyphenyl)piperazin-1-yl) | —C(CH₃)₃ | MS m/z 438 (M + H)⁺ |
| 1-329 | •—(4-(4-trifluoromethylphenyl)piperazin-1-yl) | —C(CH₃)₃ | MS m/z 490 (M + H)⁺ |
| 1-330 | •—NH—(4-(pyridin-4-ylmethyl)piperazin-1-yl) | —C(CH₃)₃ | MS m/z 437 (M + H)⁺ |
| 1-331 | •—NH—CH₂CH₂—NH—C(O)CH₃ | —C(CH₃)₃ | MS m/z 362 (M + H)⁺ |
| 1-332 | •—(4-phenyl-1H-imidazol-1-yl) | —C(CH₃)₃ | MS m/z 404 (M + H)⁺ |

[Table 1-30]

TABLE 1-30

| Compound Number | —R² | —R³ | Analytical Data |
|---|---|---|---|
| 1-333 | •—NH—CH₂CH₂—S—CH₂-(2-furyl) | •—O—CH₂CH₂—O—CH₃ | MS m/z 405 (M + H)⁺ |
| 1-334 | •—NH—CH₂CH₂CH₂—N(CH₃)—Ph | •—O—CH₂CH₂—O—CH₃ | MS m/z 412 (M + H)⁺ |
| 1-335 | •—NH—CH₂-(3,4-methylenedioxyphenyl) | •—O—CH₂CH₂—O—CH₃ | MS m/z 399 (M + H)⁺ |
| 1-336 | •—NH—CH(CH₂OH)—CH₂Ph | •—O—CH₂CH₂—O—CH₃ | MS m/z 400 (M + H)⁺ |
| 1-337 | •—NH-(1-benzylpiperidin-4-yl) | •—O—CH₂CH₂—O—CH₃ | MS m/z 438 (M + H)⁺ |
| 1-338 | •—NH—CH(CH₃)—Ph | •—O—CH₂CH₂—O—CH₃ | MS m/z 369 (M + H)⁺ |
| 1-339 | •—N(piperazinyl)-4-(pyridin-4-yl) | •—O—CH₂CH₂—O—CH₃ | MS m/z 411 (M + H)⁺ |
| 1-340 | •—N(piperazinyl)-4-(4-hydroxyphenyl) | •—O—CH₂CH₂—O—CH₃ | MS m/z 426 (M + H)⁺ |
| 1-341 | •—N(piperazinyl)-4-(4-CF₃-phenyl) | •—O—CH₂CH₂—O—CH₃ | MS m/z 478 (M + H)⁺ |
| 1-342 | •—N(piperazinyl)-4-(pyridin-4-ylmethyl) | •—O—CH₂CH₂—O—CH₃ | MS m/z 425 (M + H)⁺ |
| 1-343 | •—NH—CH₂CH₂—NH—C(O)CH₃ | •—O—CH₂CH₂—O—CH₃ | MS m/z 350 (M + H)⁺ |
| 1-344 | •—(1-imidazolyl)-4-phenyl | •—O—CH₂CH₂—O—CH₃ | MS m/z 392 (M + H)⁺ |

[Table 1-31]
TABLE 1-31
| Compound Number | —R² | —R³ | Analytical Data |
|---|---|---|---|
| 1-345 |  |  | MS m/z 401 (M + H)⁺ |
| 1-346 | 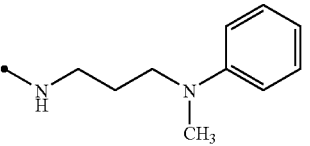 |  | MS m/z 408 (M + H)⁺ |
| 1-347 | 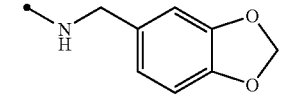 |  | MS m/z 395 (M + H)⁺ |
| 1-348 | 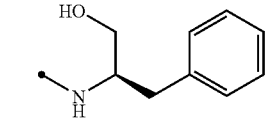 |  | MS m/z 396 (M + H)⁺ |
| 1-349 | 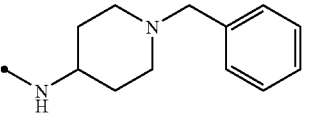 |  | MS m/z 434 (M + H)⁺ |
| 1-350 | 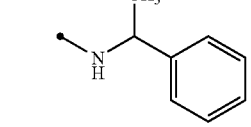 |  | MS m/z 365 (M + H)⁺ |
| 1-351 | 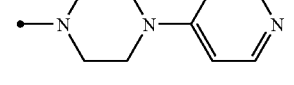 |  | MS m/z 407 (M + H)⁺ |
| 1-352 | 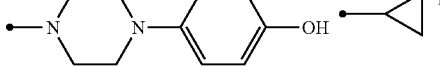 |  | MS m/z 422 (M + H)⁺ |
| 1-353 | 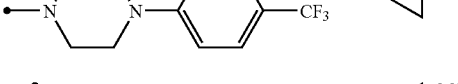 |  | MS m/z 474 (M + H)⁺ |
| 1-354 | 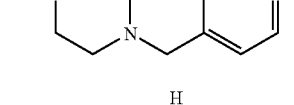 |  | MS m/z 421 (M + H)⁺ |
| 1-355 | 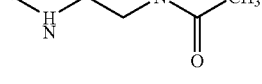 |  | MS m/z 346 (M + H)⁺ |
| 1-356 | 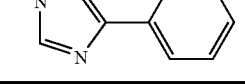 |  | MS m/z 388 (M + H)⁺ |

[Table 1-32]
TABLE 1-32
| Compound Number | •―R² | •―R³ | Analytical Data |
|---|---|---|---|
| 1-357 | 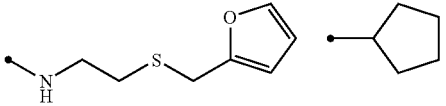 |  | MS m/z 429 (M + H)⁺ |
| 1-358 | 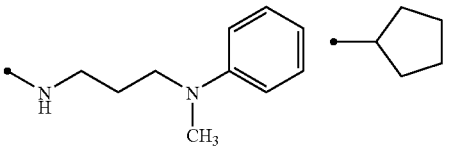 |  | MS m/z 436 (M + H)⁺ |
| 1-359 | 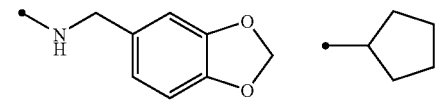 |  | MS m/z 423 (M + H)⁺ |
| 1-360 | 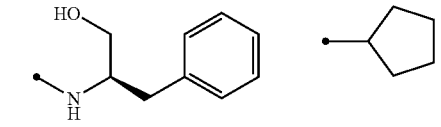 |  | MS m/z 424 (M + H)⁺ |
| 1-361 | 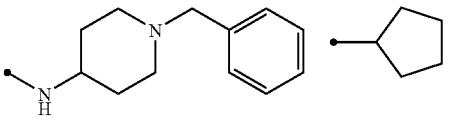 |  | MS m/z 462 (M + H)⁺ |
| 1-362 | 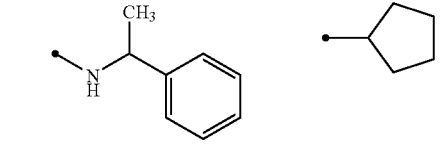 |  | MS m/z 393 (M + H)⁺ |
| 1-363 | 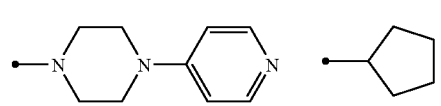 |  | MS m/z 435 (M + H)⁺ |
| 1-364 | 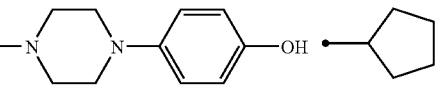 |  | MS m/z 450 (M + H)⁺ |
| 1-365 | 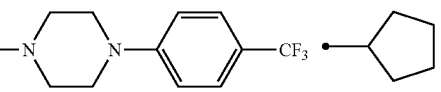 |  | MS m/z 502 (M + H)⁺ |
| 1-366 | 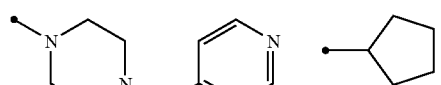 |  | MS m/z 449 (M + H)⁺ |
| 1-367 | 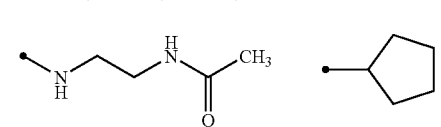 |  | MS m/z 374 (M + H)⁺ |
| 1-368 | 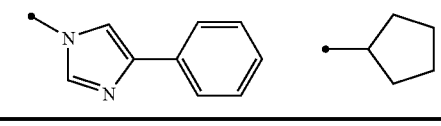 |  | MS m/z 416 (M + H)⁺ |

[Table 1-33]
TABLE 1-33
| Compound Number | —R² | —R³ | Analytical Data |
|---|---|---|---|
| 1-369 | 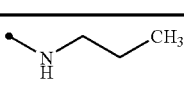 |  | MS m/z 357 (M + H)⁺ |
| 1-370 | 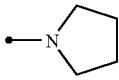 |  | MS m/z 369 (M + H)⁺ |
| 1-371 | 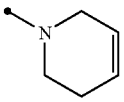 |  | MS m/z 381 (M + H)⁺ |
| 1-372 | 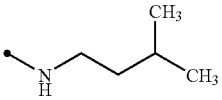 |  | MS m/z 385 (M + H)⁺ |
| 1-373 | 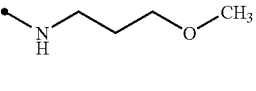 |  | MS m/z 387 (M + H)⁺ |
| 1-374 | 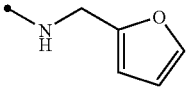 |  | MS m/z 395 (M + H)⁺ |
| 1-375 | 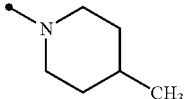 |  | MS m/z 397 (M + H)⁺ |
| 1-376 | 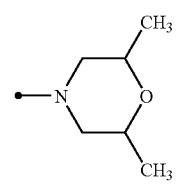 | 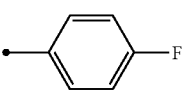 | MS m/z 413 (M + H)⁺ |
| 1-377 | 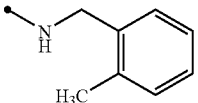 |  | MS m/z 419 (M + H)⁺ |
| 1-378 | 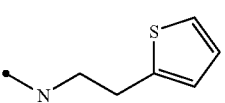 | 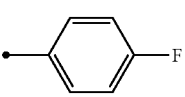 | MS m/z 425 (M + H)⁺ |
| 1-379 | 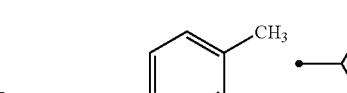 | 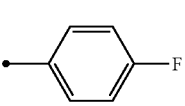 | MS m/z 433 (M + H)⁺ |
| 1-380 | 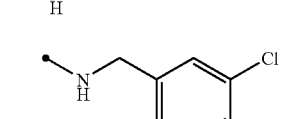 | 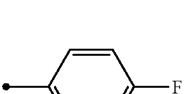 | MS m/z 438 (M + H)⁺ |

[Table 1-34]

TABLE 1-34

| Compound Number | —R² | —R³ | Analytical Data |
|---|---|---|---|
| 1-381 | -NH-CH₂CH₃ (ethylamino) | 2-methoxyphenyl | MS m/z 369 (M + H)⁺ |
| 1-382 | pyrrolidin-1-yl | 2-methoxyphenyl | MS m/z 381 (M + H)⁺ |
| 1-383 | 1,2,3,6-tetrahydropyridin-1-yl | 2-methoxyphenyl | MS m/z 393 (M + H)⁺ |
| 1-384 | -NH-CH₂CH(CH₃)₂ (isobutylamino) | 2-methoxyphenyl | MS m/z 397 (M + H)⁺ |
| 1-385 | -NH-CH₂CH₂CH₂-OCH₃ | 2-methoxyphenyl | MS m/z 399 (M + H)⁺ |
| 1-386 | -NH-CH₂-(furan-2-yl) | 2-methoxyphenyl | MS m/z 407 (M + H)⁺ |
| 1-387 | 4-methylpiperidin-1-yl | 2-methoxyphenyl | MS m/z 409 (M + H)⁺ |
| 1-388 | 2,6-dimethylmorpholin-4-yl | 2-methoxyphenyl | MS m/z 425 (M + H)⁺ |
| 1-389 | -NH-CH₂-(2-methylphenyl) | 2-methoxyphenyl | MS m/z 431 (M + H)⁺ |
| 1-390 | -NH-CH₂CH₂-(thiophen-2-yl) | 2-methoxyphenyl | MS m/z 437 (M + H)⁺ |

TABLE 1-34-continued
| Compound Number | —R² | —R³ | Analytical Data |
|---|---|---|---|
| 1-391 | 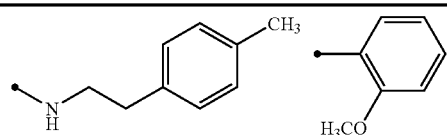 | 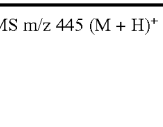 | MS m/z 445 (M + H)⁺ |
| 1-392 | 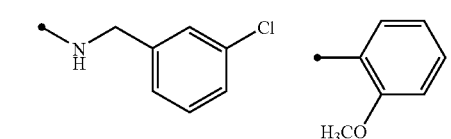 | 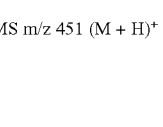 | MS m/z 451 (M + H)⁺ |
[Table 1-35]
TABLE 1-35
| Compound Number | —R² | —R³ | Analytical Data |
|---|---|---|---|
| 1-393 | 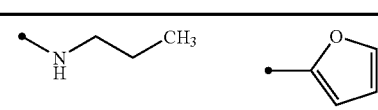 | 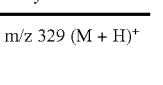 | MS m/z 329 (M + H)⁺ |
| 1-394 | 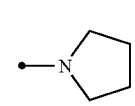 | 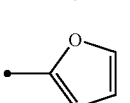 | MS m/z 341 (M + H)⁺ |
| 1-395 | 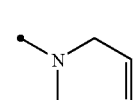 | 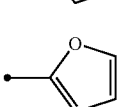 | MS m/z 353 (M + H)⁺ |
| 1-396 | 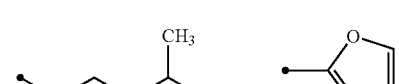 | 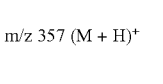 | MS m/z 357 (M + H)⁺ |
| 1-397 | 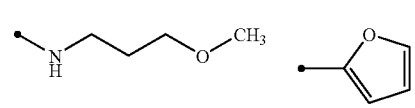 | 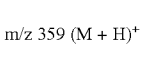 | MS m/z 359 (M + H)⁺ |
| 1-398 | 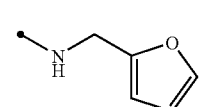 | 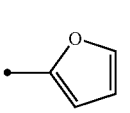 | MS m/z 367 (M + H)⁺ |
| 1-399 | 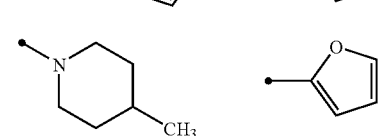 | 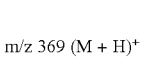 | MS m/z 369 (M + H)⁺ |
| 1-400 | 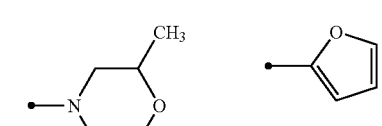 | 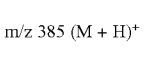 | MS m/z 385 (M + H)⁺ |
| 1-401 | 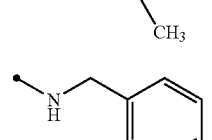 |  | MS m/z 391 (M + H)⁺ |

TABLE 1-35-continued

| Compound Number | —R² | —R³ | Analytical Data |
|---|---|---|---|
| 1-402 | —NH-CH₂CH₂-(2-thienyl) | 2-furyl | MS m/z 397 (M + H)⁺ |
| 1-403 | —NH-CH₂CH₂-(4-methylphenyl) | 2-furyl | MS m/z 405 (M + H)⁺ |
| 1-404 | —NH-CH₂-(3-chlorophenyl) | 2-furyl | MS m/z 411 (M + H)⁺ |

[Table 1-36]

TABLE 1-36

| Compound Number | —R² | —R³ | Analytical Data |
|---|---|---|---|
| 1-405 | —NH-CH₂CH₃ | 3-methoxyphenyl | MS m/z 383 (M + H)⁺ |
| 1-406 | pyrrolidin-1-yl | 3-methoxyphenyl | MS m/z 395 (M + H)⁺ |
| 1-407 | 1,2,3,6-tetrahydropyridin-1-yl | 3-methoxyphenyl | MS m/z 407 (M + H)⁺ |
| 1-408 | —NH-CH₂CH₂-CH(CH₃)₂ | 3-methoxyphenyl | MS m/z 411 (M + H)⁺ |
| 1-409 | —NH-CH₂CH₂CH₂-OCH₃ | 3-methoxyphenyl | MS m/z 413 (M + H)⁺ |
| 1-410 | —NH-CH₂-(2-furyl) | 3-methoxyphenyl | MS m/z 421 (M + H)⁺ |
| 1-411 | 4-methylpiperidin-1-yl | 3-methoxyphenyl | MS m/z 423 (M + H)⁺ |

TABLE 1-36-continued

| Compound Number | —R² | —R³ | Analytical Data |
|---|---|---|---|
| 1-412 | 2,6-dimethylmorpholin-4-yl (N-linked) | 3-methoxyphenyl | MS m/z 439 (M + H)⁺ |
| 1-413 | (2-methylbenzyl)amino | 3-methoxyphenyl | MS m/z 445 (M + H)⁺ |
| 1-414 | [2-(thiophen-2-yl)ethyl]amino | 3-methoxyphenyl | MS m/z 451 (M + H)⁺ |
| 1-415 | [2-(4-methylphenyl)ethyl]amino | 3-methoxyphenyl | MS m/z 459 (M + H)⁺ |
| 1-416 | (3-chlorobenzyl)amino | 3-methoxyphenyl | MS m/z 465 (M + H)⁺ |

[Table 1-37]

TABLE 1-37

| Compound Number | —R² | —R³ | Analytical Data |
|---|---|---|---|
| 1-417 | ethylamino | —CH₃ | MS m/z 277 (M + H)⁺ |
| 1-418 | pyrrolidin-1-yl | —CH₃ | MS m/z 289 (M + H)⁺ |
| 1-419 | 3,6-dihydro-2H-pyridin-1-yl | —CH₃ | MS m/z 301 (M + H)⁺ |
| 1-420 | (3-methylbutyl)amino (isopentylamino) | —CH₃ | MS m/z 305 (M + H)⁺ |
| 1-421 | (3-methoxypropyl)amino | —CH₃ | MS m/z 307 (M + H)⁺ |
| 1-422 | 4-methylpiperidin-1-yl | —CH₃ | MS m/z 317 (M + H)⁺ |

TABLE 1-37-continued
| Compound Number | —R² | —R³ | Analytical Data |
|---|---|---|---|
| 1-423 | 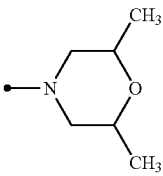 | —CH₃ | MS m/z 333 (M + H)⁺ |
| 1-424 | 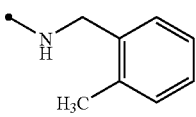 | —CH₃ | MS m/z 339 (M + H)⁺ |
| 1-425 | 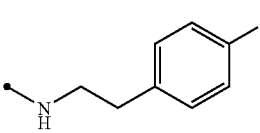 | —CH₃ | MS m/z 353 (M + H)⁺ |
| 1-426 | 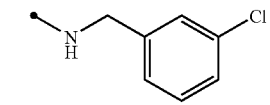 | —CH₃ | MS m/z 359 (M + H)⁺ |
[Table 1-38]
TABLE 1-38
| Compound Number | —R² | —R³ | Analytical Data |
|---|---|---|---|
| 1-427 | 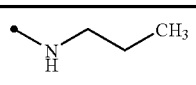 | 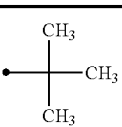 | MS m/z 319 (M + H)⁺ |
| 1-428 | 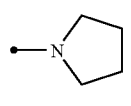 | 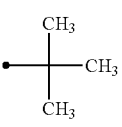 | MS m/z 331 (M + H)⁺ |
| 1-429 | 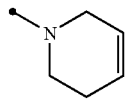 | 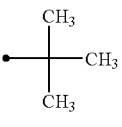 | MS m/z 343 (M + H)⁺ |
| 1-430 | 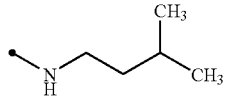 | 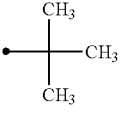 | MS m/z 347 (M + H)⁺ |
| 1-431 | 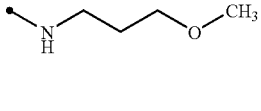 | 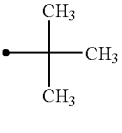 | MS m/z 349 (M + H)⁺ |
| 1-432 | 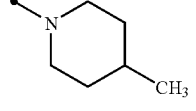 | 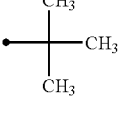 | MS m/z 359 (M + H)⁺ |

TABLE 1-38-continued

| Compound Number | —R² | —R³ | Analytical Data |
|---|---|---|---|
| 1-433 | 2,6-dimethylmorpholin-4-yl | tert-butyl | MS m/z 375 (M + H)⁺ |
| 1-434 | 2-methylbenzylamino | tert-butyl | MS m/z 381 (M + H)⁺ |
| 1-435 | 4-methylphenethylamino | tert-butyl | MS m/z 395 (M + H)⁺ |
| 1-436 | 3-chlorobenzylamino | tert-butyl | MS m/z 401 (M + H)⁺ |

[Table 1-39]

TABLE 1-39

| Compound Number | —R² | —R³ | Analytical Data |
|---|---|---|---|
| 1-437 | ethylamino | styryl | MS m/z 365 (M + H)⁺ |
| 1-438 | pyrrolidin-1-yl | styryl | MS m/z 377 (M + H)⁺ |
| 1-439 | 3,6-dihydro-2H-pyridin-1-yl | styryl | MS m/z 389 (M + H)⁺ |
| 1-440 | isobutylamino (3-methylbutan-2-ylamino) | styryl | MS m/z 393 (M + H)⁺ |
| 1-441 | 3-methoxypropylamino | styryl | MS m/z 395 (M + H)⁺ |
| 1-442 | furfurylamino | styryl | MS m/z 403 (M + H)⁺ |
| 1-443 | 4-methylpiperidin-1-yl | styryl | MS m/z 405 (M + H)⁺ |

TABLE 1-39-continued
| Compound Number | —R² | —R³ | Analytical Data |
|---|---|---|---|
| 1-444 | 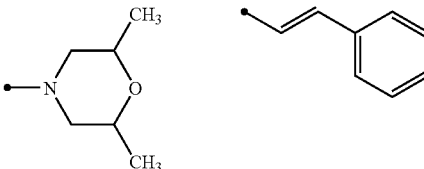 | 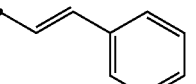 | MS m/z 421 (M + H)⁺ |
| 1-445 | 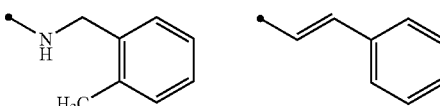 | 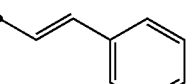 | MS m/z 427 (M + H)⁺ |
| 1-446 | 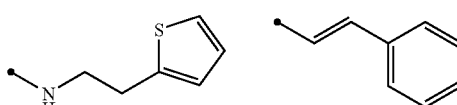 | 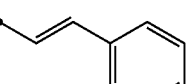 | MS m/z 433 (M + H)⁺ |
| 1-447 | 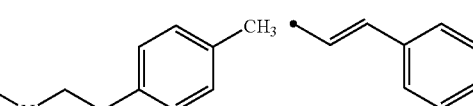 | 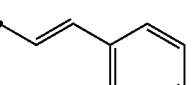 | MS m/z 441 (M + H)⁺ |
| 1-448 | 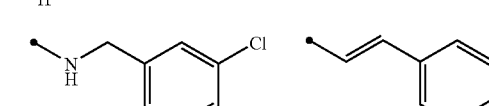 | 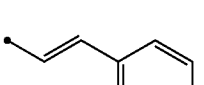 | MS m/z 447 (M + H)⁺ |
[Table 1-40]
TABLE 1-40
| Compound Number | —R² | —R³ | Analytical Data |
|---|---|---|---|
| 1-449 | 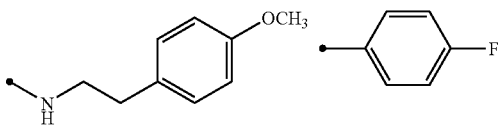 |  | MS m/z 449 (M + H)⁺ |
| 1-450 | 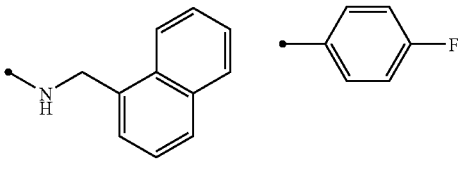 |  | MS m/z 455 (M + H)⁺ |
| 1-451 | 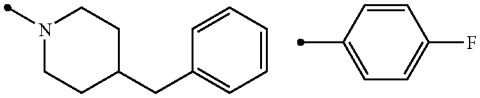 |  | MS m/z 473 (M + H)⁺ |
| 1-452 | 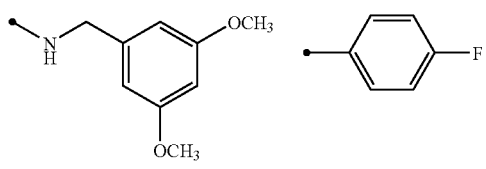 |  | MS m/z 465 (M + H)⁺ |
| 1-453 | 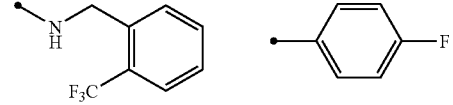 |  | MS m/z 473 (M + H)⁺ |

TABLE 1-40-continued
| Compound Number | —R² | —R³ | Analytical Data |
|---|---|---|---|
| 1-454 | 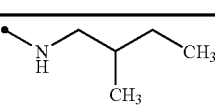 |  | MS m/z 385 (M + H)⁺ |
| 1-455 | 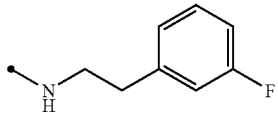 |  | MS m/z 437 (M + H)⁺ |
| 1-456 | 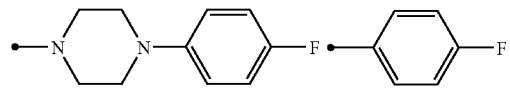 | 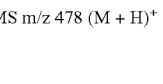 | MS m/z 478 (M + H)⁺ |
| 1-457 | 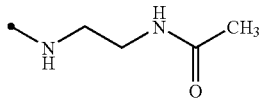 |  | MS m/z 400 (M + H)⁺ |
| 1-458 | 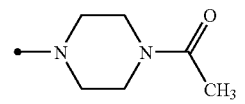 | 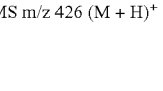 | MS m/z 426 (M + H)⁺ |
| 1-459 | 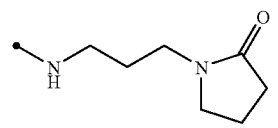 |  | MS m/z 440 (M + H)⁺ |
| 1-460 | 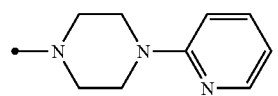 |  | MS m/z 461 (M + H)⁺ |
[Table 1-41]
TABLE 1-41
| Compound Number | —R² | —R³ | Analytical Data |
|---|---|---|---|
| 1-461 | 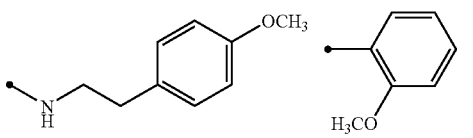 | 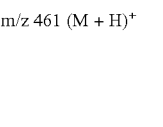 | MS m/z 461 (M + H)⁺ |
| 1-462 | 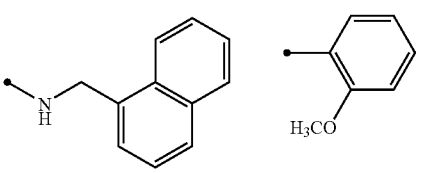 | 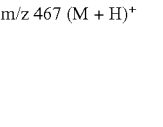 | MS m/z 467 (M + H)⁺ |

TABLE 1-41-continued
| Compound Number | —R² | —R³ | Analytical Data |
|---|---|---|---|
| 1-463 | 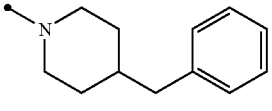 | 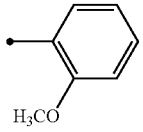 | MS m/z 485 (M + H)⁺ |
| 1-464 | 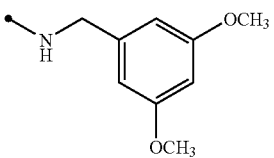 |  | MS m/z 477 (M + H)⁺ |
| 1-465 | 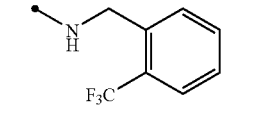 | 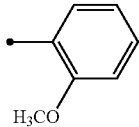 | MS m/z 485 (M + H)⁺ |
| 1-466 | 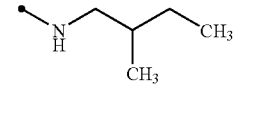 | 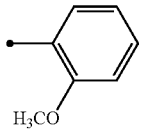 | MS m/z 397 (M + H)⁺ |
| 1-467 | 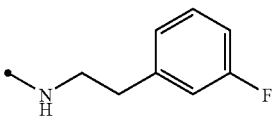 | 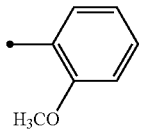 | MS m/z 449 (M + H)⁺ |
| 1-468 | 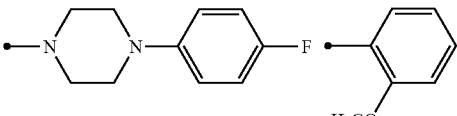 | 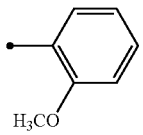 | MS m/z 490 (M + H)⁺ |
| 1-469 | 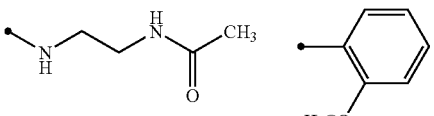 | 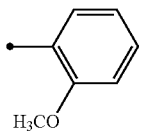 | MS m/z 412 (M + H)⁺ |
| 1-470 | 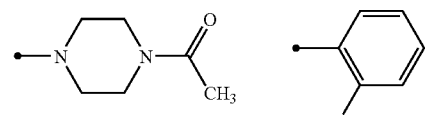 |  | MS m/z 438 (M + H)⁺ |
| 1-471 | 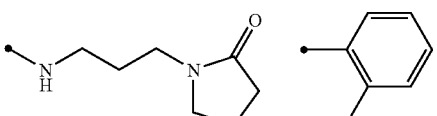 | 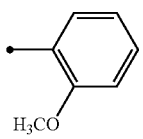 | MS m/z 452 (M + H)⁺ |
| 1-472 | 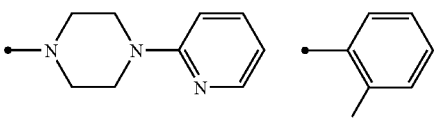 | 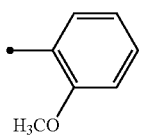 | MS m/z 473 (M + H)⁺ |

[Table 1-42]

TABLE 1-42

| Compound Number | —R² | —R³ | Analytical Data |
|---|---|---|---|
| 1-473 | 4-methoxyphenethylamino | 2-furyl | MS m/z 421 (M + H)⁺ |
| 1-474 | (naphthalen-1-ylmethyl)amino | 2-furyl | MS m/z 427 (M + H)⁺ |
| 1-475 | 4-benzylpiperidin-1-yl | 2-furyl | MS m/z 445 (M + H)⁺ |
| 1-476 | (3,5-dimethoxybenzyl)amino | 2-furyl | MS m/z 437 (M + H)⁺ |
| 1-477 | (2-trifluoromethylbenzyl)amino | 2-furyl | MS m/z 445 (M + H)⁺ |
| 1-478 | (2-methylbutyl)amino | 2-furyl | MS m/z 357 (M + H)⁺ |
| 1-479 | 3-fluorophenethylamino | 2-furyl | MS m/z 409 (M + H)⁺ |
| 1-480 | 4-(4-fluorophenyl)piperazin-1-yl | 2-furyl | MS m/z 450 (M + H)⁺ |
| 1-481 | (2-acetamidoethyl)amino | 2-furyl | MS m/z 372 (M + H)⁺ |
| 1-482 | 4-acetylpiperazin-1-yl | 2-furyl | MS m/z 398 (M + H)⁺ |
| 1-483 | 3-(2-oxopyrrolidin-1-yl)propylamino | 2-furyl | MS m/z 412 (M + H)⁺ |
| 1-484 | 4-(pyridin-2-yl)piperazin-1-yl | 2-furyl | MS m/z 433 (M + H)⁺ |

[Table 1-43]
TABLE 1-43
| Compound Number | •—R² | •—R³ | Analytical Data |
|---|---|---|---|
| 1-485 | 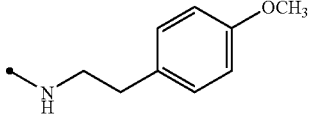 | 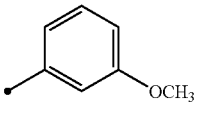 | MS m/z 475 (M + H)⁺ |
| 1-486 | 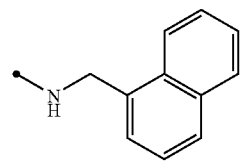 | 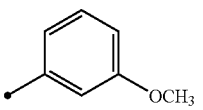 | MS m/z 481 (M + H)⁺ |
| 1-487 | 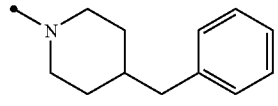 | 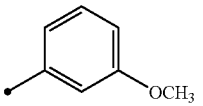 | MS m/z 499 (M + H)⁺ |
| 1-488 | 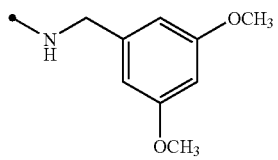 | 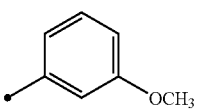 | MS m/z 491 (M + H)⁺ |
| 1-489 | 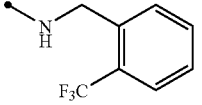 | 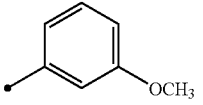 | MS m/z 499 (M + H)⁺ |
| 1-490 | 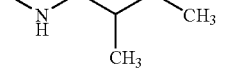 | 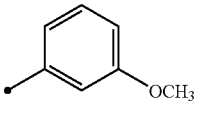 | MS m/z 411 (M + H)⁺ |
| 1-491 | 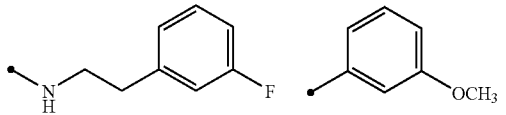 | 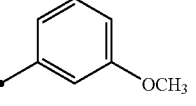 | MS m/z 463 (M + H)⁺ |
| 1-492 | 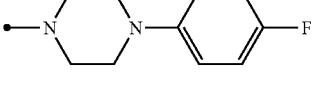 | 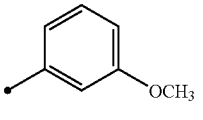 | MS m/z 504 (M + H)⁺ |
| 1-493 | 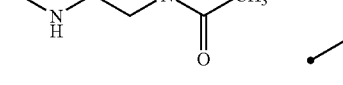 | 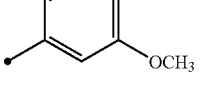 | MS m/z 426 (M + H)⁺ |
| 1-494 | 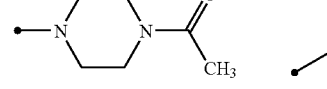 | 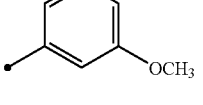 | MS m/z 452 (M + H)⁺ |
| 1-495 | 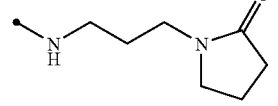 | 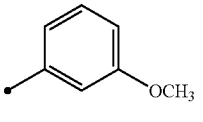 | MS m/z 466 (M + H)⁺ |

TABLE 1-43-continued

| Compound Number | —R² | —R³ | Analytical Data |
|---|---|---|---|
| 1-496 | piperazine-N-(2-pyridyl) | 3-methoxyphenyl | MS m/z 487 (M + H)⁺ |

[Table 1-44]

TABLE 1-44

| Compound Number | —R² | —R³ | Analytical Data |
|---|---|---|---|
| 1-497 | —NH-CH₂-(1-naphthyl) | —CH₃ | MS m/z 375 (M + H)⁺ |
| 1-498 | 4-benzylpiperidin-1-yl | —CH₃ | MS m/z 393 (M + H)⁺ |
| 1-499 | —NH-CH₂-(3,5-dimethoxyphenyl) | —CH₃ | MS m/z 385 (M + H)⁺ |
| 1-500 | —NH-CH₂-(2-trifluoromethylphenyl) | —CH₃ | MS m/z 393 (M + H)⁺ |
| 1-501 | —NH-CH₂-CH(CH₃)-CH₂-CH₃ | —CH₃ | MS m/z 305 (M + H)⁺ |
| 1-502 | —NH-CH₂CH₂-(3-fluorophenyl) | —CH₃ | MS m/z 357 (M + H)⁺ |
| 1-503 | 4-(4-fluorophenyl)piperazin-1-yl | —CH₃ | MS m/z 398 (M + H)⁺ |
| 1-504 | 4-acetylpiperazin-1-yl | —CH₃ | MS m/z 346 (M + H)⁺ |
| 1-505 | —NH-CH₂CH₂CH₂-(γ-butyrolacton-2-yloxy) | —CH₃ | MS m/z 360 (M + H)⁺ |
| 1-506 | 4-(2-pyridyl)piperazin-1-yl | —CH₃ | MS m/z 381 (M + H)⁺ |

[Table 1-45]

TABLE 1-45

| Compound Number | •—R² | •—R³ | Analytical Data |
|---|---|---|---|
| 1-507 | naphthalen-1-ylmethyl-NH— | —C(CH₃)₃ | MS m/z 417 (M + H)⁺ |
| 1-508 | 4-benzylpiperidin-1-yl | —C(CH₃)₃ | MS m/z 435 (M + H)⁺ |
| 1-509 | (3,5-dimethoxybenzyl)amino | —C(CH₃)₃ | MS m/z 427 (M + H)⁺ |
| 1-510 | (2-trifluoromethylbenzyl)amino | —C(CH₃)₃ | MS m/z 435 (M + H)⁺ |
| 1-511 | (2-methylbutyl)amino | —C(CH₃)₃ | MS m/z 447 (M + H)⁺ |
| 1-512 | [2-(3-fluorophenyl)ethyl]amino | —C(CH₃)₃ | MS m/z 399 (M + H)⁺ |
| 1-513 | 4-(4-fluorophenyl)piperazin-1-yl | —C(CH₃)₃ | MS m/z 440 (M + H)⁺ |
| 1-514 | 4-acetylpiperazin-1-yl | —C(CH₃)₃ | MS m/z 388 (M + H)⁺ |
| 1-515 | [3-(2-oxopyrrolidin-1-yl)propyl]amino | —C(CH₃)₃ | MS m/z 402 (M + H)⁺ |
| 1-516 | 4-(pyridin-2-yl)piperazin-1-yl | —C(CH₃)₃ | MS m/z 423 (M + H)⁺ |

[Table 1-46]
TABLE 1-46
| Compound Number | —R² | —R³ | Analytical Data |
|---|---|---|---|
| 1-517 | 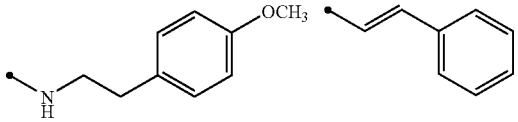 | 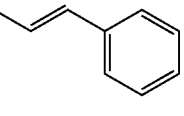 | MS m/z 457 (M + H)⁺ |
| 1-518 | 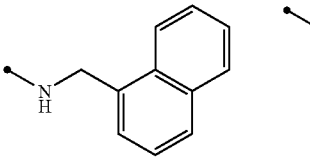 | 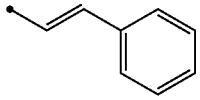 | MS m/z 463 (M + H)⁺ |
| 1-519 | 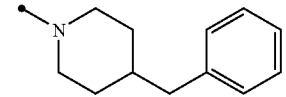 | 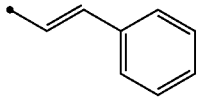 | MS m/z 481 (M + H)⁺ |
| 1-520 | 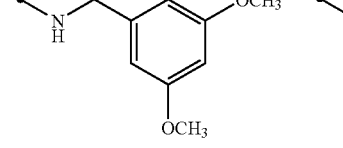 | 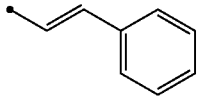 | MS m/z 473 (M + H)⁺ |
| 1-521 | 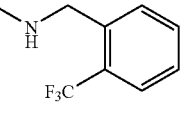 | 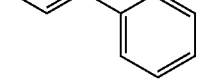 | MS m/z 481 (M + H)⁺ |
| 1-522 | 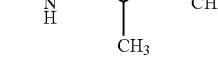 | 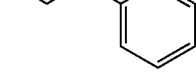 | MS m/z 493 (M + H)⁺ |
| 1-523 | 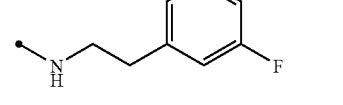 | 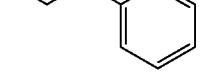 | MS m/z 445 (M + H)⁺ |
| 1-524 | 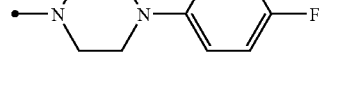 | 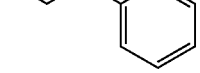 | MS m/z 486 (M + H)⁺ |
| 1-525 | 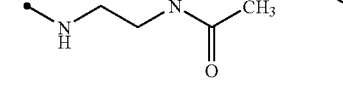 | 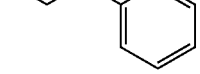 | MS m/z 408 (M + H)⁺ |
| 1-526 | 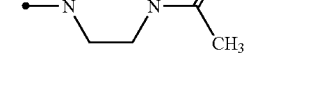 | 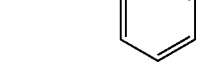 | MS m/z 434 (M + H)⁺ |
| 1-527 | 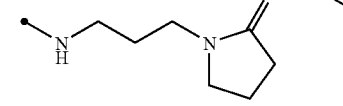 | 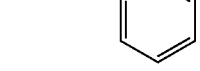 | MS m/z 448 (M + H)⁺ |

TABLE 1-46-continued

| Compound Number | —R² | —R³ | Analytical Data |
|---|---|---|---|
| 1-528 | piperazinyl-pyridin-2-yl | styryl (trans-2-phenylethenyl) | MS m/z 469 (M + H)⁺ |

[Table 1-47]

TABLE 1-47

| Compound Number | —R² | —R³ | Analytical Data |
|---|---|---|---|
| 1-529 | —NH-CH₂CH₂-(3-chlorophenyl) | —CH₃ | MS m/z 373 (M + H)⁺ |
| 1-530 | —NH-CH₂CH₂-phenyl | —CH₃ | MS m/z 339 (M + H)⁺ |
| 1-531 | —NH-CH₂CH₂-(3-methoxyphenyl) | —CH₃ | MS m/z 369 (M + H)⁺ |
| 1-532 | —NH-CH₂CH₂-(4-hydroxyphenyl) | cyclopropyl | MS m/z 381 (M + H)⁺ |
| 1-533 | —NH-CH₂CH₂-(4-(2-morpholinoethoxy)phenyl) | cyclopropyl | MS m/z 494 (M + H)⁺ |
| 1-534 | —NH-phenyl | cyclopropyl | MS m/z 337 (M + H)⁺ |
| 1-535 | —NH-(3,4,5-trimethoxyphenyl) | cyclopropyl | MS m/z 427 (M + H)⁺ |
| 1-536 | —NH-CH₂CH₂-(1H-imidazol-4-yl) | cyclopropyl | MS m/z 355 (M + H)⁺ |

TABLE 1-47-continued
| Compound Number | —R² | —R³ | Analytical Data |
|---|---|---|---|
| 1-537 | 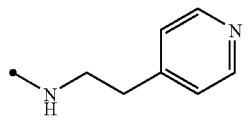 | 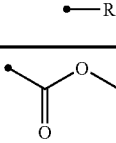 | MS m/z 398 (M + H)⁺ |
| 1-538 | 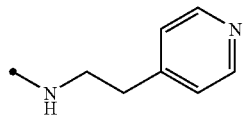 | 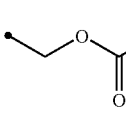 | MS m/z 398 (M + H)⁺ |
| 1-539 | 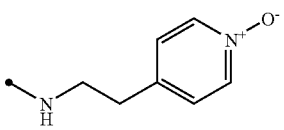 |  | MS m/z 382 (M + H)⁺ |
[Table 2-1]
TABLE 2-1
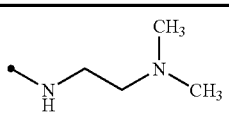
| Compound Number | —R² | —R³ | Analytical Data |
|---|---|---|---|
| 2-1 |  | —CH₃ | MS m/z 278 (M + H)⁺ |
| 2-2 | 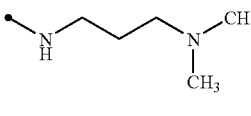 | —CH₃ | MS m/z 292 (M + H)⁺ |
| 2-3 |  | —CH₃ | MS m/z 317 (M + H)⁺ |
| 2-4 | 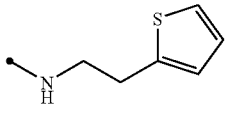 | —CH₃ | MS m/z 318 (M + H)⁺ |
| 2-5 |  | —CH₃ | MS m/z 318 (M + H)⁺ |
| 2-6 | 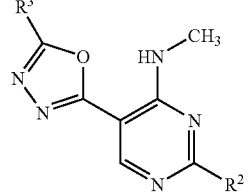 | —CH₃ | MS m/z 334 (M + H)⁺ |
| 2-7 | 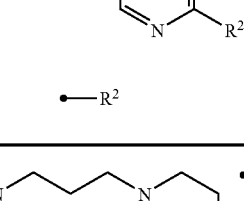 | —CH₃ | MS m/z 312 (M + H)⁺ |
| 2-8 | 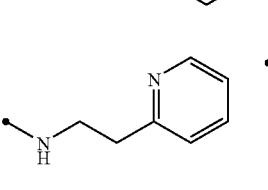 | —CH₃ | MS m/z 312 (M + H)⁺ |
| 2-9 | 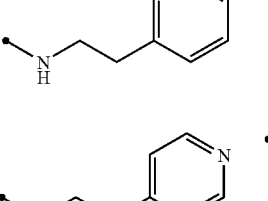 | —CH₃ | MS m/z 312 (M + H)⁺ |
| 2-10 | 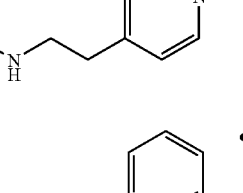 | —CH₃ | MS m/z 311 (M + H)⁺ |

[Table 2-2]
TABLE 2-2
| Compound Number | —R² | —R³ | Analytical Data |
|---|---|---|---|
| 2-11 |  |  | MS m/z 292 (M + H)⁺ |
| 2-12 |  |  | MS m/z 306 (M + H)⁺ |
| 2-13 |  |  | MS m/z 331 (M + H)⁺ |
| 2-14 |  |  | MS m/z 332 (M + H)⁺ |
| 2-15 |  |  | MS m/z 332 (M + H)⁺ |
| 2-16 |  |  | MS m/z 348 (M + H)⁺ |
| 2-17 |  |  | MS m/z 326 (M + H)⁺ |
| 2-18 |  |  | MS m/z 326 (M + H)⁺ |
| 2-19 |  |  | MS m/z 326 (M + H)⁺ |
| 2-20 |  |  | MS m/z 325 (M + H)⁺ |
[Table 2-3]
TABLE 2-3
| Compound Number | —R² | —R³ | Analytical Data |
|---|---|---|---|
| 2-21 |  |  | MS m/z 306 (M + H)⁺ |

TABLE 2-3-continued

| Compound Number | —R² | —R³ | Analytical Data |
|---|---|---|---|
| 2-22 | •-NH-CH₂CH₂CH₂-N(CH₃)₂ | •-CH₂CH₂CH₂CH₃ | MS m/z 320 (M + H)⁺ |
| 2-23 | •-NH-CH₂CH₂-(2-thienyl) | •-CH₂CH₂CH₂CH₃ | MS m/z 345 (M + H)⁺ |
| 2-24 | •-NH-CH₂CH₂CH₂-(pyrrolidin-1-yl) | •-CH₂CH₂CH₂CH₃ | MS m/z 346 (M + H)⁺ |
| 2-25 | •-NH-CH₂CH₂-(piperidin-1-yl) | •-CH₂CH₂CH₂CH₃ | MS m/z 346 (M + H)⁺ |
| 2-26 | •-NH-CH₂CH₂CH₂-(morpholin-4-yl) | •-CH₂CH₂CH₂CH₃ | MS m/z 362 (M + H)⁺ |
| 2-27 | •-NH-CH₂CH₂-(pyridin-2-yl) | •-CH₂CH₂CH₂CH₃ | MS m/z 340 (M + H)⁺ |
| 2-28 | •-NH-CH₂CH₂-(pyridin-3-yl) | •-CH₂CH₂CH₂CH₃ | MS m/z 340 (M + H)⁺ |
| 2-29 | •-NH-CH₂CH₂-(pyridin-4-yl) | •-CH₂CH₂CH₂CH₃ | MS m/z 340 (M + H)⁺ |
| 2-30 | •-NH-CH₂CH₂-phenyl | •-CH₂CH₂CH₂CH₃ | MS m/z 339 (M + H)⁺ |

[Table 2-4]

TABLE 2-4

| Compound Number | —R² | —R³ | Analytical Data |
|---|---|---|---|
| 2-31 | •-NH-CH₂CH₂-N(CH₃)₂ | •-CH(CH₃)₂ | MS m/z 306 (M + H)⁺ |
| 2-32 | •-NH-CH₂CH₂CH₂-N(CH₃)₂ | •-CH(CH₃)₂ | MS m/z 320 (M + H)⁺ |

TABLE 2-4-continued

| Compound Number | —R² | —R³ | Analytical Data |
|---|---|---|---|
| 2-33 | -NH-CH₂CH₂-(2-thienyl) | -CH(CH₃)₂ | MS m/z 345 (M + H)⁺ |
| 2-34 | -NH-(CH₂)₃-(1-pyrrolidinyl) | -CH(CH₃)₂ | MS m/z 346 (M + H)⁺ |
| 2-35 | -NH-CH₂CH₂-(1-piperidinyl) | -CH(CH₃)₂ | MS m/z 346 (M + H)⁺ |
| 2-36 | -NH-(CH₂)₃-(4-morpholinyl) | -CH(CH₃)₂ | MS m/z 362 (M + H)⁺ |
| 2-37 | -NH-CH₂CH₂-(2-pyridyl) | -CH(CH₃)₂ | MS m/z 340 (M + H)⁺ |
| 2-38 | -NH-CH₂CH₂-(3-pyridyl) | -CH(CH₃)₂ | MS m/z 340 (M + H)⁺ |
| 2-39 | -NH-CH₂CH₂-(4-pyridyl) | -CH(CH₃)₂ | MS m/z 340 (M + H)⁺ |
| 2-40 | -NH-CH₂CH₂-Ph | -CH(CH₃)₂ | MS m/z 339 (M + H)⁺ |

[Table 2-5]

TABLE 2-5

| Compound Number | —R² | —R³ | Analytical Data |
|---|---|---|---|
| 2-41 | -NH-CH₂CH₂-N(CH₃)₂ | -C(CH₃)₃ | MS m/z 320 (M + H)⁺ |
| 2-42 | -NH-(CH₂)₃-N(CH₃)₂ | -C(CH₃)₃ | MS m/z 334 (M + H)⁺ |
| 2-43 | -NH-CH₂CH₂-(2-thienyl) | -C(CH₃)₃ | MS m/z 359 (M + H)⁺ |

TABLE 2-5-continued

| Compound Number | —R² | —R³ | Analytical Data |
|---|---|---|---|
| 2-44 | •—NH—CH₂CH₂CH₂—N(pyrrolidine) | •—C(CH₃)₃ | MS m/z 360 (M + H)⁺ |
| 2-45 | •—NH—CH₂CH₂—N(piperidine) | •—C(CH₃)₃ | MS m/z 360 (M + H)⁺ |
| 2-46 | •—NH—CH₂CH₂CH₂—N(morpholine) | •—C(CH₃)₃ | MS m/z 376 (M + H)⁺ |
| 2-47 | •—NH—CH₂CH₂-(2-pyridyl) | •—C(CH₃)₃ | MS m/z 354 (M + H)⁺ |
| 2-48 | •—NH—CH₂CH₂-(3-pyridyl) | •—C(CH₃)₃ | MS m/z 354 (M + H)⁺ |
| 2-49 | •—NH—CH₂CH₂-(4-pyridyl) | •—C(CH₃)₃ | MS m/z 354 (M + H)⁺ |
| 2-50 | •—NH—CH₂CH₂—Ph | •—C(CH₃)₃ | MS m/z 353 (M + H)⁺ |

[Table 2-6]

TABLE 2-6

| Compound Number | —R² | —R³ | Analytical Data |
|---|---|---|---|
| 2-51 | •—NH—CH₂CH₂—N(CH₃)₂ | •—O—CH₂—O—CH₃ | MS m/z 308 (M + H)⁺ |
| 2-52 | •—NH—CH₂CH₂CH₂—N(CH₃)₂ | •—O—CH₂—O—CH₃ | MS m/z 322 (M + H)⁺ |
| 2-53 | •—NH—CH₂CH₂-(2-thienyl) | •—O—CH₂—O—CH₃ | MS m/z 347 (M + H)⁺ |
| 2-54 | •—NH—CH₂CH₂CH₂—N(pyrrolidine) | •—O—CH₂—O—CH₃ | MS m/z 348 (M + H)⁺ |

TABLE 2-6-continued

| Compound Number | —R² | —R³ | Analytical Data |
|---|---|---|---|
| 2-55 | N-(2-piperidin-1-yl-ethyl)amino | CH₂OCH₃ | MS m/z 348 (M + H)⁺ |
| 2-56 | N-(3-morpholin-4-yl-propyl)amino | CH₂OCH₃ | MS m/z 364 (M + H)⁺ |
| 2-57 | N-(2-pyridin-2-yl-ethyl)amino | CH₂OCH₃ | MS m/z 342 (M + H)⁺ |
| 2-58 | N-(2-pyridin-3-yl-ethyl)amino | CH₂OCH₃ | MS m/z 342 (M + H)⁺ |
| 2-59 | N-(2-pyridin-4-yl-ethyl)amino | CH₂OCH₃ | MS m/z 342 (M + H)⁺ |
| 2-60 | N-(2-phenylethyl)amino | CH₂OCH₃ | MS m/z 341 (M + H)⁺ |

[Table 2-7]

TABLE 2-7

| Compound Number | —R² | —R³ | Analytical Data |
|---|---|---|---|
| 2-61 | N-(2-dimethylaminoethyl)amino | cyclopropyl | MS m/z 304 (M + H)⁺ |
| 2-62 | N-(3-dimethylaminopropyl)amino | cyclopropyl | MS m/z 318 (M + H)⁺ |
| 2-63 | N-(2-thiophen-2-yl-ethyl)amino | cyclopropyl | MS m/z 343 (M + H)⁺ |
| 2-64 | N-(3-pyrrolidin-1-yl-propyl)amino | cyclopropyl | MS m/z 344 (M + H)⁺ |
| 2-65 | N-(2-piperidin-1-yl-ethyl)amino | cyclopropyl | MS m/z 344 (M + H)⁺ |

TABLE 2-7-continued

| Compound Number | —R² | —R³ | Analytical Data |
|---|---|---|---|
| 2-66 | -NH-CH₂CH₂CH₂-N(morpholine) | cyclopropyl | MS m/z 360 (M + H)⁺ |
| 2-67 | -NH-CH₂CH₂-(2-pyridyl) | cyclopropyl | MS m/z 338 (M + H)⁺ |
| 2-68 | -NH-CH₂CH₂-(3-pyridyl) | cyclopropyl | MS m/z 338 (M + H)⁺ |
| 2-69 | -NH-CH₂CH₂-(4-pyridyl) | cyclopropyl | MS m/z 338 (M + H)⁺ |
| 2-70 | -NH-CH₂CH₂-phenyl | cyclopropyl | MS m/z 337 (M + H)⁺ |

[Table 2-8]

TABLE 2-8

| Compound Number | —R² | —R³ | Analytical Data |
|---|---|---|---|
| 2-71 | -NH-CH₂CH₂-N(CH₃)₂ | cyclopentyl | MS m/z 332 (M + H)⁺ |
| 2-72 | -NH-CH₂CH₂CH₂-N(CH₃)₂ | cyclopentyl | MS m/z 346 (M + H)⁺ |
| 2-73 | -NH-CH₂CH₂-(2-thienyl) | cyclopentyl | MS m/z 371 (M + H)⁺ |
| 2-74 | -NH-CH₂CH₂CH₂-(pyrrolidin-1-yl) | cyclopentyl | MS m/z 372 (M + H)⁺ |
| 2-75 | -NH-CH₂CH₂-(piperidin-1-yl) | cyclopentyl | MS m/z 372 (M + H)⁺ |
| 2-76 | -NH-CH₂CH₂CH₂-(morpholin-4-yl) | cyclopentyl | MS m/z 388 (M + H)⁺ |

TABLE 2-8-continued
| Compound Number | —R² | —R³ | Analytical Data |
|---|---|---|---|
| 2-77 | 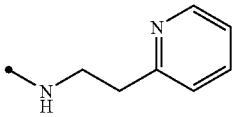 | 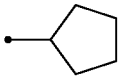 | MS m/z 366 (M + H)⁺ |
| 2-78 | 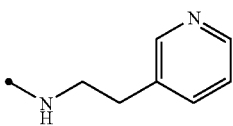 | 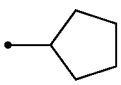 | MS m/z 366 (M + H)⁺ |
| 2-79 | 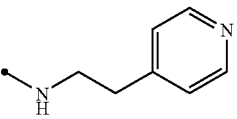 | 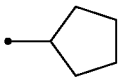 | MS m/z 366 (M + H)⁺ |
| 2-80 | 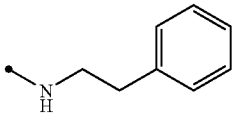 | 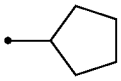 | MS m/z 365 (M + H)⁺ |
| 2-81 | 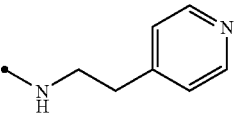 | 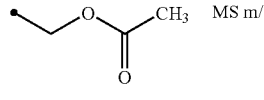 | MS m/z 370 (M + H)⁺ |
| 2-82 | 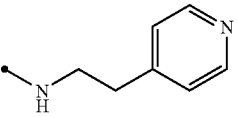 | 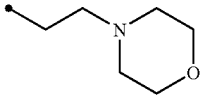 | MS m/z 411 (M + H)⁺ |
[Table 3-1]
TABLE 3-1
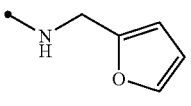
| Compound Number | —R¹ | —R² | Analytical Data |
|---|---|---|---|
| 3-1 | 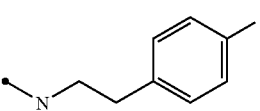 | 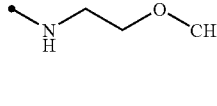 | MS m/z 421 (M + H)⁺ |
| 3-2 | 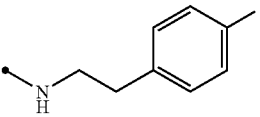 | | MS m/z 399 (M + H)⁺ |

TABLE 3-1-continued

| Compound Number | —R¹ | —R² | Analytical Data |
|---|---|---|---|
| 3-3 | •—NH—CH₂CH₂—NH—C(O)CH₃ | •—NH—CH₂CH₂—C₆H₄—F | MS m/z 426 (M + H)⁺ |
| 3-4 | •—NH—CH₂—C₆H₅ | •—NH—CH₂CH₂—C₆H₄—F | MS m/z 431 (M + H)⁺ |
| 3-5 | •—NH—CH₂CH₂—C₆H₄—OCH₃ | •—NH—CH₂CH₂—C₆H₄—F | MS m/z 475 (M + H)⁺ |
| 3-6 | •—NH—(CH₂)₃—N(pyrrolidin-2-one) | •—NH—CH₂CH₂—C₆H₄—F | MS m/z 466 (M + H)⁺ |
| 3-7 | •—N(CH₃)₂ | •—NH—CH₂CH₂—C₆H₄—F | MS m/z 369 (M + H)⁺ |
| 3-8 | •—N(CH₃)(CH₂CH₂CH₃) | •—NH—CH₂CH₂—C₆H₄—F | MS m/z 397 (M + H)⁺ |
| 3-9 | •—N(pyrrolidinyl) | •—NH—CH₂CH₂—C₆H₄—F | MS m/z 395 (M + H)⁺ |
| 3-10 | •—N(morpholinyl) | •—NH—CH₂CH₂—C₆H₄—F | MS m/z 411 (M + H)⁺ |
| 3-11 | •—N(4-acetylpiperazin-1-yl) | •—NH—CH₂CH₂—C₆H₄—F | MS m/z 452 (M + H)⁺ |

[Table 3-2]

TABLE 3-2

| Compound Number | —R¹ | —R² | Analytical Data |
|---|---|---|---|
| 3-12 | NH-CH2-furan | NH-CH2CH2-(3-F-phenyl) | MS m/z 421 (M + H)+ |
| 3-13 | NH-CH2CH2-O-CH3 | NH-CH2CH2-(3-F-phenyl) | MS m/z 399 (M + H)+ |
| 3-14 | NH-CH2CH3 | NH-CH2CH2-(3-F-phenyl) | MS m/z 383 (M + H)+ |
| 3-15 | NH-CH2CH2-NH-C(=O)CH3 | NH-CH2CH2-(3-F-phenyl) | MS m/z 426 (M + H)+ |
| 3-16 | NH-CH2-phenyl | NH-CH2CH2-(3-F-phenyl) | MS m/z 431 (M + H)+ |
| 3-17 | NH-CH2CH2-(4-OCH3-phenyl) | NH-CH2CH2-(3-F-phenyl) | MS m/z 475 (M + H)+ |
| 3-18 | NH-CH2CH2CH2-(2-oxopyrrolidin-1-yl) | NH-CH2CH2-(3-F-phenyl) | MS m/z 466 (M + H)+ |
| 3-19 | N(CH3)2 | NH-CH2CH2-(3-F-phenyl) | MS m/z 369 (M + H)+ |
| 3-20 | N(CH3)(CH2CH2CH3) | NH-CH2CH2-(3-F-phenyl) | MS m/z 397 (M + H)+ |
| 3-21 | pyrrolidin-1-yl | NH-CH2CH2-(3-F-phenyl) | MS m/z 395 (M + H)+ |
| 3-22 | morpholin-4-yl | NH-CH2CH2-(3-F-phenyl) | MS m/z 411 (M + H)+ |

TABLE 3-2-continued

| Compound Number | —R¹ | —R² | Analytical Data |
|---|---|---|---|
| 3-23 | piperazine with N-acetyl | N-methyl-2-(3-fluorophenyl)ethylamine | MS m/z 452 (M + H)⁺ |

[Table 3-3]

TABLE 3-3

| Compound Number | —R¹ | —R² | Analytical Data |
|---|---|---|---|
| 3-24 | furfurylamino | 2-(pyridin-3-yl)ethylamino | MS m/z 404 (M + H)⁺ |
| 3-25 | 2-methoxyethylamino | 2-(pyridin-3-yl)ethylamino | MS m/z 382 (M + H)⁺ |
| 3-26 | 2-acetamidoethylamino | 2-(pyridin-3-yl)ethylamino | MS m/z 409 (M + H)⁺ |
| 3-27 | benzylamino | 2-(pyridin-3-yl)ethylamino | MS m/z 414 (M + H)⁺ |
| 3-28 | 4-methoxyphenethylamino | 2-(pyridin-3-yl)ethylamino | MS m/z 458 (M + H)⁺ |
| 3-29 | 3-(2-oxopyrrolidin-1-yl)propylamino | 2-(pyridin-3-yl)ethylamino | MS m/z 449 (M + H)⁺ |
| 3-30 | dimethylamino | 2-(pyridin-3-yl)ethylamino | MS m/z 352 (M + H)⁺ |
| 3-31 | N-methyl-N-propylamino | 2-(pyridin-3-yl)ethylamino | MS m/z 380 (M + H)⁺ |
| 3-32 | pyrrolidin-1-yl | 2-(pyridin-3-yl)ethylamino | MS m/z 378 (M + H)⁺ |

TABLE 3-3-continued
| Compound Number | —R¹ | —R² | Analytical Data |
|---|---|---|---|
| 3-33 | 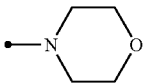 | 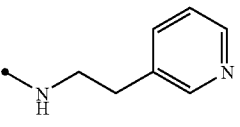 | MS m/z 394 (M + H)⁺ |
| 3-34 | 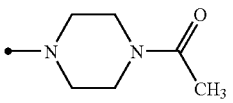 | 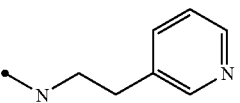 | MS m/z 435 (M + H)⁺ |
[Table 3-4]
TABLE 3-4
| Compound Number | —R¹ | —R² | Analytical Data |
|---|---|---|---|
| 3-35 | 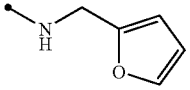 | 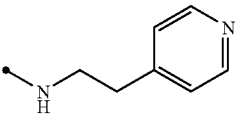 | MS m/z 404 (M + H)⁺ |
| 3-36 | 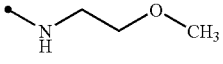 |  | MS m/z 382 (M + H)⁺ |
| 3-37 | 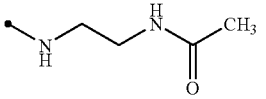 | 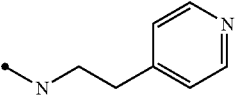 | MS m/z 409 (M + H)⁺ |
| 3-38 | 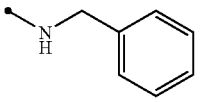 | 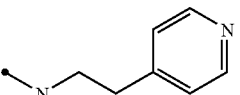 | MS m/z 414 (M + H)⁺ |
| 3-39 | 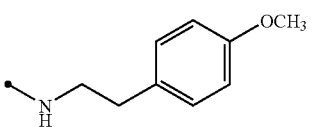 | 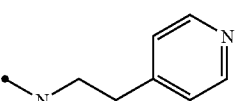 | MS m/z 458 (M + H)⁺ |
| 3-40 | 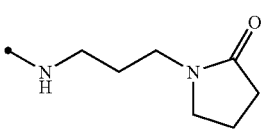 | 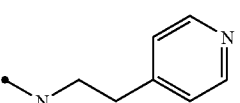 | MS m/z 449 (M + H)⁺ |
| 3-41 | 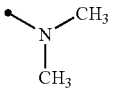 | 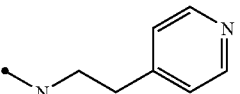 | MS m/z 352 (M + H)⁺ |
| 3-42 | 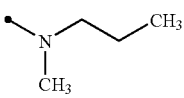 | 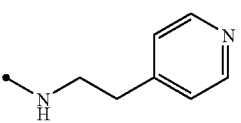 | MS m/z 380 (M + H)⁺ |

TABLE 3-4-continued

| Compound Number | —R¹ | —R² | Analytical Data |
|---|---|---|---|
| 3-43 | pyrrolidine | 2-(pyridin-4-yl)ethylamino | MS m/z 378 (M + H)⁺ |
| 3-44 | morpholine | 2-(pyridin-4-yl)ethylamino | MS m/z 394 (M + H)⁺ |
| 3-45 | 4-acetylpiperazine | 2-(pyridin-4-yl)ethylamino | MS m/z 435 (M + H)⁺ |

[Table 3-5]

TABLE 3-5

| Compound Number | —R¹ | —R² | Analytical Data |
|---|---|---|---|
| 3-46 | furfurylamino | 2-(4-hydroxyphenyl)ethylamino | MS m/z 419 (M + H)⁺ |
| 3-47 | 2-methoxyethylamino | 2-(4-hydroxyphenyl)ethylamino | MS m/z 397 (M + H)⁺ |
| 3-48 | ethylamino | 2-(4-hydroxyphenyl)ethylamino | MS m/z 381 (M + H)⁺ |
| 3-49 | 2-acetamidoethylamino | 2-(4-hydroxyphenyl)ethylamino | MS m/z 424 (M + H)⁺ |
| 3-50 | benzylamino | 2-(4-hydroxyphenyl)ethylamino | MS m/z 429 (M + H)⁺ |
| 3-51 | 2-(4-methoxyphenyl)ethylamino | 2-(4-hydroxyphenyl)ethylamino | MS m/z 473 (M + H)⁺ |
| 3-52 | 3-(2-oxopyrrolidin-1-yl)propylamino | 2-(4-hydroxyphenyl)ethylamino | MS m/z 464 (M + H)⁺ |

TABLE 3-5-continued

| Compound Number | —R¹ | —R² | Analytical Data |
|---|---|---|---|
| 3-53 | —N(CH₃)₂ | —NH-CH₂CH₂-C₆H₄-OH (para) | MS m/z 367 (M + H)⁺ |
| 3-54 | —N(CH₃)(CH₂CH₃) | —NH-CH₂CH₂-C₆H₄-OH (para) | MS m/z 395 (M + H)⁺ |
| 3-55 | pyrrolidin-1-yl | —NH-CH₂CH₂-C₆H₄-OH (para) | MS m/z 393 (M + H)⁺ |
| 3-56 | morpholin-4-yl | —NH-CH₂CH₂-C₆H₄-OH (para) | MS m/z 409 (M + H)⁺ |
| 3-57 | 4-acetylpiperazin-1-yl | —NH-CH₂CH₂-C₆H₄-OH (para) | MS m/z 450 (M + H)⁺ |

[Table 3-6]

TABLE 3-6

| Compound Number | —R¹ | —R² | Analytical Data |
|---|---|---|---|
| 3-58 | —NH-CH₂-(furan-2-yl) | —NH-CH₂CH₂-C₆H₄-OCH₃ (para) | MS m/z 433 (M + H)⁺ |
| 3-59 | —NH-CH₂CH₂-O-CH₃ | —NH-CH₂CH₂-C₆H₄-OCH₃ (para) | MS m/z 411 (M + H)⁺ |
| 3-60 | —NH-CH₂CH₂-NH-C(O)-CH₃ | —NH-CH₂CH₂-C₆H₄-OCH₃ (para) | MS m/z 438 (M + H)⁺ |
| 3-61 | —NH-CH₂-C₆H₅ | —NH-CH₂CH₂-C₆H₄-OCH₃ (para) | MS m/z 443 (M + H)⁺ |
| 3-62 | —NH-CH₂CH₂-C₆H₄-OCH₃ (para) | —NH-CH₂CH₂-C₆H₄-OCH₃ (para) | MS m/z 487 (M + H)⁺ |

TABLE 3-6-continued
| Compound Number | —R¹ | —R² | Analytical Data |
|---|---|---|---|
| 3-63 |  | 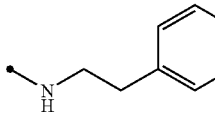 | MS m/z 478 (M + H)⁺ |
| 3-64 |  |  | MS m/z 381 (M + H)⁺ |
| 3-65 |  |  | MS m/z 409 (M + H)⁺ |
| 3-66 |  |  | MS m/z 407 (M + H)⁺ |
| 3-67 |  |  | MS m/z 423 (M + H)⁺ |
| 3-68 |  |  | MS m/z 464 (M + H)⁺ |
[Table 3-7]
TABLE 3-7
| Compound Number | —R¹ | —R² | Analytical Data |
|---|---|---|---|
| 3-69 |  |  | MS m/z 433 (M + H)⁺ |
| 3-70 |  |  | MS m/z 411 (M + H)⁺ |
| 3-71 |  |  | MS m/z 438 (M + H)⁺ |
| 3-72 |  |  | MS m/z 443 (M + H)⁺ |

TABLE 3-7-continued

| Compound Number | —R¹ | —R² | Analytical Data |
|---|---|---|---|
| 3-73 | –NH–CH₂CH₂–C₆H₄–OCH₃ (4-methoxyphenethylamino) | –NH–CH₂–(3,4-methylenedioxyphenyl) | MS m/z 487 (M + H)⁺ |
| 3-74 | –NH–(CH₂)₃–(2-oxopyrrolidin-1-yl) | –NH–CH₂–(3,4-methylenedioxyphenyl) | MS m/z 478 (M + H)⁺ |
| 3-75 | –N(CH₃)₂ | –NH–CH₂–(3,4-methylenedioxyphenyl) | MS m/z 381 (M + H)⁺ |
| 3-76 | –N(CH₃)(CH₂CH₂CH₃) | –NH–CH₂–(3,4-methylenedioxyphenyl) | MS m/z 409 (M + H)⁺ |
| 3-77 | pyrrolidin-1-yl | –NH–CH₂–(3,4-methylenedioxyphenyl) | MS m/z 407 (M + H)⁺ |
| 3-78 | morpholin-4-yl | –NH–CH₂–(3,4-methylenedioxyphenyl) | MS m/z 423 (M + H)⁺ |
| 3-79 | 4-acetylpiperazin-1-yl | –NH–CH₂–(3,4-methylenedioxyphenyl) | MS m/z 464 (M + H)⁺ |

[Table 3-8]

TABLE 3-8

| Compound Number | —R¹ | —R² | Analytical Data |
|---|---|---|---|
| 3-80 | –NH–CH₂–(2-furyl) | 4-(4-hydroxyphenyl)piperazin-1-yl | MS m/z 460 (M + H)⁺ |
| 3-81 | –NH–CH₂CH₂–OCH₃ | 4-(4-hydroxyphenyl)piperazin-1-yl | MS m/z 438 (M + H)⁺ |
| 3-82 | –NH–CH₂CH₂–NH–C(O)CH₃ | 4-(4-hydroxyphenyl)piperazin-1-yl | MS m/z 465 (M + H)⁺ |
| 3-83 | –NH–CH₂–C₆H₅ | 4-(4-hydroxyphenyl)piperazin-1-yl | MS m/z 470 (M + H)⁺ |
| 3-84 | –NH–CH₂CH₂–C₆H₄–OCH₃ (4-methoxyphenethylamino) | 4-(4-hydroxyphenyl)piperazin-1-yl | MS m/z 514 (M + H)⁺ |

TABLE 3-8-continued

| | R¹ | R² | Analytical Data |
|---|---|---|---|
| 3-85 | -NH-CH₂CH₂CH₂-N(pyrrolidin-2-one) | -N(piperazine)-C₆H₄-OH | MS m/z 505 (M + H)⁺ |
| 3-86 | -N(CH₃)₂ | -N(piperazine)-C₆H₄-OH | MS m/z 408 (M + H)⁺ |
| 3-87 | -N(CH₃)(CH₂CH₃) | -N(piperazine)-C₆H₄-OH | MS m/z 436 (M + H)⁺ |
| 3-88 | -N(pyrrolidine) | -N(piperazine)-C₆H₄-OH | MS m/z 434 (M + H)⁺ |
| 3-89 | -N(morpholine) | -N(piperazine)-C₆H₄-OH | MS m/z 450 (M + H)⁺ |
| 3-90 | -N(piperazine)-C(O)CH₃ | -N(piperazine)-C₆H₄-OH | MS m/z 491 (M + H)⁺ |

[Table 3-9]

TABLE 3-9

| Compound Number | —R¹ | —R² | Analytical Data |
|---|---|---|---|
| 3-91 | -NH-C₆H₅ | -NH-CH₂CH₂-C₆H₄-F | MS m/z 417 (M + H)⁺ |
| 3-92 | -NH-C₆H₃(F)(Cl) | -NH-CH₂CH₂-C₆H₄-F | MS m/z 469 (M + H)⁺ |
| 3-93 | -NH-C₆H₄-CN | -NH-CH₂CH₂-C₆H₄-F | MS m/z 442 (M + H)⁺ |
| 3-94 | -NH-C₆H₂(OCH₃)₃ | -NH-CH₂CH₂-C₆H₄-F | MS m/z 507 (M + H)⁺ |
| 3-95 | -NH-C₆H₄-OCH₃ | -NH-CH₂CH₂-C₆H₄-F | MS m/z 447 (M + H)⁺ |

TABLE 3-9-continued
| Compound Number | —R¹ | —R² | Analytical Data |
|---|---|---|---|
| 3-96 | 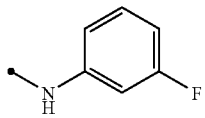 | 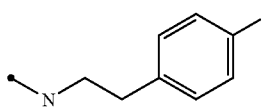 | MS m/z 435 (M + H)⁺ |
| 3-97 | 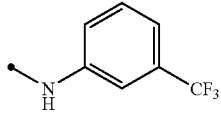 | 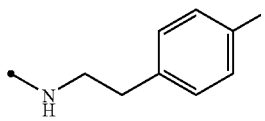 | MS m/z 485 (M + H)⁺ |
| 3-98 | 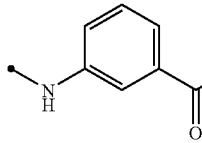 | 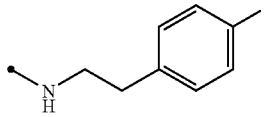 | MS m/z 460 (M + H)⁺ |
| 3-99 | 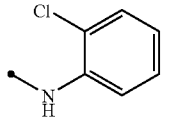 | 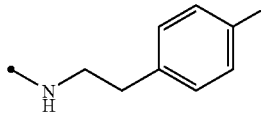 | MS m/z 451 (M + H)⁺ |
| 3-100 | 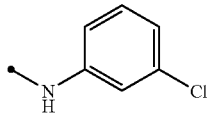 | 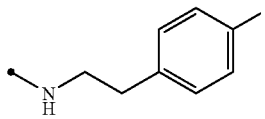 | MS m/z 451 (M + H)⁺ |
| 3-101 | 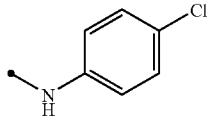 | 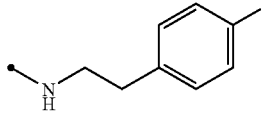 | MS m/z 451 (M + H)⁺ |
| 3-102 | 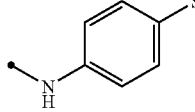 | 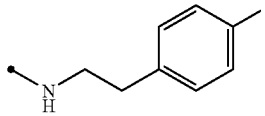 | MS m/z 496 (M + H)⁺ |
[Table 3-10]
TABLE 3-10
| Compound Number | —R¹ | —R² | Analytical Data |
|---|---|---|---|
| 3-103 | 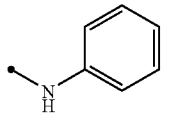 | 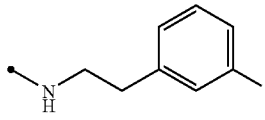 | MS m/z 417 (M + H)⁺ |
| 3-104 | 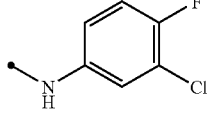 | 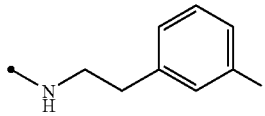 | MS m/z 469 (M + H)⁺ |
| 3-105 | 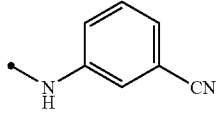 | 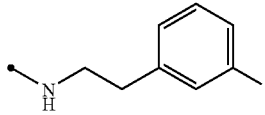 | MS m/z 442 (M + H)⁺ |

TABLE 3-10-continued

| Compound Number | •—R¹ | •—R² | Analytical Data |
|---|---|---|---|
| 3-106 | 3,4,5-trimethoxyphenyl-NH- | 3-fluorophenethyl-NH- | MS m/z 507 (M + H)⁺ |
| 3-107 | 3-methoxyphenyl-NH- | 3-fluorophenethyl-NH- | MS m/z 447 (M + H)⁺ |
| 3-108 | 3-fluorophenyl-NH- | 3-fluorophenethyl-NH- | MS m/z 435 (M + H)⁺ |
| 3-109 | 3-trifluoromethylphenyl-NH- | 3-fluorophenethyl-NH- | MS m/z 485 (M + H)⁺ |
| 3-110 | 3-carbamoylphenyl-NH- | 3-fluorophenethyl-NH- | MS m/z 460 (M + H)⁺ |
| 3-111 | 2-chlorophenyl-NH- | 3-fluorophenethyl-NH- | MS m/z 451 (M + H)⁺ |
| 3-112 | 3-chlorophenyl-NH- | 3-fluorophenethyl-NH- | MS m/z 451 (M + H)⁺ |
| 3-113 | 4-chlorophenyl-NH- | 3-fluorophenethyl-NH- | MS m/z 451 (M + H)⁺ |
| 3-114 | 4-sulfamoylphenyl-NH- | 3-fluorophenethyl-NH- | MS m/z 496 (M + H)⁺ |

[Table 3-11]

TABLE 3-11

| Compound Number | •—R¹ | •—R² | Analytical Data |
|---|---|---|---|
| 3-115 | phenyl-NH- | 2-(pyridin-3-yl)ethyl-NH- | MS m/z 400 (M + H)⁺ |

TABLE 3-11-continued

| Compound Number | —R¹ | —R² | Analytical Data |
|---|---|---|---|
| 3-116 | 4-F, 3-Cl anilino | 2-(pyridin-3-yl)ethylamino | MS m/z 452 (M + H)⁺ |
| 3-117 | 3-CN anilino | 2-(pyridin-3-yl)ethylamino | MS m/z 425 (M + H)⁺ |
| 3-118 | 3,4,5-tri(OCH₃) anilino | 2-(pyridin-3-yl)ethylamino | MS m/z 490 (M + H)⁺ |
| 3-119 | 3-OCH₃ anilino | 2-(pyridin-3-yl)ethylamino | MS m/z 430 (M + H)⁺ |
| 3-120 | 3-F anilino | 2-(pyridin-3-yl)ethylamino | MS m/z 418 (M + H)⁺ |
| 3-121 | 3-CF₃ anilino | 2-(pyridin-3-yl)ethylamino | MS m/z 468 (M + H)⁺ |
| 3-122 | 3-C(O)NH₂ anilino | 2-(pyridin-3-yl)ethylamino | MS m/z 443 (M + H)⁺ |
| 3-123 | 2-Cl anilino | 2-(pyridin-3-yl)ethylamino | MS m/z 434 (M + H)⁺ |
| 3-124 | 3-Cl anilino | 2-(pyridin-3-yl)ethylamino | MS m/z 434 (M + H)⁺ |
| 3-125 | 4-Cl anilino | 2-(pyridin-3-yl)ethylamino | MS m/z 434 (M + H)⁺ |
| 3-126 | 4-SO₂NH₂ anilino | 2-(pyridin-3-yl)ethylamino | MS m/z 479 (M + H)⁺ |

[Table 3-12]

TABLE 3-12

| Compound Number | •—R¹ | •—R² | Analytical Data |
|---|---|---|---|
| 3-127 | •—NH—C₆H₅ (phenyl) | •—NH—CH₂CH₂—(4-pyridyl) | MS m/z 400 (M + H)⁺ |
| 3-128 | •—NH—(3-Cl, 4-F-phenyl) | •—NH—CH₂CH₂—(4-pyridyl) | MS m/z 452 (M + H)⁺ |
| 3-129 | •—NH—(3-CN-phenyl) | •—NH—CH₂CH₂—(4-pyridyl) | MS m/z 425 (M + H)⁺ |
| 3-130 | •—NH—(3,4,5-triOCH₃-phenyl) | •—NH—CH₂CH₂—(4-pyridyl) | MS m/z 490 (M + H)⁺ |
| 3-131 | •—NH—(3-OCH₃-phenyl) | •—NH—CH₂CH₂—(4-pyridyl) | MS m/z 430 (M + H)⁺ |
| 3-132 | •—NH—(3-F-phenyl) | •—NH—CH₂CH₂—(4-pyridyl) | MS m/z 418 (M + H)⁺ |
| 3-133 | •—NH—(3-CF₃-phenyl) | •—NH—CH₂CH₂—(4-pyridyl) | MS m/z 468 (M + H)⁺ |
| 3-134 | •—NH—(3-C(O)NH₂-phenyl) | •—NH—CH₂CH₂—(4-pyridyl) | MS m/z 443 (M + H)⁺ |
| 3-135 | •—NH—(2-Cl-phenyl) | •—NH—CH₂CH₂—(4-pyridyl) | MS m/z 434 (M + H)⁺ |
| 3-136 | •—NH—(3-Cl-phenyl) | •—NH—CH₂CH₂—(4-pyridyl) | MS m/z 434 (M + H)⁺ |
| 3-137 | •—NH—(4-Cl-phenyl) | •—NH—CH₂CH₂—(4-pyridyl) | MS m/z 434 (M + H)⁺ |

TABLE 3-12-continued

| Compound Number | •—R¹ | •—R² | Analytical Data |
|---|---|---|---|
| 3-138 | 4-sulfamoylphenyl-NH- (SO₂NH₂ on phenyl para to NH) | -NH-CH₂CH₂-(pyridin-4-yl) | MS m/z 479 (M + H)⁺ |

[Table 3-13]

TABLE 3-13

| Compound Number | •—R¹ | •—R² | Analytical Data |
|---|---|---|---|
| 3-139 | phenyl-NH- | -NH-CH₂CH₂-C₆H₄-OH (4-OH) | MS m/z 415 (M + H)⁺ |
| 3-140 | 3-chloro-4-fluorophenyl-NH- | -NH-CH₂CH₂-C₆H₄-OH (4-OH) | MS m/z 467 (M + H)⁺ |
| 3-141 | 3-cyanophenyl-NH- | -NH-CH₂CH₂-C₆H₄-OH (4-OH) | MS m/z 440 (M + H)⁺ |
| 3-142 | 3,4,5-trimethoxyphenyl-NH- | -NH-CH₂CH₂-C₆H₄-OH (4-OH) | MS m/z 505 (M + H)⁺ |
| 3-143 | 3-methoxyphenyl-NH- | -NH-CH₂CH₂-C₆H₄-OH (4-OH) | MS m/z 445 (M + H)⁺ |
| 3-144 | 3-fluorophenyl-NH- | -NH-CH₂CH₂-C₆H₄-OH (4-OH) | MS m/z 433 (M + H)⁺ |
| 3-145 | 3-trifluoromethylphenyl-NH- | -NH-CH₂CH₂-C₆H₄-OH (4-OH) | MS m/z 483 (M + H)⁺ |
| 3-146 | 3-carbamoylphenyl-NH- | -NH-CH₂CH₂-C₆H₄-OH (4-OH) | MS m/z 458 (M + H)⁺ |

TABLE 3-13-continued

| Compound Number | —R¹ | —R² | Analytical Data |
|---|---|---|---|
| 3-147 | 2-Cl-phenyl-NH- | 4-OH-phenethyl-NH- | MS m/z 449 (M + H)⁺ |
| 3-148 | 3-Cl-phenyl-NH- | 4-OH-phenethyl-NH- | MS m/z 449 (M + H)⁺ |
| 3-149 | 4-Cl-phenyl-NH- | 4-OH-phenethyl-NH- | MS m/z 449 (M + H)⁺ |
| 3-150 | 4-SO₂NH₂-phenyl-NH- | 4-OH-phenethyl-NH- | MS m/z 494 (M + H)⁺ |

[Table 3-14]

TABLE 3-14

| Compound Number | —R¹ | —R² | Analytical Data |
|---|---|---|---|
| 3-151 | phenyl-NH- | 4-OCH₃-phenethyl-NH- | MS m/z 429 (M + H)⁺ |
| 3-152 | 4-F-3-Cl-phenyl-NH- | 4-OCH₃-phenethyl-NH- | MS m/z 481 (M + H)⁺ |
| 3-153 | 3-CN-phenyl-NH- | 4-OCH₃-phenethyl-NH- | MS m/z 454 (M + H)⁺ |
| 3-154 | 3,4,5-tri-OCH₃-phenyl-NH- | 4-OCH₃-phenethyl-NH- | MS m/z 519 (M + H)⁺ |
| 3-155 | 3-OCH₃-phenyl-NH- | 4-OCH₃-phenethyl-NH- | MS m/z 459 (M + H)⁺ |

TABLE 3-14-continued
| Compound Number | —R¹ | —R² | Analytical Data |
|---|---|---|---|
| 3-156 | 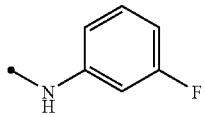 | 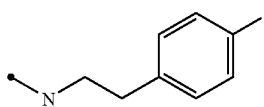 | MS m/z 447 (M + H)⁺ |
| 3-157 | 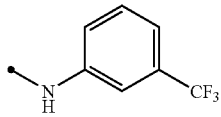 | 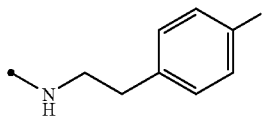 | MS m/z 497 (M + H)⁺ |
| 3-158 | 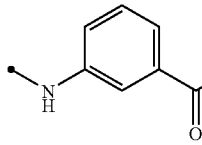 | 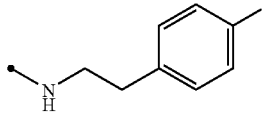 | MS m/z 472 (M + H)⁺ |
| 3-159 | 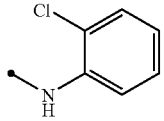 | 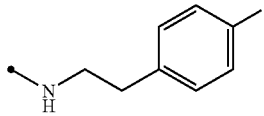 | MS m/z 463 (M + H)⁺ |
| 3-160 | 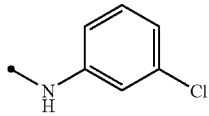 | 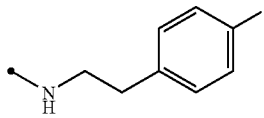 | MS m/z 463 (M + H)⁺ |
| 3-161 | 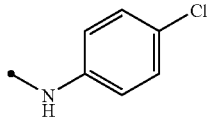 | 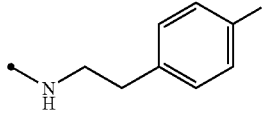 | MS m/z 463 (M + H)⁺ |
| 3-162 | 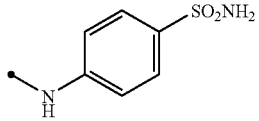 | 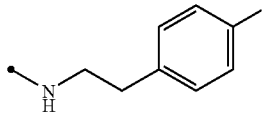 | MS m/z 508 (M + H)⁺ |
[Table 3-15]
TABLE 3-15
| Compound Number | —R¹ | —R² | Analytical Data |
|---|---|---|---|
| 3-163 | 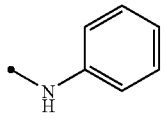 | 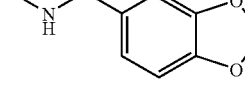 | MS m/z 429 (M + H)⁺ |
| 3-164 | 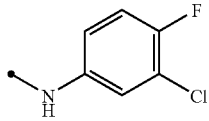 | 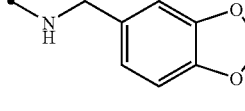 | MS m/z 481 (M + H)⁺ |
| 3-165 | 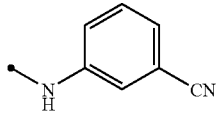 | 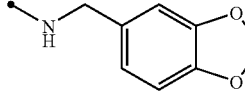 | MS m/z 454 (M + H)⁺ |

TABLE 3-15-continued

| Compound Number | —R¹ | —R² | Analytical Data |
|---|---|---|---|
| 3-166 | 3,4,5-trimethoxyphenyl-NH— | benzo[1,3]dioxol-5-ylmethyl-NH— | MS m/z 519 (M + H)⁺ |
| 3-167 | 3-methoxyphenyl-NH— | benzo[1,3]dioxol-5-ylmethyl-NH— | MS m/z 459 (M + H)⁺ |
| 3-168 | 3-fluorophenyl-NH— | benzo[1,3]dioxol-5-ylmethyl-NH— | MS m/z 447 (M + H)⁺ |
| 3-169 | 3-(trifluoromethyl)phenyl-NH— | benzo[1,3]dioxol-5-ylmethyl-NH— | MS m/z 497 (M + H)⁺ |
| 3-170 | 3-carbamoylphenyl-NH— | benzo[1,3]dioxol-5-ylmethyl-NH— | MS m/z 472 (M + H)⁺ |
| 3-171 | 2-chlorophenyl-NH— | benzo[1,3]dioxol-5-ylmethyl-NH— | MS m/z 463 (M + H)⁺ |
| 3-172 | 3-chlorophenyl-NH— | benzo[1,3]dioxol-5-ylmethyl-NH— | MS m/z 463 (M + H)⁺ |
| 3-173 | 4-chlorophenyl-NH— | benzo[1,3]dioxol-5-ylmethyl-NH— | MS m/z 463 (M + H)⁺ |
| 3-174 | 4-sulfamoylphenyl-NH— | benzo[1,3]dioxol-5-ylmethyl-NH— | MS m/z 508 (M + H)⁺ |

[Table 3-16]

TABLE 3-16

| Compound Number | —R¹ | —R² | Analytical Data |
|---|---|---|---|
| 3-175 | phenyl-NH— | 4-(4-hydroxyphenyl)piperazin-1-yl— | MS m/z 456 (M + H)⁺ |

TABLE 3-16-continued

| Compound Number | •—R¹ | •—R² | Analytical Data |
|---|---|---|---|
| 3-176 | 4-F, 3-Cl anilino | 4-(4-hydroxyphenyl)piperazin-1-yl | MS m/z 508 (M + H)⁺ |
| 3-177 | 3-CN anilino | 4-(4-hydroxyphenyl)piperazin-1-yl | MS m/z 481 (M + H)⁺ |
| 3-178 | 3,4,5-trimethoxy anilino | 4-(4-hydroxyphenyl)piperazin-1-yl | MS m/z 546 (M + H)⁺ |
| 3-179 | 3-OCH₃ anilino | 4-(4-hydroxyphenyl)piperazin-1-yl | MS m/z 486 (M + H)⁺ |
| 3-180 | 3-F anilino | 4-(4-hydroxyphenyl)piperazin-1-yl | MS m/z 474 (M + H)⁺ |
| 3-181 | 3-CF₃ anilino | 4-(4-hydroxyphenyl)piperazin-1-yl | MS m/z 524 (M + H)⁺ |
| 3-182 | 3-CONH₂ anilino | 4-(4-hydroxyphenyl)piperazin-1-yl | MS m/z 499 (M + H)⁺ |
| 3-183 | 2-Cl anilino | 4-(4-hydroxyphenyl)piperazin-1-yl | MS m/z 490 (M + H)⁺ |
| 3-184 | 3-Cl anilino | 4-(4-hydroxyphenyl)piperazin-1-yl | MS m/z 490 (M + H)⁺ |
| 3-185 | 4-Cl anilino | 4-(4-hydroxyphenyl)piperazin-1-yl | MS m/z 490 (M + H)⁺ |
| 3-186 | 4-SO₂NH₂ anilino | 4-(4-hydroxyphenyl)piperazin-1-yl | MS m/z 535 (M + H)⁺ |

[Table 3-17]
TABLE 3-17
| Compound Number | —R¹ | —R² | Analytical Data |
|---|---|---|---|
| 3-187 | 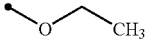 | 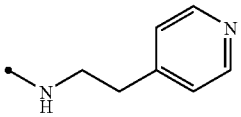 | MS m/z 353 (M + H)⁺ |
| 3-188 | 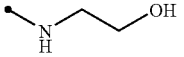 | 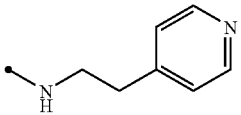 | MS m/z 368 (M + H)⁺ |
| 3-189 | 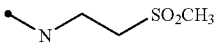 | 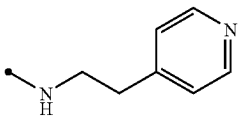 | MS m/z 430 (M + H)⁺ |
| 3-190 | 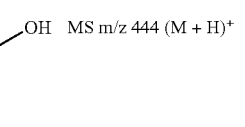 | 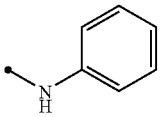 | MS m/z 444 (M + H)⁺ |
| 3-191 | 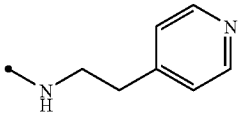 | 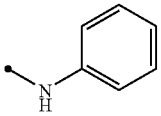 | MS m/z 400 (M + H)⁺ |
| 3-192 | 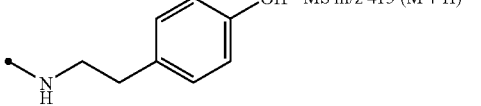 |  | MS m/z 415 (M + H)⁺ |
| 3-193 | 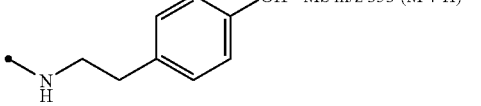 | 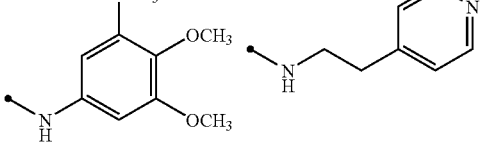 | MS m/z 353 (M + H)⁺ |
| 3-194 |  | 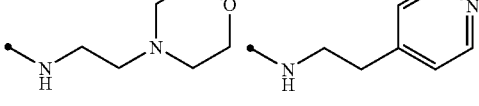 | MS m/z 490 (M + H)⁺ |
| 3-195 |  |  | MS m/z 438 (M + H)⁺ |
| 3-196 |  | 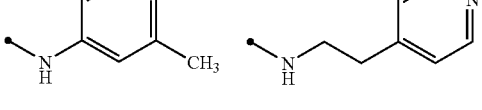 | MS m/z 414 (M + H)⁺ |
| 3-197 |  | | MS m/z 414 (M + H)⁺ |

TABLE 3-17-continued
| Compound Number | —R¹ | —R² | Analytical Data |
|---|---|---|---|
| 3-198 | 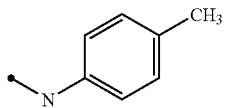 | 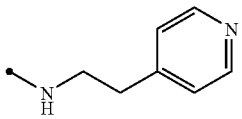 | MS m/z 414 (M + H)⁺ |
[Table 3-18]
TABLE 3-18
| Compound Number | —R¹ | —R² | Analytical Data |
|---|---|---|---|
| 3-199 | 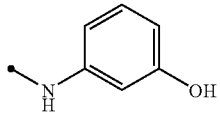 | 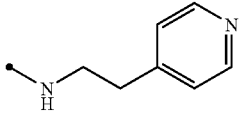 | MS m/z 416 (M + H)⁺ |
| 3-200 | 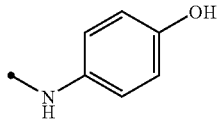 | 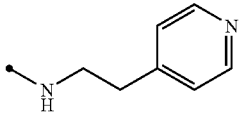 | MS m/z 416 (M + H)⁺ |
| 3-201 | 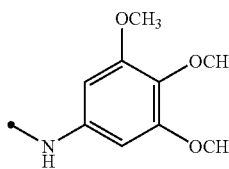 | 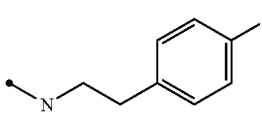 | MS m/z 505 (M + H)⁺ |
| 3-202 | 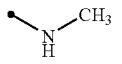 | 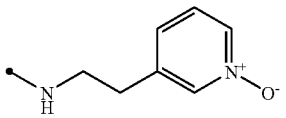 | MS m/z 354 (M + H)⁺ |
| 3-203 | 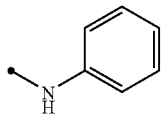 | 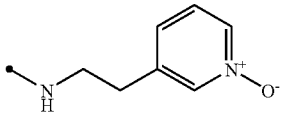 | MS m/z 416 (M + H)⁺ |
| 3-204 | 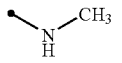 | 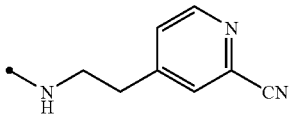 | MS m/z 363 (M + H)⁺ |
| 3-205 | 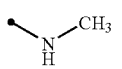 | 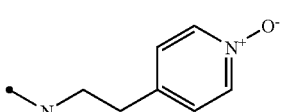 | MS m/z 354 (M + H)⁺ |
| 3-206 | 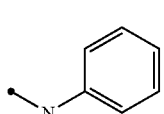 | 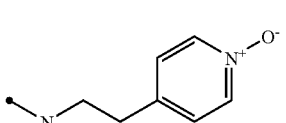 | MS m/z 416 (M + H)⁺ |
| 3-207 | 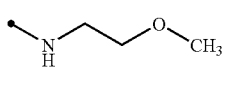 | 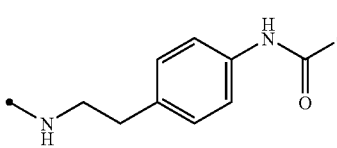 | MS m/z 438 (M + H)⁺ |

TABLE 3-18-continued

| Compound Number | •—R¹ | •—R² | Analytical Data |
|---|---|---|---|
| 3-208 | •—NH—CH₂CH₂—O—CH₃ | •—NH—CH₂CH₂—C₆H₄—NH—SO₂CH₃ | MS m/z 474 (M + H)⁺ |
| 3-209 | •—NH—CH₂CH₂—O—CH₃ | •—NH—CH₂CH₂—(pyridine-3-yl N-oxide) | MS m/z 398 (M + H)⁺ |
| 3-210 | •—NH—CH₂CH₂—O—CH₃ | •—NH—CH₂CH₂—(pyridine-4-yl N-oxide) | MS m/z 398 (M + H)⁺ |

[Table 3-19]

TABLE 3-19

| Compound Number | •—R¹ | •—R² | Analytical Data |
|---|---|---|---|
| 3-211 | •—NH—CH₃ | •—NH—CH₂CH₂—C₆H₄—NH—C(O)CH₃ | MS m/z 394 (M + H)⁺ |
| 3-212 | •—NH—CH₂CH₂—O—CH₃ | •—NH—CH₂CH₂—C₆H₄—NH—C(O)—OCH₃ | MS m/z 454 (M + H)⁺ |
| 3-213 | •—NH—CH₃ | •—NH—CH₂CH₂—C₆H₄—NH—SO₂CH₃ | MS m/z 430 (M + H)⁺ |
| 3-214 | •—NH—CH₃ | •—NH—CH₂CH₂—C₆H₄—NH—C(O)—OCH₃ | MS m/z 410 (M + H)⁺ |
| 3-215 | •—NH—C₆H₄—OCH₃ | •—NH—CH₂CH₂—(pyridin-4-yl) | MS m/z 430 (M + H)⁺ |
| 3-216 | •—NH—C₆H₅ | •—NH—CH₂CH₂—C₆H₄—NH—C(O)CH₃ | MS m/z 456 (M + H)⁺ |

TABLE 3-19-continued

| Compound Number | —R¹ | —R² | Analytical Data |
|---|---|---|---|
| 3-217 | phenyl-NH- | 4-(NHC(O)OCH₃)-phenyl-CH₂CH₂-NH- | MS m/z 472 (M + H)⁺ |
| 3-218 | phenyl-NH- | 2-cyano-pyridin-4-yl-CH₂CH₂-NH- | MS m/z 425 (M + H)⁺ |
| 3-219 | F-CH₂CH₂-NH- | pyridin-4-yl-CH₂CH₂-NH- | MS m/z 370 (M + H)⁺ |
| 3-220 | CH₃O-CH₂CH₂CH₂-NH- | pyridin-4-yl-CH₂CH₂-NH- | MS m/z 396 (M + H)⁺ |
| 3-221 | 4-F-phenyl-NH- | pyridin-4-yl-CH₂CH₂-NH- | MS m/z 418 (M + H)⁺ |
| 3-222 | CH₃O-CH₂CH₂-NH- | pyridin-4-yl-CH₂CH₂-NH- | MS m/z 382 (M + H)⁺ |

[Table 3-20]

TABLE 3-20

| Compound Number | —R¹ | —R² | Analytical Data |
|---|---|---|---|
| 3-223 | phenyl-NH- | 2-methyl-pyridin-4-yl-CH₂CH₂-NH- | MS m/z 414 (M + H)⁺ |
| 3-224 | 4-OCH₃-3-Cl-phenyl-NH- | pyridin-4-yl-CH₂CH₂-NH- | MS m/z 464 (M + H)⁺ |
| 3-225 | 4-OCH₃-3-CH₃-phenyl-NH- | pyridin-4-yl-CH₂CH₂-NH- | MS m/z 444 (M + H)⁺ |
| 3-226 | 4-OH-3-Cl-phenyl-NH- | pyridin-4-yl-CH₂CH₂-NH- | MS m/z 450 (M + H)⁺ |

TABLE 3-20-continued
| Compound Number | —R¹ | —R² | Analytical Data |
|---|---|---|---|
| 3-227 |  | 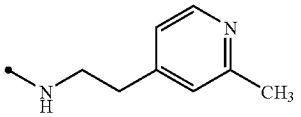 | MS m/z 352 (M + H)⁺ |
| 3-228 | 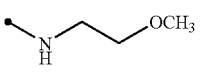 | 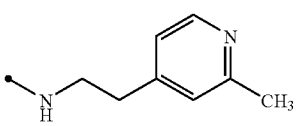 | MS m/z 396 (M + H)⁺ |
| 3-229 | 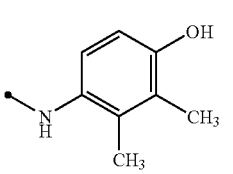 | 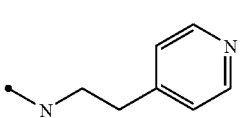 | MS m/z 444 (M + H)⁺ |
| 3-230 | 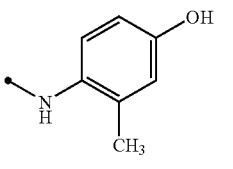 | 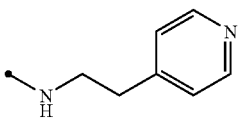 | MS m/z 430 (M + H)⁺ |
| 3-231 | 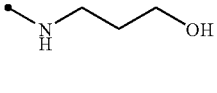 | 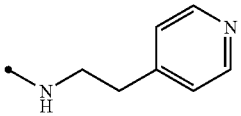 | MS m/z 382 (M + H)⁺ |
| 3-232 | 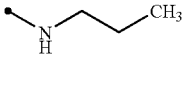 | 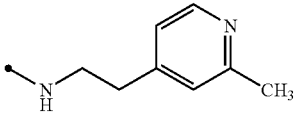 | MS m/z 380 (M + H)⁺ |
| 3-233 | 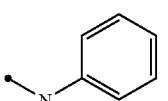 | 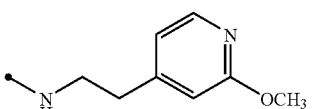 | MS m/z 430 (M + H)⁺ |
| 3-234 | 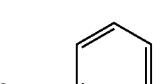 | 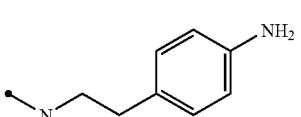 | MS m/z 414 (M + H)⁺ |
[Table 3-21]
TABLE 3-21
| Compound Number | —R¹ | —R² | Analytical Data |
|---|---|---|---|
| 3-235 |  | 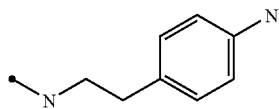 | MS m/z 352 (M + H)⁺ |
| 3-236 | 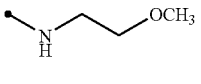 | 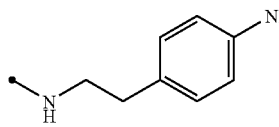 | MS m/z 396 (M + H)⁺ |

TABLE 3-21-continued

| Compound Number | —R¹ | —R² | Analytical Data |
|---|---|---|---|
| 3-237 | phenyl-NH- | 4-hydroxy-3-methylphenethyl-NH- | MS m/z 429 (M + H)⁺ |
| 3-238 | CH₃O-CH₂CH₂-NH- | 2-(pyrimidin-4-yl)ethyl-NH- | MS m/z 383 (M + H)⁺ |
| 3-239 | phenyl-NH- | 2-(pyrimidin-4-yl)ethyl-NH- | MS m/z 401 (M + H)⁺ |
| 3-240 | phenyl-NH- | 4-hydroxy-3,5-dimethylphenethyl-NH- | MS m/z 443 (M + H)⁺ |
| 3-241 | F-CH₂CH₂CH₂-NH- | 2-(pyridin-4-yl)ethyl-NH- | MS m/z 384 (M + H)⁺ |
| 3-242 | phenyl-NH- | 2-(2-hydroxypyridin-4-yl)ethyl-NH- | MS m/z 416 (M + H)⁺ |

[Table 4-1]

TABLE 4-1

| Compound Number | —R¹ | —R² | —R¹⁸ | Analytical Data |
|---|---|---|---|---|
| 4-1 | CH₃CH₂-NH- | 2-(pyridin-4-yl)ethyl-NH- | —OH | MS m/z 356 (M + H)⁺ |
| 4-2 | CH₃CH₂-NH- | 2-(pyridin-4-yl)ethyl-NH- | morpholin-4-yl | MS m/z 425 (M + H)⁺ |

TABLE 4-1-continued

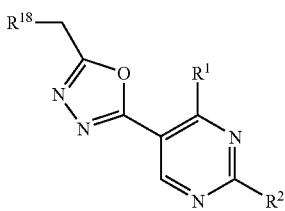

| Compound Number | •—R¹ | •—R² | •—R¹⁸ | Analytical Data |
|---|---|---|---|---|
| 4-3 | •NH-CH₂CH₃ | •NH-CH₂CH₂-(4-pyridyl) | •N(piperazinyl)N—CH₃ | MS m/z 438 (M + H)⁺ |
| 4-4 | •NH-CH₃ | •NH-CH₂CH₂-(4-pyridyl) | •—OH | MS m/z 328 (M + H)⁺ |
| 4-5 | •NH-CH₃ | •NH-CH₂CH₂-(4-pyridyl) | •N(CH₃)₂ | MS m/z 355 (M + H)⁺ |
| 4-6 | •NH-CH₃ | •NH-CH₂CH₂-(4-pyridyl) | •N(piperazinyl)N—CH₂CH₂OH | MS m/z 440 (M + H)⁺ |
| 4-7 | •NH-CH₃ | •NH-CH₂CH₂-(4-pyridyl) | •N(piperazinyl)N—C(O)CH₃ | MS m/z 438 (M + H)⁺ |
| 4-8 | •NH-CH₃ | •NH-CH₂CH₂-(4-pyridyl) | •N(piperazinyl)N—CH₃ | MS m/z 410 (M + H)⁺ |
| 4-9 | •NH-CH₂CH₂OCH₃ | •NH-CH₂CH₂-(4-pyridyl) | •—OH | MS m/z 372 (M + H)⁺ |
| 4-10 | •NH-CH₂CH₂OCH₃ | •NH-CH₂CH₂-(4-pyridyl) | •N(CH₃)₂ | MS m/z 399 (M + H)⁺ |
| 4-11 | •NH-CH₂CH₂OCH₃ | •NH-CH₂CH₂-(4-pyridyl) | •N(piperazinyl)N—CH₂CH₂OH | MS m/z 484 (M + H)⁺ |
| 4-12 | •NH-CH₂CH₂OCH₃ | •NH-CH₂CH₂-(4-pyridyl) | •N(piperazinyl)N—C(O)CH₃ | MS m/z 482 (M + H)⁺ |

[Table 4-2]

TABLE 4-2

| Compound Number | —R¹ | —R² | —R¹⁸ | Analytical Data |
|---|---|---|---|---|
| 4-13 | •—NH—CH₂CH₂—OCH₃ | •—NH—CH₂CH₂—(4-pyridyl) | •—N(piperazine)N—CH₃ | MS m/z 454 (M + H)⁺ |
| 4-14 | •—NH—CH₂CH₂—OCH₃ | •—NH—CH₂CH₂—(4-pyridyl) | •—N(piperazine)N—C₂H₅ | MS m/z 468 (M + H)⁺ |
| 4-15 | •—NH—CH₂CH₂—OCH₃ | •—NH—CH₂CH₂—(4-pyridyl) | •—N(piperazine)NH | MS m/z 440 (M + H)⁺ |
| 4-16 | •—NH—CH₂CH₂—OCH₃ | •—NH—CH₂CH₂—(4-pyridyl) | •—N(morpholine)O | MS m/z 441 (M + H)⁺ |
| 4-17 | •—NH—CH₂CH₂—OCH₃ | •—NH—CH₂CH₂—(4-pyridyl) | •—N(piperazine)N—CH(CH₃)₂ | MS m/z 482 (M + H)⁺ |
| 4-18 | •—NH—CH₂CH₂—OCH₃ | •—NH—CH₂CH₂—(4-pyridyl) | •—N(piperazine)N—cyclopentyl | MS m/z 508 (M + H)⁺ |
| 4-19 | •—NH—CH₂CH₂—OCH₃ | •—NH—CH₂CH₂—(4-pyridyl) | •—N(piperazine)N—CH₂CH₂OCH₃ | MS m/z 498 (M + H)⁺ |
| 4-20 | •—NH—CH₃ | •—NH—CH₂CH₂—(4-pyridyl) | •—N(piperazine)N—CH(CH₃)₂ | MS m/z 438 (M + H)⁺ |
| 4-21 | •—NH—CH₃ | •—NH—CH₂CH₂—(4-pyridyl) | •—N(piperazine)N—CH₂-(tetrahydrofuran-2-yl) | MS m/z 480 (M + H)⁺ |
| 4-22 | •—NH—CH₃ | •—NH—CH₂CH₂—(4-pyridyl) | •—N(piperazine)N—CHO | MS m/z 424 (M + H)⁺ |
| 4-23 | •—NH—C₂H₅ | •—NH—CH₂CH₂—(2-methyl-4-pyridyl) | •—N(piperazine)N—CH₃ | MS m/z 452 (M + H)⁺ |

TABLE 4-2-continued
| Compound Number | —R¹ | —R² | —R¹⁸ | Analytical Data |
|---|---|---|---|---|
| 4-24 | 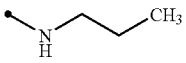 |  | 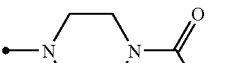 | MS m/z 466 (M + H)⁺ |
[Table 4-3]
TABLE 4-3
| Compound Number | —R¹ | —R² | —R¹⁸ | Analytical Data |
|---|---|---|---|---|
| 4-25 | 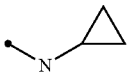 |  | 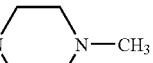 | MS m/z 436 (M + H)⁺ |
| 4-26 | 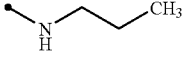 |  | 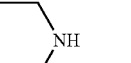 | MS m/z 424 (M + H)⁺ |
| 4-27 | 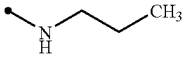 |  | 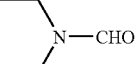 | MS m/z 452 (M + H)⁺ |
| 4-28 | 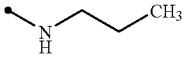 |  | 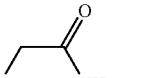 | MS m/z 438 (M + H)⁺ |
| 4-29 | 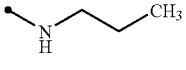 |  | 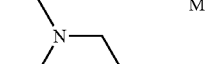 | MS m/z 468 (M + H)⁺ |
| 4-30 | 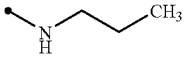 |  | 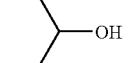 | MS m/z 439 (M + H)⁺ |
| 4-31 | 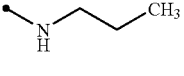 | 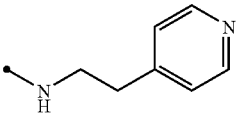 |  | MS m/z 443 (M + H)⁺ |
| 4-32 | 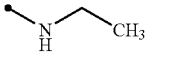 |  | 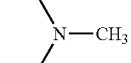 | MS m/z 424 (M + H)⁺ |
| 4-33 | 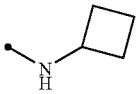 | 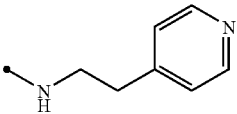 | 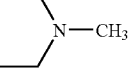 | MS m/z 450 (M + H)⁺ |

TABLE 4-3-continued

| Compound Number | —R¹ | —R² | —R¹⁸ | Analytical Data |
|---|---|---|---|---|
| 4-34 | HN—CH₂CH₂CH₂—OH | —NH—CH₂CH₂—(4-pyridyl) | —N(piperazine)N—CH₃ | MS m/z 454 (M + H)⁺ |
| 4-35 | HN—CH₂CH₂CH₂—F | —NH—CH₂CH₂—(4-pyridyl) | —N(piperazine)N—CH₃ | MS m/z 456 (M + H)⁺ |

[Table 4-4]

TABLE 4-4

| Compound Number | —R¹ | —R² | —R¹⁸ | Analytical Data |
|---|---|---|---|---|
| 4-36 | HN—CH₂CH₂—F | —NH—CH₂CH₂—(4-pyridyl) | —N(piperazine)N—CH₃ | MS m/z 456 (M + H)⁺ |
| 4-37 | HN—CH₂—cyclopropyl | —NH—CH₂CH₂—(4-pyridyl) | —N(piperazine)N—CH₃ | MS m/z 450 (M + H)⁺ |
| 4-38 | HN—phenyl | —NH—CH₂CH₂—(4-pyridyl) | —N(piperazine)N—CH₃ | MS m/z 472 (M + H)⁺ |
| 4-39 | HN—CH₂—(4-F-phenyl) | —NH—CH₂CH₂—(4-pyridyl) | —N(piperazine)N—CH₃ | MS m/z 504 (M + H)⁺ |
| 4-40 | HN—CH₂CH₂—(4-F-phenyl) | —NH—CH₂CH₂—(4-pyridyl) | —N(piperazine)N—CH₃ | MS m/z 518 (M + H)⁺ |
| 4-41 | HN—CH(CH₃)₂ | —NH—CH₂CH₂—(4-pyridyl) | —N(piperazine)N—CH₃ | MS m/z 438 (M + H)⁺ |
| 4-42 | HN—CH₂—C≡CH | —NH—CH₂CH₂—(4-pyridyl) | —N(piperazine)N—CH₃ | MS m/z 434 (M + H)⁺ |
| 4-43 | HN—CH₂—C(CH₃)₃ | —NH—CH₂CH₂—(4-pyridyl) | —N(piperazine)N—CH₃ | MS m/z 466 (M + H)⁺ |

TABLE 4-4-continued

| Compound Number | —R¹ | —R² | —R¹⁸ | Analytical Data |
|---|---|---|---|---|
| 4-44 | NHCH₂CH₃ (ethylamino) | 4-pyridyl-CH₂CH₂-NH- | -NH-CH₂CH₂-N(CH₃)₂ | MS m/z 426 (M + H)⁺ |
| 4-45 | NHCH₂CH₃ | 4-pyridyl-CH₂CH₂-NH- | -NH-CH₂CH₂-morpholine | MS m/z 468 (M + H)⁺ |
| 4-46 | NHCH₂CH₃ | 4-pyridyl-CH₂CH₂-NH- | -NH-CH₂-(tetrahydrofuran-2-yl) | MS m/z 439 (M + H)⁺ |
| 4-47 | NHCH₂CH₃ | 4-pyridyl-CH₂CH₂-NH- | -NH-CH₂CH₂-OH | MS m/z 399 (M + H)⁺ |

[Table 4-5]

TABLE 4-5

| Compound Number | —R¹ | —R² | —R¹⁸ | Analytical Data |
|---|---|---|---|---|
| 4-48 | NHCH₂CH₃ | 4-pyridyl-CH₂CH₂-NH- | -NH-CH₂CH₂-NHC(O)CH₃ | MS m/z 440 (M + H)⁺ |
| 4-49 | NHCH₂CH₃ | 4-pyridyl-CH₂CH₂-NH- | -NH-CH₂CH₂-N(CH₂CH₃)₂ | MS m/z 454 (M + H)⁺ |
| 4-50 | NHCH₂CH₃ | 4-pyridyl-CH₂CH₂-NH- | -NH-CH₂CH₂CH₂-N(CH₃)₂ | MS m/z 440 (M + H)⁺ |
| 4-51 | NHCH₂CH₃ | 4-pyridyl-CH₂CH₂-NH- | -NH-CH₂CH₂CH₂-morpholine | MS m/z 482 (M + H)⁺ |
| 4-52 | NHCH₂CH₃ | 4-pyridyl-CH₂CH₂-NH- | -NH-(piperidin-4-yl)-N-C(O)OCH₂CH₃ | MS m/z 510 (M + H)⁺ |
| 4-53 | NHCH₂CH₃ | 4-pyridyl-CH₂CH₂-NH- | -NH-CH₂CH₂CH₂-N(CH₂CH₂OH)₂ | MS m/z 500 (M + H)⁺ |

TABLE 4-5-continued
| Compound Number | —R¹ | —R² | —R¹⁸ | Analytical Data |
|---|---|---|---|---|
| 4-54 | 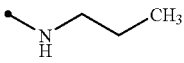 | 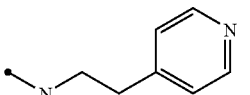 |  | MS m/z 369 (M + H)⁺ |
| 4-55 | 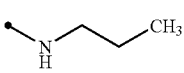 | 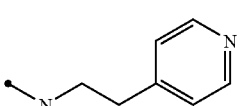 | 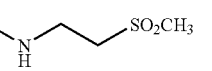 | MS m/z 461 (M + H)⁺ |
| 4-56 | 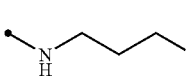 | 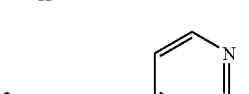 | 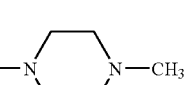 | MS m/z 468 (M + H)⁺ |
| 4-57 | 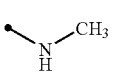 | 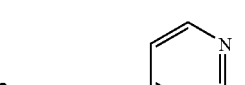 | 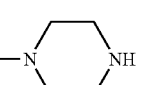 | MS m/z 396 (M + H)⁺ |
| 4-58 | 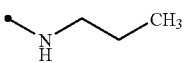 | 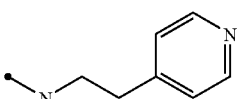 | 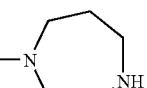 | MS m/z 438 (M + H)⁺ |
| 4-59 | 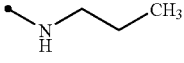 | 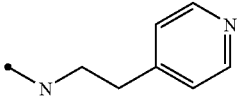 |  | MS m/z 383 (M + H)⁺ |
[Table 4-6]
TABLE 4-6
| Compound Number | —R¹ | —R² | —R¹⁸ | Analytical Data |
|---|---|---|---|---|
| 4-60 | 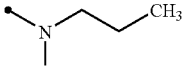 | 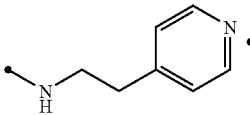 | 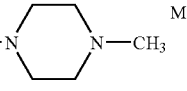 | MS m/z 452 (M + H)⁺ |
| 4-61 | 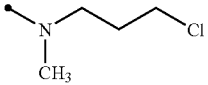 | 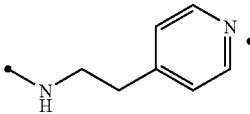 | 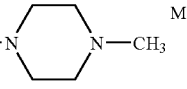 | MS m/z 472 (M + H)⁺ |
| 4-62 | 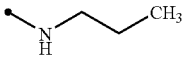 | 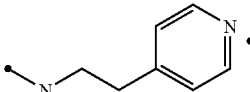 | 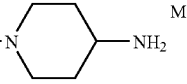 | MS m/z 438 (M + H)⁺ |
| 4-63 | 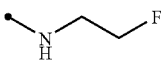 | 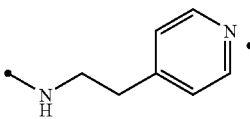 | 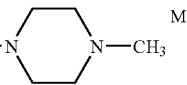 | MS m/z 442 (M + H)⁺ |

TABLE 4-6-continued
| Compound Number | —R¹ | —R² | —R¹⁸ | Analytical Data |
|---|---|---|---|---|
| 4-64 | 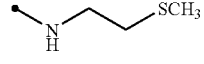 | 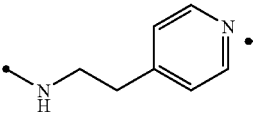 | 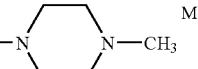 | MS m/z 470 (M + H)⁺ |
| 4-65 | 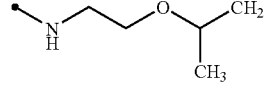 | 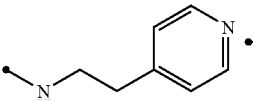 | 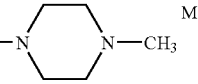 | MS m/z 482 (M + H)⁺ |
| 4-66 | 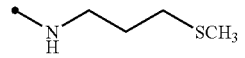 | 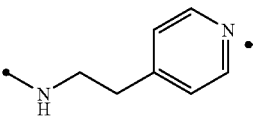 | 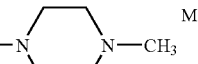 | MS m/z 484 (M + H)⁺ |
| 4-67 | 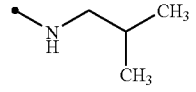 | 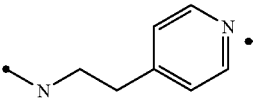 | 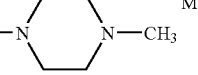 | MS m/z 452 (M + H)⁺ |
| 4-68 | 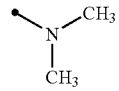 | 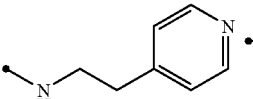 | 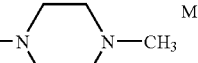 | MS m/z 424 (M + H)⁺ |
| 4-69 | 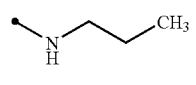 | 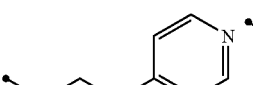 | 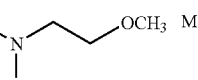 | MS m/z 427 (M + H)⁺ |
| 4-70 | 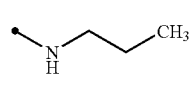 | 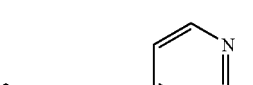 |  | MS m/z 438 (M + H)⁺ |
| 4-71 | 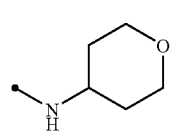 | 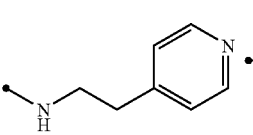 | 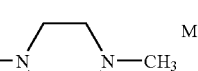 | MS m/z 480 (M + H)⁺ |
[Table 4-7]
TABLE 4-7
| Compound Number | —R¹ | —R² | —R¹⁸ | Analytical Data |
|---|---|---|---|---|
| 4-72 | 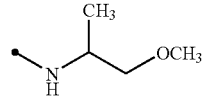 | 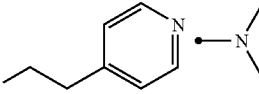 | 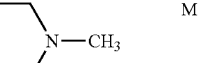 | MS m/z 468 (M + H)⁺ |
| 4-73 | 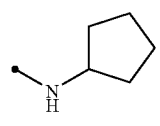 | 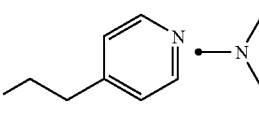 | 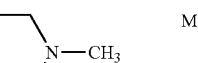 | MS m/z 464 (M + H)⁺ |

TABLE 4-7-continued
| Compound Number | —R¹ | —R² | —R¹⁸ | Analytical Data |
|---|---|---|---|---|
| 4-74 | 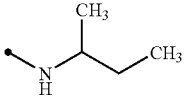 | 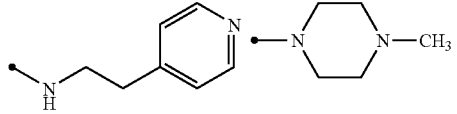 |  | MS m/z 452 (M + H)⁺ |
| 4-75 | 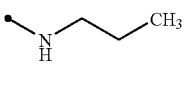 | 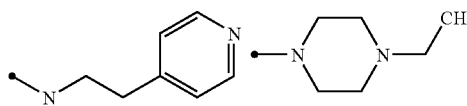 |  | MS m/z 452 (M + H)⁺ |
| 4-76 | 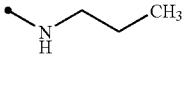 | 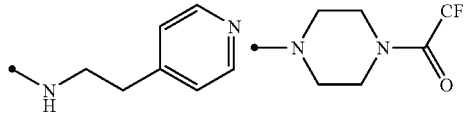 |  | MS m/z 520 (M + H)⁺ |
| 4-77 | 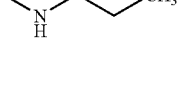 | 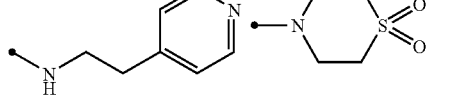 |  | MS m/z 473 (M + H)⁺ |
| 4-78 | 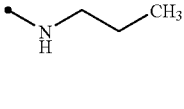 | 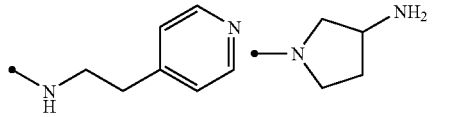 |  | MS m/z 424 (M + H)⁺ |
| 4-79 | 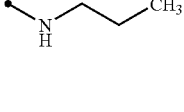 | 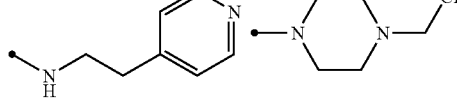 |  | MS m/z 506 (M + H)⁺ |
| 4-80 | 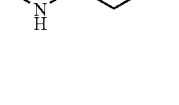 | 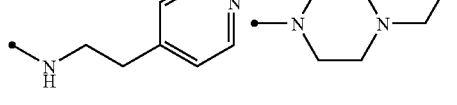 |  | MS m/z 470 (M + H)⁺ |
| 4-81 |  | 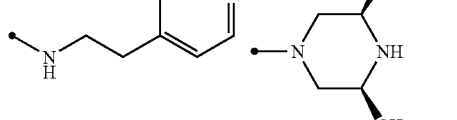 |  | MS m/z 452 (M + H)⁺ |
| 4-82 | 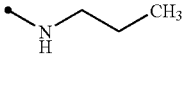 | 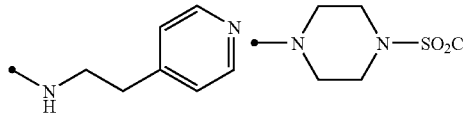 |  | MS m/z 502 (M + H)⁺ |
| 4-83 | 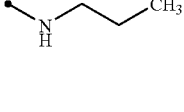 | 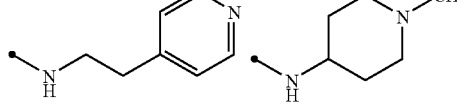 |  | MS m/z 452 (M + H)⁺ |

TABLE 4-7-continued
| Compound Number | —R¹ | —R² | —R¹⁸ | Analytical Data |
|---|---|---|---|---|
| 4-84 | 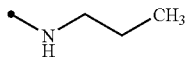 | 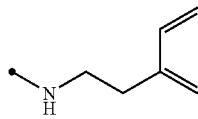 | 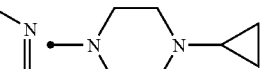 | MS m/z 464 (M + H)⁺ |
[Table 5]
TABLE 5
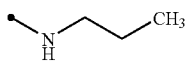
| Compound Number | —R¹ | —R² | —R¹⁹ | Analytical Data |
|---|---|---|---|---|
| 5-1 | 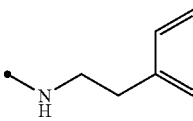 |  | —OH | MS m/z 370 (M + H)⁺ |
| 5-2 | 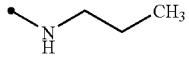 | 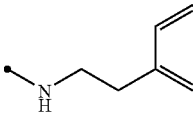 |  | MS m/z 482 (M + H)⁺ |
| 5-3 | 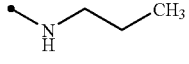 | 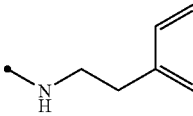 | 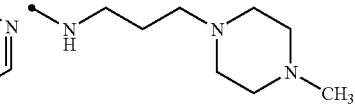 | MS m/z 509 (M + H)⁺ |
| 5-4 | 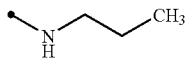 | 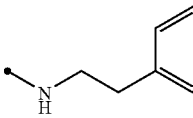 | 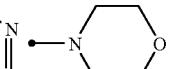 | MS m/z 439 (M + H)⁺ |
| 5-5 | 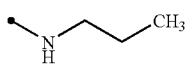 | 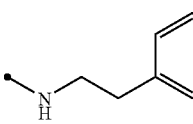 | 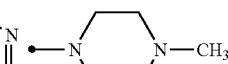 | MS m/z 452 (M + H)⁺ |
| 5-6 | 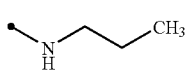 | 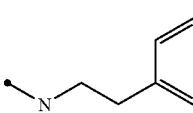 | 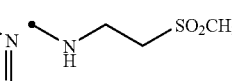 | MS m/z 475 (M + H)⁺ |

[Table 6]

TABLE 6

*Structure: 1,3,4-oxadiazol-2(3H)-one with R8 on N3, connected at C5 to a pyrimidine bearing a propylamino (HN-CH2CH2CH3) group at C4 and R2 at C2.*

| Compound Number | —R² | —R⁸ | Analytical Data |
|---|---|---|---|
| 6-1 | —NH—CH2CH2—(4-pyridyl) | —H | MS m/z 342 (M + H)⁺ |
| 6-2 | —NH—CH2CH2—(4-pyridyl) | —CH2CH2Br | MS m/z 448 (M + H)⁺ |
| 6-3 | —NH—CH2CH2—(4-pyridyl) | —CH2CH2CH2—(morpholin-4-yl) | MS m/z 455 (M + H)⁺ |
| 6-4 | —NH—CH2CH2—(4-pyridyl) | —CH2CH2CH2—(pyrrolidin-1-yl) | MS m/z 439 (M + H)⁺ |
| 6-5 | —NH—CH2CH2—(4-pyridyl) | —CH2CH2CH2—(4-methylpiperazin-1-yl) | MS m/z 468 (M + H)⁺ |
| 6-6 | —NH—CH2CH2—(4-pyridyl) | —CH2CH2CH2—(piperidin-1-yl) | MS m/z 453 (M + H)⁺ |
| 6-7 | —NH—CH2CH2—(4-pyridyl) | —CH2CH2CH2—N(CH3)2 | MS m/z 413 (M + H)⁺ |

[Table 7]

TABLE 7

General structure: pyrimidine with tetrazole (bearing R9 substituent) at position 5, HN-CH2CH2-CH3 (ethylamino with methyl) at position 4, and R2 at position 2.

| Compound Number | R² | R⁹ | Analytical Data |
|---|---|---|---|
| 7-1 | -NH-CH₂- (pyridin-4-yl) | -CH₃ | MS m/z 340 (M + H)⁺ |
| 7-2 | -NH-CH₂- (thiophen-2-yl) | -CH₃ | MS m/z 345 (M + H)⁺ |
| 7-3 | -NH-CH₂- (pyridin-4-yl) | -(CH₂)₃-morpholino | MS m/z 439 (M + H)⁺ |

Next, typical pharmacological activities of Compound (I) will be illustrated specifically below with reference to the test example.

Test Example 1

Cytostatic Activity on Leukemia Cell Line

The cytostatic rate (%) of a test compound on human acute myeloid leukemia cell line MV-4-11 was determined in the following manner.

Each cell was cultured using Roswell Park Memorial Institute's Medium (RPMI) 1640 (Gibco, Catalog No. 11875-093) containing 10% fetal bovine serum (Gibco, Catalog. No. 10437-028) and 1% penicillin/streptomycin (1:1) (Gibco, Catalog No. 15140-122). Each 80 μL of the MV-4-11 cell having a concentration of 7.5×10⁴ cells/mL (or K562 cell having a concentration of 2.5×10⁴ cells/mL) was inoculated to wells of a TC MICROWELL 96U plate (Nalge Nunc International, Catalog No. 163320) and was cultured in a 5% carbon dioxide gas incubator at 37° C. for 4 hours. As a blank, only RPMI medium (80 μL) was added to a well. Each 20 μL of a solution of the test compound in dimethyl sulfoxide (DMSO) which was prepared to make the final concentration to 10 μmol/L, was added to the MV-4-11 cell. Each 20 μL of DMSO was added to the control well and the blank well to a final concentration of 0.1%. After adding the test compound, the cells were incubated in a 5% carbon dioxide gas incubator at 37° C. for 72 hours. After adding 20 μL of WST-1 reagent {4-[3-(4-iodophenyl)-2-(4-nitrophenyl)-2H-5-tetrazolio]-1,3-benzene disulfonate sodium salt} (Roche Diagnostics K.K., Catalog No. 1644807) diluted to 50% with RPMI medium, the cells were further incubated at 37° C. for 2 hours. Then, the absorbances at 450 nm (reference wavelength: 690 nm) were determined with a microplate spectrophotometer SPECTRA max 340PC (Molecular Devices Corporation). The relative growth (%) of a well to which the test compound had been added was determined while setting the absorbance of a well to which not the test compound but DMSO alone had been added (control) at 100% and that of a well containing RPMI medium alone at 0%. The cytostatic rate (%) of the test compound was determined by subtracting the calculated relative growth from 100. The higher the cytostatic rate, the stronger the test compound exhibits cytostatic activity on the cell.

The determined cytostatic rates (%) are shown in Tables to 8-3.

TABLE 8-1

| Compound Number | MV-4-11 (%, 10 μmol/L) |
|---|---|
| 1-3 | 91 |
| 1-10 | 97 |
| 1-29 | 99 |
| 1-59 | 100 |
| 1-69 | 99 |
| 1-70 | 97 |
| 1-82 | 96 |
| 1-538 | 97 |
| 1-548 | 97 |
| 2-69 | 98 |
| 2-82 | 96 |
| 3-187 | 97 |
| 3-188 | 98 |
| 3-189 | 94 |
| 3-190 | 98 |
| 3-191 | 98 |
| 3-192 | 98 |
| 3-198 | 95 |
| 3-200 | 94 |
| 3-222 | 98 |
| 3-223 | 97 |
| 3-226 | 97 |

TABLE 8-1-continued

| Compound Number | MV-4-11 (%, 10 µmol/L) |
| --- | --- |
| 3-227 | 98 |
| 3-228 | 98 |

TABLE 8-2

| Compound Number | MV-4-11 (%, 10 µmol/L) |
| --- | --- |
| 3-229 | 99 |
| 3-230 | 90 |
| 3-232 | 98 |
| 3-234 | 95 |
| 3-236 | 96 |
| 3-237 | 99 |
| 3-239 | 90 |
| 3-241 | 99 |
| 3-242 | 91 |
| 4-2 | 100 |
| 4-3 | 99 |
| 4-5 | 99 |
| 4-8 | 98 |
| 4-10 | 97 |
| 4-13 | 98 |
| 4-23 | 100 |
| 4-24 | 100 |
| 4-25 | 99 |
| 4-26 | 99 |
| 4-27 | 99 |
| 4-28 | 99 |
| 4-29 | 99 |
| 4-30 | 96 |
| 4-32 | 99 |

TABLE 8-3

| Compound Number | MV-4-11 (%, 10 µmol/L) |
| --- | --- |
| 4-33 | 99 |
| 4-34 | 98 |
| 4-35 | 99 |
| 4-38 | 97 |
| 4-41 | 98 |
| 4-44 | 97 |
| 4-45 | 98 |
| 4-47 | 98 |
| 4-48 | 98 |
| 4-50 | 99 |
| 4-55 | 09 |
| 4-60 | 96 |
| 4-77 | 97 |
| 4-78 | 97 |
| 4-81 | 97 |
| 4-82 | 96 |
| 5-3 | 99 |
| 5-5 | 95 |
| 6-2 | 96 |
| 6-3 | 96 |
| 6-5 | 97 |
| 7-1 | 99 |
| 7-3 | 100 |

Tables 8-1 to 8-3 show that Compound (I) exhibits cytostatic activities on the human acute myeloid leukemia cell lines MV-4-11.

Compound (I) or a pharmaceutically acceptable salt thereof may be used as it is or in various pharmaceutical forms depending upon the pharmacological effect, purpose of administration, and the like. A pharmaceutical composition of the present invention can be manufactured by uniform mixing of Compound (I) or a pharmaceutically acceptable salt thereof in an amount which is effective as an active ingredient with pharmaceutically acceptable carriers. These carriers can have forms in a wide range according to desired dosage form for administration. It is preferred that the pharmaceutical composition is in a unit dosage form for oral administration or parental administration such as injection.

In the manufacture of tablets, excipient such as lactose and mannitol, disintegrator such as starch, lubricant such as magnesium stearate, binder such as polyvinyl alcohol and hydroxypropyl cellulose, and surfactant such as sucrose fatty acid esters and sorbitol fatty acid esters, and the like may be used by a conventional procedure. Tablets containing 1 to 200 mg of an active ingredient per tablet are preferred.

In the manufacture of injections, water, physiological saline, vegetable oil such as olive oil and peanut oil, solvent such as ethyl oleate and propylene glycol, dissolving agent such as sodium benzoate, sodium salicylate and urethane, isotonizing agent such as sodium chloride and glucose, preservative such as phenol, cresol, p-hydroxybenzoate and chlorobutanol, and antioxidant such as ascorbic acid and sodium pyrosulfite, and the like may be used by a conventional procedure.

Compound (I) or a pharmaceutically acceptable salt thereof can be administered either orally or parentally by means of injection solution, and the like. The effective dose and frequency of administration vary depending on the dosage form, age, body weight and symptom of a patient, and the like. In general, Compound (I) or a pharmaceutically acceptable salt thereof may preferably be administered in an amount of 0.01 to 100 mg/kg per day.

The present invention will be illustrated in further detail with examples and reference examples below which by no means limit the scope of the present invention. Here, the compound numbers in the examples and reference examples below correspond to the compound numbers mentioned in Tables 1 to 7.

The physicochemical data of each compounds in the examples and the reference examples below are measured using following equipments.

$^1$H NMR: JEOL JNM-EX270 (270 MHz) or JEOL JNM-GX270 (270 MHz) MS: Micromass LCT or Micromass Quatro (measured by APCI method or ESI method)

Reference Example 1

Synthesis of 2-methylthio-4-n-propylaminopyrimidine-5-carbohydrazide [Compound (E) in which $R^1$ is n-propylamino]

Step 1

Commercially available ethyl 4-chloro-2-methylthiopyrimidine-5-carboxylate (25.0 g) was dissolved in THF (430 mL), then n-propylamine (10.6 mL) and triethylamine (30.1 mL) were added thereto, followed by stirring at room temperature for 12 hours. After completion of the reaction was confirmed by thin-layer chromatography, water was added to the reaction mixture, and the resulting mixture was separated into organic layer and aqueous layer. The aqueous layer was extracted with ethyl acetate and the extract was combined with the organic layer. The organic layer was washed with saturated brine and dried over anhydrous sodium sulfate, and then the solvent was evaporated under reduced pressure to give crude ethyl 2-methylthio-4-n-propylaminopyrimidine-5-carboxylate.

Subsequently, the crude product was dissolved in ethanol (360 mL) and THF (180 mL), then an aqueous sodium hydroxide solution (3 mol/L, 360 mL) was added thereto, followed by stirring at room temperature for 12 hours. After completion of the reaction was confirmed by thin-layer chromatography, water was added to the reaction mixture, and the resulting mixture was acidified with hydrochloric acid to pH 4. Precipitated crystals were collected by filtration and the resulting crystals were washed with water and dried thoroughly under reduced pressure to give 2-methylthio-4-n-propylaminopyrimidine-5-carboxylic acid (22.6 g, yield 92%).

Step 2

2-Methylthio-4-n-propylaminopyrimidine-5-carboxylic acid (22.6 g) obtained in Step 1 was dissolved in THF (360 mL), then carbonyldiimidazole (16.9 g) was added thereto, followed by stirring at room temperature for 1.5 hours. Then, a THF (100 mL) solution of hydrazine monohydrate (14.5 mL) was added dropwise to the reaction mixture over 30 minutes, followed by stirring at room temperature for 2.5 hours. After completion of the reaction was confirmed by thin-layer chromatography, water was added to the reaction mixture. Precipitated crystals were collected by filtration and the resulting crystals were washed with water and dried thoroughly under reduced pressure to give 2-methylthio-4-n-propylaminopyrimidine-5-carbohydrazide (20.1 g, yield 84%).

Reference Example 2

Synthesis of 4-methylamino-2-methylthiopyrimidine-5-carbohydrazide [Compound (E) in which $R^1$ is methylamino]

Commercially available ethyl 4-chloro-2-methylthiopyrimidine-5-carboxylate (9.70 g) was reacted with methylamine in a similar manner to the second stage in Step 1 of Reference Example 1. The reaction mixture was purified by silica gel chromatography (chloroform/methanol) to give ethyl 4-methylamino-2-methylthiopyrimidine-5-carboxylate (8.37 g, yield 88%). Subsequently, the resulting compound was treated in a similar manner to Steps 1 and 2 of Reference Example 1 to give 4-methylamino-2-methylthiopyrimidine-5-carbohydrazide (5.78 g, yield 74%).

ESI m/z: 214 [M+H]$^+$; $^1$H NMR (DMSO-$d_6$) δ (ppm): 2.46 (s, 3H), 2.93 (d, J=4.8 Hz, 3H), 3.32 (br s, 1H), 4.46 (br s, 2H), 8.59 (br d, J=4.8 Hz, 1H), 9.75 (br s, 1H).

Reference Example 3

Synthesis of 4-chloro-5-(5-cyclopropyl[1,3,4]oxadiazol-2-yl)-2-methylthiopyrimidine [Compound (AC) in which Q is a Chlorine Atom, $R^{2B}$ Represents methylthio, and —X—Y—Z— is —O—C(c-$C_3H_5$) =N— (wherein c-$C_3H_5$ is cyclopropyl)]

Step 1

Ethyl 4-hydroxy-2-methylthiopyrimidine-5-carboxylate [Compound (A-ii)] (6.70 g) obtained by a method described in the literature [Journal of Heterocyclic Chemistry, vol. 38, p. 93 (2001)] was dissolved in THF (300 mL), then triphenylphosphine (16.5 g), 2-(trimethylsilyl)ethanol (9.0 mL), and DEAD (10.9 g) were added thereto, followed by stirring at room temperature for 12 hours. After completion of the reaction was confirmed by thin-layer chromatography, the reaction mixture was concentrated under reduced pressure, and the residue was purified by silica gel chromatography to give ethyl 2-methylthio-4-(2-trimethylsilylethoxy)pyrimidine-5-carboxylate [Compound (C) in which $R^1$ is 2-trimethylsilylethoxy](4.14 g, yield 42%).

Step 2

The ethyl 2-methylthio-4-(2-trimethylsilylethoxy)pyrimidine-5-carboxylate (4.14 g) obtained in Step 1 was dissolved in ethanol (200 mL), then an aqueous sodium hydroxide solution (2.0 mol/L, 13 mL) was added thereto, followed by stirring at room temperature for 12 hours. After completion of the reaction was confirmed by thin-layer chromatography, water was added to the reaction mixture, and the resulting mixture was acidified with hydrochloric acid to pH 4. Precipitated crystals were collected by filtration and the resulting crystals were washed with water and dried thoroughly under reduced pressure to give 2-methylthio-4-(2-trimethylsilylethoxy)pyrimidine-5-carboxylic acid [Compound (D) in which $R^1$ is 2-trimethylsilylethoxy] (3.52 g, yield 89%).

Step 3

2-Methylthio-4-(2-trimethylsilylethoxy)pyrimidine-5-carboxylic acid (9.73 g) obtained in Step 2 was dissolved in THF (100 mL), carbonyldiimidazole (5.5 g) was added thereto, followed by stirring at room temperature for 1.5 hours. Then, hydrazine monohydrate (4.70 mL) was added dropwise to the reaction mixture, and the resulting mixture was stirred at room temperature for 2.5 hours. After completion of the reaction was confirmed by thin-layer chromatography, water was added to the reaction mixture, followed by extraction with ethyl acetate. The organic layer was sequentially washed with a saturated aqueous sodium hydrogencarbonate solution and saturated brine, and dried over anhydrous magnesium sulfate. The solvent was evaporated under reduced pressure, and the mixture was dried under reduced pressure to give crude 2-methylthio-4-(2-trimethylsilylethoxy)pyrimidine-5-carbohydrazide [Compound (E) in which $R^1$ is 2-trimethylsilylethoxy].

Step 4

The total amount of crude 2-methylthio-4-(2-trimethylsilylethoxy)pyrimidine-5-carbohydrazide obtained in Step 3 was dissolved in chloroform (150 mL), a saturated aqueous sodium hydrogencarbonate solution (150 mL) was added thereto, and then cyclopropanecarbonyl chloride (7.0 mL) was added thereto under ice cooling. The temperature of the reaction mixture was raised to room temperature, and the mixture was stirred for 12 hours. After completion of the reaction was confirmed by thin-layer chromatography, the reaction mixture was separated into organic layer and aqueous layer. The aqueous layer was extracted with dichloromethane and the extract was combined with the organic layer. The organic layer was washed sequentially with water and saturated brine and dried over anhydrous magnesium sulfate. The solvent was evaporated under reduced pressure, and diethyl ether was added to the residue to precipitate crystals. The resulting crystals were collected by filtration and dried thoroughly under reduced pressure to give N'-cyclopropanecarbonyl-2-methylthio-4-(2-trimethylsilylethoxy)pyrimidine-5-carbohydrazide [Compound (G) in which $R^1$ is 2-trimethylsilylethoxy, and $R^{3B}$ represents cyclopropyl] (9.27 g, yield 78%).

Step 5

N'-cyclopropanecarbonyl-2-methylthio-4-(2-trimethylsilylethoxy)pyrimidine-5-carbohydrazide (9.27 g) obtained in Step 4 was dissolved in acetonitrile (250 mL), and triphenylphosphine (7.90 g) and triethylamine (7.0 mL) were added thereto. The mixture was stirred at 40° C. for 1 hour. Then, carbon tetrachloride (4.7 g) was added, and the mixture was stirred at 40° C. for 3 hours. After completion of the reaction was confirmed by thin-layer chromatography, the reaction mixture was concentrated under reduced pressure, and the residue was purified by silica gel chromatography. The fraction of the desired product was collected, and the solvent was evaporated under reduced pressure. Diethyl ether was added to the residue to precipitate crystals. The resulting crystals were collected by filtration and dried thoroughly under reduced pressure to give 5-(5-cyclopropyl[1,3,4]oxadiazol-2-yl)-4-(2-trimethylsilylethoxy)-2-methylthiopyrimidine [Compound (AA) in which —X—Y—Z— is —O—C(c-$C_3H_5$)=N—] (5.18 g, yield 59%).

Step 6

5-(5-Cyclopropyl[1,3,4]oxadiazol-2-yl)-4-(2-trimethylsilylethoxy)-2-methylthiopyrimidine (10.0 g) obtained in Step 5 was dissolved in THF (100 mL), and a TBAF-THF solution (1.0 mol/L, 42.8 mL) was added thereto. The mixture was stirred at room temperature for 12 hours. After completion of the reaction was confirmed by thin-layer chromatography, the solvent was evaporated under reduced pressure, and the residue was purified by silica gel chromatography. The fraction of the desired product was collected, and the solvent was evaporated under reduced pressure. Diisopropyl ether was added to the residue to precipitate crystals. The resulting crystals were collected by filtration and dried thoroughly under reduced pressure to give 5-(5-cyclopropyl[1,3,4]oxadiazol-2-yl)-4-hydroxy-2-methylthiopyrimidine [Compound (AB) in which —X—Y—Z— represents —O—C(c-$C_3H_5$)=N—, and $R^{2B}$ is methylthio] (6.26 g, yield 88%).

Step 7

Phosphorus oxychloride (15 mL) was added to 5-(5-cyclopropyl[1,3,4]oxadiazol-2-yl)-4-hydroxy-2-methylthiopyrimidine (6.26 g) obtained in Step 6, and the mixture was stirred at 60° C. for 30 minutes. After completion of the reaction was confirmed by thin-layer chromatography, the reaction mixture was added to a saturated aqueous sodium hydrogencarbonate solution, and the resulting mixture was extracted with ethyl acetate. The organic layer was washed with saturated brine and dried over anhydrous magnesium sulfate, and then the solvent was evaporated under reduced pressure. Diethyl ether was added to the residue to precipitate crystals. The resulting crystals were collected by filtration and dried thoroughly under reduced pressure to give 4-chloro-5-(5-cyclopropyl[1,3,4]oxadiazol-2-yl)-2-methylthiopyrimidine (5.31 g, yield 79%).

ESI m/z: 269 [M+H]$^+$; $^1$H NMR (CDCl$_3$) δ (ppm): 1.24 (d, J=6.9 Hz, 4H), 2.27 (quintet, J=6.9 Hz, 1H), 2.63 (s, 3H), 9.02 (s, 1H).

Reference Example 4

Synthesis of 4-chloro-5-cyano-2-methylthiopyrimidine [Compound (V)]

Step 1

Methylisothiourea sulfate [Compound (T)] (90.5 g, 0.325 mmol) was dissolved in an aqueous sodium hydroxide solution (2 mol/L, 325 mL), then an ethanol solution (350 mL) of ethyl 2-ethoxymethylene-2-cyanoacetate [Compound (S)] (100 g, 0.591 mmol) was gradually added dropwise thereto under ice-cooling to avoid the internal temperature to raise over 15° C. After addition of all the ethanol solution, an aqueous sodium hydroxide solution (2 mol/L, 300 mL) was gradually added to the mixture, and ethanol (150 mL) was further added thereto. The resulting mixture was stirred overnight at room temperature. After completion of the reaction was confirmed by thin-layer chromatography, precipitated crystals were collected by filtration and washed with ethanol (500 mL). The resulting white crystals were dried under reduced pressure to give 5-cyano-3,4-dihydro-2-methylthiopyrimidin-4-one [Compound (U)] (113.3 g, yield 100%).

Step 2

Phosphorus oxychloride (150 mL) was added to 5-cyano-3,4-dihydro-2-methylthiopyrimidin-4-one (30.0 g, 0.159 mmol) obtained in Step 1, and the mixture was heated under reflux for 7 hours. The reaction mixture was left to stand to cool, and then phosphorus oxychloride was evaporated under reduced pressure. The residue was poured into ice water (about 1,000 mL), and the precipitated light yellow solid was collected by filtration and washed with water. The resulting solid was dried under reduced pressure to give 4-chloro-5-cyano-2-methylthiopyrimidine (11.9 g, yield 40%).

Reference Example 5

Synthesis of 5-(5-acetoxymethyl[1,3,4]oxadiazol-2-yl)-2-methylthio-4-(2-trimethylsilylethoxy)pyrimidine [Compound (AA) in which —X—Y—Z— is —O—C(CH$_2$OCOCH$_3$)=N—]

Step 1

2-Methylthio-4-(2-trimethylsilylethoxy)pyrimidine-5-carbohydrazide [Compound (E) in which $R^1$ represents 2-trimethylsilylethoxy] (1.00 g, 3.33 mmol) obtained in Step 3 of Reference Example 3 was dissolved in chloroform (10 mL), and a saturated aqueous sodium hydrogencarbonate solution (10 mL) was added thereto. While stirring the mixture under ice-cooling, a chloroform (10 mL) solution of methyl chlorocarbonylacetate (0.477 g, 3.50 mmol) was added to the mixture, and was stirred at the same temperature for 1 hour. After completion of the reaction was confirmed by thin-layer chromatography, the reaction mixture was separated into organic layer and aqueous layer. The aqueous layer was extracted with chloroform and the extract was combined with the organic layer. The organic layer was washed with saturated brine and dried over anhydrous magnesium sulfate, and then the solvent was evaporated under reduced pressure to give crude N'-acetoxymethylcarbonyl-2-methylthio-4-(2-trimethylsilylethoxy)pyrimidine-5-carbohydrazide [Compound (G) in which $R^1$ is 2-trimethylsilylethoxy, and $R^{3B}$ represents acetoxymethyl].

Step 2

The total amount of the N'-acetoxymethylcarbonyl-2-methylthio-4-(2-trimethylsilylethoxy)pyrimidine-5-carbohydrazide, the crude product, obtained in Step 1 was dissolved in acetonitrile (30 mL), then triphenylphosphine (1.31 g, 5.00 mmol), carbon tetrachloride (2.05 g, 13.3 mmol), and triethylamine (0.67 g, 6.66 mmol) were added thereto, followed by stirring at room temperature for 12 hours. After completion of the reaction was confirmed by thin-layer chromatography, the reaction mixture was concentrated under reduced pressure, and the residue was purified by silica gel chromatography (chloroform/methanol) to give the title compound (1.00 g, overall yield in two steps 79%).

Reference Example 6

Synthesis of 4-(2-aminoethyl)pyridine-N-oxide Used for Synthesis of Compounds 1-539, 3-205, 3-206, and 3-210

Step 1

Commercially available 4-(2-aminoethyl)pyridine (5.00 g, 40.9 mmol) was dissolved in THF (200 mL), then di-tert-butyl dicarbonate (8.93 g, 40.9 mmol) was added thereto, followed by stirring at room temperature for 3 hours. The reaction mixture was concentrated under reduced pressure to give 4-[2-(N-tert-butoxycarbonyl)aminoethyl]pyridine (9.07 g, quantitative yield). This compound was used in the subsequent reaction without purification.

Step 2

4-[2-(N-tert-butoxycarbonyl)aminoethyl]pyridine (0.222 g, 1.00 mmol) obtained in Step 1 was dissolved in dichloromethane (2.00 mL), then methyltrioxorhenium (VII) (0.001 g, 0.005 mmol) and 30% aqueous hydrogen peroxide (1.00 mL) were added thereto, followed by stirring at room temperature for 2 hours. After completion of the reaction was confirmed by thin-layer chromatography, water was added to the reaction mixture, and the resulting mixture was extracted with dichloromethane. The organic layer was dried over anhydrous magnesium sulfate, and then the solvent was evaporated under reduced pressure to give 4-[2-(N-tertbutoxycarbonyl)aminoethyl]pyridine-N-oxide (0.153 g, yield 64%).

Step 3

4-[2-(N-tert-butoxycarbonyl)aminoethyl]pyridine-N-oxide (572 mg, 2.40 mmol) was dissolved in dichloromethane (10.0 mL), then trifluoroacetic acid (2.00 mL) was added thereto, followed by stirring at room temperature for 1 hour. After completion of the reaction was confirmed by thin-layer chromatography, the reaction mixture was concentrated under reduced pressure to give a trifluoroacetate of 4-(2-aminoethyl)pyridine-N-oxide (quantitative yield).

Reference Example 7

Synthesis of 3-(2-aminoethyl)pyridine-N-oxide Used for Synthesis of Compounds 3-202, 3-203, and 3-209

3-(2-Aminoethyl)pyridine-N-oxide was synthesized from 3-(2-aminoethyl)pyridine according to the method described in Reference Example 6.

Reference Example 8

Synthesis of N-tert-butoxycarbonyl-2-(4-aminophenyl)ethylamine Used for Synthesis of Compounds 3-234, 3-235, and 3-236

Commercially available 2-(4-aminophenyl)ethylamine (14.2 g, 0.104 mol) was dissolved in dichloromethane (400 mL), then a dichloromethane solution (100 mL) of di-tert-butyl dicarbonate (24.0 g, 0.110 mol) was added thereto under ice-cooling, followed by stirring at the same temperature for 30 minutes. After completion of the reaction was confirmed by thin-layer chromatography, Chromatorex (NH, DM1020, 100 g, manufactured by Fuji Silysia Chemical Ltd.) was added thereto, and the mixture was stirred at room temperature for 1 hour. Subsequently, the reaction mixture was filtered, and the filtrate was concentrated under reduced pressure to give N-tertbutoxycarbonyl-2-(4-aminophenyl)ethylamine (22.8 g, yield 93%).

Reference Example 9

Synthesis of N-substituted-2-(4-aminophenyl)ethylamine Used for Synthesis of Compounds 3-207, 3-208, 3-211 to 3-214, 3-216, and 3-217

N-tert-butoxycarbonyl-2-(4-aminophenyl)ethylamine (0.024 g, 0.102 mmol) obtained in Reference Example 8 was dissolved in THF (0.400 mL), then N,N'-diisopropylaminomethyl polystyrene (2% divinylbenzene copolymer, about 3.90 mmol/g, 77 mg, Argonaut Technology Ltd.) and a chloroform solution (1.00 mol/L, 0.130 mL, 0.130 mmol) of acid chloride, sulfonyl chloride, or chloroformate were added thereto, followed by stirring at room temperature for 1 hour. After completion of the reaction was confirmed by thin-layer chromatography, tris(2-aminoethyl)amine polystyrene (1% divinylbenzene copolymer, about 3.4 mmol/g, 44 mg, Novabiochem Corp.) was added thereto, followed by stirring at room temperature for 12 hours. Subsequently, the resins were filtered off, then the filtrate was concentrated and dried to obtain title compound group.

Reference Example 10

Synthesis of 4-(2-aminoethyl)pyridine-2-carbonitrile dihydrochloride Used for Synthesis of Compounds 3-204 and 3-218

Step 1

Commercially available 4-(2-hydroxyethyl)pyridine (10.0 g, 81.2 mmol) was dissolved in dichloromethane (400 mL), then 2,6-lutidine (26.1 g, 244 mmol) and chloro-tert-butyldimethylsilane (32.0 g, 121 mmol) were added thereto, followed by stirring at room temperature for 3 hours. After completion of the reaction was confirmed by thin-layer chromatography, water was added to the reaction mixture, and the resulting mixture was separated into organic layer and aqueous layer. The organic layer was dried over anhydrous magnesium sulfate, then the solvent was evaporated under reduced pressure to give 4-[2-(tert-butyldimethylsiloxy)ethyl]pyridine (19.2 g, quantitative yield).

Step 2

4-[2-(tert-Butyldimethylsiloxy)ethyl]pyridine (0.222 g, 1.00 mmol) obtained in Step 1 was dissolved in dichloromethane (2.00 mL), then methyltrioxorhenium (VII) (0.001 g, 0.005 mmol) and 30% aqueous hydrogen peroxide (1.00 mL) were added thereto, followed by stirring at room temperature for 2 hours. After completion of the reaction was confirmed by thin-layer chromatography, water was added to the reaction mixture, and the resulting mixture was extracted with dichloromethane. The organic layer was dried over anhydrous magnesium sulfate, and then the solvent was evaporated under reduced pressure to give 4-[2-(tert-butyldimethylsiloxy)ethyl]pyridine-N-oxide (0.153 g, yield 64%).

Step 3

4-[2-(tert-Butyldimethylsiloxy)ethyl]pyridine-N-oxide (12.5 g, 49.3 mmol) was dissolved in dichloromethane (100 mL), then trimethylsilyl cyanide (5.31 g, 53.5 mmol) was added thereto at room temperature, and dimethylcarbamoyl chloride (5.76 g, 53.5 mmol) was added thereto over 30 minutes. Then, the mixture was stirred for 24 hours. After completion of the reaction was confirmed by thin-layer chromatography, a 10% aqueous potassium carbonate solution (150 mL) was added to the mixture, and the mixture was further stirred for 10 minutes. The reaction mixture was extracted with dichloromethane. The organic layer was dried over anhydrous magnesium sulfate, and then the solvent was evaporated under reduced pressure to give 4-[2-(tert-butyldimethylsiloxy)ethyl]pyridine-2-carbonitrile (12.5 g, yield 97%).

Step 4

4-[2-(tert-Butyldimethylsiloxy)ethyl]pyridine-2-carbonitrile (6.5 g, 24.8 mmol) obtained in Step 3 was dissolved in THF (100 mL), then a TBAF-THF solution (1.00 mol/L, 49.6 mL, 49.6 mmol) was added thereto, followed by stirring at room temperature for 10 hours. After completion of the reaction was confirmed by thin-layer chromatography, the reaction mixture was concentrated under reduced pressure. The concentrate was diluted with ethyl acetate, water was added thereto, and the mixture was separated into organic layer and aqueous layer. The organic layer was dried over anhydrous magnesium sulfate, and then the solvent was evaporated under reduced pressure. The residue was purified by silica gel column chromatography (ethyl acetate) to give 4-(2-hydroxyethyl)pyridine-2-carbonitrile (2.53 g, yield 69%).

Step 5

4-(2-Hydroxyethyl)pyridine-2-carbonitrile (2.53 g, 17.1 mmol) obtained in Step 4 was dissolved in THF (40.0 mL), then phthalimide (3.02 g, 20.5 mmol), triphenylphosphine (5.38 g, 20.5 mmol), and a DEAD-toluene solution (40.0%, 8.93 g, 20.5 mmol) were added thereto, followed by stirring at room temperature for 1 hour. After completion of the reaction was confirmed by thin-layer chromatography, the reaction mixture was concentrated under reduced pressure. Diethyl ether was added to the residue, and the resulting precipitate was collected by filtration. Ethanol (200 mL) and hydrazine monohydrate (2.57 g, 51.3 mmol) were added to the resulting solid, and the mixture was stirred at 70° C. for 2 hours. After the resulting precipitate was collected by filtration, the filtrate was concentrated under reduced pressure, and a further precipitate was collected by filtration. A hydrogen chloride-ethyl acetate solution (4.00 mol/L, 50.0 mL, 200 mmol) was added to the filtrate, and precipitated crystals were collected by filtration to give 4-(2-aminoethyl)pyridine-2-carbonitrile dihydrochloride (2.05 g, yield 55%).

Reference Example 11

Synthesis of 4-(2-aminoethyl)-2-methylpyridine dihydrochloride Used for Synthesis of Compounds 3-223, 3-227, 3-228, 3-232, and 4-23

Step 1

An LDA-THF solution (2.00 mol/L, 65.0 mL, 130 mmol) was cooled to −78° C., then a THF solution (50.0 mL) of 2,4-lutidine (10.7 g) was added thereto, followed by stirring for 2 hours. Then, the temperature was raised to 0° C., and a THF solution (50.0 mL) of dimethyl carbonate (11.7 g) was added dropwise to the mixture, followed by stirring for 30 minutes. Water was added to the reaction mixture, and the resulting mixture was concentrated under reduced pressure and extracted with ethyl acetate. The organic layer was dried over anhydrous magnesium sulfate, and then the solvent was evaporated under reduced pressure. The residue was purified by silica gel column chromatography (hexane:ethyl acetate=3:1) to give methyl 2-methylpyridin-4-ylacetate (2.69 g, yield 16%).

Step 2

Methyl 2-methylpyridin-4-ylacetate (1.78 g, 10.8 mmol) obtained in Step 1 was dissolved in THF (70 mL), then Lithium aluminum hydride (451 mg, 11.9 mmol) was added thereto at 0° C., followed by stirring at the same temperature for 1 hour. After completion of the reaction was confirmed by thin-layer chromatography, sodium sulfate decahydrate (3.22 g, 10.0 mmol) was added thereto, and the resulting mixture was further stirred at room temperature for 1 hour. The resulting precipitate was filtered out, and the filtrate was concentrated under reduced pressure. The residue was purified by silica gel column chromatography [chloroform:ammonia-methanol solution (2.00 mol/L)=40:1] to give 4-(2-hydroxyethyl)-2-methylpyridine (900 mg, yield 61%). Subsequently, 4-(2-aminoethyl)-2-methylpyridine dihydrochloride was obtained in a similar manner to Step 5 of Reference Example 9.

Reference Example 12

Synthesis of 4-(2-aminoethyl)-2-methoxypyridine dihydrochloride Used for Synthesis of Compound 3-233

Commercially available 2-chloro-4-methylpyridine (25.5 g, 200 mmol) and a sodium methoxide-methanol solution (28.0%, 77.0 g, 399 mmol) were mixed, and the mixture was heated under reflux for 15 hours. After completion of the reaction was confirmed by thin-layer chromatography, the resulting precipitate was filtered out, and the filtrate was concentrated under reduced pressure. Water was added to the residue, and the resulting mixture was extracted with dichloromethane. The organic layer was dried over anhydrous magnesium sulfate, and the solvent was, evaporated under reduced pressure to give 2-methoxy-4-methylpyridine (18.4 g, yield 75%).

An LDA-THF solution (2.00 mol/L, 2.00 mL, 4.00 mmol) was cooled to −78° C., and a THF solution (2.00 mL) of the compound (369 mg, 3.00 mmol) obtained in the step described above was added thereto, followed by stirring for 30 minutes. Then, a THF solution (2.00 mL) of dimethyl carbonate (297 mg, 3.30 mmol) was added to the mixture, and the temperature was raised to 0° C. over 2 hours. Water was added to the reaction mixture, and the resulting mixture was concentrated under reduced pressure and extracted with ethyl acetate. The organic layer was dried over anhydrous magnesium sulfate, and then the solvent was evaporated under reduced pressure. The residue was purified by silica gel column chromatography (ethyl acetate) to give methyl 2-methoxypyridin-4-ylacetate (60.0 mg, yield 11%). Subsequently, 4-(2-aminoethyl)-2-methoxypyridine dihydrochloride was obtained in a similar manner to Step 2 of Reference Example 11 and Step 5 of Reference Example 10.

Reference Example 13

Synthesis of 4-(2-aminoethyl)-2-hydroxypyridine dihydrobromide Used for Synthesis of Compound 3-242

4-(2-Aminoethyl)-2-methoxypyridine dihydrochloride (225 mg, 1.00 mmol) synthesized in Reference Example 12 was mixed with 48% hydrobromic acid (3.0 mL) and acetic acid (3.0 mL), and the mixture was heated under reflux for 4 hours. The reaction mixture was concentrated under reduced pressure to give 4-(2-aminoethyl)-2-hydroxypyridine dihydrobromide (150 mg, yield 50%).

Reference Example 14

Synthesis of 2-methyl-4-(2-aminoethyl)phenol hydrochloride Used for Synthesis of Compound 3-237

Commercially available 3-methyl-4-hydroxybenzaldehyde (1.00 g, 7.34 mmol), ammonium acetate (850 mg, 11.0 mmol), and nitromethane (7.00 mL) were mixed, and the mixture was stirred at 45° C. for 5 hours. Then, the reaction mixture was filtered through Celite, and the filtrate was concentrated under reduced pressure to give 2-methyl-4-(2-nitrovinyl)phenol (1.05 g, yield 80%). This compound (1.05 g, 5.86 mmol) was dissolved in THF (30.0 mL), then lithium aluminum hydride (642 mg, 16.9 mmol) was added thereto, followed by stirring at room temperature for 30 minutes. Subsequently, sodium sulfate decahydrate (5.45 g, 16.9 mmol) was added to the reaction mixture, and the resulting mixture was stirred at room temperature for 30 minutes. The resulting precipitate was filtered out, and the filtrate was concentrated under reduced pressure. A hydrogen chloride-ethyl acetate solution (4.00 mol/L, 10.0 mL, 40.0 mmol) was added thereto, and precipitated crystals were collected by filtration to give 2-methyl-4-(2-aminoethyl)phenol hydrochloride (188 mg, yield 17%).

Reference Example 15

Synthesis of 2,6-dimethyl-4-(2-aminoethyl)phenol hydrochloride Used for Synthesis of Compound 3-240

Commercially available 3,5-dimethyl-4-hydroxybenzaldehyde (1.50 g, 10.0 mmol), ammonium acetate (850 mg, 11.0 mmol), and nitromethane (7.00 mL) were mixed, and the mixture was stirred at 45° C. for 5 hours. Then, the reaction mixture was filtered through Celite, and the filtrate was concentrated under reduced pressure to give 2,6-dimethyl-4-(2-nitrovinyl)phenol (1.82 g, yield 94%). This compound (1.82 g, 9.42 mmol) was dissolved in THF (60.0 mL), then lithium aluminum hydride (1.14 g, 30.0 mmol) was added thereto, followed by stirring at room temperature for 30 minutes. Subsequently, sodium sulfate decahydrate (9.67 g, 30.0 mmol) was added to the reaction mixture, and the resulting mixture was stirred at room temperature for 30 minutes. The resulting precipitate was filtered out, and the filtrate was concentrated under reduced pressure. A hydrogen chloride-ethyl acetate solution (4.00 mol/L, 10.0 mL, 40.0 mmol) was added thereto, and precipitated crystals were collected by filtration to give 2,6-dimethyl-4-(2-aminoethyl)phenol hydrochloride (477 mg, yield 25%).

Reference Example 16

Synthesis of 1-amino-3-fluoropropane hydrobromide Used for Synthesis of Compound 3-241

An ammonia-methanol solution (7.00 mol/L, 20.0 mL, 140 mmol) was added to commercially available 3-bromo-1-fluoropropane (4.65 g, 30.0 mmol), followed by stirring at room temperature for 12 hours. Then, the reaction mixture was concentrated under reduced pressure to give 1-amino-3-fluoropropane hydrobromide (2.32 g, yield 49%). This compound was used in the subsequent reaction without purification.

Example 1

Synthesis of Compound 1-1 to Compound 1-539

Step 1

2-Methylthio-4-n-propylaminopyrimidine-5-carbohydrazide (12 mg, 0.050 mmol) [Compound (E) in which $R^1$ is n-propylamino] obtained in Reference Example 1 was dissolved in THF (0.60 mL), then a chloroform solution (1.0 mol/L, 0.070 mL) of Compound (F) in which V represents —COCl or —CO$_2$COR$^{3B}$ (wherein R$^{3B}$ has the same definition as described above) and morpholinomethyl polystyrene (42 mg) were added thereto, followed by stirring at room temperature for 5 hours with hermetic sealing. After completion of the reaction was confirmed by thin-layer chromatography, tris(2-aminomethyl)amine polystyrene (44 mg) was added to the reaction mixture, followed by stirring at room temperature for 12 hours. The resins were filtered off from the reaction mixture, and the filtrate was concentrated and dried to give 2-methylthio-4-propylaminopyrimidine-5-carboxylic acid N'-substituted hydrazide [Compound (G) in which $R^1$ is n-propylamino].

Step 2

The total amount of 2-methylthio-4-propylaminopyrimidine-5-carboxylic acid N'-substituted hydrazide obtained in Step 1 was dissolved in dichloromethane (0.40 mL), then a triethylamine-dichloromethane solution (1.0 mol/L, 0.15 mL), a carbon tetrachloride-dichloromethane solution (1.0 mol/L, 0.50 mL), and triphenylphosphine polystyrene (45 mg) were added thereto, followed by stirring at room temperature for 12 hours with hermetic sealing. After completion of the reaction was confirmed by thin-layer chromatography, the resin was filtered off from the reaction mixture, and the filtrate was concentrated and dried. The residue was purified by silica gel chromatography to give 4-propylamino-5-(5-substituted [1,3,4]oxadiazol-2-yl)-2-methylthiopyrimidine [Compound (H) in which $R^1$ is n-propylamino].

Step 3

The total amount of 4-propylamino-5-(5-substituted [1,3,4]oxadiazol-2-yl)-2-methylthiopyrimidine obtained in Step 2 was dissolved in dichloromethane (0.30 mL), then an mCPBA-dichloromethane solution (0.50 mol/L, 0.175 mL) was added thereto, followed by stirring at room temperature for 1 hour with hermetic sealing. After completion of the reaction was confirmed by thin-layer chromatography, a saturated aqueous sodium hydrogencarbonate solution was added to the reaction mixture, and the resulting mixture was separated into organic layer and aqueous layer. The organic layer was washed with water, dried over anhydrous sodium sulfate, and then concentrated and dried to give a mixture of sulfoxide at position 2 and sulfone at position 2 [Compound (J) in which $R^1$ is n-propylamino].

Step 4

The total amount of the mixture obtained in Step 3 was dissolved in THF (0.30 mL), then a chloroform solution (1.0 mol/L, 0.090 mL) of Compound (K) was added thereto, followed by stirring at 60° C. for 24 hours with hermetic sealing. After completion of the reaction was confirmed by thin-layer chromatography, chloroform (0.40 mL), benzoyl chloride polymer-bound [about 2.5 mmol/g, 23 mg, Canadian Journal of Chemistry, vol. 55, p. 3351 (1977)], and poly(4-vinylpyridine) (23 mg) were added to the reaction mixture, followed by further stirring at room temperature for 12 hours. The resin was filtered off from the reaction mixture, and the filtrate was concentrated and dried to give Compounds 1-1 to 1-539 (average overall yield from 4-n-propylamino-2-methylthiopyrimidine-5-carbohydrazide: about 70%).

Example 2

Synthesis of Compound 2-1 to Compound 2-82

Compounds 2-1 to 2-82 were obtained by treating 4-methylamino-2-methylthiopyrimidine-5-carbohydrazide (11 mg, 0.050 mmol) [Compound (E) in which $R^1$ is methylamino] obtained in Reference Example 2, in a similar manner to the each steps of Example 1 (average overall yield from 4-methylamino-2-methylthiopyrimidine-5-carbohydrazide: about 70%).

Example 3

Synthesis of Compound 3-1 to Compound 3-90, Compounds 3-202, 3-204, and 3-205, Compound 3-207 to Compound 3-214, Compounds 3-219 and 3-220, Compound 3-222, Compound 3-227, Compound 3-228, Compound 3-231, Compound 3-232, Compound 3-235, Compound 3-236, Compound 3-238, and Compound 3-241

Step 1

4-Chloro-5-(5-cyclopropyl[1,3,4]oxadiazol-2-yl)-2-methylthiopyrimidine (13 mg, 0.050 mmol) [Compound (AC) in which Q is a chlorine atom, $R^{2B}$ is methylthio, and —X—Y—Z— is —O—C(c-$C_3H_5$)=N—] obtained in Reference Example 3 was dissolved in THF (0.50 mL), then triethylamine (0.007 mL) and a chloroform solution (1.0 mol/L, 0.10 mL) of $R^1$—H [wherein $R^1$ is the same as that defined above: Compound (B)] were added thereto, followed by stirring at 60° C. for 12 hours with hermetic sealing. After completion of the reaction was confirmed by thin-layer chromatography, the reaction mixture was concentrated and dried. The residue was dissolved in chloroform (0.60 mL), then benzoyl chloride polymer-bound [about 2.5 mmol/g, 23 mg, Canadian Journal of Chemistry, vol. 55, p. 3351 (1977)], and poly(4-vinylpyridine) (23 mg) were added thereto, followed by further stirring at room temperature for 12 hours. The resin was filtered off from the reaction mixture, and the filtrate was concentrated and dried to give 4-amino-5-(5-cyclopropyl[1,3,4]oxadiazol-2-yl)-2-methylthiopyrimidine [Compound (AD) in which —X—Y—Z— is —O—C(c-$C_3H_5$)=N—].

Steps 2 and 3

The title compounds were each obtained from the compounds obtained in Step 1, in a similar manner to Steps 3 and 4 of Example 1.

Example 4

Synthesis of Compound 3-91 to Compound 3-201, Compounds 3-203 and 3-206, Compound 3-215 to Compound 3-218, Compound 3-221, Compound 3-223 to Compound 3-226, Compound 3-229, Compound 3-230, Compound 3-233, Compound 3-234, Compound 3-237, Compound 3-239, Compound 3-240, and Compound 3-242

Step 1

4-Chloro-5-(5-cyclopropyl[1,3,4]oxadiazol-2-yl)-2-methylthiopyrimidine (13 mg, 0.050 mmol) [Compound (AC) in which Q is a chlorine atom, $R^{2B}$ is methylthio, and —X—Y—Z— is —O—C(c-$C_3H_5$)=N—] obtained in Reference Example 3 was dissolved in THF (0.50 mL), then triethylamine (0.007 mL) and a chloroform solution (1.0 mol/L, 0.20 mL) of $R^1$—H [wherein $R^1$ has the same definition as described above: Compound (B)] were added thereto, followed by stirring at 60° C. for 12 hours with hermetic sealing. After completion of the reaction was confirmed by thin-layer chromatography, the reaction mixture was concentrated and dried. The residue was dissolved in chloroform/methanol (chloroform:methanol=3:1, 0.50 mL), then benzoyl chloride polymer-bound [about 2.5 mmol/g, 46 mg, Canadian Journal of Chemistry, vol. 55, p. 3351 (1977)], and poly(4-vinylpyridine) (46 mg) were added thereto, followed by further stirring at room temperature for 12 hours. The resin was filtered off from the reaction mixture, and the filtrate was concentrated and dried to give 4-amino-5-(5-cyclopropyl[1,3,4]oxadiazol-2-yl)-2-methylthiopyrimidine [Compound (AD) in which —X—Y—Z— is —O—C(c-$C_3H_5$)=N—].

Steps 2 and 3

The title compounds were each obtained from the 4-amino-5-(5-cyclopropyl[1,3,4]oxadiazol-2-yl)-2-methylthiopyrimidine obtained in Step 1, in a similar manner to Steps 3 and 4 of Example 1.

Example 5

Synthesis of Compound 4-1

Compound 1-538 (315 mg) obtained in the Example 1 was dissolved in methanol (6.0 mL), then an aqueous sodium hydroxide solution (2.0 mmol/L, 0.59 mL) was added thereto, followed by stirring at room temperature for 20 minutes. After completion of the reaction was confirmed by thin-layer chromatography, the reaction mixture was added with water and the precipitated crystals were collected by filtration. The crystals were fully dried under reduced pressure to give compound 4-1 (264 mg, yield 94%).

Example 6

Synthesis of Compounds 4-4 and 4-9

Each of Compounds 4-4 and 4-9 were obtained in a similar manner to Example 4, using 5-(5-acetoxymethyl[1,3,4]oxadiazol-2-yl)-4-methylamino-2-[2-(4-pyridyl)ethylamino] pyrimidine or 5-(5-acetoxymethyl[1,3,4]oxadiazol-2-yl)-4-(2-methoxyethylamino)-2-[2-(4-pyridyl)ethylamino] pyrimidine synthesized in a similar manner to Example 1.

Example 7

Synthesis of Compound 4-2

Step 1

Compound 4-1 (50.0 mg, 0.14 mmol) obtained in Example 5 was dissolved in dichloromethane (2.0 mL), then triethylamine (0.029 mL, 21 mg) and methanesulfonyl chloride (0.013 mL, 0.17 mmol) were added thereto, followed by stirring at room temperature for 2 hours. After completion of the reaction was confirmed by thin-layer chromatography, the reaction mixture was added with saturated aqueous sodium hydrogen carbonate solution and was extracted with ethyl acetate. The organic layer was washed with saturated brine and dried over anhydrous magnesium sulfate. Then the solvent was evaporated under reduced pressure to give crude product of 5-(5-methanesulfonyloxymethyl[1,3,4]oxadiazol-2-yl)-4-n-propylamino-2-[2-(4-pyridyl)ethylamino]pyrimidine.

Step 2

The total amount of the crude product of 5-(5-methanesulfonyloxymethyl[1,3,4]oxadiazol-2-yl)-4-n-propylamino-2-[2-(4-pyridyl)ethylamino]pyrimidine obtained in Step 1 was dissolved in THF (2.0 mL), then morpholine (0.024 mL, 24 mg) was added thereto, followed by stirring at room temperature for 12 hours. After completion of the reaction was confirmed by thin-layer chromatography, the reaction mixture was concentrated under reduced pressure, and the residue was purified by silica gel column chromatography (chloroform/methanol). The product was crystallized from hexane/ethyl acetate and the obtained crystals were fully dried under reduced pressure to give Compound 4-2 (30.0 mg, 50% yield from Compound 4-1).

Example 8

Synthesis of Compound 4-3, Compound 4-24, Compound 4-26 to Compound 4-31, Compound 4-44 to Compound 4-55, Compound 4-58, Compound 4-59, Compound 4-62, Compound 4-69, Compound 4-70, Compound 4-75 to Compound 4-84

Each of Compound 4-3, Compound 4-24, Compound 4-26 to Compound 4-31 were obtained by reacting the crude product of 5-(5-methanesulfonyloxymethyl[1,3,4]oxadiazol-2-yl)-4-n-propylamino-2-[2-(4-pyridyl)ethylamino]pyrimidine obtained in Step 1 of Example 7 with various amine corresponding to each product in a similar manner to Step 2 of Example 7.

Example 9

Synthesis of Compound 4-5 to Compound 4-8, Compound 4-20 to Compound 4-22, and Compound 4-57

A crude product of 5-(5-methanesulfonyloxymethyl[1,3,4]oxadiazol-2-yl)-4-methylamino-2-[2-(4-pyridyl)ethylamino]pyrimidine was obtained in a similar manner to Step 1 of Example 7 using Compound 4-4 obtained in Example 6. Each of Compound 4-5 to Compound 4-8, and Compound 4-20 to Compound 4-22 were obtained by reacting the crude product with various amine corresponding to each product in a similar manner to Step 2 of Example 7.

Example 10

Synthesis of Compound 4-10 to Compound 4-19

A crude product of 5-(5-methanesulfonyloxymethyl[1,3,4]oxadiazol-2-yl)-4-(2-methoxyethylamino)-2-[2-(4-pyridyl)ethylamino]pyrimidine was obtained in a similar manner to Step 1 of Example 7 using Compound 4-9 obtained in Example 6. Each of Compound 4-10 to Compound 4-19 were obtained by reacting the crude product with various amine corresponding to each product in a similar manner to Step 2 of Example 7.

Example 11

Synthesis of Compound 4-32

Step 1

To 30 mL of dichloromethane, 5-(5-acetoxymethyl[1,3,4]oxadiazol-2-yl)-2-methylthio-4-(2-trimethylsilylethoxy)pyrimidine [Compound (AA) in which —X—Y—Z— represents —O—C(CH$_2$OCOCH$_3$)=N—] (1.00 g, 2.61 mmol) obtained in Reference Example 5 was dissolved, then mCPBA (purity about 65%, 1.04 g) was added to the solution, followed by stirring at room temperature for 30 minutes. After completion of the reaction was confirmed by thin-layer chromatography, saturated aqueous sodium hydrogen carbonate solution was added and the mixture was separated into organic layer and aqueous layer. Further, an aqueous layer was extracted with dichloromethane and those organic layers were combined. The organic layer was washed with saturated aqueous sodium hydrogen carbonate solution, dried over anhydrous magnesium sulfate and then the solvent was evaporated under reduced pressure. The residue was dissolved in THF (30 mL), then 2-(4-pyridyl)ethylamine (351 mg, 2.87 mmol) was added thereto, followed by stirring at room temperature for 12 hours. After completion of the reaction was confirmed by thin-layer chromatography, saturated aqueous sodium hydrogen carbonate solution was added to the reaction mixture and the mixture was extracted with ethyl acetate. An organic layer was washed with saturated brine, dried over anhydrous magnesium sulfate and then the solvent was evaporated under reduced pressure. The residue was purified by silica gel chromatography (chloroform/methanol) to give 5-(5-acetoxymethyl[1,3,4]oxadiazol-2-yl)-2-[2-(4-pyridyl)ethylamino]-4-(2-trimethylsilylethoxy)pyrimidine [Compound (IB-i) in which R$^1$ is 2-trimethylsilylethoxy, and R$^2$ is 2-(4-pyridyl)ethylamino] (1.01 g, yield 85%)

Step 2

To 20 mL of methanol, 5-(5-acetoxymethyl[1,3,4]oxadiazol-2-yl)-2-(2-pyridin-4-yl-ethylamino)-4-[2-(4-pyridyl)ethylamino]pyrimidine (1.00 g, 2.19 mmol) obtained in Step 1 was dissolved, then an aqueous sodium hydroxide solution (2.0 mol/L, 1.64 mL) was added thereto, followed by stirring at room temperature for 1 hour. After completion of the reaction was confirmed by thin-layer chromatography, the reaction mixture was concentrated under reduced pressure, water was added thereto and the mixture was extracted with ethyl acetate. The organic layer was washed with saturated brine, dried over anhydrous magnesium sulfate and then the solvent was evaporated under reduced pressure to give 5-(5-hydroxymethyl[1,3,4]oxadiazol-2-yl)-2-[2-(4-pyridyl)ethylamino]-4-(2-trimethylsilylethoxy)pyrimidine [Compound (IB-ii) in which R$^1$ is 2-trimethylsilylethoxy, and R$^2$ is 2-(4-pyridyl)ethylamino] (0.76 g, yield 84%).

Step 3

To 20 mL of dichloromethane, 5-(5-hydroxymethyl[1,3,4]oxadiazol-2-yl)-2-[2-(4-pyridyl)ethylamino]-4-(2-trimethylsilylethoxy)pyrimidine (0.76 g, 1.83 mmol) obtained in Step 2 was dissolved, then methanesulfonic anhydride (0.48 g, 2.75 mmol) and triethylamine (0.37 g, 3.66 mmol) were added thereto, followed by stirring at room temperature for 1 hour. After completion of the reaction was confirmed by thin-layer chromatography, saturated aqueous sodium hydrogen carbonate solution was added and the reaction mixture was separated. Further, an aqueous layer was extracted with dichloromethane and those organic layers were combined. The organic layer was washed with saturated brine, dried over anhydrous magnesium sulfate and then the solvent was evaporated under reduced pressure. The residue was dissolved in dichloromethane (50 mL), then 1-methylpiperazine (403 mg, 4.03 mmol) was added thereto, followed by stirring at room temperature for 12 hours. After completion of the reaction was confirmed by thin-layer chromatography, the mixture was treated as described above. The residue was purified by silica gel chromatography (chloroform/methanol) to give 5-[5-(4-methylpiperazinyl)methyl[1,3,4]oxadiazol-2-yl]-2-[2-(4-pyridyl)ethylamino]-4-(2-trimethylsilylethoxy)pyrimidine [Compound (IH) in which $R^{2B}$ is 2-(4-pyridyl)ethylamino and —X—Y—Z— is

[Chemical Formula 13]

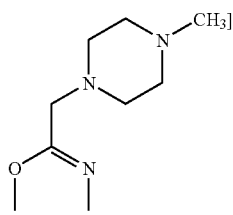

(0.738 g, yield 81)%

Step 4

To 80 mL of THF, 5-[5-(4-methylpiperazinyl)methyl[1,3,4]oxadiazol-2-yl]-2-[2-(4-pyridyl)ethylamino]-4-(2-trimethylsilylethoxy)pyrimidine (3.83 g, 7.71 mmol) obtained in Step 3 was dissolved, then TBAF-THF solution (1.0 mol/L, 15.8 mL, 15.8 mmol) was added thereto, followed by stirring at a temperature between room temperature and 50° C. in total of 5 hours. After completion of the reaction was confirmed by thin-layer chromatography, the reaction mixture was concentrated under reduced pressure and the residue was purified by silica gel column chromatography (chloroform/methanol). Then, the residue was crystallized from hexane/ethyl acetate to give 4-hydroxy-5-[5-(4-methylpiperazinyl)methyl[1,3,4]oxadiazol-2-yl]-2-[2-(4-pyridyl)ethylamino]pyrimidine [Compound (AB) in which $R^{2B}$ is [2-(4-pyridyl)ethylamino] and —X—Y—Z— is

[Chemical Formula 14]

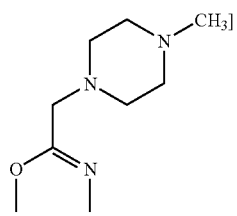

(1.71 g, yield 56%)

Step 5

To 3.0 mL of dichrolomethane, 4-hydroxy-5-[5-(4-methylpiperazinyl)methyl[1,3,4]oxadiazol-2-yl]-2-[2-(4-pyridyl)ethylamino]pyrimidine (100 mg, 0.252 mmol) obtained in Step 4 was dissolved, then triethylamine (0.14 mL, 1.0 mmol) and methanesulfonic anhydride (110 mg, 0.63 mmol) were added thereto under ice-cooling, followed by stirring at the same temperature for 1 hour. After completion of the reaction was confirmed by thin-layer chromatography, triethylamine (0.14 mL, 1.0 mmol) and ethylamine hydrochloride (81 mg, 1.0 mmol) were added to the reaction mixture, followed by stirring at room temperature for 12 hours. After completion of the reaction was confirmed by thin-layer chromatography, saturated aqueous sodium hydrogen carbonate solution was added and the reaction mixture was separated into organic layer and aqueous layer. Further, the aqueous layer was extracted with dichloromethane and those organic layers were combined. The organic layer was washed with saturated brine, dried over anhydrous magnesium sulfate, and then evaporated under reduced pressure. The residue was purified by silica gel column chromatography to give Compound 4-32 (47 mg, yield 44%).

Example 12

Synthesis of Compound 4-25, Compound 4-33 to Compound 4-43, Compound 4-56, Compound 4-60, Compound 4-61, Compound 4-63 to Compound 4-68, Compound 4-71 to Compound 4-74

Each of Compound 4-25, Compound 4-33 to Compound 4-35 were obtained by reacting 4-hydroxy-5-[5-(4-methylpiperazinyl)methyl[1,3,4]oxadiazol-2-yl]-2-[2-(4-pyridyl)ethylamino]pyrimidine obtained in Step 4 of Example 11 with various amine corresponding to each compound in a similar manner to Step 5 of Example 11.

Example 13

Synthesis of Compound 4-23

In a similar manner to Example 5, 5-(5-hydroxymethyl[1,3,4]oxadiazol-2-yl)-2-{2-[4-(2-methyl)pyridyl]ethylamino}-4-n-propylaminopyrimidine was synthesized using 5-(5-acetoxymethyl[1,3,4]oxadiazol-2-yl)-2-{2-[4-(2-methyl)pyridyl]ethylamino}-4-n-propylaminopyrimidine synthesized according to Example 1. Then; using this compound, crude product of 5-(5-methanesulfonyloxymethyl[1,3,4]oxadiazol-2-yl)-2-{2-[4-(2-methyl)pyridyl]ethylamino}-4-n-propylaminopyrimidine was obtained according to Step 1 of Example 7. Compound 4-23 was obtained by reacting this crude product with 1-methylpiperazine according to Step 2 of Example 7.

Example 14

Synthesis of Compound 5-1

Compound 1-537 (100 mg) obtained in the Example 1 was dissolved in methanol (4.0 mL), then aqueous sodium hydroxide solution (2.0 mmol/L, 0.19 mL) was added thereto, followed by stirring at room temperature for 12 hours. Precipitated crystals were collected by filtration, washed with methanol and were dried fully under reduced pressure to give sodium salt of Compound 5-1 (82 mg, yield 84%).

Example 15

Synthesis of Compound 5-2

Compound 1-537 (50 mg) obtained in the Example 1 was dissolved in THF (5.0 mL), then 2-morpholinoethylamine (16 mg) was added thereto, followed by stirring with heating under reflux for 3 days. After completion of the reaction was confirmed by thin-layer chromatography, the reaction mixture was added with water and then extracted with chloroform. The organic layer was washed with saturated aqueous sodium hydrogen carbonate solution, dried over anhydrous magnesium sulfate, and then evaporated under reduced pressure. The residue was purified by silica gel column chromatography (chloroform/methanol) to give Compound 5-2 (48 mg, yield 79%).

Example 16

Synthesis of Compound 5-3 to Compound 5-6

Each of Compound 5-3 to Compound 5-6 were obtained by reacting Compound 1-537 obtained in Example 1 with 3-(4-methylpiperazinyl)propylamine, morpholine, 1-methylpiperazine, 2-methanesulfonylethylamine in a similar manner to Example 15.

Example 17

Synthesis of Compound 6-1

Step 1

To 60 mL of THF, 2-methylthio-4-n-propylaminopyrimidine-5-carbohydrazide (3.00 g) [Compound (E) in which $R^1$ is n-propylamino] obtained in Reference Example 1 was dissolved, then triethylamine (1.39 g) and carbonyldiimidazole (2.22 g) were added thereto, followed by stirring at room temperature for 1 hour. After completion of the reaction was confirmed by thin-layer chromatography, the reaction mixture was added with water and the precipitated crystals were collected by filtration. After washing with water, the crystals were dried fully under reduced pressure to give 5-(2-methylthio-4-propylaminopyrimidin-5-yl)-3H-[1,3,4]oxadiazol-2-one [Compound (N) in which $R^1$ is n-propylamino] (2.47 g, yield 75%).

Step 2

Compound 6-1 (102 mg, yield 40%) was obtained in a similar manner to Step 3 and Step 4 of Example 1 using 5-(2-methylthio-4-propylaminopyrimidin-5-yl)-3H-[1,3,4]oxadiazol-2-one (200 mg) obtained in Step 1.

Example 18

Synthesis of Compound 6-2

Step 1

To 5.0 mL of THF, 5-(2-methylthio-4-propylaminopyrimidin-5-yl)-3H-[1,3,4]oxadiazol-2-one (200 mg) obtained in Step 1 of Example 17 was dissolved, then triphenylphosphine (588 mg), DEAD (40% toluene solution, 1.02 mL, 2.34 mmol) and 2-bromoethanol (280 mg) were added thereto, followed by stirring at room temperature for 1 hour. After completion of the reaction was confirmed by thin-layer chromatography, the reaction mixture was added with water and was extracted with ethyl acetate. The organic layer was washed with saturated brine, dried over anhydrous magnesium sulfate, and then the solvent was evaporated under reduced pressure. The residue was purified by silica gel column chromatography (chloroform/methanol) to give 3-bromoethyl-5-(2-methylthio-4-propylaminopyrimidin-5-yl)-3H-[1,3,4]oxadiazol-2-one [Compound (P) in which $R^1$ represents n-propylamino, $R^{8A}$ represents 2-bromoethyl] (210 mg, yield 75%).

Step 2

Compound 6-2 (173 mg, yield 73%) was obtained in a similar manner to Steps 3 and 4 of Example 1 using 3-bromoethyl-5-(2-methylthio-4-propylaminopyrimidin-5-yl)-3H-[1,3,4]oxadiazol-2-one (200 mg) obtained in Step 1.

Example 19

Synthesis of Compound 6-3

Compound 6-2 (100 mg) obtained in Example 18 was dissolved in DMF (2.0 mL), then potassium carbonate (92 mg) and morpholine-DMF solution (1.0 mol/L, 0.66 mL) were added thereto, followed by stirring at 60° C. for 2 days. The reaction mixture was added with water and was extracted with ethyl acetate. The organic layer was sequentially washed with water and saturated brine and then dried over anhydrous magnesium sulfate. The solvent was evaporated under reduced pressure and the residue was purified by silica gel column chromatography (chloroform/methanol). Then, the mixture was crystallized from hexane/ethylacetate to give Compound 6-3 (44 mg, yield 44%).

Example 20

Synthesis of Compound 6-4 to Compound 6-7

Each of Compound 6-4 to Compound 6-7 were obtained by reacting Compound 6-1 obtained in Example 18 with pyrrolidine, 1-methylpiperazine, piperidine, and dimethylamine in a similar manner to Example 19.

Example 21

Synthesis of Compound 7-1

Step 1

To 40 mL of THF, 4-chloro-5-cyano-2-methylthiopyrimidine [Compound (V)] (1.86 g, 10.0 mmol) obtained in Reference Example 4 was dissolved, then n-propylamine (709 mg, 12.0 mmol) and morpholinomethylpolystyrene (7.0 g) were added thereto, followed by stirring at room temperature for 12 hours. After completion of the reaction was confirmed by thin-layer chromatography, chloroform (100 mL) and benzoylchloride polymer bound [about 2.5 mmol/g, 4.6 g, Canadian Journal of Chemistry, Vol. 55, p. 3351 (1977)] were added thereto, followed by further stirring at room temperature for 12 hours. After resins in the reaction mixture were filtered out, the filtrate was concentrated under reduced pressure to give 4-n-propylamino-5-cyano-2-methylthiopyrimidine [Compound (W) in which $R^1$ represents n-propylamino].

Step 2

To 40 mL of dichloromethane, 4-n-propylamino-5-cyano-2-methylthiopyrimidine obtained in Step 1 was dissolved, then mCPBA-dichloromethane solution (0.50 mol/L, 25 mL, 12.5 mmol) was added thereto over 5 minutes, followed by stirring at room temperature for 2 hours. The reaction mixture was added with saturated aqueous sodium hydrogen carbonate solution and extracted with dichloromethane. The organic layer was washed with saturated brine, dried over anhydrous magnesium sulfate and then the solvent evaporated under reduced pressure. The residue was dissolved in THF (40 mL), then 2-(4-pyridyl)ethylamine (1.47 g, 12.0 mmol) was added thereto, followed by stirring at room temperature for 12 hours. After completion of the reaction was confirmed by thin-layer chromatography, chloroform (80 mL), benzoylchloride polymer bound [about 2.5 mmol/g, 4.6 g, Canadian Journal of Chemistry, Vol. 55, p. 3351 (1977)] and poly(4-vinylpyridine) (4.6 g) were added thereto, followed by further stirring at room temperature for 12 hours. After resins in the reaction mixture were filtered out, the filtrate was concentrated to give 5-cyano-4-n-propylamino-2-[2-(4-pyridyl)ethylamino]pyrimidine [Compound (Y) in which $R^1$ is n-propylamino and $R^1$ is 2-(4-pyridyl)ethylamino].

Step 3

To 20 mL of DMF, the total amount of 5-cyano-4-n-propylamino-2-[2-(4-pyridyl)ethylamino]pyrimidine obtained in Step 2 was dissolved, then DMF (16 mL) solution of ammonium chloride (856 mg) and sodium azide (1.04 g) was added thereto, followed by stirring at 100° C. for 24 hours. After completion of the reaction was confirmed by thin-layer chromatography, the reaction mixture was added with chloroform and 5% an aqueous citric acid solution, and then the mixture was separated. The pH of an aqueous layer was adjusted to about 6 and the crystals were precipitated. The crystals were collected by filtration, washed with water, then dried fully under reduced pressure to give 4-n-propylamino-2-[2-(4-pyridyl)ethylamino]-5-tetrazolylpyrimidine [Compound (Z) in which $R^1$ is n-propylamino and $R^2$ is 2-(4-pyridyl)ethylamino] (700 mg, overall yield from 4-chloro-5-cyano-2-methylthiopyrimidine: 22%).

Step 4

To 7.2 mL of THF, 4-n-propylamino-2-[2-(4-pyridyl)ethylamino]-5-tetrazolylpyrimidine (390 mg) obtained in Step 3 was dissolved, then triphenylphosphine-THF solution (1.0 mol/L, 2.4 mL), methanol-THF solution (1.0 mol/L, 2.4 mL) and DEAD-THF solution (1.0 mol/L, 2.4 mL) were added thereto, followed by stirring at room temperature for 12 hours. After completion of the reaction was confirmed by thin-layer chromatography, the reaction mixture was concentrated under reduced pressure, and the residue was purified by silica gel column chromatography (chloroform/methanol) to give Compound 7-2 (149 mg, yield 37%).

Example 22

Synthesis of Compound 7-2

Compound 7-2 was obtained in a similar manner to Example 21 except for using 2-(2-thienyl)ethylamine instead of 2-(4-pyridyl)ethylamine in Step 2 of Example 21.

Example 23

Synthesis of Compound 7-3

Compound 7-3 (15 mg, yield 34%) was obtained by reacting 4-n-propylamino-2-[2-(4-pyridyl)ethylamino]-5-tetrazolylpyrimidine (32 mg) obtained in Step 3 of Example 21 with 2-morpholinoethanol in a similar manner to Step 4 of Example 21.

The compounds obtained in each of the above examples were identified by mass spectrometry. The results of spectrometry in each compound were described in tables 1 to 7 as an equipment data.

The results of mass spectrometry and proton nuclear magnetic resonance spectra of typical compounds are listed below.

Compound 1-3: ESI m/z: 345 [M+H]$^+$; $^1$H NMR (CDCl$_3$) δ(ppm): 1.00 (t, J=7.3 Hz, 3H), 1.70 (sextet, J=7.3 Hz, 2H), 2.57 (s, 3H), 3.16 (t, J=6.8 Hz, 2H), 3.54 (br s, 2H), 3.73 (q, J=6.8 Hz, 2H), 5.35 (br s, 1H), 6.86 (dd, J=3.5, 1.2 Hz, 1H), 6.95 (dd, J=5.1, 3.5 Hz, 1H), 7.17 (dd, J=5.1, 1.2 Hz, 1H), 8.07 (br s, 1H), 8.38 (br s, 1H).

Compound 1-9: ESI m/z: 340 [M+H]$^+$; $^1$H NMR (CDCl$_3$) δ(ppm): 1.01 (t, J=7.4 Hz, 3H), 1.71 (m, 2H), 2.58 (s, 3H), 2.95 (t, J=7.1 Hz, 2H), 3.53 (m, 2H), 3.73 (q, J=6.9 Hz, 2H), 5.42 (br s, 1H), 7.17 (dd, J=1.6, 4.5 Hz, 2H), 8.11 (br s, 1H), 8.38 (br s, 1H), 8.52 (dd, J=1.6, 4.5 Hz, 2H).

Compound 1-29: ESI m/z: 368 [M+H]$^+$; $^1$H NMR (CDCl$_3$) δ(ppm): 1.01 (t, J=7.4 Hz, 3H), 1.06 (t, J=7.4 Hz, 3H), 1.71 (m, 2H), 1.86 (m, 2H), 2.87 (t, J=7.4 Hz, 2H), 2.95 (t, J=7.1 Hz, 2H), 3.54 (m, 2H), 3.73 (q, J=7.1 Hz, 2H), 5.45 (br s, 1H), 7.17 (dd, J=1.6, 4.4 Hz, 2H), 8.14 (br s, 1H), 8.39 (br s, 1H), 8.52 (dd, J=1.4, 4.4 Hz, 2H).

Compound 1-43: ESI m/z: 387 [M+H]$^+$; $^1$H NMR (CDCl$_3$) δ(ppm): 1.01 (t, J=7.4 Hz, 3H), 1.46 (s, 9H), 1.68 (m, 2H), 3.16 (t, J=6.8 Hz, 2H), 3.55 (m, 2H), 3.73 (q, J=6.6 Hz, 2H), 5.32 (br s, 1H), 6.86 (dd, J=3.5, 1.2 Hz, 1H), 6.95 (dd, J=5.1, 3.5 Hz, 1H), 7.17 (dd, J=5.1, 1.2 Hz, 1H), 8.14 (br s, 1H), 8.40 (br s, 1H).

Compound 1-69: ESI m/z: 366 [M+H]$^+$; $^1$H NMR (CDCl$_3$) δ(ppm): 1.00 (t, J=7.4 Hz, 3H), 1.17 (d, J=7.1 Hz, 4H), 1.70 (m, 2H), 2.18 (quintet, J=6.7 Hz, 1H), 2.94 (t, J=7.1 Hz, 2H), 3.53 (m, 2H), 3.72 (dt, J=7.1 Hz, 2H), 5.32 (br s, 1H), 7.16 (dd, J=1.6, 4.5 Hz, 2H), 8.10 (br s, 1H), 8.33 (br s, 1H), 8.52 (dd, J=1.4, 4.5 Hz, 2H).

Compound 1-420: ESI m/z: 305 [M+H]$^+$; $^1$H NMR (CDCl$_3$) δ(ppm): 0.95 (d, J=6.6 Hz, 6H), 0.99 (t, J=7.3 Hz, 3H), 1.46-1.76 (m, 5H), 2.56 (s, 3H), 3.42-3.57 (m, 4H), 5.15 (br s, 1H), 8.03 (br s, 1H), 8.37 (br s, 1H).

Compound 1-426: ESI m/z: 359 [M+H]$^+$; $^1$H NMR (CDCl$_3$) δ(ppm): 0.95 (t, J=7.2 Hz, 3H), 1.61 (m, 2H), 2.57 (s, 3H), 3.49 (q, J=6.6 Hz, 2H), 4.75 (d, J=6.2 Hz, 2H), 5.76 (br s, 1H), 7.18-7.46 (m, 4H), 8.07 (br s, 1H), 8.39 (br s, 1H)

Compound 1-502: ESI m/z: 357 [M+H]$^+$; $^1$H NMR (CDCl$_3$) δ(ppm): 1.01 (t, J=7.3 Hz, 3H), 1.71 (sextet, J=7.3 Hz, 2H), 2.57 (s, 3H), 2.93 (t, J=7.1 Hz, 2H), 3.55 (br s, 2H), 3.70 (q, J=6.8 Hz, 2H), 5.21 (br s, 1H), 6.87-7.03 (m, 3H), 7.23-7.30 (m, 1H), 8.08 (br s, 1H), 8.38 (br s, 1H).

Compound 1-529: ESI m/z: 373 [M+H]$^+$; $^1$H NMR (CDCl$_3$) δ(ppm): 1.01 (t, J=7.4 Hz, 3H), 1.73 (m, 2H), 2.58 (s, 3H), 2.91 (t, J=7.2 Hz, 2H), 3.54 (br s, 2H), 3.70 (q, J=6.8 Hz, 2H), 5.36 (br s, 1H), 7.09-7.27 (m, 4H), 8.11 (br s, 1H), 8.37 (br s, 1H).

Compound 1-530: ESI m/z: 339 [M+H]$^+$; $^1$H NMR (CDCl$_3$) δ(ppm): 1.01 (t, J=7.4 Hz, 3H), 1.71 (m, 2H), 2.57 (s, 3H), 2.913 (t, J=7.1 Hz, 2H), 3.55 (br s, 2H), 3.70 (q, J=6.8 Hz, 2H), 5.31 (br s, 1H), 7.19-7.35 (m, 5H), 8.07 (br s, 1H), 8.37 (br s, 1H).

Compound 1-531: ESI m/z: 369 [M+H]$^+$; $^1$H NMR (CDCl$_3$) δ(ppm): 1.01 (t, J=7.4 Hz, 3H), 1.70 (m, 2H), 2.57 (s, 3H), 2.91 (t, J=7.1 Hz, 2H), 3.56 (br s, 2H), 3.70 (q, J=6.6 Hz, 2H), 3.80 (s, 3H), 5.34 (br s, 1H), 6.75-6.86 (m, 3H), 7.19-7.27 (m, 1H), 8.08 (br s, 1H), 8.37 (br s, 1H).

Compound 1-532: ESI m/z: 381 [M+H]$^+$; $^1$H NMR (CDCl$_3$) δ(ppm): (major peaks) 1.01 (t, J=7.4 Hz, 3H), 1.16 (d, J=6.8 Hz, 4H), 1.71 (m, 2H), 2.17 (quintet, J=6.8 Hz, 1H), 2.85 (t, J=6.4 Hz, 2H), 3.55 (m, 2H), 3.67 (q, J=6.4 Hz, 2H), 5.25 (br s, 1H), 6.71 (d, J=8.4 Hz, 2H), 7.02 (d, J=8.4 Hz, 2H), 8.17 (br s, 1H), 8.31 (br s, 1H).

Compound 1-533: ESI m/z: 494 [M+H]$^+$; $^1$H NMR (CDCl$_3$) δ(ppm): 1.00 (t, J=7.4 Hz, 3H), 1.17 (d, J=36.6 Hz, 4H), 1.69 (m, 2H), 2.17 (quintet, J=6.6 Hz, 1H), 2.58 (m, 4H), 2.80 (t, J=5.7 Hz, 2H), 2.86 (t, J=7.0 Hz, 2H), 3.54 (m, 2H), 3.66 (q, J=6.7 Hz, 2H), 3.74 (m, 4H), 4.09 (t, J=5.7 Hz, 2H), 5.22 (br s, 1H), 6.85 (d, J=8.6 Hz, 2H), 7.14 (d, J=8.6 Hz, 2H), 8.06 (br s, 1H), 8.32 (br s, 1H).

Compound 1-534: ESI m/z: 337 [M+H]$^+$; $^1$H NMR (CDCl$_3$) δ(ppm): 1.03 (t, J=7.3 Hz, 3H), 1.19 (d, J=6.7 Hz, 4H), 1.74 (m, 2H), 2.20 (quintet, J=6.7 Hz, 1H), 3.58 (m, 2H), 7.05 (m, 1H), 7.2-7.3 (m, 1H), 7.34 (m, 2H), 7.67 (m, 2H), 8.22 (br s, 1H), 8.45 (s, 1H).

Compound 1-535: ESI m/z: 427 [M+H]⁺; ¹H NMR (CDCl₃) δ(ppm): 1.01 (t, J=7.3 Hz, 3H), 1.19 (d, J=6.6 Hz, 4H), 1.73 (m, 2H), 2.19 (quintet, J=6.6 Hz, 1H), 3.61 (m, 2H), 3.84 (s, 3H), 3.88 (s, 6H), 6.99 (s, 2H), 7.39 (br s, 1H), 8.22 (br s, 1H), 8.46 (s, 1H).

Compound 1-536: ESI m/z: 355 [M+H]⁺; ¹H NMR (CDCl₃) δ(ppm): (major peaks) 0.99 (t, J=7.3 Hz, 3H), 1.17 (d, J=6.6 Hz, 4H), 1.68 (m, 2H), 2.17 (quintet, J=6.6 Hz, 1H), 2.94 (t, J=6.5 Hz, 2H), 3.51 (m, 2H), 3.75 (q, J=6.4 Hz, 2H), 5.63 (br s, 1H), 6.83 (d, J=0.8 Hz, 1H), 7.57 (d, J=0.8 Hz, 1H), 8.05 (br s, 1H), 8.32 (br s, 1H).

Compound 1-537: ESI m/z: 398 [M+H]⁺; ¹H NMR (DMSO-d₆) δ(ppm): 0.93 (t, J=7.3 Hz, 3H), 1.36 (t, J=7.1 Hz, 3H), 1.63 (m, 2H), 2.90 (m, 2H), 3.3-3.6 (m, 4H), 4.44 (q, J=7.1 Hz, 2H), 7.26 (dd, J=1.5, 4.6 Hz, 2H), 7.81 (m, 1H), 7.96 (m, 1H), 8.38 (s, 1H), 8.46 (dd, J=1.5, 4.6 Hz, 2H).

Compound 1-538: ESI m/z: 398 [M+H]⁺; ¹H NMR (CDCl₃) δ(ppm): 1.01 (t, J=7.4 Hz, 3H), 1.72 (m, 2H), 2.18 (s, 3H), 2.95 (t, J=7.1 Hz, 2H), 3.53 (m, 2H), 3.74 (m, 2H), 5.31 (s, 2H), 5.34 (br s, 1H), 7.17 (dd, J=1.5, 4.5 Hz, 2H), 8.08 (br s, 1H), 8.41 (s, 1H), 8.53 (dd, J=1.5, 4.5 Hz, 2H).

Compound 1-539: ESI m/z: 382 [M+H]⁺; ¹H-NMR (CDCl₃) δ(ppm): 1.00 (t, J=7.3 Hz, 3H), 1.18 (d, J=6.5 Hz, 4H), 1.62-1.73 (m, 2H), 2.18 (quintet, J=6.5 Hz, 1H), 2.95 (t, J=6.8 Hz, 2H), 3.51 (br s, 2H), 3.71 (dt, J=6.8, 6.8 Hz, 2H), 5.30 (br s, 1H), 7.14 (d, J=6.5 Hz, 2H), 8.13-8.16 (m, 3H), 8.34 (br s, 1H)

Compound 2-69: ESI m/z: 338 [M+H]⁺; ¹H NMR (DMSO-d₆) δ(ppm): 1.0-1.2 (m, 4H), 2.25 (m, 1H), 2.8-3.0 (m, 2H), 3.03 (d, J=4.0 Hz, 3H), 3.57 (m, 2H), 7.26 (dd, J=1.5, 4.8 Hz, 2H), 7.56 (br s, 1H), 7.78 (br s, 1H), 8.30 (s, 1H), 8.46 (dd, J=1.5, 4.8 Hz, 2H).

Compound 2-81: ESI m/z: 370 [M+H]⁺; ¹H NMR (DMSO-d₆) δ(ppm): 2.13 (s, 3H), 2.91 (br t, J=7.2 Hz, 2H), 3.05 (d, J=4.4 Hz, 3H), 3.59 (m, 2H), 5.33 (s, 2H), 7.27 (dd, J=1.7, 4.4 Hz, 2H), 7.66 (br s, 1H), 7.81 (br s, 1H), 8.32 (s, 1H), 8.46 (dd, J=1.7, 4.4 Hz, 2H).

Compound 2-82: ESI m/z: 411 [M+H]⁺; ¹H NMR (CDCl₃) δ(ppm): (major peaks) 2.51 (t, J=6.2 Hz, 2H), 2.60 (m, 4H), 2.62 (s, 1H), 2.71 (t, J=6.2 Hz, 2H), 2.93 (t, J=7.2 Hz, 2H), 3.70 (q, J=8.2 Hz, 2H), 3.83 (m, 4H), 7.16 (d, J=6.0 Hz, 2H), 8.33 (m, 2H), 8.50 (d, J=6.0 Hz, 2H).

Compound 3-187: ESI m/z: 353 [M+H]⁺; ¹H NMR (CDCl₃) δ(ppm): (major peaks) 1.16 (d, J=6.3 Hz, 4H), 1.44 (br t, 3H), 2.22 (quintet, J=6.3 Hz, 1H), 2.95 (br t, J=6.9 Hz, 2H), 3.75 (m, 2H), 4.49 (br, 2H), 7.15 (d, J=5.6 Hz, 2H), 8.54 (d, J=5.6 Hz, 2H), 8.63 (s, 1H).

Compound 3-188: ESI m/z: 368 [M+H]⁺; ¹H NMR (CDCl₃) δ(ppm): 1.18 (d, J=6.6 Hz, 4H), 2.19 (quintet, J=6.6 Hz, 1H), 2.93 (t, J=7.0 Hz, 2H), 3.6-4.0 (m, 7H), 5.45 (br s, 1H), 7.16 (dd, J=1.5, 4.5 Hz, 2H), 8.2-8.5 (m, 2H), 8.52 (dd, J=1.5, 4.5 Hz, 2H).

Compound 3-189: ESI m/z: 430 [M+H]⁺; ¹H NMR (CDCl₃) δ(ppm): 1.18 (d, J=6.8 Hz, 4H), 2.19 (quintet, J=6.8 Hz, 1H), 2.8-3.0 (m, 2H), 2.93 (s, 3H), 3.40 (t, J=6.8 Hz, 2H), 3.77 (q, J=6.7 Hz, 2H), 4.08 (m, 2H), 5.34 (br s, 1H), 7.18 (dd, J=1.5, 4.5 Hz, 2H), 8.2-8.5 (m, 2H), 8.53 (dd, J=1.5, 4.5 Hz, 2H).

Compound 3-190: ESI m/z: 444 [M+H]⁺; ¹H NMR (CDCl₃) δ(ppm): (major peaks) 1.18 (d, J=6.6 Hz, 4H), 2.19 (quintet, J=6.6 Hz, 1H), 2.83 (t, J=7.4 Hz, 2H), 2.99 (m, 2H), 3.63 (t, J=7.4 Hz, 2H), 3.83 (m, 2H), 6.70 (m, 2H), 6.97 (m, 2H), 7.17 (d, J=6.0 Hz, 2H), 8.25 (br s, 1H), 8.32 (s, 1H), 8.42 (d, J=6.0 Hz, 2H).

Compound 3-191: ESI m/z: 400 [M+H]⁺; ¹H NMR (CDCl₃) δ(ppm): 1.22 (d, J=6.8 Hz, 4H), 2.22 (quintet, J=6.8 Hz, 1H), 2.94 (t, J=7.3 Hz, 2H), 3.74 (q, J=6.9 Hz, 2H), 5.83 (br s, 1H), 7.0-7.5 (m, 5H), 7.74 (m, 2H), 8.51 (m, 3H), 10.21 (br s, 1H).

Compound 3-192: ESI m/z: 415 [M+H]⁺; ¹H NMR (CDCl₃) δ(ppm): (major peaks) 1.20 (d, J=6.6 Hz, 4H), 2.21 (quintet, J=6.6 Hz, 1H), 2.86 (t, J=6.7 Hz, 2H), 3.69 (q, J=6.4 Hz, 2H), 5.55 (br s, 1H), 6.73 (d, J=8.4 Hz, 2H), 7.0-7.5 (m, 3H), 7.04 (d, J=8.4 Hz, 2H), 7.80 (m, 2H), 8.46 (br s, 1H), 10.26 (br s, 1H).

Compound 3-194: ESI m/z: 490 [M+H]⁺; ¹H NMR (CDCl₃) δ(ppm): 1.22 (d, J=6.7 Hz, 4H), 2.22 (quintet, J=6.7 Hz, 1H), 2.92 (t, J=7.1 Hz, 2H), 3.7-3.9 (m, 2H), 3.82 (s, 6H), 3.85 (s, 3H), 5.34 (br s, 1H), 7.03 (br s, 2H), 7.10 (m, 2H), 8.5 (br s, 1H), 8.51 (dd, J=1.6, 4.4 Hz, 2H), 10.2 (br s, 1H).

Compound 3-195: ESI m/z: 437 [M+H]⁺; ¹H NMR (CDCl₃) δ(ppm): 1.16 (d, J=6.7 Hz, 4H), 2.19 (quintet, J=6.7 Hz, 1H), 2.5-2.7 (m, 4H), 2.82 (m, 2H), 2.94 (t, J=6.9 Hz, 2H), 3.7-3.8 (nm, 6H), 4.55 (m, 2H), 5.6 (br s, 1H), 7.16 (dd, J=1.7, 4.3 Hz, 2H), 8.54 (dd, J=1.7, 4.3 Hz, 2H), 8.65 (br s, 1H).

Compound 3-196: ESI m/z: 414 [M+H]⁺; ¹H NMR (CDCl₃) δ(ppm): 1.20 (m, 4H), 2.21 (m, 1H), 2.41 (s, 3H), 2.86 (m, 2H), 3.64 (m, 2H), 5.36 (br s, 1H), 6.9-7.4 (m, 5H), 8.02 (m, 1H), 8.48 (m, 3H), 9.89 (br s, 1H).

Compound 3-197: ESI m/z: 414 [M+H]⁺; ¹H NMR (CDCl₃) δ(ppm): (major peaks) 1.21 (d, J=6.7 Hz, 4H), 2.22 (quintet, J=6.7 Hz, 1H), 2.34 (s, 3H), 2.94 (t, J=7.2 Hz, 2H), 3.75 (q, J=6.8 Hz, 2H), 5.36 (br s, 1H), 6.9-7.3 (m, 4H), 7.51 (br s, 1H), 7.62 (m, 1H), 8.50 (s, 1H), 8.51 (m, 2H).

Compound 3-198: ESI m/z: 414 [M+H]⁺; ¹H NMR (CDCl₃) δ(ppm): (major peaks) 1.21 (d, J=6.6 Hz, 4H), 2.21 (quintet, J=6.6 Hz, 1H), 2.36 (s, 3H), 2.92 (t, J=7.1 Hz, 2H), 3.72 (m, 2H), 5.36 (m, 1H), 7.0-7.1 (m, 2H), 7.15 (d, J=8.1 Hz, 2H), 7.59 (d, J=8.1 Hz, 2H), 8.5 (1H, overlapping with other peaks), 8.51 (d, J=5.3 Hz, 2H).

Compound 3-199: ESI m/z: 416 [M+H]⁺; ¹H NMR (DMSO-d₆) δ(ppm): 1.0-1.2 (m, 4H), 2.28 (m, 2H), 2.87 (m, 2H), 3.59 (m, 2H), 6.4-6.6 (m, 1H), 7.13 (m, 2H), 7.2-7.3 (m, 2H), 7.83 (br s, 1H), 8.42 (m, 2H), 8.48 (s, 1H), 9.46 (s, 1H), 9.91 (s, 1H).

Compound 3-200: ESIMS m/z: 416 [M+H]⁺; ¹H NMR (CDCl₃) δ(ppm): 1.0-1.2 (m, 4H), 2.26 (m, 1H), 2.80 (m, 2H), 3.4-3.6 (m, 2H), 6.74 (d, J=7.9 Hz, 2H), 7.14 (m, 2H), 7.44 (d, J=7.9 Hz, 2H), 7.73 (m, 1H), 8.43 (d, J=4.6 Hz, 2H), 8.44 (s, 1H), 9.33 (s, 1H), 9.66 (s, 1H).

Compound 3-202: ESIMS m/z: 354 [M+H]⁺; ¹H NMR (CDCl₃) δ(ppm): 1.18 (d, J=6.8 Hz, 4H), 2.19 (quintet, J=6.8 Hz, 1H), 2.94 (t, J=6.8 Hz, 2H), 3.08 (br s, 3H), 3.73 (dt, J=6.8, 6.8 Hz, 2H), 5.50 (br s, 1H), 7.15-7.24 (m, 2H), 8.00 (br s, 1H), 8.10 (dt, J=1.6, 5.9 Hz, 1H), 8.18 (br s, 1H), 8.32 (br s, 1H).

Compound 3-203: ESIMS m/z: 416 [M+H]⁺; ¹H NMR (CDCl₃) δ(ppm): (d, J=7.2 Hz, 4H), 2.22 (quintet, J=7.2 Hz, 1H), 2.89 (t, J=6.9 Hz, 2H), 3.69-3.71 (m, 2H), 5.59 (br s, 1H), 7.05 (br s, 1H), 7.14-7.16 (m, 2H), 7.33-7.39 (m, 2H), 7.69-7.72 (m, 2H), 8.08 (d, J=6.0 Hz, 1H), 8.13 (br s, 1H), 8.48 (br s, 1H), 10.17 (br s, 1H).

Compound 3-204: ESIMS m/z: 363 [M+H]⁺; ¹H NMR (CDCl₃) δ(ppm): 1.18 (d, J=6.5 Hz, 4H), 2.19 (quintet, J=6.5 Hz, 1H), 3.03 (t, J=7.0 Hz, 2H), 3.09 (br s, 3H), 3.77 (dt, J=6.5, 7.0 Hz, 2H), 5.27 (br s, 1H), 7.39 (dd, J=1.6, 5.2 Hz, 1H), 7.60 (br s, 1H), 8.04 (br s, 1H), 8.33 (br s, 1H), 8.61 (d, J=5.2 Hz, 1H).

Compound 3-205: ESIMS m/z: 354 [M+H]⁺; ¹H NMR (CDCl₃) δ(ppm): 1.18 (d, J=6.5 Hz, 4H), 2.19 (quintet, J=6.5 Hz, 1H), 2.96 (t, J=7.0 Hz, 2H), 3.08 (br s, 3H), 3.73 (dt, J=6.5, 7.0 Hz, 2H), 5.38 (br s, 1H), 7.15 (d, J=7.0 Hz, 1H), 8.02 (br s, 1H), 8.14 (d, J=7.0 Hz, 2H), 8.33 (br s, 1H).

Compound 3-206: ESIMS m/z: 416 [M+H]⁺; ¹H NMR (CDCl₃) δ(ppm): 1.22 (d, J=6.8 Hz, 4H), 2.22 (quintet, J=6.8 Hz, 1H), 2.90 (t, J=6.8 Hz, 2H), 3.68-3.71 (m, 2H), 5.52 (br s, 1H), 7.01-7.18 (m, 3H), 7.32-7.38 (m, 2H), 7.69 (d, J=7.6 Hz, 2H), 8.09 (d, J=7.6 Hz, 2H), 8.49 (br s, 1H), 10.16 (br s, 1H).

Compound 3-207: ESIMS m/z: 438 [M+H]⁺; ¹H NMR (CDCl₃) δ(ppm): 1.17 (d, J=6.5 Hz, 4H), 2.13-2.20 (m, 4H), 2.88 (t, J=7.0 Hz, 2H), 3.40 (s, 3H), 3.61-3.71 (m, 4H), 3.77 (br s, 2H), 5.66 (br s, 1H), 7.16-7.22 (m, 3H), 7.42 (d, J=8.1 Hz, 2H), 8.31 (br s, 2H).

Compound 3-208: ESIMS m/z: 474 [M+H]⁺; ¹H NMR (CDCl₃) δ(ppm): 1.17 (d, J=6.2 Hz, 4H), 2.18 (quintet, J=6.2 Hz, 1H), 2.91 (t, J=7.0 Hz, 2H), 3.00 (s, 3H), 3.41 (s, 3H), 3.61-3.72 (m, 4H), 3.77 (br s, 2H), 5.35 (br s, 1H), 6.66 (br s, 1H), 7.14-7.24 (m, 4H), 8.22 (br s, 1H), 8.33 (br s, 1H).

Compound 3-209: ESIMS m/z: 398 [M+H]⁺; ¹H NMR (CDCl₃) δ(ppm): 1.18 (d, J=6.2 Hz, 4H), 2.13-2.23 (m, 1H), 2.92 (t, J=7.0 Hz, 2H), 3.40 (s, 3H), 3.59-3.75 (m, 6H), 5.31 (br s, 1H), 7.14-7.24 (m, 2H), 8.10 (d, J=6.2 Hz, 1H), 8.15 (br s, 1H), 8.25 (br s, 1H), 8.35 (br s, 1H).

Compound 3-210: ESIMS m/z: 398 [M+H]⁺; ¹H NMR (CDCl₃) δ(ppm): 1.18 (d, J=6.2 Hz, 4H), 2.13-2.23 (m, 1H), 2.95 (t, J=7.0 Hz, 2H), 3.40 (s, 3H), 3.58-3.62 (m, 2H), 3.67-3.77 (m, 4H), 5.30 (br s, 1H), 7.15 (d, J=6.5 Hz, 2H), 8.14 (d, J=6.5 Hz, 2H), 8.25 (br s, 1H), 8.35 (br s, 1H).

Compound 3-211: ESIMS m/z: 394 [M+H]⁺; ¹H NMR (CDCl₃) δ(ppm): 1.17 (t, J=6.8 Hz, 4H), 2.13-2.21 (m, 4H), 2.90 (t, J=6.8 Hz, 2H), 3.09 (br s, 3H), 3.69 (dt, J=6.8, 6.8 Hz, 2H), 5.21 (br s, 1H), 7.19 (d, J=8.4 Hz, 2H), 7.43 (d, J=8.4 Hz, 2H), 7.95 (br s, 1H), 8.32 (br s, 1H).

Compound 3-212: ESIMS m/z: 454 [M+H]⁺; ¹H NMR (CDCl₃) δ(ppm): 1.15-1.18 (m, 4H), 2.12-2.22 (m, 1H), 2.88 (t, J=6.8 Hz, 2H), 3.40 (s, 3H), 3.59-3.77 (m, 9H), 5.29 (br s, 1H), 6.60 (br s, 1H), 7.17 (d, J=8.6 Hz, 2H), 7.31 (d, J=8.6 Hz, 2H), 8.20 (br s, 1H), 8.33 (br s, 1H).

Compound 3-213: ESIMS m/z: 430 [M+H]⁺; ¹H NMR (CDCl₃) δ(ppm): 1.16-1.19 (m, 4H), 2.14-2.24 (m, 1H), 2.87-2.92 (m, 5H), 3.10 (br s, 3H), 3.68 (dt, J=6.8, 6.8 Hz, 2H), 5.62 (br s, 1H), 7.16-7.25 (m, 4H), 7.92 (br s, 1H), 8.33 (br s, 1H), 9.14 (br s, 1H).

Compound 3-214: ESIMS m/z: 410 [M+H]⁺; ¹H NMR (CDCl₃) δ(ppm): 1.17 (d, J=6.8 Hz, 4H), 2.13-2.23 (m, 1H), 2.88 (t, J=6.8 Hz, 2H), 3.09 (br s, 3H), 3.67 (dt, J=6.6, 6.8 Hz, 2H), 3.76 (m, 3H), 5.47 (br s, 1H), 7.14-7.17 (m, 3H), 7.38 (d, J=8.4 Hz, 2H), 7.91 (br s, 1H), 8.32 (br s, 1H).

Compound 3-215: ESI m/z: 430 [M+H]⁺; ¹H NMR (DMSO-d₆) δ(ppm): 1.0-1.2 (m, 4H), 2.29 (m, 1H), 2.84 (m, 2H), 3.51 (m, 2H), 3.76 (s, 3H), 6.91 (d, J=8.8 Hz, 2H), 7.16 (d, J=5.3 Hz, 2H), 7.59 (d, J=8.8 Hz, 2H), 7.82 (br s, 1H), 8.43 (d, J=5.3 Hz, 2H), 8.47 (s, 1H), 9.76 (s, 1H).

Compound 3-216: ESIMS m/z: 456 [M+H]⁺; ¹H NMR (CDCl₃) δ(ppm): 1.11 (d, J=6.5 Hz, 4H), 2.15 (s, 3H), 2.22 (quintet, J=6.5 Hz, 1H), 2.89 (t, J=7.3 Hz, 2H), 3.68 (dt, J=6.8, 7.3 Hz, 2H), 5.75 (br s, 1H), 7.08-7.16 (m, 4H), 7.32-7.38 (m, 1H), 7.50 (d, J=8.4 Hz, 2H), 7.78 (br s, 2H), 8.47 (br s, 1H), 8.62 (br s, 1H), 10.19 (br s, 1H).

Compound 3-217: ESIMS m/z: 472 [M+H]⁺; ¹H NMR (CDCl₃) δ(ppm): 1.20-1.22 (m, 4H), 2.21 (quintet, J=6.5 Hz, 1H), 2.89 (t, J=6.8 Hz, 2H), 3.70 (dt, J=6.8, 7.3 Hz, 2H), 3.78 (s, 3H), 5.37 (br s, 1H), 6.55 (br s, 1H), 7.14-7.17 (m, 3H), 7.30-7.38 (m, 4H), 7.78 (br s, 2H), 8.47 (br s, 1H), 10.20 (br s, 1H).

Compound 3-218: ESIMS m/z: 425 [M+H]⁺; ¹H NMR (CDCl₃) δ(ppm): 1.22 (d, J=6.5 Hz, 4H), 2.22 (quintet, J=6.5 Hz, 1H), 2.95-3.00 (m, 2H), 3.77 (br s, 2H), 5.43 (br s, 1H), 7.20-7.46 (m, 5H), 7.67-7.70 (m, 2H), 8.50 (br s, 1H), 8.57 (d, J=4.9 Hz, 1H), 10.16 (br s, 1H).

Compound 3-219: ESI m/z: 370 [M+H]⁺; ¹H NMR (DMSO-d₆) δ(ppm): 1.0-1.2 (m, 4H), 2.26 (m, 1H), 2.88 (br t, J=7.1 Hz, 2H), 3.54 (m, 2H), 3.7-4.0 (m, 2H), 4.53 (m, 1H), 4.71 (m, 1H), 7.25 (dd, J=1.5, 4.5 Hz, 2H), 7.64 (br s, 1H), 8.06 (br s, 1H), 8.32 (s, 1H), 8.45 (dd, J=1.5, 4.5 Hz, 2H).

Compound 3-220: ESI m/z: 396 [M+H]⁺; ¹H NMR (DMSO-d₆) δ(ppm): 1.0-1.2 (m, 4H), 1.84 (m, 2H), 2.25 (m, 1H), 2.88 (br t, J=6.8 Hz, 2H), 3.23 (s, 3H), 3.40 (t, J=6.1 Hz, 2H), 3.57 (m, 4H), 7.26 (d, J=5.8 Hz, 2H), 7.57 (br s, 1H), 7.96 (br s, 1H), 8.31 (s, 1H), 8.46 (d, J=5.8 Hz, 2H).

Compound 3-221: ESI m/z: 418 [M+H]⁺; ¹H NMR (DMSO-d₆) δ(ppm): 1.0-1.2 (m, 4H), 2.29 (m, 1H), 2.85 (m, 2H), 3.5-3.7 (m, 2H), 7.1-7.3 (m, 4H), 7.6-7.8 (m, 2H), 7.87 (br s, 1H), 8.44 (m, 2H), 8.49 (s, 1H), 9.87 (s, 1H).

Compound 3-222: ESI m/z: 382 [M+H]⁺; ¹H NMR (CDCl₃) δ(ppm): 1.17 (d, J=6.5 Hz, 4H), 2.18 (quintet, J=6.5 Hz, 1H), 2.94 (t, J=7.0 Hz, 2H), 3.40 (s, 3H), 3.61 (t, J=5.7 Hz, 2H), 3.69-3.76 (m, 4H), 5.22 (br s, 1H), 7.16 (d, J=5.9 Hz, 2H), 8.24 (br s, 1H), 8.35 (br s, 1H), 8.52-8.54 (m, 2H).

Compound 3-223: ESI m/z: 414 [M+H]⁺; ¹H NMR (CDCl₃) δ(ppm): 1.21 (d, J=6.8 Hz, 4H), 2.22 (quintet, J=6.8 Hz, 1H), 2.52 (s, 3H), 2.89 (t, J=6.5 Hz, 2H), 3.72 (dt, J=6.5, 6.5 Hz, 2H), 5.44 (br s, 1H), 6.94-7.00 (m, 2H), 7.10-7.16 (m, 1H), 7.32-7.38 (m, 2H), 7.77 (br s, 2H), 8.40 (d, J=5.4 Hz, 1H), 8.49 (br s, 1H), 10.21 (br s, 1H).

Compound 3-224: ESI m/z: 464 [M+H]⁺; ¹H NMR (DMSO-d₆) δ(ppm): 1.1-1.2 (m, 4H), 2.51 (m, 1H), 2.86 (m, 2H), 3.5-3.7 (m, 2H), 3.85 (s, 3H), 7.11 (d, J=8.9 Hz, 1H), 7.18 (d, J=5.7 Hz, 2H), 7.43 (dd, J=2.5, 8.9 Hz, 1H), 7.89 (m, 1H), 8.02 (d, J=2.5 Hz, 1H), 8.42 (d, J=5.7 Hz, 2H), 8.48 (s, 1H), 9.82 (s, 1H).

Compound 3-225: ESI m/z: 444 [M+H]⁺; ¹H NMR (DMSO-d₆) δ(ppm) 1.1-1.2 (m, 4H), 2.2-2.3 (1H, overlapping with other peaks), 2.26 (s, 3H), 2.84 (m, 2H), 3.57 (m, 2H), 3.85 (s, 3H), 6.75 (dd, J=2.7, 8.8 Hz, 1H), 6.90 (d, J=2.7 Hz, 1H), 7.05 (d, J=5.6 Hz, 2H), 7.7-7.8 (1H, overlapping with other peaks), 7.78 (d, J=8.8 Hz, 1H), 8.41° (d, J=5.6 Hz, 2H), 8.47 (s, 1H), 9.50 (s, 1H).

Compound 3-226: ESI m/z: 450 [M+H]⁺; ¹H NMR (DMSO-d₆) δ(ppm) 1.1-1.2 (m, 4H), 2.29 (m, 1H), 2.86 (m, 2H), 3.5-3.7 (m, 2H), 6.96 (d, J=8.6 Hz, 1H), 7.19 (d, J=5.9 Hz, 2H), 7.29 (dd, J=2.6, 8.6 Hz, 1H), 7.8-7.9 (1H, overlapping with other peaks), 7.90 (d, J=2.6 Hz, 1H), 8.45 (d, J=5.9 Hz, 2H), 8.47 (s, 1H), 9.75 (s, 1H), 10.1 (s, 1H).

Compound 3-227: ESI m/z: 352 [M+H]⁺; ¹H NMR (CDCl₃) δ(ppm): 1.18 (t. J=6.8 Hz, 4H), 2.19 (quintet, J=6.8 Hz, 1H), (s, 3H), 2.90 (t, J=7.0 Hz, 2H), 3.11 (br s, 3H), (dt, J=6.8, 7.0 Hz, 2H), 5.22 (br s, 1H), 6.98 (d, J=4.9 Hz, 1H), 7.03 (br s, 1H), 7.99 (br s, 1H), 8.34 (br s, 1H), 8.41 (d, J=4.9 Hz, 1H).

Compound 3-228: ESI m/z: 396 [M+H]⁺; ¹H NMR (CDCl₃) δ(ppm): 1.17 (t, J=6.8 Hz, 4H), 2.18 (quintet, J=6.8 Hz, 1H), 2.54 (s, 3H), 2.89 (t, J=7.0 Hz, 2H), 3.40 (s, 3H), 3.61-3.78 (m, 6H), 5.19 (br s, 1H), 6.97 (d, J=5.1 Hz, 1H), 7.03 (br s, 1H), 8.23 (br s, 1H), 8.36 (br s, 1H), 8.41 (d, J=5.1 Hz, 1H).

Compound 3-229: ESI m/z: 444 [M+H]⁺; ¹H NMR (DMSO-d₆) δ(ppm): (major peaks) 1.0-1.2 (m, 4H), 2.10 (s, 6H), 2.23 (m, 1H), 2.73 (br t, J=7.4 Hz, 2H), 3.39 (m, 2H), 6.68 (d, J=8.3 Hz, 1H), 7.00 (m, 2H), 7.21 (d, J=8.3 Hz, 1H), 8.39 (dd, J 1.6, 4.4 Hz, 2H), 8.43 (s, 1H), 8.86 (s, 1H), 9.26 (s, 1H).

Compound 3-230: ESI m/z: 430 [M+H]⁺; ¹H NMR (DMSO-d₆) δ(ppm): 1.0-1.2 (m, 4H), 2.18 (s, 3H), 2.28 (m, 1H), 2.70 (br t, J=7.4 Hz, 2H), 3.3-3.4 (m, 2H), 6.62 (dd, J=2.2, 8.6 Hz, 1H), 6.71 (br s, 1H), 7.01 (d, J=5.4 Hz, 2H), 7.58 (d, J=8.6 Hz, 1H), 7.73 (br t, J=5.6 Hz, 1H), 8.42 (d, J=5.4 Hz, 2H), 8.46 (s, 1H), 9.35 (br s, 1H), 9.40 (s, 1H).

Compound 3-231: ESI m/z: 382 [M+H]$^+$; $^1$H NMR (DMSO-d$_6$) δ(ppm): 1.0-1.2 (m, 4H), 1.76 (m, 2H), 2.25 (m, 1H), 2.89 (br t, J=6.7 Hz, 2H), 3.4-3.7 (m, 6H), 4.57 (br t, J=4.8 Hz, 1H), 7.26 (dd, J=1.6, 4.4 Hz, 2H), 7.56 (br s, 1H), 7.93 (br s, 1H), 8.32 (s, 1H), 8.45 (dd, J=1.6, 4.4 Hz, 2H).

Compound 3-232: ESI m/z: 380 [M+H]$^+$; $^1$H NMR (CDCl$_3$) δ(ppm): 1.01 (t, J=7.6 Hz, 3H), 1.17 (d, J=6.5 Hz, 4H), 1.64-1.74 (m, 2H), 2.18 (quintet, J=6.5 Hz, 1H), 2.54 (s, 3H), 2.90 (t, J=7.0 Hz, 2H), 3.54 (br s, 2H), 3.71 (dt, J=7.0, 7.0 Hz, 2H), 5.21 (br s, 1H), 6.97 (d, J=4.9 Hz, 1H), 7.03 (br s, 1H), 8.10 (br s, 1H), 8.34 (br s, 1H), 8.41 (d, J=4.9 Hz, 1H).

Compound 3-233: ESI m/z: 430 [M+H]$^+$; $^1$H NMR (CDCl$_3$) δ(ppm): 1.20-1.33 (m, 4H), 2.22 (quintet, J=6.6 Hz, 1H), 2.89 (t, J=7.3 Hz, 2H), 3.72 (dt, J=7.1, 7.3 Hz, 2H), 3.93 (s, 3H), 5.39 (br s, 1H), 6.60 (br s, 1H), 6.72 (br s, 1H), 7.10-7.16 (m, 1H), 7.32-7.38 (m, 2H), 7.74 (br s, 2H), 8.06-8.08 (m, 1H), 8.48 (m, 1H), 10.21 (br s, 1H).

Compound 3-234: ESI m/z: 414 [M+H]$^+$; $^1$H NMR (CDCl$_3$) δ(ppm): (d, J=6.6 Hz, 4H), 2.22 (quintet, J=6.6 Hz, 1H), (t, J=7.2 Hz, 2H), 3.61-3.89 (m, 2H), 5.28 (br s, 1H), (br s, 2H), 6.62-6.67 (m, 2H), 7.00 (d, J=7.8 Hz, 2H), 7.12-7.17 (m, 1H), 7.37 (t, J=7.8 Hz, 2H), 7.77-7.79 (m, 2H), 8.42 (br s, 1H), 10.34 (br s, 1H).

Compound 3-235: ESI m/z: 352 [M+H]$^+$; $^1$H NMR (CDCl$_3$) δ(ppm): 1.17 (d, J=6.2 Hz, 4H), 2.11-2.13 (m, 1H), 2.82 (t, J=7.0 Hz, 2H), 3.10 (br s, 3H), 3.60-3.70 (m, 4H), 5.23 (br s, 1H), 6.65 (d, J=8.4 Hz, 2H), 7.03 (d, J=8.4 Hz, 2H), 7.94 (br s, 1H), 8.32 (br s, 1H).

Compound 3-236: ESI m/z: 396 [M+H]$^+$; $^1$H NMR (CDCl$_3$) δ(ppm): 1.16-1.18 (m, 4H), 2.13-2.22 (m, 1H), 2.81 (t, J=6.9 Hz, 2H), 3.40 (s, 3H), 3.60-3.66 (m, 6H), 3.77 (br s, 2H), 5.24 (br s, 1H), 6.65 (d, J=7.8 Hz, 2H), 7.02 (d, J=7.8 Hz, 2H), 8.19 (br s, 1H), 8.33 (br s, 1H).

Compound 3-237: ESI m/z: 429 [M+H]$^+$; $^1$H NMR (CDCl$_3$) δ(ppm): 1.23-1.46 (m, 4H), 2.17-2.27 (m, 4H), 2.82 (t, J=7.0 Hz, 2H), 3.65 (t, J=7.0 Hz, 2H), 5.80 (br s, 1H), 6.71 (d, J=8.1 Hz, 1H), 6.87-6.96 (m, 2H), 7.11-7.16 (m, 1H), 7.33-7.39 (m, 2H), 7.68 (br s, 1H), 7.79-7.81 (m, 2H), 8.42 (br s, 1H), 10.18 (br s, 1H)

Compound 3-238: ESI m/z: 401 [M+H]$^+$; $^1$H NMR (CDCl$_3$) δ(ppm): 1.17 (d, J=6.5 Hz, 4H), 2.17 (quintet, J=6.5 Hz, 1H), 3.10 (t, J=6.5 Hz, 2H), 3.40 (s, 3H), 3.59-3.63 (m, 2H), 3.71-3.79 (m, 2H), 3.90 (dt, J=6.2, 6.5 Hz, 2H), 5.11 (br s, 1H), 7.21 (dd, J=1.4, 5.1 Hz, 1H), 8.23 (br s, 1H), 8.34 (br s, 1H), 8.61 (d, J=5.1 Hz, 1H), 9.16 (d, J=1.4 Hz, 1H).

Compound 3-239: ESI m/z: 383 [M+H]$^+$; $^1$H NMR (CDCl$_3$) δ(ppm): (d, J=6.6 Hz, 4H), 2.21 (quintet, J=6.6 Hz, 1H), (t, J=6.5 Hz, 2H), 3.92 (dt, J=6.2, 6.5 Hz, 2H), (br s, 1H), 7.09-7.15 (m, 2H), 7.32-7.38 (m, 2H), 7.71-7.85 (m, 2H), 8.59 (d, J=5.1 Hz, 1H), 8.47 (br s, 1H), 9.15 (br s, 1H), 10.21 (br s, 1H).

Compound 3-240: ESI m/z: 443 [M+H]$^+$; $^1$H NMR (CDCl$_3$) δ(ppm): 1.23-1.26 (m, 4H), 2.23 (br s, 7H), 2.79 (t, J=7.2 Hz, 2H), 3.64 (t, J=7.2 Hz, 2H), 5.84 (br s, 1H), 6.82 (br s, 2H), 7.11-7.16 (m, 1H), 7.34-7.39 (m, 2H), 7.66 (br s, 1H), 7.80-7.82 (m, 2H), 8.42 (br s, 1H), 10.18 (br s, 1H).

Compound 3-241: ESI m/z: 384 [M+H]$^+$; $^1$H NMR (CDCl$_3$) δ(ppm): 1.18 (d, J=6.8 Hz, 4H), 1.99-2.24 (m, 3H), 2.94 (t, J=7.0 Hz, 2H), 3.70-3.77 (m, 4H), 4.56 (dt, J=5.7, 47 Hz, 2H), 5.32 (br s, 1H), 7.17 (d, J=5.4 Hz, 2H), 8.16 (br s 1H), 8.35 (br s, 1H), 8.52 (d, J=5.4 Hz, 2H).

Compound 3-242: ESI m/z: 416 [M+H]$^+$; $^1$H NMR (DMSO) δ(ppm): 1.11-1.16 (m, 4H), 2.19-2.27 (m, 1H), 2.59-2.64 (m, 2H), 3.42-3.48 (m, 2H), 5.26 (br s, 1H), 5.95-6.02 (m, 1H), 6.09 (br s, 1H), 7.02-7.07 (m, 1H), 7.19-7.32 (m, 3H), 7.67-7.83 (m, 2H), 8.45 (br s, 1H), 9.94 (br s, 1H), 11.32 (br s, 1H).

Compound 4-1: ESI m/z: 356 [M+H]$^+$; $^1$H NMR (DMSO-d$_6$) δ(ppm): 0.93 (t, J=7.4 Hz, 3H), 1.62 (m, 2H), 2.90 (m, 2H), 3.4-3.6 (m, 4H), 4.67 (d, J=6.1 Hz, 2H), 5.90 (t, J=6.1 Hz, 1H), 7.26 (dd, J=1.5, 4.4 Hz, 2H), 7.60 (br s, 1H), 7.98 (br s, 1H), 8.34 (s, 1H), 8.46 (dd, J=1.5, 4.4 Hz, 2H).

Compound 4-2: ESI m/z: 425 [M+H]$^+$; $^1$H NMR (CDCl$_3$) δ(ppm): 1.02 (t, J=7.4 Hz, 3H), 1.71 (m, 2H), 2.63 (m, 4H), 2.95 (t, J=7.0 Hz, 2H), 3.54 (m, 2H), 3.7-3.8 (m, 6H), 3.84 (s, 2H), 5.33 (br s, 1H), 7.17 (dd, J=1.7, 4.5 Hz, 2H), 8.10 (br s, 1H), 8.43 (s, 1H), 8.53 (dd, J=1.7, 4.5 Hz, 2H).

Compound 4-3: ESI m/z: 438 [M+H]$^+$; $^1$H NMR (DMSO-d$_6$) δ(ppm): 0.92 (t, J=7.4 Hz, 3H), 1.61 (m, 2H), 2.13 (s, 3H), 2.31 (m, 4H), 2.49 (m, 4H), 2.88 (br t, J=6.8 Hz, 2H), 3.4-3.6 (m, 4H), 3.80 (s, 2H), 7.24 (dd, J=1.5, 4.4 Hz, 2H), 7.59 (br s, 1H), 7.95 (br s, 1H), 8.32 (s, 1H), 8.44 (dd, J=1.5, 4.4 Hz, 2H).

Compound 4-4: ESI m/z: 328 [M+H]$^+$; $^1$H NMR (DMSO-d$_6$) δ(ppm): 2.91 (m, 2H), 3.04 (br s, 3H), 3.59 (m, 2H), 4.67 (s, 2H), 5.87 (s, 1H), 7.26 (dd, J=1.6, 4.4 Hz, 2H), 7.55 (br s, 1H), 7.83 (br s, 1H), 8.33 (s, 1H), 8.45 (dd, J=1.6, 4.4 Hz, 2H).

Compound 4-5: ESI m/z: 355 [M+H]$^+$; $^1$H NMR (DMSO-d$_6$) δ(ppm): 2.26 (s, 6H), 2.91 (br t, J=7.2 Hz, 2H), 3.05 (br d, J=4.0 Hz, 3H), 3.59 (m, 2H), 3.78 (s, 2H), 7.27 (dd, J=1.5, 4.4 Hz, 2H), 7.61 (br s, 1H), 7.85 (br s, 1H), 8.32 (s, 1H), 8.46 (dd, J=1.5, 4.4 Hz, 2H).

Compound 4-6: ESI m/z: 440 [M+H]$^+$; $^1$H NMR (DMSO-d$_6$) δ(ppm): 2.3-2.6 (m, 10H), 2.91 (br t, J=7.2 Hz, 2H), 3.05 (br d, J=4.0 Hz, 3H), 3.47 (q, J=5.9 Hz, 2H), 3.58 (m, 2H), 3.81 (s, 2H), 4.38 (s, 1H), 7.27 (dd, J=1.5, 4.8 Hz, 2H), 7.61 (br s, 1H), 7.84 (br s, 1H), 8.32 (s, 1H), 8.46 (dd, J=1.4, 4.8 Hz, 2H).

Compound 4-7: ESI m/z: 438 [M+H]$^+$; $^1$H NMR (DMSO-d$_6$) δ(ppm): 1.97 (s, 3H), 2.4-2.6 (m, 4H), 2.90 (br t, J=7.0 Hz, 2H), 3.05 (br d, J=4.0 Hz, 3H), 3.43 (m, 4H), 3.58 (m, 2H), 3.88 (s, 2H), 7.27 (dd, J=1.1, 4.8 Hz, 2H), 7.62 (br s, 1H), 7.83 (br s, 1H), 8.32 (s, 1H), 8.45 (dd, J=1.1, 4.8 Hz, 2H).

Compound 4-8: ESI m/z: 410 [M+H]$^+$; $^1$H NMR (DMSO-d$_6$) δ(ppm): 2.15 (s, 3H), 2.33 (m, 4H), 2.50 (m, 4H), 2.90 (br t, J=6.8 Hz, 2H), 3.05 (br d, J=4.0 Hz, 3H), 3.58 (m, 2H), 3.82 (s, 2H), 7.27 (d, J=5.5 Hz, 2H), 7.62 (br s, 1H), 7.84 (br s, 1H), 8.31 (s, 1H), 8.46 (d, J=5.5 Hz, 2H).

Compound 4-10: ESI m/z: 399 [M+H]$^+$; $^1$H NMR (DMSO-d$_6$) δ(ppm): 2.25 (s, 6H), 2.89 (br t, J=6.7 Hz, 2H), 3.30 (s, 3H), 3.5-3.8 (m, 6H), 3.77 (s, 2H), 7.26 (d, J=5.7 Hz, 2H), 7.65 (br s, 1H), 8.06 (br s, 1H), 8.34 (s, 1H), 8.46 (d, J=5.7 Hz, 2H).

Compound 4-11: ESI m/z: 484 [M+H]$^+$; $^1$H NMR (DMSO-d$_6$) δ(ppm): 2.3-2.6 (m, 8H), 2.36 (t, J=6.2 Hz, 2H), 2.89 (br t, J=7.1 Hz, 2H), 3.30 (s, 3H), 3.45 (m, 2H), 3.5-3.8 (m, 6H), 3.82 (s, 2H), 4.36 (t, J=5.3 Hz, 1H), 7.26 (dd, J=1.7, 4.4 Hz, 2H), 7.66 (br s, 1H), 8.05 (br s, 1H), 8.34 (s, 1H), 8.46 (dd, J=1.7, 4.4 Hz, 2H).

Compound 4-12: ESI m/z: 482 [M+H]$^+$; $^1$H NMR (DMSO-d$_6$) δ(ppm): (hydrochloride, major peaks) 2.03 (s, 3H), 3.1-3.4 (m, 6H), (br t, J=5.1 Hz, 2H), 3.80 (m, 8H), 4.68 (s, 2H), (d, J=6.2 Hz, 2H), 8.59 (s, 1H), 8.8-8.9 (br, 1H), (d, J=6.2 Hz, 2H).

Compound 4-13: ESI m/z: 454 [M+H]$^+$; $^1$H NMR (DMSO-d$_6$) δ(ppm): 2.14 (s, 3H), 2.32 (m, 4H), 2.50 (m, 4H), 2.89 (br t, J=6.9 Hz, 2H), 3.30 (s, 3H), 3.5-3.8 (m, 6H), 3.81 (s, 2H), 7.26 (dd, J=1.6, 4.5 Hz, 2H), 7.66 (br s, 1H), 8.05 (br s, 1H), 8.34 (s, 1H), 8.46 (dd, J=1.6, 4.5 Hz, 2H).

Compound 4-14: ESI m/z: 468 [M+H]$^+$; $^1$H NMR (DMSO-d$_6$) δ(ppm): 0.96 (t, J=7.2 Hz, 3H), 2.29 (q, J=7.2 Hz, 2H), 2.36 (m, 4H), 2.50 (m, 4H), 2.89 (br t, J=7.0 Hz, 2H), 3.30 (s, 3H), 3.5-3.8 (m, 6H), 3.81 (s, 2H), 7.26 (dd, J=1.5, 4.4 Hz, 2H), 7.66 (br s, 1H), 8.06 (br s, 1H), 8.34 (s, 1H), 8.46 (dd, J=1.5, 4.4 Hz, 2H).

Compound 4-15: ESI m/z: 440 [M+H]$^+$; $^1$H NMR (DMSO-d$_6$) δ(ppm): (major peaks) 2.41 (m, 4H), 2.68 (m, 4H), 2.89 (m, 2H), 3.30 (s, 3H), 3.5-3.8 (m, 6H), 3.78 (s, 2H), 7.26 (dd, J=1.5, 4.4 Hz, 2H), 7.66 (br s, 1H), 8.05 (br s, 1H), 8.34 (s, 1H), 8.46 (dd, J=1.5, 4.4 Hz, 2H).

Compound 4-16: ESI m/z: 441 [M+H]$^+$; $^1$H NMR (DMSO-d$_6$) δ(ppm): 2.50 (m, 4H), 2.89 (br t, J=6.8 Hz, 2H), 3.34 (s, 3H), 3.5-3.8 (m, 10H), 3.83 (s, 2H), 7.26 (dd, J=1.6, 4.5 Hz, 2H), 7.66 (br s, 1H), 8.05 (br s, 1H), 8.35 (s, 1H), 8.46 (dd, J=1.6, 4.5 Hz, 2H).

Compound 4-17: ESI m/z: 482 [M+H]$^+$; $^1$H NMR (DMSO-d$_6$) δ(ppm): 0.94 (d, J=6.6 Hz, 6H), 2.3-2.6 (m, 8H), 2.59 (septet, J=6.6 Hz, 1H), 2.89 (br t, J=6.9 Hz, 2H), 3.30 (s, 3H), 3.5-3.8 (m, 6H), 3.80 (br s, 2H), 7.26 (dd, J=1.7, 4.5 Hz, 2H), 7.64 (br s, 1H), 8.06 (br s, 1H), 8.34 (s, 1H), 8.46 (dd, J=1.7, 4.5 Hz, 2H).

Compound 4-18: ESI m/z: 508 [M+H]$^+$; $^1$H NMR (DMSO-d$_6$) δ(ppm): 1.2-1.8 (m, 8H), 2.3-2.6 (m, 9H), 2.89 (br t, J=6.9 Hz, 2H), 3.30 (s, 3H), 3.5-3.8 (m, 6H), 3.80 (s, 2H), 7.26 (dd, J=1.6, 4.4 Hz, 2H), 7.66 (br s, 1H), 8.05 (br s, 1H), 8.34 (s, 1H), 8.46 (dd, J=1.6, 4.4 Hz, 2H).

Compound 4-19: ESI m/z: 498 [M+H]$^+$; $^1$H NMR (DMSO-d$_6$) δ(ppm): 2.3-2.6 (m, 10H), 2.89 (br t, J=6.9 Hz, 2H), 3.21 (s, 3H), 3.30 (s, 3H), 3.40 (t, J=5.8 Hz, 2H), 3.5-3.8 (m, 6H), 3.81 (s, 2H), 7.26 (dd, J=1.6, 4.4 Hz, 2H), 7.66 (br s, 1H), 8.05 (br s, 1H), 8.34 (s, 1H), 8.46 (dd, J=1.4, 4.4 Hz, 2H).

Compound 4-20: ESI m/z: 438 [M+H]$^+$; $^1$H NMR (DMSO-d$_6$) δ(ppm): 0.94 (d, J=6.6 Hz, 6H), 2.3-2.5 (m, 8H), 2.59 (m, 1H), 2.91 (br t, J=6.6 Hz, 2H), 3.05 (d, J=4.4 Hz, 3H), 3.58 (m, 2H), 3.80 (s, 2H), 7.26 (dd, J=1.5, 4.4 Hz, 2H), 7.62 (br s, 1H), 7.85 (br d, J=4.4 Hz, 1H), 8.32 (s, 1H), 8.46 (dd, J=1.5, 4.4 Hz, 2H).

Compound 4-21: ESI m/z: 480 [M+H]$^+$; $^1$H NMR (DMSO-d$_6$) δ(ppm): 1.4-2.0 (m, 4H), 2.3-2.6 (m, 10H), 2.90 (br t, J=7.0 Hz, 2H), 3.04 (d, J=4.4 Hz, 3H), 3.5-3.9 (m, 3H), 3.58 (m, 2H), 3.81 (s, 2H), 7.26 (dd, J=1.8, 4.4 Hz, 2H), 7.62 (br s, 1H), 7.84 (br d, J=4.4 Hz, 1H), 8.32 (s, 1H), 8.46 (dd, J=1.8, 4.4 Hz, 2H).

Compound 4-22: ESI m/z: 424 [M+H]$^+$; $^1$H NMR (DMSO-d$_6$) δ(ppm): 2.4-2.6 (m, 4H), 2.91 (br t, J=7.0 Hz, 2H), 3.05 (d, J=4.4 Hz, 3H), 3.3-3.5 (m, 4H), 3.58 (m, 2H), 3.90 (s, 2H), (dd, J=1.5, 4.4 Hz, 2H), 7.62 (br t, J=5.4 Hz, 1H), (br d, J=4.4 Hz, 1H), 7.98 (s, 1H), 8.32 (s, 1H), (dd, J=1.5, 4.4 Hz, 2H).

Compound 4-23: ESIMS m/z: 452 [M+H]$^+$; $^1$H NMR (CDCl$_3$) δ(ppm): (t, J=7.6 Hz, 3H), 1.67-1.76 (m, 2H), 2.29 (s, 3H), (br s, 4H), 2.54 (s, 3H), 2.67 (br s, 4H), 2.90 (t, J=6.8 Hz, 2H), 3.56 (br s, 2H), 3.72 (dt, J=6.8, 6.8 Hz, 2H), 3.86 (s, 2H), 5.28 (br s, 1H), 6.98 (d, J=5.1 Hz, 1H), 7.03 (br s, 1H), 8.11 (br s, 1H), 8.40-8.44 (m, 2H).

Compound 4-25: ESI m/z: 436 [M+H]$^+$; $^1$H NMR (DMSO-d$_6$) δ(ppm): 0.59 (m, 2H), 0.83 (m, 2H), 2.14 (s, 3H), 2.2-2.6 (m, 8H), 2.94 (m, 3H), 3.60 (m, 2H), 3.81 (s, 2H), 7.27 (d, J=5.7 Hz, 2H), 7.70 (br t, J=5.7 Hz, 1H), 7.91 (br s, 1H), 8.33 (s, 1H), 8.46 (d, J=5.7 Hz, 2H).

Compound 4-32: ESI m/z: 424 [M+H]$^+$; $^1$H NMR (DMSO-d$_6$) δ(ppm): (br t, J=7.3 Hz, 3H), 2.14 (s, 3H), 2.2-2.5 (m, 8H), br t, J=6.8 Hz, 2H), 3.4-3.6 (m, 4H), 3.81 (s, 2H), (dd, J=1.5, 4.4 Hz, 2H), 7.62 (br s, 1H), 7.92 (br s, 1H), 8.33 (s, 1H), 8.46 (dd, J=1.5, 4.4 Hz, 2H).

Compound 4-33: ESI m/z: 450 [M+H]$^+$; $^1$H NMR (DMSO-d$_6$) δ(ppm): 1.77 (m, 2H), 2.00 (m, 2H), 2.14 (s, 3H), 2.3-2.6 (m, 10H), 2.90 (br t, J=6.5 Hz, 2H), 3.58 (m, 2H), 3.82 (s, 2H), 4.60 (m, 1H), 7.27 (br d, J=5.3 Hz, 2H), 7.66 (br s, 1H), 8.02 (br s, 1H), 8.33 (s, 1H), 8.47 (br d, J=5.3 Hz, 2H).

Compound 4-34: ESI m/z: 454 [M+H]$^+$; $^1$H NMR (DMSO-d$_6$) δ(ppm): 1.77 (m, 2H), 2.14 (s, 3H), 2.2-2.6 (m, 8H), 2.89 (br t, J=6.8 Hz, 2H), 3.4-3.7 (m, 6H), 3.81 (s, 2H), 4.59 (br s, 1H), 7.27 (dd, J=1.5, 4.5 Hz, 2H), 7.62 (br s, 1H), 7.98 (br s, 1H), 8.32 (s, 1H), 8.46 (dd, J=1.5, 4.5 Hz, 2H).

Compound 4-35: ESI m/z: 456 [M+H]$^+$; $^1$H NMR (DMSO-d$_6$) δ(ppm): 1.9-2.1 (m, 2H), 2.14 (s, 3H), 2.2-2.6 (m, 8H), 2.89 (br t, J=7.0 Hz, 2H), 3.5-3.8 (m, 4H), 3.81 (s, 2H), 4.44 (t, J=5.8 Hz, 1H), 4.62 (t, J=5.8 Hz, 1H), 7.25 (dd, J=1.7, 4.5 Hz, 2H), 7.65 (br t, J=5.5 Hz, 1H), 8.01 (br t, J=5.5 Hz, 1H), 8.33 (s, 1H), 8.45 (dd, J=1.7, 4.5 Hz, 2H).

Compound 5-1: ESI m/z: 370 [M+H]$^+$; $^1$H NMR (DMSO-d$_6$) δ(ppm): (Na salt) 0.92 (t, J=7.4 Hz, 3H), 1.62 (m, 2H), 2.88 (m, 2H), 3.4-3.6 (m, 4H), 7.25 (d, J=5.7 Hz, 2H), 7.55 (br s, 1H), 8.06 (br s, 1H), 8.38 (s, 1H), 8.45 (m, 2H).

Compound 5-2: ESI m/z: 482 [M+H]$^+$; $^1$H NMR (DMSO-d$_6$) δ(ppm): 0.94 (t, J=7.4 Hz, 3H), 1.64 (m, 2H), 2.4-2.6 (m, 6H), 2.90 (t, J=7.0 Hz, 2H), 3.41 (m, 2H), 3.5-3.6 (m, 8H), 7.26 (dd, J=1.5, 4.6 Hz, 2H), 7.76 (br t, J=5.6 Hz, 1H), 7.92 (br t, J=5.2 Hz, 1H), 8.4-8.5 (m, 3H), 9.08 (br t, J=5.9 Hz, 1H).

Compound 5-3: ESI m/z: 509 [M+H]$^+$; $^1$H NMR (DMSO-d$_6$) δ(ppm): 0.94 (t, J=7.3 Hz, 3H), 1.5-1.8 (m, 4H), 2.13 (s, 3H), 2.2-2.5 (m, 10H), 2.90 (t, J=7.0 Hz, 2H), 3.3-3.4 (m, 2H), 3.4-3.7 (m, 4H), 7.26 (d, J=5.9 Hz, 2H), 7.76 (br t, J=5.5 Hz, 1H), 7.93 (br t, J=5.3 Hz, 1H), 8.4-8.5 (m, 3H), 9.24 (br t, J=5.1 Hz, 1H).

Compound 5-4: ESI m/z: 439 [M+H]$^+$; $^1$H NMR (DMSO-d$_6$) δ(ppm): 0.93 (t, J=7.4 Hz, 3H), 1.61 (m, 2H), 2.89 (m, 2H), 3.3-3.7 (m, 10H), 3.96 (m, 2H), 7.24 (d, J=5.8 Hz, 2H), 7.71 (br s, 1H), 7.93 (br s, 1H), 8.36 (s, 1H), 8.45 (d, J=5.8 Hz, 2H).

Compound 5-5: ESI m/z: 452 [M+H]$^+$; $^1$H NMR (DMSO-d$_6$) δ(ppm): 0.94 (t, J=7.3 Hz, 3H), 1.63 (m, 2H), 2.32 (s, 3H), 2.56 (m, 4H), 2.90 (t, J=6.9 Hz, 2H), 3.4-3.6 (m, 4H), 3.72 (m, 2H), 3.97 (m, 2H), 7.26 (d, J=5.7 Hz, 2H), 7.72 (br s, 1H), 7.93 (br s, 1H), 8.37 (s, 1H), 8.46 (d, J=5.7 Hz, 2H).

Compound 5-6: ESI m/z: 475 [M+H]$^+$; $^1$H NMR (DMSO-d$_6$) δ(ppm): 0.93 (t, J=7.4 Hz, 3H), 1.63 (m, 2H), 2.90 (m, 2H), 3.06 (s, 3H), 3.4-3.6 (m, 4H), 3.41 (t, J=6.8 Hz, 2H), 3.71 (br t, J=6.8 Hz, 2H), 7.26 (d, J=5.9 Hz, 2H), 7.78 (br t, J=5.6 Hz, 1H), 7.91 (br t, J=5.4 Hz, 1H), 8.45 (s, 1H), 8.46 (d, J=5.9 Hz, 2H), 9.39 (s, 1H).

Compound 6-1: ESI m/z: 342 [M+H]$^+$; $^1$H NMR (DMSO-d$_6$) δ(ppm): 0.91 (t, J=7.4 Hz, 3H), 1.58 (m, 2H), 2.87 (t, J=7.0 Hz, 2H), 3.3-3.6 (m, 4H), 7.1-7.6 (m, 2H), 7.24 (dd, J=1.5, 4.4 Hz, 2H), 8.13 (s, 1H), 8.45 (dd, J=1.5, 4.4 Hz, 2H), 12.4 (br s, 1H).

Compound 6-2: ESI m/z: 448 [M+H]$^+$; $^1$H NMR (CDCl$_3$) δ(ppm): 1.01 (t, J=7.4 Hz, 3H), 1.69 (m, 2H), 2.93 (t, J=7.0 Hz, 2H), 3.52 (m, 2H), 3.64 (t, J=6.4 Hz, 2H), 3.72 (dt, J=6.6, 7.0 Hz, 2H), 4.17 (t, J=6.4 Hz, 2H), 5.3 (br s, 1H), 7.08 (br s, 1H), 7.16 (dd, J=1.5, 4.5 Hz, 2H), 8.32 (s, 1H), 8.53 (dd, J=1.5, 4.5 Hz, 2H).

Compound 6-3: ESI m/z: 455 [M+H]$^+$; $^1$H NMR (CDCl$_3$) δ(ppm): 1.01 (t, J=7.4 Hz, 3H), 1.68 (m, 2H), 2.52 (m, 4H), 2.71 (t, J=6.3 Hz, 2H), 2.93 (t, J=7.0 Hz, 2H), 3.52 (m, 2H), 3.68 (m, 6H), 3.88 (t, J=6.3 Hz, 2H), 5.50 (br s, 1H), 7.1-7.2 (br, 1H), 7.16 (d, J=5.9 Hz, 2H), 8.31 (br s, 1H), 8.52 (d, J=5.9 Hz, 2H).

Compound 6-4: ESI m/z: 439 [M+H]$^+$; $^1$H NMR (CDCl$_3$) δ(ppm): 1.01 (t, J=7.4 Hz, 3H), 1.67 (m, 2H), 1.7-1.9 (m, 4H), 2.58 (m, 4H), 2.84 (t, J=6.6 Hz, 2H), 2.92 (t, J=6.9 Hz, 2H), 3.52 (m, 2H), 3.71 (m, 2H), 3.89 (t, J=6.6 Hz, 2H), 5.41 (br s, 1H), 7.0-7.2 (br, 1H), 7.15 (d, J=4.6 Hz, 2H), 8.29 (s, 1H), 8.52 (d, J=4.6 Hz, 2H).

Compound 6-5: ESI m/z: 468 [M+H]$^+$; $^1$H NMR (CDCl$_3$) δ(ppm): 1.01 (t, J=7.3 Hz, 3H), 1.68 (m, 2H), 2.27 (s, 3H), 2.43 (m, 4H), 2.55 (m, 4H), 2.72 (t, J=6.5 Hz, 2H), 2.93 (t, J=6.9 Hz, 2H), 3.51 (m, 2H), 3.72 (m, 2H), 3.87 (t, J=6.5 Hz, 2H), 5.45 (br s, 1H), 7.0-7.2 (br, 1H), 7.16 (d, J=4.8 Hz, 2H), 8.42 (br s, 1H), 8.52 (d, J=4.8 Hz, 2H).

Compound 6-6: ESI m/z: 453 [M+H]$^+$; $^1$H NMR (CDCl$_3$) δ(ppm): 1.01 (t, J=6.8 Hz, 3H), 1.3-1.8 (m, 8H), 2.44 (m, 4H), 2.68 (t, J=6.0 Hz, 2H), 2.93 (t, J=6.8 Hz, 2H), 3.50 (m, 2H), 3.71 (m, 2H), 3.87 (t, J=6.0 Hz, 2H), 5.41 (br s, 1H), 7.0-7.2 (br, 1H), 7.15 (m, 2H), 8.29 (s, 1H), 8.51 (m, 2H).

Compound 6-7: ESI m/z: 413 [M+H]$^+$; $^1$H NMR (CDCl$_3$) δ(ppm): 1.01 (t, J=6.6 Hz, 3H), 1.68 (m, 2H), 2.29 (s, 6H), 2.67 (t, J=5.5 Hz, 2H), 2.92 (t, J=6.9 Hz, 2H), 3.51 (m, 2H), 3.71 (m, 2H), 3.85 (t, J=5.5 Hz, 2H), 5.53 (br s, 1H), 7.0-7.2 (br, 1H), 7.15 (d, J=4.0 Hz, 2H), 8.28 (s, 1H), 8.51 (d, J=4.0 Hz, 2H).

Compound 7-1: ESI m/z: 340 [M+H]$^+$; $^1$H NMR (CDCl$_3$) δ(ppm): 1.02 (t, J=7.4 Hz, 3H), 1.72 (m, 2H), 2.95 (t, J=7.1 Hz, 2H), 3.54 (m, 2H), 3.73 (m, 2H), 4.38 (s, 3H), 5.24 (br s, 1H), 7.17 (dd, J=1.7, 4.5 Hz, 2H), 7.76 (br s, 1H), 8.52 (dd, J=1.7, 4.5 Hz, 2H), 8.72 (s, 1H).

Compound 7-2: ESI m/z: 345 [M+H]$^+$; $^1$H NMR (CDCl$_3$) δ(ppm): 1.02 (t, J=7.4 Hz, 3H), 1.6-1.8 (m, 2H), 3.16 (m, 2H), 3.5-3.6 (m, 2H), 3.7-3.8 (m, 2H), 4.37 (s, 3H), 5.25 (br s, 1H), 6.8-7.0 (m, 2H), 7.1-7.2 (m, 1H), 7.73 (br s, 1H), 8.72 (s, 1H).

Compound 7-3: ESI m/z: 439 [M+H]$^+$; $^1$H NMR (CDCl$_3$) δ(ppm): 1.03 (t, J=7.4 Hz, 3H), 1.72 (m, 2H), 2.53 (m, 4H), 2.95 (t, J=7.1 Hz, 2H), 3.01 (t, J=6.5 Hz, 2H), 3.55 (m, 2H), 3.66 (m, 4H), 3.73 (m, 2H), 4.75 (t, J=6.5 Hz, 2H), 5.18 (br s, 1H), 7.17 (dd, J=1.5, 4.5 Hz, 2H), 7.79 (br s, 1H), 8.52 (dd, J=1.5, 4.5 Hz, 2H), 8.72 (s, 1H).

Example 24

A tablet having the following formulation is prepared in a conventional manner.
Formulation:

| | |
|---|---|
| Compound 2 | 5 mg |
| Lactose | 60 mg |
| Potato starch | 30 mg |
| Polyvinyl alcohol | 2 mg |
| Magnesium stearate | 1 mg |
| Tar dye | trace amount |

INDUSTRIAL APPLICABILITY

The present invention provides an antitumor agent comprising, as an active ingredient, a pyrimidine derivative or a pharmaceutically acceptable salt thereof; a pyrimidine derivative or a pharmaceutically acceptable salt thereof having an antitumor activity etc.; and the like.

The invention claimed is:
1. A pyrimidine derivative represented by Formula (I):

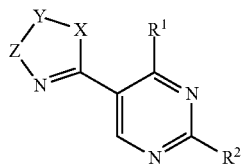

(I)

[wherein
—X—Y—Z— represents —O—CR$^3$=N— {wherein R$^3$ represents a hydrogen atom, hydroxy, carboxy, lower alkyl, lower alkyl substituted with one to four substituents, which may be the same or different and selected from the following substituent group A [substituent group A: halogen, amino, aminosulfonyl, nitro, hydroxy, mercapto, cyano, formyl, carboxy, carbamoyl, lower alkanoyloxy, lower alkanoylamino, mono- or di-(lower alkyl)aminocarbonyl, lower alkoxycarbonyl, mono- or di-(lower alkyl)amino, N-aryl-N-(lower alkyl) amino, lower alkylsulfonyl, lower alkylsulfinyl, mono- or di-(lower alkylsulfonyl)amino, mono- or di-(arylsulfonyl)amino, tri-(lower alkyl)silyl, lower alkylthio, aromatic heterocyclic alkylthio, lower alkanoyl, lower alkanoyl substituted with one to three substituents, which may be the same or different and selected from the following substituent group a (substituent group a: halogen and hydroxy), lower alkoxy, lower alkoxy substituted with one to three substituents, which may be the same or different and selected from the substituent group a, aryloxy, aryloxy substituted with one to three substituents, which may be the same or different and selected from the substituent group a, aralkyloxy, and aralkyloxy substituted with one to three substituents, which may be the same or different and selected from the substituent group a; wherein, when the substituted lower alkyl is substituted methyl, substituted ethyl, or substituted propyl, the substituent may be —NR$^4$R$^5$ (wherein R$^4$ and R$^5$ may be the same or different, and each represents a hydrogen atom, substituted or unsubstituted lower alkyl, substituted or unsubstituted lower alkenyl, substituted or unsubstituted lower alkynyl, substituted or unsubstituted aralkyl, substituted or unsubstituted aromatic heterocyclic alkyl, substituted or unsubstituted heteroalicyclic alkyl, substituted or unsubstituted aryl, a substituted or unsubstituted aromatic heterocyclic group, or a substituted or unsubstituted heteroalicyclic group)], substituted or unsubstituted lower alkenyl, substituted or unsubstituted lower alkynyl, substituted or unsubstituted aralkyl, substituted or unsubstituted aromatic heterocyclic alkyl, substituted or unsubstituted heteroalicyclic alkyl, substituted or unsubstituted aryl, a substituted or unsubstituted aromatic heterocyclic group, a substituted or unsubstituted heteroalicyclic group, substituted or unsubstituted lower alkoxy, substituted or unsubstituted lower alkoxycarbonyl, substituted or unsubstituted lower alkylthio, substituted or unsubstituted lower alkanoyl, or —C(=O)NR$^6$R$^7$ (wherein R$^6$ and R$^7$ may be the same or different, and each represents a hydrogen atom, substituted or unsubstituted lower alkyl, substituted or unsubstituted lower alkenyl, substituted or unsubstituted lower alkynyl, substituted or unsubstituted aralkyl, substituted or unsubstituted aromatic heterocyclic alkyl, substituted or unsubstituted heteroalicyclic alkyl, substituted or unsubstituted aryl, a substituted or unsubstituted aromatic heterocyclic group, or a substituted or unsubstituted heteroalicyclic group, or R$^6$ and R$^7$ are combined together with the adjacent nitrogen atom thereto to form a substituted or unsubstituted heteroalicyclic group)}
R$^1$ represents —NR$^{10}$R$^{11}$ (wherein R$^{10}$ and R$^{11}$ may be the same or different, and each represents a hydrogen atom, substituted or unsubstituted lower alkyl, substituted or unsubstituted lower alkenyl, substituted or unsubstituted lower alkynyl, substituted or unsubstituted aralkyl, substituted or unsubstituted aromatic heterocyclic alkyl, substituted or unsubstituted heteroalicyclic alkyl, substituted or unsubstituted monocyclic aryl, a substituted or unsubstituted aromatic monoheterocyclic group, or a substituted or unsubstituted heteroalicyclic group, or

243

$R^{10}$ and $R^{11}$ are combined together with the adjacent nitrogen atom thereto to form a substituted or unsubstituted heteroalicyclic group; wherein, when one of $R^{10}$ and $R^{11}$ is a hydrogen atom, the other of $R^{10}$ and $R^{11}$ is not a group selected from substituted or unsubstituted pyrazol-3-yl and substituted or unsubstituted 1,2,4-triazol-3-yl), or —$OR^{12}$ (wherein $R^{12}$ represents a hydrogen atom, substituted or unsubstituted lower alkyl, substituted or unsubstituted lower alkenyl, substituted or unsubstituted lower alkynyl, substituted or unsubstituted aralkyl, substituted or unsubstituted aromatic heterocyclic alkyl, substituted or unsubstituted heteroalicyclic alkyl, substituted or unsubstituted aryl, a substituted or unsubstituted aromatic heterocyclic group, or a substituted or unsubstituted heteroalicyclic group); and $R^2$ represents —$NR^{13}R^{14}$ (wherein $R^{13}$ and $R^{14}$ may be the same or different, and each represents a hydrogen atom, substituted or unsubstituted lower alkyl, substituted or unsubstituted lower alkenyl, substituted or unsubstituted lower alkynyl, substituted or unsubstituted aralkyl, substituted or unsubstituted aromatic heterocyclic alkyl, substituted or unsubstituted heteroalicyclic alkyl, substituted or unsubstituted monocyclic aryl, a substituted or unsubstituted aromatic monoheterocyclic group, or a substituted or unsubstituted heteroalicyclic group; wherein $R^{13}$ and $R^{14}$ do not simultaneously represent a hydrogen atom, and when one of $R^{13}$ and $R^{14}$ is a hydrogen atom, the other of $R^{13}$ and $R^{14}$ is not substituted or unsubstituted pyrazol-3-yl)]

or a pharmaceutically acceptable salt thereof.

2. A pyrimidine derivative represented by Formula (IA):

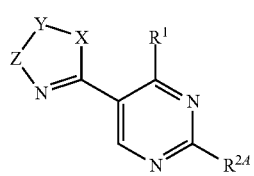

(IA)

[wherein

—X—Y—Z— represents —O—$CR^3$=N— {wherein $R^3$ represents a hydrogen atom, hydroxy, carboxy, lower alkyl, lower alkyl substituted with one to four substituents, which may be the same or different and selected from the following substituent group A [substituent group A: halogen, amino, aminosulfonyl, nitro, hydroxy, mercapto, cyano, formyl, carboxy, carbamoyl, lower alkanoyloxy, lower alkanoylamino, mono- or di-(lower alkyl)aminocarbonyl, lower alkoxycarbonyl, mono- or di-(lower alkyl)amino, N-aryl-N-(lower alkyl) amino, lower alkylsulfonyl, lower alkylsulfonyl, mono- or di-(lower alkylsulfonyl)amino, mono- or di-(arylsulfonyl)amino, tri-(lower alkyl)silyl, lower alkylthio, aromatic heterocyclic alkylthio, lower alkanoyl, lower alkanoyl substituted with one to three substituents, which may be the same or different and selected from the following substituent group a (substituent group a: halogen and hydroxy), lower alkoxy, lower alkoxy substituted with one to three substituents, which may be the same or different and selected from the substituent group a, aryloxy, aryloxy substituted with one to three substituents, which may be the same or different and selected from the substituent group a, aralkyloxy, and aralkyloxy substituted with one to three substituents,

244 which may be the same or different and selected from the substituent group a; wherein, when the substituted lower alkyl is substituted methyl, substituted ethyl, or substituted propyl, the substituent may be —$NR^4R^5$ (wherein $R^4$ and $R^5$ may be the same or different, and each represents a hydrogen atom, substituted or unsubstituted lower alkyl, substituted or unsubstituted lower alkenyl, substituted or unsubstituted lower alkynyl, substituted or unsubstituted aralkyl, substituted or unsubstituted aromatic heterocyclic alkyl, substituted or unsubstituted heteroalicyclic alkyl, substituted or unsubstituted aryl, a substituted or unsubstituted aromatic heterocyclic group, or a substituted or unsubstituted heteroalicyclic group)], substituted or unsubstituted lower alkenyl, substituted or unsubstituted lower alkynyl, substituted or unsubstituted aralkyl, substituted or unsubstituted aromatic heterocyclic alkyl, substituted or unsubstituted heteroalicyclic alkyl, substituted or unsubstituted aryl, a substituted or unsubstituted aromatic heterocyclic group, a substituted or unsubstituted heteroalicyclic group, substituted or unsubstituted lower alkoxy, substituted or unsubstituted lower alkoxycarbonyl, substituted or unsubstituted lower alkylthio, substituted or unsubstituted lower alkanoyl, or —C(=O)$NR^6R^7$ (wherein $R^6$ and $R^7$ may be the same or different, and each represents a hydrogen atom, substituted or unsubstituted lower alkyl, substituted or unsubstituted lower alkenyl, substituted or unsubstituted lower alkynyl, substituted or unsubstituted aralkyl, substituted or unsubstituted aromatic heterocyclic alkyl, substituted or unsubstituted heteroalicyclic alkyl, substituted or unsubstituted aryl, a substituted or unsubstituted aromatic heterocyclic group, or a substituted or unsubstituted heteroalicyclic group, or $R^6$ and $R^7$ are combined together with the adjacent nitrogen atom thereto to form a substituted or unsubstituted heteroalicyclic group)}, $R^1$ represents —$NR^{10}R^{11}$ (wherein $R^{10}$ and $R^{11}$ may be the same or different, and each represents a hydrogen atom, substituted or unsubstituted lower alkyl, substituted or unsubstituted lower alkenyl, substituted or unsubstituted lower alkynyl, substituted or unsubstituted aralkyl, substituted or unsubstituted aromatic heterocyclic alkyl, substituted or unsubstituted heteroalicyclic alkyl, substituted or unsubstituted monocyclic aryl, a substituted or unsubstituted aromatic monoheterocyclic group, or a substituted or unsubstituted heteroalicyclic group, or $R^{10}$ and $R^{11}$ are combined together with the adjacent nitrogen atom thereto to form a substituted or unsubstituted heteroalicyclic group; wherein, when one of $R^{10}$ and $R^{11}$ is a hydrogen atom, the other of $R^{10}$ and $R^{11}$ is not a group selected from substituted or unsubstituted pyrazol-3-yl and substituted or unsubstituted 1,2,4-triazol-3-yl), or —$OR^{12}$ (wherein $R^{12}$ represents a hydrogen atom, substituted or unsubstituted lower alkyl, substituted or unsubstituted lower alkenyl, substituted or unsubstituted lower alkynyl, substituted or unsubstituted aralkyl, substituted or unsubstituted aromatic heterocyclic alkyl, substituted or unsubstituted heteroalicyclic alkyl, substituted or unsubstituted aryl, a substituted or unsubstituted aromatic heterocyclic group, or a substituted or unsubstituted heteroalicyclic group); and $R^{2A}$ represents —$NR^{13A}R^{14A}$ {wherein $R^{13A}$ and $R^{14A}$ may be the same or different, and each represents a hydrogen atom, lower alkyl, lower alkyl substituted with one to four substituents, which may be the same or different and selected from the following substituent group B [substituent group B: halogen, amino, aminosulfonyl, nitro, hydroxy, mercapto, cyano, formyl, carboxy, carbamoyl, lower alkanoyloxy, lower alkanoylamino, mono- or di-(lower alkyl)aminocarbonyl, lower alkoxycarbonyl, mono- or di-(lower alkyl)amino, N-aryl-N-(lower alkyl)amino, lower alkylsulfonyl, lower alkylsulfinyl, mono- or di-(lower alkylsulfonyl)amino, mono- or di-(arylsulfonyl)amino, tri-(lower alkyl)silyl, lower alkylthio, aromatic heterocyclic alkylthio, lower alkanoyl, lower alkanoyl substituted with one to three substituents, which may be the same or different and selected from the following substituent group a (substituent group a: halogen and hydroxy), lower alkoxy, lower alkoxy substituted with one to three substituents, which may be the same or different and selected from the substituent group a, aryloxy, aryloxy substituted with one to three substituents, which may be the same or different and selected from the substituent group a, aralkyloxy, and aralkyloxy substituted with one to three substituents, which may be the same or different and selected from the substituent group a], substituted or unsubstituted lower alkenyl, substituted or unsubstituted lower alkynyl, substituted or unsubstituted heteroalicyclic alkyl, substituted or unsubstituted monocyclic aryl, or a substituted or unsubstituted heteroalicyclic group, wherein $R^{13A}$ and $R^{14A}$ do not simultaneously represent a hydrogen atom}, —$NR^{15}CR^{16A}R^{16B}$—Ar {wherein $R^{15}$ represents a hydrogen atom or lower alkyl; $R^{16A}$ and $R^{16B}$ may be the same or different, and each represents a hydrogen atom, lower alkyl, or lower alkyl substituted with one to three substituents, which may be the same or different and selected from the following substituent group b (substituent group b: halogen, hydroxy, and hydroxymethyl); and Ar represents aryl, aryl substituted with one to three substituents, which may be the same or different and selected from the following substituent group c [substituent group c: halogen, amino, nitro, hydroxy, mercapto, cyano, carboxy, aminosulfonyl, lower alkyl, lower alkyl substituted with one to three substituents, which may be the same or different and selected from the substituent group b, lower alkoxy, lower alkylthio, mono- or di-(lower alkyl) amino, lower alkanoylamino, mono- or di-(lower alkylsulfonyl)amino, lower alkoxycarbonylamino, heteroalicyclic alkyloxy, and alkylenedioxy], an aromatic heterocyclic group, or an aromatic heterocyclic group substituted with one to three substituents, which may be the same or different and selected from the substituent group c}, or —$NR^{15}CR^{16A}R^{16B}CR^{17A}R^{17B}$—Ar (wherein $R^{15}$, $R^{16B}$, and Ar have the same definitions as described above, respectively; and $R^{17A}$ and $R^{17B}$ have the same definition as $R^{16A}$ and $R^{16B}$ described above, respectively)]

or a pharmaceutically acceptable salt thereof.

3. The pyrimidine derivative or the pharmaceutically acceptable salt thereof according to claim 2, wherein —X—Y—Z— is —O—$CR^{3A}$=N— (wherein $R^{3A}$ represents lower alkyl, lower alkyl substituted with one to four substituents, which may be the same or different and selected from the substituent group a, or heteroalicyclic alkyl).

4. The pyrimidine derivative or the pharmaceutically acceptable salt thereof according to claim 3, wherein $R^1$ is —$NR^{10}R^{11}$, and $R^{2A}$ is —$NR^{15}CR^{16A}R^{16B}$—Ar or —$NR^{15}CR^{16A}R^{16B}CR^{17A}R^{17B}$—Ar.

5. The pyrimidine derivative or the pharmaceutically acceptable salt thereof according to claim 4, wherein $R^1$ is —$NHR^{10A}$ (wherein $R^{10A}$ represents substituted or unsubstituted lower alkyl or substituted or unsubstituted monocyclic aryl).

6. The pyrimidine derivative or the pharmaceutically acceptable salt thereof according to claim 5, wherein $R^{2A}$ is —$NH(CH_2)_2$—Ar.

7. The pyrimidine derivative or the pharmaceutically acceptable salt thereof according to claim 5, wherein $R^{2A}$ is —$NH(CH_2)_2$—$Ar^1$ (wherein $Ar^1$ represents phenyl or phenyl substituted with one to three substituents, which may be the same or different and selected from the substituent group c).

8. The pyrimidine derivative or the pharmaceutically acceptable salt thereof according to claim 5, wherein $R^{2A}$ is —$NH(CH_1)_2$—$Ar^2$ (wherein $Ar^2$ represents pyridyl or pyridyl substituted with one to three substituents, which may be the same or different and selected from the substituent group c).

* * * * *

UNITED STATES PATENT AND TRADEMARK OFFICE
CERTIFICATE OF CORRECTION

PATENT NO. : 7,956,060 B2
APPLICATION NO. : 10/594369
DATED : June 7, 2011
INVENTOR(S) : Hitoshi Arai et al.

It is certified that error appears in the above-identified patent and that said Letters Patent is hereby corrected as shown below:

COLUMN 4:

Line 26, "heteroalicyclic-alkyl," should read --heteroalicyclic alkyl,--.

COLUMN 7:

Line 31, "represents each" should read --each represents--.

COLUMN 8:

Line 26, "1,2,3,4-tetrahydronaphtyl," should read --1,2,3,4-tetrahydronaphthyl,--.

COLUMN 19:

Line 36, "Step 11" should read --Step 12--.

COLUMN 22:

Line 5, "Compound (o)." should read --Compound (O).--.

COLUMN 199:

Compound Number 461 " 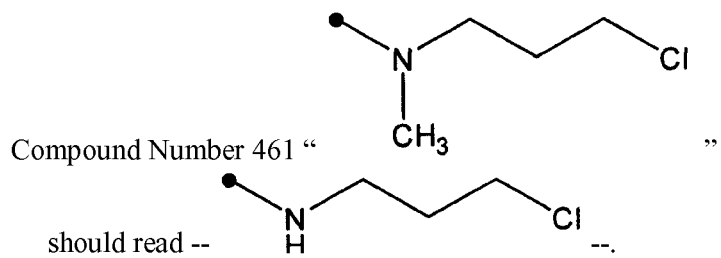 "

should read -- --.

Signed and Sealed this
Twenty-fifth Day of October, 2011

David J. Kappos
*Director of the United States Patent and Trademark Office*

COLUMN 212:

Line 35, "compounds" should read --compound--; and
Line 37, "equipments." should read --equipment.--.

COLUMN 216:

Line 4, "to raise" should read --rising--.

COLUMN 220:

Line 18, "Lithium" should read --lithium--.

COLUMN 223:

Line 29, "the each" should read --each of the--.

COLUMN 224:

Line 54, "were" should read --was--.

COLUMN 225:

Line 37, "were" should read --was--;
Line 40, "amine" should read --amine compounds--;
Line 55, "were" should read --was--;
Line 56, "amine" should read --amine compounds--; and
Line 67, "were" should read --was--.

COLUMN 226:

Line 1, "amine" should read --amine compounds--.

COLUMN 227:

Line 18, "CH$_3$]" should read --CH$_3$--; and
Line 48, "CH$_3$]" should read --CH$_3$--.

COLUMN 228:
Line 22, "were" should read --was--; and
Line 25, "amine" should read --amine compounds--.

COLUMN 229:

Line 11, "were" should read --was--.

COLUMN 230:

Line 25, "were" should read --was--.

COLUMN 231:

Line 12, "the reaction mixture was added with" should read
--to the reaction mixture was added--;
Line 13, "5% an" should read --a 5%--; and
Line 55, "an" should be deleted.

COLUMN 232:

Line 42, "2.913" should read --2.93--.

COLUMN 233:

Line 41, "(s, 1H)," should read --(s, 3H),--.

COLUMN 236:

Line 38, "8.41°" should read --8.41--;
Line 47, "(t. J=6.8 Hz, 4H)," should read --(t, J=6.8 Hz, 4H),--;
Line 48, "(dt," should read --3.73 (dt,--; and
Line 62, "J 1.6," should read --J=1.6,--.

COLUMN 237:

Line 21, "(CDCl$_3$) δ (ppm):" should read --(CDCl$_3$ δ(ppm):1.22--;
Line 22, "(br s, 1H)," should read --(br s, 1H), 6.04--; and
Line 51, "1H)," should read --1H), 3.11-- and
"6.5 Hz, 2H)," should read --6.5 Hz, 2H), 5.98--.

COLUMN 238:

Line 57, "3.1-3.4 (m, 6H)," should read --3.1-3.4 (m, 6H), 3.59--; and
Line 58, "(s, 2H)," should read --(s, 2H), 8.01-- and
"(br, 1H)," should read --(br, 1H), 8.86--.

CERTIFICATE OF CORRECTION (continued)
U.S. Pat. No. 7,956,060 B2

COLUMN 239:

Line 46, "3.90 (s, 2H)," should read --3.90 (s, 2H), 7.27-- and
"J=5.4 Hz, 1H)," should read --J=5.4 Hz, 1H), 7.84--;
Line 47, "(s, 1H)," should read --(s, 1H), 8.46--;
Line 50, "(CDCl$_3$) δ (ppm):" should read --(CDCl$_3$) δ (ppm): 1.01--;
Line 51, "(s, 3H)," should read --(s, 3H), 2.49--;
Line 61, "(DMSO-d$_6$) δ (ppm):" should read --(DMSO-d$_6$) δ (ppm): 1.22--; and
Line 62, "(m, 8H)," should read --(m, 8H), 2.90)--
and "(s, 2H)," should read --(s,2H), 7.26--.

COLUMN 243:

Line 54, "lower alkylsulfonyl," (2$^{nd}$ occurrence) should read --lower alkylsulfinyl,--.